United States Patent
Cunningham et al.

(10) Patent No.: US 10,858,385 B2
(45) Date of Patent: *Dec. 8, 2020

(54) METHODS AND COMPOSITIONS FOR NUCLEOSIDE TRIPHOSPHATE AND RIBONUCLEIC ACID PRODUCTION

(71) Applicant: GreenLight Biosciences, Inc., Medford, MA (US)

(72) Inventors: Drew S. Cunningham, Winchester, MA (US); Daniel MacEachran, Medford, MA (US); James Robbins Abshire, Cambridge, MA (US); Himanshu Dhamankar, Arlington, MA (US); Ifeyinwa Iwuchukwu, Billerica, MA (US); Mehak Gupta, Medford, MA (US); Matthew Eduardo Moura, Cambridge, MA (US); Naveen Sudharsan, Malden, MA (US); Nicholas Skizim, Dedham, MA (US); Rachit Jain, Medford, MA (US); Karthikeyan Ramachandriya, Winchester, MA (US)

(73) Assignee: GreenLight Biosciences, Inc., Medford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/196,059

(22) Filed: Nov. 20, 2018

(65) Prior Publication Data
US 2019/0144489 A1 May 16, 2019

Related U.S. Application Data

(63) Continuation of application No. PCT/US2018/055353, filed on Oct. 11, 2018.

(60) Provisional application No. 62/571,071, filed on Oct. 11, 2017.

(51) Int. Cl.
| | |
|---|---|
| *C07H 21/02* | (2006.01) |
| *C12P 19/32* | (2006.01) |
| *C12P 19/30* | (2006.01) |
| *C12P 19/34* | (2006.01) |
| *C12N 9/12* | (2006.01) |
| *C12N 9/22* | (2006.01) |
| *C12N 9/90* | (2006.01) |
| *C12N 15/11* | (2006.01) |

(52) U.S. Cl.
CPC .......... *C07H 21/02* (2013.01); *C12N 9/1229* (2013.01); *C12N 9/22* (2013.01); *C12N 9/90* (2013.01); *C12N 15/11* (2013.01); *C12P 19/30* (2013.01); *C12P 19/32* (2013.01); *C12P 19/34* (2013.01); *C12Y 108/99002* (2013.01); *C12Y 204/02* (2013.01); *C12Y 207/0104* (2013.01); *C12Y 207/0401* (2013.01); *C12Y 207/04003* (2013.01); *C12Y 207/04004* (2013.01); *C12Y 207/04006* (2013.01); *C12Y 207/04014* (2013.01); *C12Y 207/07001* (2013.01); *C12Y 207/07004* (2013.01); *C12Y 207/07005* (2013.01)

(58) Field of Classification Search
None
See application file for complete search history.

(56) References Cited

U.S. PATENT DOCUMENTS

| | | |
|---|---|---|
| 3,223,592 A | 12/1965 | Sakaguchi et al. |
| 3,684,652 A | 8/1972 | Nakayama et al. |
| 3,950,357 A | 4/1976 | Kahan et al. |
| RE28,886 E | 6/1976 | Nakayama et al. |
| 4,006,060 A | 2/1977 | Kahan et al. |
| 4,194,047 A | 3/1980 | Christensen et al. |
| 4,248,966 A | 2/1981 | Demain et al. |
| 4,266,034 A | 5/1981 | Patel |
| 4,270,537 A | 6/1981 | Romaine |
| 4,292,436 A | 8/1981 | Liu et al. |
| 4,329,481 A | 5/1982 | Liu et al. |
| 4,374,772 A | 2/1983 | Hazen et al. |
| 4,438,201 A | 3/1984 | Kubo et al. |
| 4,458,066 A | 7/1984 | Caruthers et al. |
| 4,460,689 A | 7/1984 | Foor et al. |
| 4,596,556 A | 6/1986 | Morrow et al. |
| 4,790,824 A | 12/1988 | Morrow et al. |
| 4,886,499 A | 12/1989 | Cirelli et al. |
| 4,940,460 A | 7/1990 | Casey et al. |
| 4,941,880 A | 7/1990 | Burns |
| 4,946,783 A | 8/1990 | Beckwith et al. |
| 4,950,603 A | 8/1990 | Ingolia et al. |
| 5,000,000 A | 3/1991 | Ingram et al. |
| 5,001,055 A | 3/1991 | Imahori |
| 5,015,235 A | 5/1991 | Crossman |
| 5,064,413 A | 11/1991 | McKinnon et al. |
| 5,070,020 A | 12/1991 | Ingolia et al. |

(Continued)

FOREIGN PATENT DOCUMENTS

| | | |
|---|---|---|
| CN | 1329506 C | 8/2007 |
| CN | 105219822 | 1/2016 |

(Continued)

OTHER PUBLICATIONS

Extended European Search Report for EP 16774076.0, dated Apr. 24, 2019.

(Continued)

*Primary Examiner* — Nancy A Treptow
(74) *Attorney, Agent, or Firm* — Wolf, Greenfield & Sacks, P.C.

(57) ABSTRACT

Provided herein, in some embodiments, are methods and composition for the production of nucleoside triphosphates and ribonucleic acids.

30 Claims, 17 Drawing Sheets
Specification includes a Sequence Listing.

(56) References Cited

U.S. PATENT DOCUMENTS

| | | |
|---|---|---|
| 5,141,496 A | 8/1992 | Dalto et al. |
| 5,190,521 A | 3/1993 | Hubbard et al. |
| 5,312,335 A | 5/1994 | McKinnon et al. |
| 5,319,122 A | 6/1994 | Friedman |
| 5,328,483 A | 7/1994 | Jacoby |
| 5,334,144 A | 8/1994 | Alchas et al. |
| 5,339,163 A | 8/1994 | Homma et al. |
| 5,417,662 A | 5/1995 | Hjertman et al. |
| 5,436,131 A | 7/1995 | Condra et al. |
| 5,466,220 A | 11/1995 | Brenneman |
| 5,383,851 A | 12/1995 | McKinnon et al. |
| 5,480,381 A | 1/1996 | Weston |
| 5,503,627 A | 4/1996 | McKinnon et al. |
| 5,520,639 A | 5/1996 | Peterson et al. |
| 5,527,288 A | 6/1996 | Gross et al. |
| 5,569,189 A | 10/1996 | Parsons |
| 5,593,856 A | 1/1997 | Choi et al. |
| 5,599,302 A | 2/1997 | Lilley et al. |
| 5,649,912 A | 7/1997 | Peterson |
| 5,665,566 A | 9/1997 | Lavaille |
| 5,672,497 A | 9/1997 | Cox et al. |
| 5,704,911 A | 1/1998 | Parsons |
| 5,871,922 A | 2/1999 | Salmond et al. |
| 5,893,397 A | 4/1999 | Peterson et al. |
| 5,993,412 A | 11/1999 | Deily et al. |
| 6,159,693 A | 12/2000 | Shultz et al. |
| 6,168,931 B1 | 1/2001 | Swartz et al. |
| 6,387,667 B1 | 5/2002 | Maruyama et al. |
| 6,440,688 B1 | 8/2002 | Bruce et al. |
| 6,472,169 B1 | 10/2002 | Frost et al. |
| 6,531,299 B1 | 3/2003 | Khosla et al. |
| 6,613,552 B1 | 9/2003 | Frost et al. |
| 6,746,859 B1 | 6/2004 | LaVallie |
| 6,921,659 B2 | 7/2005 | Joly |
| 6,994,986 B2 | 2/2006 | Swartz et al. |
| 7,041,479 B2 | 5/2006 | Swartz et al. |
| 7,223,390 B2 | 5/2007 | Brown |
| 7,226,767 B2 | 6/2007 | Maruyama et al. |
| 7,312,049 B2 | 12/2007 | Calhoun et al. |
| 7,338,789 B2 | 3/2008 | Swartz et al. |
| 7,341,852 B2 | 3/2008 | Voloshin et al. |
| 7,351,563 B2 | 4/2008 | Swartz et al. |
| 7,579,005 B2 | 8/2009 | Keeler et al. |
| 8,876,443 B2 | 7/2014 | Chan et al. |
| 8,859,247 B2 | 10/2014 | Koltermann et al. |
| 8,916,358 B2 | 12/2014 | Swartz |
| 8,956,833 B2 | 2/2015 | Swartz |
| 9,469,861 B2 | 10/2016 | Blake et al. |
| 9,611,487 B2 | 4/2017 | Blake et al. |
| 9,637,746 B2 | 5/2017 | Klein-Marcuschamer |
| 9,688,977 B2 | 6/2017 | Blake et al. |
| 10,036,001 B2 | 7/2018 | Swartz |
| 10,316,342 B2 | 6/2019 | MacEachran et al. |
| 10,421,953 B2 | 9/2019 | Blake et al. |
| 2002/0058303 A1 | 5/2002 | Swartz et al. |
| 2002/0127633 A1 | 9/2002 | Dilley et al. |
| 2002/0160459 A1 | 10/2002 | Berry et al. |
| 2003/0022178 A1 | 1/2003 | Schneewind et al. |
| 2003/0040086 A1 | 2/2003 | Dodge et al. |
| 2003/0113778 A1 | 6/2003 | Schulte et al. |
| 2004/0002103 A1 | 1/2004 | Short |
| 2004/0038250 A1 | 2/2004 | Nunez et al. |
| 2004/0091976 A1 | 5/2004 | Deng et al. |
| 2004/0209321 A1 | 10/2004 | Swartz et al. |
| 2005/0054044 A1 | 3/2005 | Swartz et al. |
| 2005/0239174 A1 | 10/2005 | Bao et al. |
| 2006/0234358 A1 | 10/2006 | Anderlei et al. |
| 2006/0281148 A1 | 12/2006 | Swartz et al. |
| 2007/0111283 A1 | 5/2007 | Cannon et al. |
| 2007/0154983 A1 | 7/2007 | Calhoun et al. |
| 2007/0161092 A1 | 7/2007 | Townsend et al. |
| 2007/0202198 A1 | 8/2007 | Purcell |
| 2008/0021205 A1 | 1/2008 | Blau et al. |
| 2008/0131925 A1 | 6/2008 | Berk et al. |
| 2009/0042244 A1 | 2/2009 | Voloshin et al. |
| 2009/0053779 A1 | 2/2009 | Lee et al. |
| 2009/0124012 A1 | 5/2009 | Nikolsky et al. |
| 2009/0155867 A1 | 6/2009 | Soucaille |
| 2009/0275096 A1 | 11/2009 | Burgard et al. |
| 2009/0275097 A1 | 11/2009 | Sun et al. |
| 2009/0312539 A1 | 12/2009 | Gnanaprakasam et al. |
| 2009/0325245 A1 | 12/2009 | Soucaille et al. |
| 2010/0120105 A1 | 5/2010 | Anthony et al. |
| 2010/0136640 A1 | 6/2010 | Lee et al. |
| 2010/0143997 A1 | 6/2010 | Buelter et al. |
| 2010/0291653 A1 | 11/2010 | Ness et al. |
| 2011/0008867 A1 | 1/2011 | Zarur et al. |
| 2011/0099670 A1 | 4/2011 | Koops et al. |
| 2011/0124069 A1 | 5/2011 | Mampel et al. |
| 2011/0262946 A1 | 10/2011 | Roy et al. |
| 2011/0269198 A1 | 11/2011 | Klein-Marcuschamer |
| 2011/0275116 A1 | 11/2011 | Swartz |
| 2011/0312052 A1 | 12/2011 | Koltermann et al. |
| 2012/0052547 A1 | 3/2012 | Swartz |
| 2012/0070870 A1 | 3/2012 | Way et al. |
| 2013/0065878 A1 | 3/2013 | Blake et al. |
| 2014/0193869 A1 | 7/2014 | Blake et al. |
| 2014/0271559 A1 | 9/2014 | Baum et al. |
| 2015/0037868 A1 | 2/2015 | Blake et al. |
| 2015/0064751 A1 | 3/2015 | Swartz |
| 2015/0191753 A1 | 7/2015 | Swartz |
| 2016/0028101 A1 | 1/2016 | Zhang et al. |
| 2016/0115558 A1 | 4/2016 | Swartz |
| 2017/0044554 A1 | 2/2017 | Zhang et al. |
| 2017/0096692 A1 | 4/2017 | Blake et al. |
| 2017/0159058 A1 | 6/2017 | Blake et al. |
| 2017/0247724 A1 | 8/2017 | Klein-Marcuschamer |
| 2017/0253866 A1 | 9/2017 | Blake et al. |
| 2017/0292138 A1 | 10/2017 | Blake et al. |
| 2018/0030416 A1 | 2/2018 | Beltran Pavez et al. |
| 2018/0087045 A1 | 3/2018 | Blake et al. |
| 2018/0273985 A1 | 9/2018 | Blake |
| 2018/0320210 A1 | 11/2018 | MacEachran et al. |

FOREIGN PATENT DOCUMENTS

| | | |
|---|---|---|
| CN | 105219822 A | 1/2016 |
| EP | 0377295 A1 | 7/1990 |
| EP | 0444775 A1 | 9/1991 |
| EP | 0553821 A1 | 8/1993 |
| EP | 1261696 A1 | 12/2002 |
| EP | 1264894 A1 | 12/2002 |
| EP | 1279736 A1 | 1/2003 |
| EP | 1433856 A1 | 6/2004 |
| EP | 1502956 A1 | 2/2005 |
| EP | 1514927 A1 | 3/2005 |
| EP | 1631675 A1 | 3/2006 |
| EP | 1939210 A1 | 7/2008 |
| EP | 1587947 B1 | 1/2010 |
| EP | 2204453 A1 | 7/2010 |
| EP | 2377928 A2 | 10/2011 |
| GB | 2 018 822 A | 10/1979 |
| JP | S61-260895 A | 11/1986 |
| JP | S63-7788 A | 1/1988 |
| JP | H01-228473 A | 9/1989 |
| JP | H07-298893 A | 11/1995 |
| JP | H08-502176 A | 3/1996 |
| JP | H08-196284 A | 8/1996 |
| JP | H10-500849 A | 1/1998 |
| JP | 2002-535008 A | 10/2002 |
| JP | 2007-534338 A | 11/2007 |
| JP | 2009-531050 A | 9/2009 |
| JP | 2013-021967 A | 2/2013 |
| JP | 2013-526277 | 6/2013 |
| JP | 2013-537802 | 10/2013 |
| JP | 5800218 B2 | 10/2015 |
| WO | WO 1995/032294 A1 | 11/1995 |
| WO | WO 1997/013537 A1 | 4/1997 |
| WO | WO 1997/13537 A1 | 4/1997 |
| WO | WO 1997/037705 A1 | 10/1997 |
| WO | WO 1997/37705 A1 | 10/1997 |
| WO | WO 1998/007690 A1 | 2/1998 |
| WO | WO 1999/034850 A1 | 7/1999 |
| WO | WO 1999/50389 | 10/1999 |

(56) References Cited

FOREIGN PATENT DOCUMENTS

| WO | WO 2000/003581 A1 | 1/2000 |
|---|---|---|
| WO | WO 2000/039288 A1 | 7/2000 |
| WO | WO 2000/044923 A1 | 8/2000 |
| WO | WO 2000/055353 A1 | 9/2000 |
| WO | WO 2000/061768 A2 | 10/2000 |
| WO | WO 2003/038117 A2 | 5/2003 |
| WO | WO 2003/054792 A2 | 7/2003 |
| WO | WO 2005/030949 A1 | 4/2005 |
| WO | WO 2005/030995 A1 | 4/2005 |
| WO | WO 2005/052117 A2 | 6/2005 |
| WO | WO 2005/098048 A1 | 10/2005 |
| WO | WO 2006/001382 A1 | 1/2006 |
| WO | WO 2006/090385 A1 | 8/2006 |
| WO | WO 2007/053655 A2 | 5/2007 |
| WO | WO 2007/110619 A1 | 10/2007 |
| WO | WO 2007/137144 A2 | 11/2007 |
| WO | WO 2008/002661 A2 | 1/2008 |
| WO | WO 2008/002663 A2 | 1/2008 |
| WO | WO 2008/002673 A2 | 1/2008 |
| WO | WO 2008/066583 A2 | 6/2008 |
| WO | WO 2008/088884 A2 | 7/2008 |
| WO | WO 2008/094546 A2 | 8/2008 |
| WO | WO 2010/046713 A2 | 4/2010 |
| WO | WO 2010/074760 A1 | 7/2010 |
| WO | WO 2010/077806 A1 | 7/2010 |
| WO | WO 2011/017560 A1 | 2/2011 |
| WO | WO 2011/072287 A2 | 6/2011 |
| WO | WO 2011/140516 A2 | 11/2011 |
| WO | WO 2012/030980 A1 | 3/2012 |
| WO | WO 2012/135902 A1 | 10/2012 |
| WO | WO 2014/151190 A1 | 9/2014 |
| WO | WO 2014/197655 A1 | 12/2014 |
| WO | WO 2014/197702 A1 | 12/2014 |
| WO | WO 2015/021058 A2 | 2/2015 |
| WO | WO 2016/160936 A1 | 10/2016 |
| WO | WO 2017/176963 A1 | 10/2017 |
| WO | WO 2018/126287 A1 | 7/2018 |

OTHER PUBLICATIONS

International Search Report and Written Opinion for PCT/US2018/055353, dated Jan. 7, 2019.
Partial Supplementary European Search Report for EP 16774076.0, dated Jan. 21, 2019.
[No Author Listed] Biapenem. Drugs Fut. 1994;19(7):631-637.
[No Author Listed] Biolistic® Particle Delivery System Bibliography. Bio-Rad Technical Bulletin #1687. Bio-Rad Laboratories. 12 pages.
[No Author Listed] Crude Lysate. Wikipedia entry for Crude Lysate, http://en.wikipedia.org/wiki/Crude_lysate downloaded on Mar. 3, 2015. Page Last Modified on Nov. 3, 2013. 1 page.
Adams et al., Hindered dialkylamino nucleoside phosphite reagents in the synthesis of two DNA 51-mers. J Am Chem Soc. 1983;105(3):661-3.
Alber et al., Malonyl-coenzyme A reductase in the modified 3-hydroxypropionate cycle for autotrophic carbon fixation in archaeal Metallosphaera and *Sulfolobus* spp. J Bacteriol. Dec. 2006;188(24):8551-9. Epub Oct. 13, 2006.
Allain, Cell-free ethanol production: the future of fuel ethanol? J Chem Technol Biotechnol. 2007;82:117-20.
Alper et al., Tuning genetic control through promoter engineering. Proc Natl Acad Sci U S A. Sep. 6, 2005;102(36):12678-83. Epub Aug. 25, 2005.
Alves-Pereira et al., CDP-alcohol hydrolase, a very efficient activity of the 5'-nucleotidase/udp-sugar hydrolase encoded by the usha gene of yersinia intermedia and *Escherichia coli*. J Bacteriol. Sep. 15, 2008;190(18):6153-61. Published ahead of print Jul. 18, 2008 , doi:10.1128/JB.00658-08.
Anthony et al., Optimization of the mevalonate-based isoprenoid biosynthetic pathway in *Escherichia coli* for production of the anti-malarial drug precursor amorpha-4,11-diene. Metab Eng. Jan. 2009;11(1):13-9. Epub Aug. 12, 2008.
Arnold et al., Proteolytic degradation of ribonuclease A in the pretransition region of thermally and urea-induced unfolding. Eur J Biochem. Jan. 2001;268(1):93-7.
Atsumi et al., Acetolactate synthase from Bacillus subtilis serves as a 2-ketoisovalerate decarboxylase for isobutanol biosynthesis in *Escherichia coli*. Appl. Environ. Microbial. 2009;75:6306-11.
Atsumi et al., Metabolic engineering of *Escherichia coli* for 1-butanol production. Metab Eng. Nov. 2008;10(6):305-11. Epub Sep. 14, 2007.
Atsumi et al., Non-fermentative pathways for synthesis of branched-chain higher alcohols as biofuels. Nature. Jan. 3, 2008;451(7174):86-9.
Baba et al., Construction of *Escherichia coli* K-12 in-frame, single-gene knockout mutants: the Keio collection. Mol Syst Biol. 2006;2:2006. 0008. Epub Feb. 21, 2006.
Bastian et al. Engineered ketol-acid reductoisomerase and alcohol dehydrogenase enable anaerobic 2-methylpropan-1-ol production at theoretical yield in *Escherichia coli*. Metab. Eng. 2011;13:345-52.
Bateson et al., Olivanic acid analogues. Part 6. Biomimetic synthesis of (±)-PS-5, (±)-6-Epi-PS-5, and (±)-benzyl MM22381. J Chem Soc Perkin Trans 1. 1990;1793-1801.
Baum et al., beta-Galactosidase containing a human immunodeficiency virus protease cleavage site is cleaved and inactivated by human immunodeficiency virus protease. Proc Natl Acad Sci U S A. Dec. 1990;87(24):10023-7.
Beaucage et al., Deoxynucleoside phosphoramidites—A new class of key intermediates for deoxypolynucleotide synthesis. Tetra Lett. 1981;22(20):1859-62.
Belousov et al., Sequence-specific targeting and covalent modification of human genomic DNA. Nucleic Acids Res. Sep. 1, 1997;25(17):3440-4.
Benton et al., Screening lambdagt recombinant clones by hybridization to single plaques in situ Science. Apr. 8, 1977;196(4286):180-2.
Berge et al., Pharmaceutical salts. J Pharmaceut Sci. Jan. 1977;66(1):1-19.
Blattner et al., Analysis of the *Escherichia coli* genome. IV. DNA sequence of the region from 89.2 to 92.8 minutes. Nucleic Acids Res. Nov. 25, 1993;21(23):5408-17.
Blommers et al., Effects of the introduction of L-nucleotides into DNA. Solution structure of the heterochiral duplex d(G-C-G-(L)T-G-C-G).d(C-G-C-A-C-G-C) studied by NMR spectroscopy Biochemistry. Jun. 28, 1994;33(25):7886-96.
Bodner et al., Definition of the common and divergent steps in carbapenem β-lactam antibiotic biosynthesis. Chembiochem. Sep. 19, 2011;12(14):2159-65. doi: 10.1002/cbic.201100366. Epub Aug. 24, 2011.
Bodner et al., Non-heme iron oxygenases generate natural structural diversity in carbapenem antibiotics. J Am Chem Soc. Jan. 13, 2010;132(1):12-3.
Boiteux et al., Design of glycolysis. Philos Trans R Soc Lond B Biol Sci. Jun. 26, 1981;293(1063):5-22.
Bongaerts et al., Metabolic engineering for microbial production of aromatic amino acids and derived compounds. Metab Eng. Oct. 2001;3(4):289-300.
Boyer et al., Cell-free synthesis and maturation of [FeFe] hydrogenases. Biotechnol Bioeng. Jan. 1, 2008;99(1):59-67.
Bradley, Star role for bacteria in controlling flu pandemic? Nat Rev Drug Discov. Dec. 2005;4(12):945-6.
Brady et al., Transfer of Pantoea citrea, Pantoea punctata and Pantoea terrea to the genus *Tatumella* emend. as *Tatumella citrea* comb. nov., *Tatumella punctata* comb. nov. and *Tatumella terrea* comb. nov. and description of *Tatumella morbirosei* sp. nov. Int J Syst Evol Microbiol. Mar. 2010;60(Pt 3):484-94. doi: 10.1099/ijs. 0.012070-0. Epub Aug. 4, 2009.
Brown et al., Chemical synthesis and cloning of a tyrosine tRNA gene. Methods Enzymol. 1979;68:109-51.
Buist et al., Different subcellular locations of secretome components of Gram-positive bacteria. Microbiology. Oct. 2006;152(Pt 10):2867-74.

(56) References Cited

OTHER PUBLICATIONS

Bujara et al., Exploiting cell-free systems: Implementation and debugging of a system of biotransformations. Biotechnol Bioeng. Jun. 15, 2010;106(3):376-89. doi: 10.1002/bit.22666.

Bujara et al., Optimization of a blueprint for in vitro glycolysis by metabolic real-time analysis. Nat Chem Biol. May 2011;7(5):271-7. doi: 10.1038/nchembio.541. Epub Mar. 20, 2011.

Calhoun et al., An economical method for cell-free protein synthesis using glucose and nucleoside monophosphates. Biotechnol Prog. Jul.-Aug. 2005;21(4):1146-53.

Calhoun et al., Energizing cell-free protein synthesis with glucose metabolism. Biotechnol Bioeng. Jun. 5, 2005;90(5):606-13.

Calhoun et al., Energy systems for ATP regeneration in cell-free protein synthesis reactions. Methods in Molecular Biology. In vitro transcription and translation protocols. 2007;375(2):3-17.

Calhoun et al., Total amino acid stabilization during cell-free protein synthesis reactions. J Biotechnol. May 17, 2006;123(2):193-203. Epub Jan. 26, 2006.

Campbell et al., The CTP:phosphocholine cytidylyltransferase encoded by the licC gene of *Streptococcus pneumoniae:* cloning, expression, purification, and characterization. Biochim Biophys Acta. Dec. 30, 2001;1534(2-3):85-95.

Chandran et al., Phosphoenolpyruvate availability and the biosynthesis of shikimic acid. Biotechnol Prog. May-Jun. 2003;19(3):808-14.

Chang et al., YPA: an integrated repository of promoter features in *Saccharomyces cerevisiae.* Nucleic Acids Res. Jan. 2011;39(Database issue):D647-52. Epub Nov. 2, 2010.

Chen et al., A modified osmotic shock for periplasmic release of a recombinant creatinase from *Escherichia coli.* Biochem Eng J. 2004;19:211-5.

Chen et al., Crystal structures of penicillin-binding protein 6 from *Escherichia coli.* J Am Chem Soc. Oct. 14, 2009;131(40):14345-54.

Chen et al., High-level accumulation of a recombinant antibody fragment in the periplasm of *Escherichia coli* requires a triple-mutant (degP prc spr) host strain. Biotechnol Bioeng. Mar. 5, 2004;85(5):463-74.

Chisti et al., Disruption of microbial cells for intracellular products. Enzyme Micro Technol 1986;8(4):194-204. doi 10.1016/0141-0229(86)90087-6.

Chiu et al., Site-directed, Ligase-Independent Mutagenesis (SLIM): a single-tube methodology approaching 100% efficiency in 4 h. Nucleic Acids Res. Dec. 7, 2004;32(21):e174.

Chong et al., Single-column purification of free recombinant proteins using a self-cleavable affinity tag derived from a protein splicing element. Gene. Jun. 19, 1997;192(2):271-81.

Choubey et al., Molecular characterization and localization of Plasmodium falciparum choline kinase. Biochim Biophys Acta. Jul. 2006;1760(7):1027-38.

Collins-Racie et al., Production of recombinant bovine enterokinase catalytic subunit in *Escherichia coli* using the novel secretory fusion partner DsbA. Biotechnology (N Y). Sep. 1995;13(9):982-7.

Coulthurst et al., Regulation and biosynthesis of carbapenem antibiotics in bacteria. Nat Rev Microbiol. Apr. 2005;3(4):295-306. Erratum included.

Dahiyat et al., De novo protein design: fully automated sequence selection. Science. Oct. 3, 1997;278(5335):82-7.

Dancz et al., Inducible control of virulence gene expression in Listeria monocytogenes: temporal requirement of listeriolysin O during intracellular infection. J Bacteriol. Nov. 2002;184(21):5935-45.

Danese et al., Targeting and assembly of periplasmic and outer-membrane proteins in *Escherichia coli.* Annu Rev Genet. 1998;32:59-94.

Dani et al., Isolation and characterization of a thylakoid membrane module showing partial light and dark reactions. Biochim Biophys Acta. May 15, 2005;1669(1):43-52.

Daniell et al., Transformation of the cyanobacterium Anacystis nidulans 6301 with the *Escherichia coli* plasmid pBR322. Proc Natl Acad Sci U S A. Apr. 1986;83(8):2546-50.

Datsenko et al., One-step inactivation of chromosomal genes in *Escherichia coli* K-12 using PCR products. Proc Natl Acad Sci U S A. Jun. 6, 2000;97(12):6640-5.

Daube et al., Cell-free co-synthesis of protein nanoassemblies: tubes, rings, and doughnuts. Nano Lett. Mar. 2007;7(3):638-41. Epub Feb. 2, 2007.

De Boer et al., Protein targeting towards the thylakoid lumen of chloroplasts: proper localization of fusion proteins is only observed in vivo. EMBO J. Oct. 1991;10(10):2765-72.

De La Plaza et al., Biochemical and molecular characterization of alpha-ketoisovalerate decarboxylase, an enzyme involved in the formation of aldehydes from amino acids by Lactococcus lactis. FEMS Microbial. Lett. 2004;238:367-374.

De Mey et al., Construction and model-based analysis of a promoter library for *E. coli:* an indispensable tool for metabolic engineering. BMC Biotechnol. Jun. 18, 2007;7:34.

De Vries et al., Cloning, expression, and sequence analysis of the Bacillus methanolicus C1 methanol dehydrogenase gene. J Bacteriol. Aug. 1992;174(16):5346-53.

Dietrich et al., A novel semi-biosynthetic route for artemisinin production using engineered substrate-promiscuous P450(BM3). ACS Chem Biol. Apr. 17, 2009;4(4):261-7.

Ding et al., Functional analysis of the essential bifunctional tobacco enzyme 3-dehydroquinate dehydratase/shikimate dehydrogenase in transgenic tobacco plants. J Exp Bot. 2007;58(8):2053-67. Epub Apr. 26, 2007.

Dingwall et al., The nucleoplasmin nuclear location sequence is larger and more complex than that of SV-40 large T antigen. J Cell Biol. Sep. 1988;107(3):841-9.

Draper et al., Ti plasmid homologous sequences present in tissues from agrobacterium plasmid-transformed petunia protoplasts. Plant Cell Physiol. 1982;23(3):451-8.

Egan et al., Transketolase kinetics. The slow reconstitution of the holoenzyme is due to rate-limiting dimerization of the subunits. J Biol Chem. May 25, 1981;256(10):4877-83.

Ehrmann et al., TnTIN and TnTAP: mini-transposons for site-specific proteolysis in vivo. Proc Natl Acad Sci U S A. Nov. 25, 1997;94(24):13111-5.

Elander, Industrial production of beta-lactam antibiotics. Appl Microbiol Biotechnol. Jun. 2003;61(5-6):385-92. Epub Apr. 3, 2003.

Ellermeier et al., Construction of targeted single copy lac fusions using lambda Red and FLP-mediated site-specific recombination in bacteria. Gene. May 15, 2002;290(1-2):153-61.

Erb et al., Carboxylation mechanism and stereochemistry of crotonyl-CoA carboxylase/reductase, a carboxylating enoyl-thioester reductase. Proc Natl Acad Sci U S A. Jun. 2, 2009;106(22):8871-6. Epub May 20, 2009.

Erb et al., Synthesis of C5-dicarboxylic acids from C2-units involving crotonyl-CoA carboxylase/reductase: The ethylmalonyl-CoA pathway. Proc Nat Acad Sci. Jun. 4, 2007;104(25):10631-6.

Eser et al.,Target-directed proteolysis in vivo. Methods Enzymol. 2007;421:68-83.

Evans et al., The asymmetric synthesis of β-lactam antibiotics—IV. A formal synthesis of thienamycin. Tetra Lett. 1986;27(41):4961-4.

Fischer et al., Metabolic flux profiling of *Escherichia coli* mutants in central carbon metabolism using GC-MS. Eur J Biochem. Mar. 2003;270(5):880-91.

Flores et al., Pathway engineering for the production of aromatic compounds in *Escherichia coli.* Nat Biotechnol. May 1996;14(5):620-3.

Flores et al., Analysis of carbon metabolism in *Escherichia coli* strains with an inactive phosphotransferase system by (13)C labeling and NMR spectroscopy. Metab Eng. Apr. 2002;4(2):124-37.

Flores et al., Growth-rate recovery of *Escherichia coli* cultures carrying a multicopy plasmid, by engineering of the pentose-phosphate pathway. Biotechnol Bioeng. Aug. 20, 2004;87(4):485-94.

Fox et al., Methane monooxygenase from Methylosinus trichosporium OB3b. Purification and properties of a three-component system with high specific activity from a type II methanotroph. J Biol Chem. Jun. 15, 1989;264(17):10023-33.

(56) References Cited

OTHER PUBLICATIONS

Fradejas et al., The control of shikimic acid synthesis by tyrosine and phenylalamine. Biochem Biophys Res Commun. Jul. 26, 1961;5:320-3.
Freeman et al., Four enzymes define the incorporation of coenzyme A in thienamycin biosynthesis. Proc Natl Acad Sci U S A. Aug. 12, 2008;105(32):11128-33. Epub Aug. 4, 2008. Supplemental material included.
Freeman et al., A comparison of methods for plasmid delivery into plant protoplasts. Plant Cell Physiol. 1984;25(8):1353-65.
Frenkel et al., 7,12-dimethylbenz[a]anthracene induces oxidative DNA modification in vivo. Free Radic Biol Med. Sep. 1995;19(3):373-80.
Friesen et al., Purification and Kinetic Characterization of CTP-:Phosphocholine Cytidylyltransferase from *Saccharomyces cerevisiae*. Protein Expression and Purification. Feb. 2001;21(1):141-8.
Fujio et al., Construction of a plasmid carrying both CTP synthetase and a fused gene formed from cholinephosphate cytidylyltransferase and choline kinase genes and its application to industrial CDP-choline production: enzymatic production of CDP-choline from orotic acid (Part II). Biosci Biotechnol Biochem. Jun. 1997;61(6):960-4.
Fujio et al., Production of ATP from Adenine by Brevibacterium ammoniagenes, J Ferment Technol. 1983;61(3):261-267.
Gaspar et al., High yields of 2,3-butanediol and mannitol in Lactococcus lactis through engineering of $NAD^+$ cofactor recycling. Appl Environ Microbiol. Oct. 2011;77(19):6826-35. Epub Aug. 12, 2011. Supplemental material included.
Genbank Accession No. AAC43119. Analysis of the *Escherichia coli* genome. IV. DNA sequence of the region from 89.2 to 92.8 minutes. Sep. 3, 1993. 4 pages. Last accessed Jul. 26, 2016.
Genbank Submission; NIH/NCBI, Accession No. AAB59985; Ling et al., Sequence analysis identifies the proline dehydrogenase and delta 1-pyrroline-5-carboxylate dehydrogenase domains of the multifunctional *Escherichia coli* PutA protein. Nov. 24, 1994.
Genbank Submission; NIH/NCBI, Accession No. AAC73225; Blattner et al., pyruvate dehydrogenase, decarboxylase component E1, thiamine triphosphate-binding [*Escherichia coli* str. K-12 substr. MG1655]. Sep. 1, 2011.
Genbank Submission; NIH/NCBI, Accession No. AAC73226; Blattner et al., pyruvate dehydrogenase, dihydrolipoyltransacetylase component E2 [*Escherichia coli* str. K-12 substr. MG1655]. Sep. 1, 2011.
Genbank Submission; NIH/NCBI, Accession No. AAC73296; Blattner et al., acetyl-CoA carboxylase, carboxytransferase, alpha subunit [*Escherichia coli* str. K-12 substr. MG1655]. Sep. 1, 2011.
Genbank Submission; NIH/NCBI, Accession No. AAC73346; Blattner et al., gamma-glutamate kinase [*Escherichia coli* str. K-12 substr. MG1655]. Sep. 1, 2011.
Genbank Submission; NIH/NCBI, Accession No. AAC73347; Blattner et al., gamma-glutamylphosphate reductase [*Escherichia coli* str. K-12 substr. MG1655]. Sep. 1, 2011.
Genbank Submission; NIH/NCBI, Accession No. AAC73842; Blattner et al., phosphoglyceromutase 1 [*Escherichia coli* str. K-12 substr. MG1655]. Sep. 1, 2011.
Genbank Submission; NIH/NCBI, Accession No. AAC73957; Blattner et al., L-allo-threonine aldolase, PLP-dependent [*Escherichia coli* str. K-12 substr. MG1655]. Sep. 1, 2011.
Genbank Submission; NIH/NCBI, Accession No. AAC74746; Blattner et al., pyruvate kinase I [*Escherichia coli* str. K-12 substr. MG1655]. Sep. 1, 2011.
Genbank Submission; NIH/NCBI, Accession No. AAC74849; Blattner et al., glyceraldehyde-3-phosphate dehydrogenase a [*Escherichia coli* str. K-12 substr. MG1655]. Sep. 1, 2011.
Genbank Submission; NIH/NCBI, Accession No. AAC74924; Blattner et al., pyruvate kinase II [*Escherichia coli* str. K-12 substr. MG1655]. Sep. 1, 2011.
Genbank Submission; NIH/NCBI, Accession No. AAC75447; Blattner et al., glucokinase [*Escherichia coli* str. K-12 substr. MG1655]. Sep. 1, 2011.
Genbank Submission; NIH/NCBI, Accession No. AAC75821; Blattner et al., enolase [*Escherichia coli* str. K-12 substr. MG1655]. Sep. 1, 2011.
Genbank Submission; NIH/NCBI, Accession No. AAC75962; Blattner et al., fructose-bisphosphate aldolase, class II [*Escherichia coli* str. K-12 substr. MG1655]. Sep. 1, 2011.
Genbank Submission; NIH/NCBI, Accession No. AAC75963; Blattner et al., phosphoglycerate kinase [*Escherichia coli* str. K-12 substr. MG1655]. Sep. 1, 2011.
Genbank Submission; NIH/NCBI, Accession No. AAC76849; Blattner et al., fused 3-hydroxybutyryl-CoA epimerase/delta(3)-cis-delta(2)-trans-enoyl-CoA isomerase/enoyl-CoA hydratase/3-hydroxyacyl-CoA dehydrogenase [*Escherichia coli* str. K-12 substr. MG1655]. Sep. 1, 2011.
Genbank Submission; NIH/NCBI, Accession No. AAC76898; Blattner et al.; Sep. 1, 2011.
Genbank Submission; NIH/NCBI, Accession No. AAC76901; Blattner et al., triosephosphate isomerase [*Escherichia coli* str. K-12 substr. MG1655]. Sep. 1, 2011.
Genbank Submission; NIH/NCBI, Accession No. AAC76995; Blattner et al., glucosephosphate isomerase [*Escherichia coli* str. K-12 substr. MG1655]. Sep. 1, 2011.
Genbank Submission; NIH/NCBI, Accession No. AAD38229; McGowan et al., CarA [*Pectobacterium carotovorum*]. Jul. 14, 1999.
Genbank Submission; NIH/NCBI, Accession No. AAD38230; McGowan et al., CarB [*Pectobacterium carotovorum*]. Jul. 14, 1999.
Genbank Submission; NIH/NCBI, Accession No. AAD38231; McGowan et al., CarC [*Pectobacterium carotovorum*]. Jul. 14, 1999.
Genbank Submission; NIH/NCBI, Accession No. ABA79923; Copeland et al., acetyl-CoA acetyltransferase [Rhodobacter sphaeroides 2.4.1]. Nov. 21, 2011.
Genbank Submission; NIH/NCBI, Accession No. ACJ71669; Erb et al., crotonyl-CoA carboxylase/reductase, partial [Rhodobacter sphaeroides]. Dec. 10, 2008.
Genbank Submission; NIH/NCBI, Accession No. AEW99093; Ou et al., putative methyltransferase (plasmid) [Streptomyces cattleya NRRL 8057 = DSM 46488]. Dec. 29, 2011.
Genbank Submission; NIH/NCBI, Accession No. AEW99097; Ou et al., putative methyltransferase (plasmid) [Streptomyces cattleya NRRL 8057 = DSM 46488]. Dec. 29, 2011.
Genbank Submission; NIH/NCBI, Accession No. AEW99098; Ou et al., putative methyltransferase (plasmid) [Streptomyces cattleya NRRL 8057 = DSM 46488]. Dec. 29, 2011.
Genbank Submission; NIH/NCBI, Accession No. BAA22406; Mori et al., L-proline 3-hydroxylase [*Streptomyces sp.*]. Sep. 20, 1997.
Genbank Submission; NIH/NCBI, Accession No. BAB67276; Kawarabayasi et al., malonyl-CoA/succinyl-CoA reductase [Sulfolobus tokodaii str. 7]. Aug. 17, 2011.
Genbank Submission; NIH/NCBI, Accession No. CAD18973; Nunez et al., enoyl-CoA hydratase carB homologue [Streptomyces cattleya]. Apr. 15, 2005.
Genbank Submission; NIH/NCBI, Accession No. CAD18975; Nunez et al., putative hydroxylase [Streptomyces cattleya]. Apr. 15, 2005.
Genbank Submission; NIH/NCBI, Accession No. CAD18981; Nunez et al., putative beta-lactam synthetase [Streptomyces cattleya]. Apr. 15, 2005.
Genbank Submission; NIH/NCBI, Accession No. CAD18985; Nunez et al., putative oxigenase [Streptomyces cattleya]. Apr. 15, 2005.
Genbank Submission; NIH/NCBI, Accession No. CAD18990; Nunez et al., putative cysteine transferase [Streptomyces cattleya]. Apr. 15, 2005.
Ger et al., A single Ser-180 mutation desensitizes feedback inhibition of the phenylalanine-sensitive3-deoxy-D-arabino-heptulosonate 7-phosphate (DAHP) synthetase in *Escherichia coli*. J Biochem. Nov. 1994;116(5):986-90.
Gibellini et al., Biochemical characterization of the initial steps of the Kennedy pathway in Trypanosoma brucei: the ethanolamine and choline kinases. Biochem J. 2008;415:135-44. Supplemental material included.

(56) References Cited

OTHER PUBLICATIONS

Goerke et al., Cell-free metabolic engineering promotes high-level production of bioactive Gaussia princeps luciferase.Metab Eng. May-Jul. 2008;10(3-4):187-200. doi: 10.1016/j.ymben.2008.04.001. Epub May 2, 2008.

Goerke et al., Development of cell-free protein synthesis platforms for disulfide bonded proteins. Biotechnol Bioeng. Feb. 1, 2008;99(2):351-67. Epub Jul. 11, 2007.

Gordon-Kamm et al., Transformation of Maize Cells and Regeneration of Fertile Transgenic Plants. Plant Cell. Jul. 1990;2(7):603-618.

Gosset et al., A direct comparison of approaches for increasing carbon flow to aromatic biosynthesis in *Escherichia coli*. J Ind Microbiol. Jul. 1996;17(1):47-52.

Grabowski, Enantiopure drug synthesis: from methyldopa to imipenem to efavirenz. Chirality. 2005;17 Suppl:S249-59.

Grieco et al., β-Lactam antibiotics: a formal stereocontrolled total synthesis of (.+−.)-thienamycin. J Am Chem Soc. 1984;106(21):6414-7.

Grunstein et al., Colony hybridization: a method for the isolation of cloned DNAs that contain a specific gene. Proc Natl Acad Sci U S A. Oct. 1975;72(10):3961-5.

Hamed et al., Carboxymethylproline synthase catalysed syntheses of functionalized N-heterocycles. Chem Commun (Camb). Mar. 7, 2010;46(9):1413-5. Epub Jan. 12, 2010.

Hamed et al., Crotonase catalysis enables flexible production of functionalized prolines and carbapenams. J Am Chem Soc. Jan. 11, 2012;134(1):471-9. doi: 10.1021/ja208318d. Epub Dec. 14, 2011.

Hamed et al., Evidence that thienamycin biosynthesis proceeds via C-5 epimerization: I catalyzes the formation of (2S,5S)-trans-carboxymethylproline. Chembiochem. Jan. 26, 2009;10(2):246-50.

Hamed et al., The enzymes of β-lactam biosynthesis. Nat Prod Rep. Jan. 2013;30(1):21-107. doi: 10.1039/c2np20065a.

Han et al., Paraffin oil as a "methane vector" for rapid and high cell density cultivation of Methylosinus trichosporium OB3b. Appl Microbiol Biotechnol. Jun. 2009;83(4):669-77. doi: 10.1007/s00253-009-1866-2. Epub Feb. 12, 2009.

Hardy et al., Hepatitis C virus RNA synthesis in a cell-free system isolated from replicon-containing hepatoma cells. J Virol. Feb. 2003;77(3):2029-37.

Hawley et al., Compilation and analysis of *Escherichia coli* promoter DNA sequences. Nucleic Acids Res. Apr. 25, 1983;11(8):2237-55.

Herrmann, The shikimate pathway as an entry to aromatic secondary metabolism. Plant Physiol. Jan. 1995;107(1):7-12.

Hethke et al., Cell-free transcription at 95 degrees: thermostability of transcriptional components and DNA topology requirements of Pyrococcus transcription. Genetics. Aug. 1999;152(4):1325-33.

Hikita et al., Effects of total hydrophobicity and length of the hydrophobic domain of a signal peptide on in vitro translocation efficiency. J Biol Chem. 1992;267:4882-8.

Hikita et al., The requirement of a positive charge at the amino terminus can be compensated for by a longer central hydrophobic stretch in the functioning of signal peptides. J Biol Chem. 1992;267:12375-9.

Hodgson et al., π-Allyltricarbonyliron lactone complexes in synthesis: application to the synthesis of the β-lactam antibiotic (+)-thienamycin. J Chem Soc Chem Comm. 1984;8:494-6.

Horak et al., Two distinct proteolytic systems responsible for glucose-induced degradation of fructose-1,6-bisphosphatase and the Gal2p transporter in the yeast *Saccharomyces cerevisiae* share the same protein components of the glucose signaling pathway. J Biol Chem. Mar. 8, 2002;277(10):8248-54. Epub Dec. 28, 2001.

Hryniewicz et al., Sulfate and thiosulfate transport in *Escherichia coli* K-12: identification of a gene encoding a novel protein involved in thiosulfate binding. J Bacteriol. Jun. 1990;172(6):3358-66.

Inouye, The discovery of mRNA interferases: implication in bacterial physiology and application to biotechnology. J Cell Physiol. Dec. 2006;209(3):670-6.

Ishii et al., DBTBS: a database of Bacillus subtilis promoters and transcription factors. Nucleic Acids Res. Jan. 1, 2001;29(1):278-80.

Jacobi et al., Formal Total Syntheses of the β-Lactam Antibiotics Thienamycin and PS-5. J Org Chem. 1996;61(7):2413-27.

Jang et al., Sugar sensing in higher plants. Plant Cell. Nov. 1994;6(11):1665-79.

Jenny et al., A critical review of the methods for cleavage of fusion proteins with thrombin and factor Xa. Protein Expr Purif. Sep. 2003;31(1):1-11.

Jermutus et al., Recent advances in producing and selecting functional proteins by using cell-free translation. Curr Opin Biotechnol. Oct. 1998;9(5):534-48.

Jewett et al., An integrated cell-free metabolic platform for protein production and synthetic biology. Mol Syst Biol. 2008;4:220. Epub Oct. 14, 2008.

Jewett et al., Mimicking the *Escherichia coli* cytoplasmic environment activates long-lived and efficient cell-free protein synthesis. Biotechnol Bioeng. Apr. 5, 2004;86(1):19-26.

Jonnalagadda et al., Flux regulation in glycogen-induced oscillatory glycolysis in cell-free extracts of *Saccharomyces carlsbergensis*. Biosystems. 1982;15(1):49-58.

Kahan et al., Thienamycin, a new beta-lactam antibiotic. I. Discovery, taxonomy, isolation and physical properties. J Antibiot (Tokyo). Jan. 1979;32(1):1-12.

Kahan et al., Thienamycin: development of imipenen-cilastatin. J Antimicrob Chemother. Dec. 1983;12 Suppl D:1-35.

Kalderon et al., A short amino acid sequence able to specify nuclear location. Cell. Dec. 1984;39(3 Pt 2):499-509.

Kametani et al., Studies on the syntheses of heterocyclic compounds. 800. A formal total synthesis of (.+−.)-thienamycin and a (.+−.)-decysteaminylthienamycin derivative. J Am Chem Soc. 1980;102(6):2060-5.

Kang et al., Enhanced biodegradation of toxic organophosphate compounds using recombinant *Escherichia coli* with sec pathway-driven periplasmic secretion of organophosphorus hydrolase. Biotechnol Prog. Mar.-Apr. 2006;22(2):406-10.

Kawarasaki et al., Prolonged cell-free protein synthesis in a batch system using wheat germ extract.Biosci Biotechnol Biochem. Oct. 1994;58(10):1911-3.

Kern et al., Engineering primary metabolic pathways of industrial micro-organisms. J Biotechnol. Mar. 30, 2007;129(1):6-29. Epub Dec. 2, 2006.

Kikuchi et al., Mutational analysis of the feedback sites of phenylalanine-sensitive 3-deoxy-D-arabino-heptulosonate-7-phosphate synthase of *Escherichia coli*. Appl Environ Microbiol. Feb. 1997;63(2):761-2.

Kim et al., Expression, purification, and characterization of choline kinase, product of the cki gene from *Saccharomyces cerevisiae*. J Bio Chem. 1998;273(12):6844-6852.

Kim et al., Metabolic flux analysis for calcium dependent antibiotic (CDA) production in Streptomyces coelicolor. Metab Eng. Oct. 2004;6(4):313-25.

Kim et al., Prolonged cell-free protein synthesis using dual energy sources: Combined use of creatine phosphate and glucose for the efficient supply of ATP and retarded accumulation of phosphate. Biotechnol Bioeng. Aug. 15, 2007;97(6):1510-5.

Kim et al., Regeneration of adenosine triphosphate from glycolytic intermediates for cell-free protein synthesis.Biotechnol Bioeng. Aug. 20, 2001;74(4):309-16.

Kimmel, Identification and characterization of specific clones: strategy for confirming the validity of presumptive clones. Methods Enzymol. 1987;152:507-11.

Kindle, High-frequency nuclear transformation of Chlamydomonas reinhardtii. Proc Natl Acad Sci U S A. Feb. 1990;87(3):1228-32.

Klemme, Photoproduction of hydrogen by purple bacteria: A critical evaluation of the rate limiting enzymatic steps. J Bioscience 1993;48:482-87.

Klimov et al., New phelonic inhibitors of electron transfer in photosystem II. Biologichesksie Membrany. 1992;9(6):565-575.

Knapp et al., Cell-free production of active *E. coli* thioredoxin reductase and glutathione reductase. FEBS Lett. Feb. 13, 2004;559(1-3):66-70.

Knop et al., Hydroaromatic equilibration during biosynthesis of shikimic acid. J Am Chem Soc. Oct. 24, 2001;123(42):10173-82.

(56) References Cited

OTHER PUBLICATIONS

Ko et al., Targeting of proteins to the thylakoid lumen by the bipartite transit peptide of the 33 kd oxygen-evolving protein. EMBO J. Nov. 1989;8(11):3187-94.

Krämer et al., Metabolic engineering for microbial production of shikimic acid. Metab Eng. Oct. 2003;5(4):277-83.

Krell et al., Crystallization and preliminary X-ray crystallographic analysis of shikimate kinase from Erwinia chrysanthemi. Acta Crystallogr D Biol Crystallogr. Sep. 1, 1997;53(Pt 5):612-4.

Krutsakorn et al., In vitro production of n-butanol from glucose. Metab Eng. Nov. 2013;20:84-91. doi: 10.1016/j.ymben.2013.09.006. Epub Sep. 19, 2013.

Kumagai et al., Current status of oral carbapenem development. Curr Med Chem—Anti-Infective Agents. Jan. 2002;1(1):1-14.

Kunkel, Rapid and efficient site-specific mutagenesis without phenotypic selection. Proc Natl Acad Sci U S A. Jan. 1985;82(2):488-92.

Kuroda et al., Polyphosphate kinase as a nucleoside diphosphate kinase in Escherichia coli and Pseudomonas aeruginosa. Proc Natl Acad Sci U S A. Jan. 21, 1997;94(2):439-442.

Lee et al., Fermentative production of thymidine by a metabolically engineered Escherichia coli strain. Appl Environ Microbiol. Apr. 2009;75(8):2423-32. Epub Feb. 27, 2009.

Lee et al., Systems metabolic engineering of Escherichia coli for L-threonine production. Mol Syst Biol. 2007;3:149. Epub Dec. 4, 2007.

Lee, High cell-density culture of Escherichia coli. Trends Biotechnol. Mar. 1996;14(3):98-105.

Li et al., Improved cell-free RNA and protein synthesis system. PLoS One. Sep. 2, 2014;9(9):e106232. doi: 10.1371/journal.pone.0106232. eCollection 2014.

Li et al., Rational strain improvement for enhanced clavulanic acid production by genetic engineering of the glycolytic pathway in Streptomyces clavuligerus. Metab Eng. May 2006;8(3):240-52. Epub Mar. 10, 2006.

Liu et al., Streamlining Escherichia coli S30 extract preparation for economical cell-free protein synthesis. Biotechnol Prog. Mar.-Apr. 2005;21(2):460-5.

Ludwig et al., Mutations affecting export and activity of cytolysin A from Escherichia coli. J Bacteriol. Aug. 2010;192(15):4001-11. Epub May 28, 2010.

Luli et al., Comparison of growth, acetate production, and acetate inhibition of Escherichia coli strains in batch and fed-batch fermentations. Appl Environ Microbiol. Apr. 1990;56(4):1004-11.

Mackle et al., Role of signal peptides in targeting of proteins in cyanobacteria. J Bacteriol. Apr. 1994;176(7):1857-64.

Mandel et al., Modular synthesis of pantetheine and phosphopantetheine. Org Lett. Dec. 23, 2004;6(26):4801-3.

Martin et al., Engineering a mevalonate pathway in Escherichia coli for production of terpenoids. Nat Biotechnol. Jul. 2003;21(7):796-802. Epub Jun. 1, 2003.

Mayes, Metabolism of Glycogen. In: Harper's Biochemistry—A LANGE medical book. 1990. Twenty-second edition. Murray et al., Eds. Chapter 20: 171-178.

Mergulhão et al., Analysis of factors affecting the periplasmic production of recombinant proteins in Escherichia coli. J Microbiol Biotechnol. Aug. 2007;17(8):1236-41.

Mergulhão et al., Recombinant protein secretion in Escherichia coli. Biotechnol Adv. May 2005;23(3):177-202. Epub Jan. 8, 2005.

Meyerhof, New investigations in the kinetics of cell free alcoholic fermentation. Antonie Van Leeuwenhoek. Jan.-Apr. 1947;12(1-4):140-4.

Meynial-Salles et al., New tool for metabolic pathway engineering in Escherichia coli: one-step method to modulate expression of chromosomal genes. Appl Environ Microbiol. Apr. 2005;71(4):2140-4.

Michel-Reydellet et al., Amino acid stabilization for cell-free protein synthesis by modification of the Escherichia coli genome. Metab Eng. Jul. 2004;6(3):197-203.

Muchmore et al., Crystal structure of glutamine phosphoribosylpyrophosphate amidotransferase from Escherichia coli.Protein Sci. Jan. 1998;7(1):39-51.

Muktiono et al., Isolation and purification assay of ex vivo photosystem II D1 protein toward integrated biointeraction analysis. Anal Bioanal Chem. Feb. 2008;390(4):1195-202. Epub Jan. 3, 2008.

Murphy, Use of bacteriophage lambda recombination functions to promote gene replacement in Escherichia coli. J Bacteriol. Apr. 1998;180(8):2063-71.

Myers et al., Determination of imipenem and cilastatin in serum by high-pressure liquid chromatography. Antimicrob Agents Chemother. Jul. 1984;26(1):78-81.

Narang et al., Improved phosphotriester method for the synthesis of gene fragments. Methods Enzymol. 1979;68:90-8.

Neidhardt et al., Culture medium for enterobacteria. J Bacteriol. Sep. 1974;119(3):736-47.

Ninh et al., Assembly and multiple gene expression of thermophilic enzymes in Escherichia coli for in vitro metabolic engineering. Biotechnol Bioeng. Jul. 26, 2014. doi: 10.1002/bit.25338.

Niu et al., Benzene-free synthesis of adipic acid. Biotechnol Prog. Mar.-Apr. 2002;18(2):201-11.

Noireaux et al., Principles of cell-free genetic circuit assembly. Proc Natl Acad Sci U S A. Oct. 28, 2003;100(22):12672-7. Epub Oct. 14, 2003.

Nunez et al., The Biosynthetic Gene Cluster for the ≠-Lactam Carbapenem Thienamycin in Streptomyces cattleya. Chem Biol. Apr. 2003;10(4):301-11.

Ono et al., Photosynthetic electron transport and phosphorylation reactions in thylakoid membranes from the blue-green alga Anacystis nidulans. Biochim Biophys Acta. Jun. 8, 1978;502(3):477-85.

Pace et al., Photosynthetic regeneration of ATP using bacterial chromatophores. Biotechnol Bioeng. Oct. 1976;18(10):1413-23.

Park et al., Metal-catalyzed oxidation of phenylalanine-sensitive 3-deoxy-D-arabino heptulosonate-7-phosphate synthase from Escherichia coli: inactivation and destabilization by oxidation of active-site cysteines. J Bacteriol. Mar. 1999;181(5):1636-42.

Patnaik et al., Engineering of Escherichia coli central metabolism for aromatic metabolite production with near theoretical yield. Appl Environ Microbiol. Nov. 1994;60(11):3903-8.

Paul et al., Photophosphorylation in bacterial chromatophores entrapped in alginate gel: Improvement of the physical and biochemical properties of gel beads with barium as gel-inducing agent. Enzyme Microb Technol. 1980;2(4):281-87.

Peralta-Yahya et al., Microbial engineering for the production of advanced biofuels. Nature. Aug. 16, 2012;488(7411):320-8. doi: 10.1038/nature11478.

Pines et al., Expression and secretion of proteins in E. coli. Mol Biotechnol. Aug. 1999;12(1):25-34.

Pitera et al., Balancing a heterologous mevalonate pathway for improved isoprenoid production in Escherichia coli. Metab Eng. Mar. 2007;9(2):193-207. Epub Nov. 23, 2006.

Pravdic et al., Isoflurane protects cardiomyocytes and mitochondria by immediate and cytosol-independent action at reperfusion. Br J Pharmacol. May 2010;160(2):220-32. doi: 10.1111/j.1476-5381.2010.00698.x.

Qi et al., A one-step PCR-based method for rapid and efficient site-directed fragment deletion, insertion, and substitution mutagenesis. J Virolog Meth. Apr. 2008;149(1):85-90.

Ray et al., Mutational analysis of the catalytic and feedback sites of the tryptophan-sensitive 3-deoxy-D-arabino-heptulosonate-7-phosphate synthase of Escherichia coli. J Bacteriol. Dec. 1988;170(12):5500-6.

Reider et al., Total synthesis of thienamycin: a new approach from aspartic acid. Tetra Lett. 1982;23(22):2293-6.

Reyes et al., Genomic library screens for genes involved in n-butanol tolerance in Escherichia coli. PloS One. Mar. 8, 2011;6(3):e17678.

Rodríguez et al., Identification of transcriptional activators for thienamycin and cephamycin C biosynthetic genes within the thienamycin gene cluster from Streptomyces cattleya. Mol Microbiol. Aug. 2008;69(3):633-45.

Rodríguez et al., Transcriptional organization of ThnI-regulated thienamycin biosynthetic genes in Streptomyces cattleya. J Antibiot (Tokyo). Mar. 2010;63(3):135-8. Epub Jan. 22, 2010.

(56) References Cited

OTHER PUBLICATIONS

Romanowski et al., Crystal structure of the *Escherichia coli* shikimate kinase I (AroK) that confers sensitivity to mecillinam. Proteins. Jun. 1, 2002;47(4):558-62.
Sagui et al., Enzymatic synthesis of ω-carboxy-β-hydroxy-(1)-α-amino acids. Tetrahedron. May 26, 2008;64(22):5079-84.
Salis et al., Automated design of synthetic ribosome binding sites to control protein expression. Nat Biotechnol. Oct. 2009;27(10):946-50. Epub Oct. 4, 2009. Supplemental material included.
Salzmann et al., A stereocontrolled synthesis of (+)-thienamycin. J Am Chem Soc. 1980;102(19);6161-3.
Salzmann et al., A stereocontrolled, enantiomerically specific total synthesis of thienamycin. Philos Trans R Soc Lond B Biol Sci. May 16, 1980;289(1036):191-5.
Sarath et al., Use of GFP as a reporter for the analysis of sequence-specific proteases. Curr Protoc Protein Sci. Feb. 2001;Chapter 21 Unit 9 Suppl. 26: 21.9.1-.10.
Sato et al., Poly[(R)-3-hydroxybutyrate] formation in *Escherichia coli* from glucose through an enoyl-CoA hydratase-mediated pathway. J Biosci Bioeng, Jan. 2007;103(1):38-44.
Sauer et al., The soluble and membrane-bound transhydrogenases UdhA and PntAB have divergent functions in NADPH metabolism of *Escherichia coli*. J Biol Chem. Feb. 20, 2004;279(8):6613-9. Epub Dec. 3, 2004.
Schierle et al., The DsbA signal sequence directs efficient, cotranslational export of passenger proteins to the *Escherichia coli* periplasm via the signal recognition particle pathway. J Bacteriol. Oct. 2003;185(19):5706-13.
Schlehuber et al., Prediction and identification of a permissive epitope insertion site in the vesicular stomatitis virus glycoprotein. J Virol. May 2004;78(10):5079-87.
Schnell, Protein targeting to the thylakoid membrane. Annu Rev Plant Physiol Plant Mol Biol. Jun. 1998;49:97-126.

Scopes, Glycolysis in cell-free systems. New beer in an old bottle: Eduard Buchner and the growth of biochemical knowledge. Ed A. Cornish-Bowden. 1997;151-8.

Sheen, Metabolic repression of transcription in higher plants. Plant Cell. Oct. 1990;2(10):1027-38.

Shi et al., Molecular properties, functions, and potential applications of NAD kinases. Acta Biochim Biophys Sin (Shanghai). May 2009;41(5):352-61.

Shine et al., Determinant of cistron specificity in bacterial ribosomes. Nature. Mar. 6, 1975;254(5495):34-8.

Simmons et al., Translational level is a critical factor for the secretion of heterologous proteins in *Escherichia coli*. Nat Biotechnol. May 1996;14(5):629-34.

Sleeman et al., Carboxymethylproline synthase (CarB), an unusual carbon-carbon bond-forming enzyme of the crotonase superfamily involved in carbapenem biosynthesis. J Biol Chem. Feb. 20, 2004;279(8):6730-6. Epub Nov. 18, 2003.

Soares et al., Periplasmic expression of human growth hormone via plasmid vectors containing the lambdaPL promoter: use of HPLC for product quantification. Protein Eng. Dec. 2003;16(12):1131-8.

Sorci et al., Nicotinamide mononucleotide synthetase is the key enzyme for an alternative route of NAD biosynthesis in Francisella tularensis.Proc Natl Acad Sci U S A. Mar. 3, 2009;106(9):3083-8. Epub Feb. 9, 2009. Supplemental material included.

Spirin, High-throughput cell-free systems for synthesis of functionally active proteins.Trends Biotechnol. Oct. 2004;22(10):538-45. With Supplementary data.

Srinivasan et al., The Enzymatic Synthesis of Shikimic Acid From D-Erythrose-4-Phosphate and Phosphoenolpyruvate1,2,3. J. Am. Chem. Soc. 1955;77(18):4943-4944.

Sroga et al., Periplasmic expression as a basis for whole cell kinetic screening of unnatural enzyme reactivities. Methods Enzymol. 2004;388:145-56.

Stadtman et al., Metal-catalyzed oxidation of proteins. Physiological consequences. J Biol Chem. Feb. 5, 1991;266(4):2005-8.

Stapon et al., Carbapenem biosynthesis: confirmation of stereochemical assignments and the role of CarC in the ring stereoinversion process from L-proline. J Am Chem Soc. Jul. 16, 2003;125(28):8486-93.

Stapon et al., Synthesis of (3S,5R)-carbapenam-3-carboxylic acid and its role in carbapenem biosynthesis and the stereoinversion problem. J Am Chem Soc. Dec. 24, 2003;125(51):15746-7.

Stephanopoulos et al., Exploiting biological complexity for strain improvement through systems biology. Nat Biotechnol. Oct. 2004;22(10):1261-7.

Suzuki et al., Single protein production (SPP) system in *Escherichia coli*. Nat Protoc. 2007;2(7):1802-10.

Suzuki et al., Single protein production in living cells facilitated by an mRNA interferase. Mol Cell. Apr. 15, 2005;18(2):253-61.

Swartz et al., Advances in *Escherichia coli* production of therapeutic proteins. Curr Opin Biotechnol. Apr. 2001;12(2):195-201.

Swartz, Developing cell-free biology for industrial applications. J Ind Microbiol Biotechnol. Jul. 2006;33(7):476-85. Epub May 9, 2006. Review.

Swartz, Transforming biochemical engineering with cell-free biology. AlChE J. 2012;58(1):5-13.

Swartz, Universal cell-free protein synthesis. Nat Biotechnol. Aug. 2009;27(8):731-2. doi: 10.1038/nbt0809-731.

Thöny-Meyer et al., Translocation to the periplasm and signal sequence cleavage of preapocytochrome c depend on sec and lep, but not on the ccm gene products. Eur J Biochem. Jun. 15, 1997;246(3):794-9.

Tjalsma et al., Proteomics of protein secretion by Bacillus subtilis: separating the "secrets" of the secretome. Microbiol Mol Biol Rev. Jun. 2004;68(2):207-33.

Tracewell et al., Directed enzyme evolution: climbing fitness peaks one amino acid at a time. Curr Opin Chem Biol. Feb. 2009;13(1):3-9. Epub Feb. 25, 2009.

Tyo et al., Analysis of polyhydroxybutyrate flux limitations by systematic genetic and metabolic perturbations. Metab Eng. May 2010;12(3):187-95. Epub Oct. 30, 2009.

UniProtKB/Swiss-Prot; Accession No. P28269; Yonaha et al., The primary structure of omega-amino acid:pyruvate aminotransferase. Jul. 11, 2012.

Van Bloois et al., Export of functional Streptomyces coelicolor alditol oxidase to the periplasm or cell surface of *Escherichia coli* and its application in whole-cell biocatalysis. Appl Microbiol Biotechnol. Jun. 2009;83(4):679-87. Epub Feb. 18, 2009.

Van Hees et al., Determination of low molecular weight organic acids in soil solution by HPLC. Talanta. Jan. 5, 1999;48(1):173-9.

Vander Heiden et al., Understanding the Warburg effect: the metabolic requirements of cell proliferation. Science. May 22, 2009;324(5930):1029-33. doi: 10.1126/science.1160809.

Voloshin et al., Efficient and scalable method for scaling up cell free protein synthesis in batch mode. Biotechnol Bioeng. Aug. 20, 2005;91(4):516-21.

Wahl et al., Molecular hybridization of immobilized nucleic acids: theoretical concepts and practical considerations. Methods Enzymol. 1987;152:399-407.

Wang et al., Programming cells by multiplex genome engineering and accelerated evolution. Nature. Aug. 13, 2009;460(7257):894-8. Epub Jul. 26, 2009.

Ward et al., Genomic insights into methanotrophy: the complete genome sequence of Methylococcus capsulatus (Bath). PLOS Biology. 2004;2(10):1616-28.

Weaver et al., Cloning of an aroF allele encoding a tyrosine-insensitive 3-deoxy-D-arabino-heptulosonate 7-phosphate synthase. J Bacteriol. Nov. 1990;172(11):6581-4.

Welch et al., Studies on cell-free metabolism: Ethanol production by a yeast glycolytic system reconstituted from purified enzymes. J Biotechnol. 1985;2:257-73.

Wiechert et al., A universal framework for 13C metabolic flux analysis. Metab Eng. Jul. 2001;3(3):265-83.

Wiechert, 13C metabolic flux analysis. Metab Eng. Jul. 2001;3(3):195-206.

Wilen et al., Tetrahedron report No. 38: Strategies in optical resolutions. Tetrahedron. 1977;33:2725-2736.

(56) References Cited

OTHER PUBLICATIONS

Williamson et al., Biosynthesis of the beta-lactam antibiotic, thienamycin, by Streptomyces cattleya. J Biol Chem. Apr. 25, 1985;260(8):4637-47.
Wilson et al., The shikimic acid pathway and polyketide biosynthesis. J Indust Microbiol Biotechnol. 1998;20:299-303.
Withers et al., Identification of isopentenol biosynthetic genes from Bacillus subtilis by a screening method based on isoprenoid precursor toxicity. Appl Environ Microbiol. Oct. 2007;73(19):6277-83. Epub Aug. 10, 2007.
Woodrow et al., A sequential expression system for high-throughput functional genomic analysis. Proteomics. Nov. 2007;7(21):3870-9.
Woodrow et al., Rapid expression of functional genomic libraries. J Proteome Res. Dec. 2006;5(12):3288-300.
Wuu et al., High yield cell-free production of integral membrane proteins without refolding or detergents. Biochim Biophys Acta. May 2008;1778(5):1237-50. doi: 10.1016/j.bbamem.2008.01.023. Epub Feb. 11, 2008.
Wylie et al., A single point mutation in ctp synthetase of chlamydia trachomatis confers resistance to cyclopentenyl cytosine. J Biol Chem. 1996;271:15393-400.
Yamaguchi et al., MqsR, a crucial regulator for quorum sensing and biofilm formation, is a GCU-specific mRNA interferase in *Escherichia coli*. J Biol Chem. Oct. 16, 2009;284(42):28746-53. Epub Aug. 18, 2009.
Yamaguchi et al., mRNA interferases, sequence-specific endoribonucleases from the toxin-antitoxin systems. Prog Mol Biol Transl Sci. 2009;85:467-500.
Yang et al., Export of methyl parathion hydrolase to the periplasm by the twin-arginine translocation pathway in *Escherichia coli*. J Agric Food Chem. Oct. 14, 2009;57(19):8901-5.
Yang et al., Rapid expression of vaccine proteins for B-cell lymphoma in a cell-free system. Biotechnol Bioeng. Mar. 5, 2005;89(5):503-11.
Ye et al., Synthetic metabolic engineering-a novel, simple technology for designing a chimeric metabolic pathway. Microb Cell Fact. Sep. 6, 2012;11:120. doi: 10.1186/1475-2859-11-120.
Yeo et al., Plasmodium falciparum CTP:phosphocholine cytidylyltransferase expressed in *Escherichia coli*: purification, characterization and lipid regulation. Biochem J. 1997;324:903-10.
Yu et al., Production of high-quality particulate methane monooxygenase in high yields from Methylococcus capsulatus (bath) with a hollow-fiber membrane bioreactor. J Bacteriol. Oct. 2003;185(20):5915-24.
Zamboni et al., 13C-based metabolic flux analysis. Nat Protoc. 2009;4(6):878-92. Epub May 21, 2009.
Zawada et al., Effects of growth rate on cell extract performance in cell-free protein synthesis. Biotechnol Bioeng. Jul. 5, 2006;94(4):618-24.
Zhang et al., Characterization of ChpBK, an mRNA interferase from *Escherichia coli*. J Biol Chem. Jul. 15, 2005;280(28):26080-8. Epub May 18, 2005.
Zhang et al., Characterization of YafO, an *Escherichia coli* toxin. J Biol Chem. Sep. 18, 2009;284(38):25522-31. Epub Jul. 17, 2009.
Zhang et al., Efficient regeneration of transgenic plants from rice protoplasts and correctly regulated expression of the foreign gene in the plants. Theor Appl Genet. 1988;76(6):835-40.
Zhang et al., Insights into the mRNA cleavage mechanism by MazF, an mRNA interferase. J Biol Chem. Feb. 4, 2005;280(5):3143-50. Epub Nov. 10, 2004.
Zhao et al., A novel high-throughput screening method for microbial transglutaminases with high specificity toward Gln141 of human growth hormone. J Biomol Screen. Feb. 2010;15(2):206-12. doi: 10.1177/1087057109356206. Epub Jan. 19, 2010.
International Search Report and Written Opinion for PCT/US2016/024937, dated Sep. 9, 2016.
International Preliminary Report on Patentability for PCT/US2016/024937, dated Oct. 12, 2017.
Invitation to Pay Additional Fees for PCT/US2017/026285, dated Jul. 6, 2017.
International Search Report and Written Opinion for PCT/US2017/026285, dated Aug. 28, 2017.
International Preliminary Report on Patentability for PCT/US2017/026285, dated Oct. 18, 2018.
Cheng et al., Purification and characterization of the *Escherichia coli* exoribonuclease RNase R. Comparison with RNase II. J Biol Chem. Jun. 14, 2002;277(24):21624-9. Epub Apr. 10, 2002.
Dahl et al., Isolation and characterization of Chinese hamster ovary cells defective in the intracellular metabolism of low density lipoprotein-derived cholesterol. J Biol Chem. Mar. 5, 1992;267(7):4889-96.
Endoh et al., Cell-free protein synthesis at high temperatures using the lysate of a hyperthermophile. J Biotechnol. Nov. 1, 2006;126(2):186-95. Epub May 30, 2006.
Goody, A simple and rapid method for the synthesis of nucleoside 5'-monophosphates enriched with 17O or 18O on the phosphate group. Anal Biochem. Jan. 15, 1982;119(2):322-4.
Kapust et al., Tobacco etch virus protease: mechanism of autolysis and rational design of stable mutants with wild-type catalytic proficiency. Protein Eng. Dec. 2001;14(12):993-1000.
Liu et al., Combined biosynthetic pathway for de novo production of UDP-galactose: catalysis with multiple enzymes immobilized on agarose beads. Chembiochem. Apr. 2, 2002;3(4):348-55.
Motomura et al., A new subfamily of polyphosphate kinase 2 (class III PPK2) catalyzes both nucleoside monophosphate phosphorylation and nucleoside diphosphate phosphorylation. Appl Environ Microbiol. Apr. 2014;80(8):2602-8. doi: 10.1128/AEM.03971-13. Epub Feb. 14, 2014.
Nilsen, Selective precipitation of large RNAs. Cold Spring Harb Protoc. Dec. 1, 2012;2012(12). pii: pdb.prot072322. doi: 10.1101/pdb.prot072322.
Ninh et al., Development of a continuous bioconversion system using a thermophilic whole-cell biocatalyst. Appl Environ Microbiol. Mar. 2013;79(6):1996-2001. doi: 10.1128/AEM.03752-12. Epub Jan. 18, 2013.
Restiawaty et al., Feasibility of thermophilic adenosine triphosphate-regeneration system using Thermus thermophilus polyphosphate kinase. Process Biochemistry, Sep. 2011;46(9):1747-52.
Schultheisz et al., Pathway engineered enzymatic de novo purine nucleotide synthesis. ACS Chem Biol. Aug. 15, 2008;3(8):499-511. doi: 10.1021/cb800066p.
Scopes, Studies with a reconstituted muscle glycolytic system. The anaerobic glycolytic response to simulated tetanic contraction. Biochem J. Jan. 1974;138(1):119-23.
Shiba et al., Inorganic polyphosphate and polyphosphate kinase: their novel biological functions and applications. Biochemistry (Mosc). Mar. 2000;65(3):315-23.
Spickler et al., Action of RNase II and polynucleotide phosphorylase against RNAs containing stem-loops of defined structure. J Bacteriol. May 2000;182(9):2422-7.
Stazic et al., Antisense RNA protects mRNA from RNase E degradation by RNA-RNA duplex formation during phage infection. Nucleic Acids Res. Jun. 2011;39(11):4890-9. doi: 10.1093/nar/gkr037. Epub Feb. 15, 2011.
Sybesma et al., Increased production of folate by metabolic engineering of Lactococcus lactis. Appl Environ Microbiol. Jun. 2003;69(6):3069-76.
Wong et al., Preparation of a mixture of nucleoside triphosphates from yeast RNA: use in enzymic synthesis requiring nucleoside triphosphate regeneration and conversion to nucleoside diphosphate sugars. J. Am. Chem. Soc. 1983;105(1):115-7.
Zago et al., Cloning and characterization of polyphosphate kinase and exopolyphosphatase genes from Pseudomonas aeruginosa 8830. Appl Environ Microbiol. May 1999;65(5):2065-71.
Zawada et al., Maintaining rapid growth in moderate-density *Escherichia coli* fermentations. Biotechnol Bioeng. Feb. 20, 2005;89(4):407-15.
Zhu et al., A high-energy-density sugar biobattery based on a synthetic enzymatic pathway. Nat Commun. 2014;5:3026. doi: 10.1038/ncomms4026.
Awano et al., *Escherichia coli* Rnase R Has Dual Activities, Helicase and Rnase. Journal of Bacteriology. Mar. 2010;192(5):1344-52.

SEQUENCE LISTING

```
<160> NUMBER OF SEQ ID NOS: 16

<210> SEQ ID NO 1
<211> LENGTH: 266
<212> TYPE: PRT
<213> ORGANISM: Deinococcus  geothermalis

<400> SEQUENCE: 1

Met Gln Leu Asp Arg Tyr Arg Val Pro Pro Gly Gln Arg Val Arg Leu
1               5                   10                  15

Ser Asn Trp Pro Thr Asp Asp Gly Gly Leu Ser Lys Ala Glu Gly
            20                  25                  30

Glu Ala Leu Leu Pro Asp Leu Gln Gln Arg Leu Ala Asn Leu Gln Glu
        35                  40                  45

Arg Leu Tyr Ala Glu Ser Gln Gln Ala Leu Leu Ile Val Leu Gln Ala
    50                  55                  60

Arg Asp Ala Gly Gly Lys Asp Gly Thr Val Lys His Val Ile Gly Ala
65                  70                  75                  80

Phe Asn Pro Ser Gly Val Gln Val Ser Asn Phe Lys Val Pro Thr Glu
                85                  90                  95

Glu Glu Arg Ala His Asp Phe Leu Trp Arg Ile His Arg Gln Thr Pro
            100                 105                 110
```

```
Arg Leu Gly Met Ile Gly Val Phe Asn Arg Ser Gln Tyr Glu Asp Val
            115                 120                 125

Leu Val Thr Arg Val His His Leu Ile Asp Asp Gln Thr Ala Gln Arg
        130                 135                 140

Arg Leu Lys His Ile Cys Ala Phe Glu Ser Leu Leu Thr Asp Ser Gly
145                 150                 155                 160

Thr Arg Ile Val Lys Phe Tyr Leu His Ile Ser Pro Glu Glu Gln Lys
                165                 170                 175

Lys Arg Leu Glu Ala Arg Leu Ala Asp Pro Ser Lys His Trp Lys Phe
            180                 185                 190

Asn Pro Gly Asp Leu Gln Glu Arg Ala His Trp Asp Ala Tyr Thr Ala
        195                 200                 205

Val Tyr Glu Asp Val Leu Thr Thr Ser Thr Pro Ala Ala Pro Trp Tyr
    210                 215                 220

Val Val Pro Ala Asp Arg Lys Trp Phe Arg Asn Leu Leu Val Ser Gln
225                 230                 235                 240

Ile Leu Val Gln Thr Leu Glu Glu Met Asn Pro Gln Phe Pro Ala Pro
                245                 250                 255

Ala Phe Asn Ala Ala Asp Leu Arg Ile Val
            260                 265

<210> SEQ ID NO 2
<211> LENGTH: 280
<212> TYPE: PRT
<213> ORGANISM: Meiothermus ruber

<400> SEQUENCE: 2

Met Gly Phe Cys Ser Ile Glu Phe Leu Met Gly Ala Gln Met Lys Lys
1               5                   10                  15

Tyr Arg Val Gln Pro Asp Gly Arg Phe Glu Leu Lys Arg Phe Asp Pro
            20                  25                  30

Asp Asp Thr Ser Ala Phe Glu Gly Gly Lys Gln Ala Ala Leu Glu Ala
        35                  40                  45

Leu Ala Val Leu Asn Arg Arg Leu Glu Lys Leu Gln Glu Leu Leu Tyr
    50                  55                  60

Ala Glu Gly Gln His Lys Val Leu Val Val Leu Gln Ala Met Asp Ala
65                  70                  75                  80

Gly Gly Lys Asp Gly Thr Ile Arg Val Val Phe Asp Gly Val Asn Pro
                85                  90                  95

Ser Gly Val Arg Val Ala Ser Phe Gly Val Pro Thr Glu Gln Glu Leu
            100                 105                 110

Ala Arg Asp Tyr Leu Trp Arg Val His Gln Gln Val Pro Arg Lys Gly
        115                 120                 125

Glu Leu Val Ile Phe Asn Arg Ser His Tyr Glu Asp Val Leu Val Val
    130                 135                 140

Arg Val Lys Asn Leu Val Pro Gln Gln Val Trp Gln Lys Arg Tyr Arg
145                 150                 155                 160

His Ile Arg Glu Phe Glu Arg Met Leu Ala Asp Glu Gly Thr Thr Ile
                165                 170                 175

Leu Lys Phe Phe Leu His Ile Ser Lys Asp Glu Gln Arg Gln Arg Leu
            180                 185                 190

Gln Glu Arg Leu Asp Asn Pro Glu Lys Arg Trp Lys Phe Arg Met Gly
        195                 200                 205

Asp Leu Glu Asp Arg Arg Leu Trp Asp Arg Tyr Gln Glu Ala Tyr Glu
    210                 215                 220
```

```
Ala Ala Ile Arg Glu Thr Ser Thr Glu Tyr Ala Pro Trp Tyr Val Ile
225                 230                 235                 240

Pro Ala Asn Lys Asn Trp Tyr Arg Asn Trp Leu Val Ser His Ile Leu
            245                 250                 255

Val Glu Thr Leu Glu Gly Leu Ala Met Gln Tyr Pro Gln Pro Glu Thr
            260                 265                 270

Ala Ser Glu Lys Ile Val Ile Glu
        275                 280

<210> SEQ ID NO 3
<211> LENGTH: 268
<212> TYPE: PRT
<213> ORGANISM: Meiothermus silvanus

<400> SEQUENCE: 3

Met Ala Lys Thr Ile Gly Ala Thr Leu Asn Leu Gln Asp Ile Asp Pro
1               5                   10                  15

Arg Ser Thr Pro Gly Phe Asn Gly Asp Lys Glu Lys Ala Leu Ala Leu
            20                  25                  30

Leu Glu Lys Leu Thr Ala Arg Leu Asp Glu Leu Gln Glu Gln Leu Tyr
        35                  40                  45

Ala Glu His Gln His Arg Val Leu Val Ile Leu Gln Gly Met Asp Thr
    50                  55                  60

Ser Gly Lys Asp Gly Thr Ile Arg His Val Phe Lys Asn Val Asp Pro
65                  70                  75                  80

Leu Gly Val Arg Val Ala Phe Lys Ala Pro Thr Pro Pro Glu Leu
                85                  90                  95

Glu Arg Asp Tyr Leu Trp Arg Val His Gln His Val Pro Ala Asn Gly
            100                 105                 110

Glu Leu Val Ile Phe Asn Arg Ser His Tyr Glu Asp Val Leu Val Ala
        115                 120                 125

Arg Val His Asn Leu Val Pro Pro Ala Ile Trp Ser Arg Arg Tyr Asp
    130                 135                 140

His Ile Asn Ala Phe Glu Lys Met Leu Val Asp Glu Gly Thr Thr Val
145                 150                 155                 160

Leu Lys Phe Phe Leu His Ile Ser Lys Glu Glu Gln Lys Lys Arg Leu
                165                 170                 175

Leu Glu Arg Leu Val Glu Ala Asp Lys His Trp Lys Phe Asp Pro Gln
            180                 185                 190

Asp Leu Val Glu Arg Gly Tyr Trp Glu Asp Tyr Met Glu Ala Tyr Gln
        195                 200                 205

Asp Val Leu Asp Lys Thr His Thr Gln Tyr Ala Pro Trp His Val Ile
    210                 215                 220

Pro Ala Asp Arg Lys Trp Tyr Arg Asn Leu Gln Val Ser Arg Leu Leu
225                 230                 235                 240

Val Glu Ala Leu Glu Gly Leu Arg Met Lys Tyr Pro Arg Pro Lys Leu
                245                 250                 255

Asn Ile Pro Arg Leu Lys Ser Glu Leu Glu Lys Met
            260                 265

<210> SEQ ID NO 4
<211> LENGTH: 300
<212> TYPE: PRT
<213> ORGANISM: Thermosynechococcus elongatus

<400> SEQUENCE: 4
```

```
Met Ile Pro Gln Asp Phe Leu Asp Glu Ile Asn Pro Asp Arg Tyr Ile
1               5                   10                  15

Val Pro Ala Gly Gly Asn Phe His Trp Lys Asp Tyr Asp Pro Gly Asp
            20                  25                  30

Thr Ala Gly Leu Lys Ser Lys Val Glu Ala Gln Glu Leu Leu Ala Ala
        35                  40                  45

Gly Ile Lys Lys Leu Ala Ala Tyr Gln Asp Val Leu Tyr Ala Gln Asn
50                  55                  60

Ile Tyr Gly Leu Leu Ile Ile Phe Gln Ala Met Asp Ala Ala Gly Lys
65                  70                  75                  80

Asp Ser Thr Ile Lys His Val Met Ser Gly Leu Asn Pro Gln Ala Cys
                85                  90                  95

Arg Val Tyr Ser Phe Lys Ala Pro Ser Ala Glu Glu Leu Asp His Asp
            100                 105                 110

Phe Leu Trp Arg Ala Asn Arg Ala Leu Pro Glu Arg Gly Cys Ile Gly
        115                 120                 125

Ile Phe Asn Arg Ser Tyr Tyr Glu Glu Val Leu Val Val Arg Val His
130                 135                 140

Pro Asp Leu Leu Asn Arg Gln Gln Leu Pro Pro Glu Thr Lys Thr Lys
145                 150                 155                 160

His Ile Trp Lys Glu Arg Phe Glu Asp Ile Asn His Tyr Glu Arg Tyr
                165                 170                 175

Leu Thr Arg Asn Gly Ile Leu Ile Leu Lys Phe Phe Leu His Ile Ser
            180                 185                 190

Lys Ala Glu Gln Lys Lys Arg Phe Leu Glu Arg Ile Ser Arg Pro Glu
        195                 200                 205

Lys Asn Trp Lys Phe Ser Ile Glu Asp Val Arg Asp Arg Ala His Trp
210                 215                 220

Asp Asp Tyr Gln Gln Ala Tyr Ala Asp Val Phe Arg His Thr Ser Thr
225                 230                 235                 240

Lys Trp Ala Pro Trp His Ile Ile Pro Ala Asn His Lys Trp Phe Ala
                245                 250                 255

Arg Leu Met Val Ala His Phe Ile Tyr Gln Lys Leu Ala Ser Leu Asn
            260                 265                 270

Leu His Tyr Pro Met Leu Ser Glu Ala His Arg Glu Gln Leu Leu Glu
        275                 280                 285

Ala Lys Ala Leu Leu Glu Asn Glu Pro Asp Glu Asp
290                 295                 300

<210> SEQ ID NO 5
<211> LENGTH: 281
<212> TYPE: PRT
<213> ORGANISM: Anaerolinea thermophila

<400> SEQUENCE: 5

Met Gly Glu Ala Met Glu Arg Tyr Phe Ile Lys Pro Gly Glu Lys Val
1               5                   10                  15

Arg Leu Lys Asp Trp Ser Pro Asp Pro Lys Asp Phe Glu Gly Asp
            20                  25                  30

Lys Glu Ser Thr Arg Ala Ala Val Ala Glu Leu Asn Arg Lys Leu Glu
        35                  40                  45

Val Leu Gln Glu Arg Leu Tyr Ala Glu Arg Lys His Lys Val Leu Val
50                  55                  60

Ile Leu Gln Gly Met Asp Thr Ser Gly Lys Asp Gly Val Ile Arg Ser
```

```
                65                  70                  75                  80
Val Phe Glu Gly Val Asn Pro Gln Gly Val Lys Val Ala Asn Phe Lys
                    85                  90                  95

Val Pro Thr Gln Glu Glu Leu Asp His Asp Tyr Leu Trp Arg Val His
                100                 105                 110

Lys Val Val Pro Gly Lys Gly Glu Ile Val Ile Phe Asn Arg Ser His
                115                 120                 125

Tyr Glu Asp Val Leu Val Val Arg Val His Asn Leu Val Pro Pro Glu
            130                 135                 140

Val Trp Lys Lys Arg Tyr Glu Gln Ile Asn Gln Phe Glu Arg Leu Leu
145                 150                 155                 160

His Glu Thr Gly Thr Thr Ile Leu Lys Phe Phe Leu Phe Ile Ser Arg
                165                 170                 175

Glu Glu Gln Lys Gln Arg Leu Leu Glu Arg Leu Ala Asp Pro Ala Lys
            180                 185                 190

His Trp Lys Phe Asn Pro Gly Asp Leu Lys Glu Arg Ala Leu Trp Glu
        195                 200                 205

Glu Tyr Glu Lys Ala Tyr Glu Asp Val Leu Ser Arg Thr Ser Thr Glu
    210                 215                 220

Tyr Ala Pro Trp Ile Leu Val Pro Ala Asp Lys Lys Trp Tyr Arg Asp
225                 230                 235                 240

Trp Val Ile Ser Arg Val Leu Val Glu Thr Leu Glu Gly Leu Glu Ile
                245                 250                 255

Gln Leu Pro Pro Pro Leu Ala Asp Ala Glu Thr Tyr Arg Arg Gln Leu
            260                 265                 270

Leu Glu Glu Asp Ala Pro Glu Ser Arg
            275                 280

<210> SEQ ID NO 6
<211> LENGTH: 270
<212> TYPE: PRT
<213> ORGANISM: Caldilinea aerophila

<400> SEQUENCE: 6

Met Asp Val Asp Arg Tyr Arg Val Pro Pro Gly Ser Thr Ile His Leu
1               5                   10                  15

Ser Gln Trp Pro Pro Asp Asp Arg Ser Leu Tyr Glu Gly Asp Lys Lys
                20                  25                  30

Gln Gly Lys Gln Asp Leu Ser Ala Leu Asn Arg Arg Leu Glu Thr Leu
            35                  40                  45

Gln Glu Leu Leu Tyr Ala Glu Gly Lys His Lys Val Leu Ile Ile Leu
        50                  55                  60

Gln Gly Met Asp Thr Ser Gly Lys Asp Gly Val Ile Arg His Val Phe
65                  70                  75                  80

Asn Gly Val Asn Pro Gln Gly Val Lys Val Ala Ser Phe Lys Val Pro
                85                  90                  95

Thr Ala Val Glu Leu Ala His Asp Phe Leu Trp Arg Ile His Arg Gln
                100                 105                 110

Thr Pro Gly Ser Gly Glu Ile Val Ile Phe Asn Arg Ser His Tyr Glu
            115                 120                 125

Asp Val Leu Val Val Arg Val His Gly Leu Val Pro Pro Glu Val Trp
        130                 135                 140

Ala Arg Arg Tyr Glu His Ile Asn Ala Phe Glu Lys Leu Leu Val Asp
145                 150                 155                 160
```

Glu Gly Thr Thr Ile Leu Lys Phe Phe Leu His Ile Ser Lys Glu Glu
            165                 170                 175

Gln Arg Gln Arg Leu Leu Glu Arg Leu Glu Met Pro Gly Lys Arg Trp
        180                 185                 190

Lys Phe Ser Val Gly Asp Leu Ala Glu Arg Lys Arg Trp Asp Glu Tyr
        195                 200                 205

Met Ala Ala Tyr Glu Ala Val Leu Ser Lys Thr Ser Thr Glu Tyr Ala
210                 215                 220

Pro Trp Tyr Ile Val Pro Ser Asp Arg Lys Trp Tyr Arg Asn Leu Val
225                 230                 235                 240

Ile Ser His Val Ile Asn Ala Leu Glu Gly Leu Asn Met Arg Tyr
            245                 250                 255

Pro Gln Pro Glu Asp Ile Ala Phe Asp Thr Ile Val Ile Glu
        260                 265                 270

<210> SEQ ID NO 7
<211> LENGTH: 294
<212> TYPE: PRT
<213> ORGANISM: Chlorobaculum tepidum

<400> SEQUENCE: 7

Met Lys Leu Asp Leu Asp Ala Phe Arg Ile Gln Pro Gly Lys Lys Pro
1               5                   10                  15

Asn Leu Ala Lys Arg Pro Thr Arg Ile Asp Pro Val Tyr Arg Ser Lys
            20                  25                  30

Gly Glu Tyr His Glu Leu Leu Ala Asn His Val Ala Glu Leu Ser Lys
        35                  40                  45

Leu Gln Asn Val Leu Tyr Ala Asp Asn Arg Tyr Ala Ile Leu Leu Ile
50                  55                  60

Phe Gln Ala Met Asp Ala Ala Gly Lys Asp Ser Ala Ile Lys His Val
65                  70                  75                  80

Met Ser Gly Val Asn Pro Gln Gly Cys Gln Val Tyr Ser Phe Lys His
            85                  90                  95

Pro Ser Ala Thr Glu Leu Glu His Asp Phe Leu Trp Arg Thr Asn Cys
        100                 105                 110

Val Leu Pro Glu Arg Gly Arg Ile Gly Ile Phe Asn Arg Ser Tyr Tyr
    115                 120                 125

Glu Glu Val Leu Val Val Arg Val His Pro Gly Ile Leu Glu Met Gln
130                 135                 140

Asn Ile Pro His Asn Leu Ala His Asn Gly Lys Val Trp Asp His Arg
145                 150                 155                 160

Tyr Arg Ser Ile Val Ser His Glu Gln His Leu His Cys Asn Gly Thr
                165                 170                 175

Arg Ile Val Lys Phe Tyr Leu His Leu Ser Lys Glu Glu Gln Arg Lys
            180                 185                 190

Arg Phe Leu Glu Arg Ile Asp Asp Pro Asn Lys Asn Trp Lys Phe Ser
        195                 200                 205

Thr Ala Asp Leu Glu Glu Arg Lys Phe Trp Asp Gln Tyr Met Glu Ala
210                 215                 220

Tyr Glu Ser Cys Leu Gln Glu Thr Ser Thr Lys Asp Ser Pro Trp Phe
225                 230                 235                 240

Ala Val Pro Ala Asp Asp Lys Lys Asn Ala Arg Leu Ile Val Ser Arg
            245                 250                 255

Ile Val Leu Asp Thr Leu Glu Ser Leu Asn Leu Lys Tyr Pro Glu Pro
        260                 265                 270

Ser Pro Glu Arg Arg Lys Glu Leu Leu Asp Ile Arg Lys Arg Leu Glu
    275                 280                 285

Asn Pro Glu Asn Gly Lys
    290

<210> SEQ ID NO 8
<211> LENGTH: 269
<212> TYPE: PRT
<213> ORGANISM: Oceanithermus profundus

<400> SEQUENCE: 8

Met Asp Val Ser Arg Tyr Arg Val Pro Pro Gly Ser Gly Phe Asp Pro
1               5                   10                  15

Glu Ala Trp Pro Thr Arg Glu Asp Asp Phe Ala Gly Gly Lys Lys
            20                  25                  30

Glu Ala Lys Lys Glu Leu Ala Arg Leu Ala Val Arg Leu Gly Glu Leu
        35                  40                  45

Gln Ala Arg Leu Tyr Ala Glu Gly Arg Gln Ala Leu Leu Ile Val Leu
    50                  55                  60

Gln Gly Met Asp Thr Ala Gly Lys Asp Gly Thr Ile Arg His Val Phe
65                  70                  75                  80

Arg Ala Val Asn Pro Gln Gly Val Arg Val Thr Ser Phe Lys Lys Pro
                85                  90                  95

Thr Ala Leu Glu Leu Ala His Asp Tyr Leu Trp Arg Val His Arg His
            100                 105                 110

Ala Pro Ala Arg Gly Glu Ile Gly Ile Phe Asn Arg Ser His Tyr Glu
        115                 120                 125

Asp Val Leu Val Val Arg Val His Glu Leu Val Pro Pro Glu Val Trp
    130                 135                 140

Gly Arg Arg Tyr Asp His Ile Asn Ala Phe Glu Arg Leu Leu Ala Asp
145                 150                 155                 160

Glu Gly Thr Arg Ile Val Lys Phe Phe Leu His Ile Ser Lys Asp Glu
                165                 170                 175

Gln Lys Arg Arg Leu Glu Ala Arg Leu Glu Asn Pro Arg Lys His Trp
            180                 185                 190

Lys Phe Asn Pro Ala Asp Leu Ser Glu Arg Ala Arg Trp Gly Asp Tyr
        195                 200                 205

Ala Ala Ala Tyr Ala Glu Ala Leu Ser Arg Thr Ser Ser Asp Arg Ala
    210                 215                 220

Pro Trp Tyr Ala Val Pro Ala Asp Arg Lys Trp Gln Arg Asn Arg Ile
225                 230                 235                 240

Val Ala Gln Val Leu Val Asp Ala Leu Glu Ala Met Asp Pro Arg Phe
                245                 250                 255

Pro Arg Val Asp Phe Asp Pro Ala Ser Val Arg Val Glu
            260                 265

<210> SEQ ID NO 9
<211> LENGTH: 290
<212> TYPE: PRT
<213> ORGANISM: Roseiflexus castenholzii

<400> SEQUENCE: 9

Met Tyr Ala Gln Arg Val Val Pro Gly Met Arg Val Arg Leu His Asp
1               5                   10                  15

Ile Asp Pro Asp Ala Asn Gly Gly Leu Asn Lys Asp Glu Gly Arg Ala
            20                  25                  30

```
Arg Phe Ala Glu Leu Asn Ala Glu Leu Asp Val Met Gln Glu Glu Leu
            35                  40                  45

Tyr Ala Ala Gly Ile His Ala Leu Leu Leu Ile Leu Gln Gly Met Asp
     50                  55                  60

Thr Ala Gly Lys Asp Gly Ala Ile Arg Asn Val Met Leu Asn Leu Asn
 65                  70                  75                  80

Pro Gln Gly Cys Arg Val Glu Ser Phe Lys Val Pro Thr Glu Glu
                85                  90                  95

Leu Ala His Asp Phe Leu Trp Arg Val His Arg Val Val Pro Arg Lys
             100                 105                 110

Gly Met Val Gly Val Phe Asn Arg Ser His Tyr Glu Asp Val Leu Val
             115                 120                 125

Val Arg Val His Ser Leu Val Pro Glu Ser Val Trp Arg Ala Arg Tyr
        130                 135                 140

Asp Gln Ile Asn Ala Phe Glu Arg Leu Leu Ala Asp Thr Gly Thr Ile
145                 150                 155                 160

Ile Val Lys Cys Phe Leu His Ile Ser Lys Glu Gln Glu Gln Arg
                 165                 170                 175

Leu Leu Ala Arg Glu Arg Asp Val Ser Lys Ala Trp Lys Leu Ser Ala
             180                 185                 190

Gly Asp Trp Arg Glu Arg Ala Phe Trp Asp Asp Tyr Met Ala Ala Tyr
             195                 200                 205

Glu Glu Ala Leu Thr Arg Cys Ser Thr Asp Tyr Ala Pro Trp Tyr Ile
     210                 215                 220

Ile Pro Ala Asn Arg Lys Trp Tyr Arg Asp Leu Ala Ile Ser Glu Ala
225                 230                 235                 240

Leu Val Glu Thr Leu Arg Pro Tyr Arg Asp Asp Trp Arg Arg Ala Leu
                 245                 250                 255

Asp Ala Met Ser Arg Ala Arg Arg Ala Glu Leu Glu Ala Phe Arg Ala
             260                 265                 270

Glu Gln His Ala Met Glu Gly Arg Pro Gln Gly Ala Gly Gly Val Ser
         275                 280                 285

Arg Arg
    290

<210> SEQ ID NO 10
<211> LENGTH: 282
<212> TYPE: PRT
<213> ORGANISM: Roseiflexus castenholzii

<400> SEQUENCE: 10

Met His Tyr Ala His Thr Val Ile Pro Gly Thr Gln Val Arg Leu Arg
 1               5                  10                  15

Asp Ile Asp Pro Asp Ala Ser Gly Gly Leu Thr Lys Asp Glu Gly Arg
                 20                  25                  30

Glu Arg Phe Ala Ser Phe Asn Ala Thr Leu Asp Ala Met Gln Glu Glu
             35                  40                  45

Leu Tyr Ala Ala Gly Val His Ala Leu Leu Leu Ile Leu Gln Gly Met
     50                  55                  60

Asp Thr Ala Gly Lys Asp Gly Ala Ile Arg Asn Val Met His Asn Leu
 65                  70                  75                  80

Asn Pro Gln Gly Cys Arg Val Glu Ser Phe Lys Val Pro Thr Glu Glu
                 85                  90                  95

Glu Leu Ala His Asp Phe Leu Trp Arg Val His Lys Val Val Pro Arg
```

```
                100                 105                 110
Lys Gly Met Val Gly Val Phe Asn Arg Ser His Tyr Glu Asp Val Leu
        115                 120                 125

Val Val Arg Val His Ser Leu Val Pro Glu His Val Trp Arg Ala Arg
    130                 135                 140

Tyr Asp Gln Ile Asn Ala Phe Glu Arg Leu Leu Thr Asp Thr Gly Thr
145                 150                 155                 160

Ile Ile Val Lys Cys Phe Leu His Ile Ser Lys Asp Glu Gln Glu Lys
                165                 170                 175

Arg Leu Leu Ala Arg Glu Gln Asp Val Thr Lys Ala Trp Lys Leu Ser
            180                 185                 190

Ala Gly Asp Trp Arg Glu Arg Glu Arg Trp Asp Glu Tyr Met Ala Ala
        195                 200                 205

Tyr Glu Glu Ala Leu Thr Arg Cys Ser Thr Glu Tyr Ala Pro Trp Tyr
    210                 215                 220

Ile Ile Pro Ala Asn Arg Lys Trp Tyr Arg Asp Leu Ala Ile Ser Glu
225                 230                 235                 240

Val Leu Val Glu Thr Leu Arg Pro Tyr Arg Asp Asp Trp Gln Arg Ala
                245                 250                 255

Leu Asp Ala Met Ser Gln Ala Arg Leu Ala Glu Leu Lys Ala Phe Arg
            260                 265                 270

His Gln Gln Thr Ala Gly Ala Thr Arg Leu
        275                 280

<210> SEQ ID NO 11
<211> LENGTH: 274
<212> TYPE: PRT
<213> ORGANISM: Truepera radiovictrix

<400> SEQUENCE: 11

Met Ser Gln Gly Ser Ala Lys Gly Leu Gly Lys Leu Asp Lys Lys Val
1               5                   10                  15

Tyr Ala Arg Glu Leu Ala Leu Leu Gln Leu Glu Leu Val Lys Leu Gln
                20                  25                  30

Gly Trp Ile Lys Ala Gln Gly Leu Lys Val Val Leu Phe Glu Gly
            35                  40                  45

Arg Asp Ala Ala Gly Lys Gly Ser Thr Ile Thr Arg Ile Thr Gln Pro
        50                  55                  60

Leu Asn Pro Arg Val Cys Arg Val Val Ala Leu Gly Ala Pro Thr Glu
65                  70                  75                  80

Arg Glu Arg Thr Gln Trp Tyr Phe Gln Arg Tyr Val His His Leu Pro
                85                  90                  95

Ala Ala Gly Glu Met Val Leu Phe Asp Arg Ser Trp Tyr Asn Arg Ala
            100                 105                 110

Gly Val Glu Arg Val Met Gly Phe Cys Thr Glu Ala Glu Tyr Arg Glu
        115                 120                 125

Phe Leu His Ala Cys Pro Thr Phe Glu Arg Leu Leu Leu Asp Ala Gly
    130                 135                 140

Ile Ile Leu Ile Lys Tyr Trp Phe Ser Val Ser Ala Ala Glu Gln Glu
145                 150                 155                 160

Arg Arg Met Arg Arg Arg Asn Glu Asn Pro Ala Lys Arg Trp Lys Leu
                165                 170                 175

Ser Pro Met Asp Leu Glu Ala Arg Ala Arg Trp Val Ala Tyr Ser Lys
            180                 185                 190
```

```
Ala Lys Asp Ala Met Phe Tyr His Thr Asp Thr Lys Ala Ser Pro Trp
            195                 200                 205

Tyr Val Val Asn Ala Glu Asp Lys Arg Arg Ala His Leu Ser Cys Ile
    210                 215                 220

Ala His Leu Leu Ser Leu Ile Pro Tyr Glu Asp Leu Thr Pro Pro Pro
225                 230                 235                 240

Leu Glu Met Pro Pro Arg Asp Leu Ala Gly Ala Asp Glu Gly Tyr Glu
                245                 250                 255

Arg Pro Asp Lys Ala His Gln Thr Trp Val Pro Asp Tyr Val Pro Pro
            260                 265                 270

Thr Arg

<210> SEQ ID NO 12
<211> LENGTH: 186
<212> TYPE: PRT
<213> ORGANISM: Thermus thermophilus

<400> SEQUENCE: 12

Met Asp Val Gly Gln Ala Val Ile Phe Leu Gly Pro Pro Gly Ala Gly
1               5                   10                  15

Lys Gly Thr Gln Ala Ser Arg Leu Ala Gln Glu Leu Gly Phe Lys Lys
            20                  25                  30

Leu Ser Thr Gly Asp Ile Leu Arg Asp His Val Ala Arg Gly Thr Pro
        35                  40                  45

Leu Gly Glu Arg Val Arg Pro Ile Met Glu Arg Gly Asp Leu Val Pro
    50                  55                  60

Asp Asp Leu Ile Leu Glu Leu Ile Arg Glu Glu Leu Ala Glu Arg Val
65                  70                  75                  80

Ile Phe Asp Gly Phe Pro Arg Thr Leu Ala Gln Ala Glu Ala Leu Asp
                85                  90                  95

Arg Leu Leu Ser Glu Thr Gly Thr Arg Leu Leu Gly Val Val Leu Val
            100                 105                 110

Glu Val Pro Glu Glu Glu Leu Val Arg Arg Ile Leu Arg Arg Ala Glu
        115                 120                 125

Leu Glu Gly Arg Ser Asp Asp Asn Glu Glu Thr Val Arg Arg Arg Leu
    130                 135                 140

Glu Val Tyr Arg Glu Lys Thr Glu Pro Leu Val Gly Tyr Tyr Glu Ala
145                 150                 155                 160

Arg Gly Val Leu Lys Arg Val Asp Gly Leu Gly Thr Pro Asp Glu Val
                165                 170                 175

Tyr Ala Arg Ile Arg Ala Ala Leu Gly Ile
            180                 185

<210> SEQ ID NO 13
<211> LENGTH: 208
<212> TYPE: PRT
<213> ORGANISM: Thermus thermophilus

<400> SEQUENCE: 13

Met Arg Gly Ile Val Thr Ile Asp Gly Pro Ser Ala Ser Gly Lys Ser
1               5                   10                  15

Ser Val Ala Arg Arg Val Ala Ala Leu Gly Val Pro Tyr Leu Ser
            20                  25                  30

Ser Gly Leu Leu Tyr Arg Ala Ala Ala Phe Leu Ala Leu Arg Ala Gly
        35                  40                  45

Val Asp Pro Gly Asp Glu Glu Gly Leu Leu Ala Leu Leu Glu Gly Leu
```

```
            50                  55                  60
Gly Val Arg Leu Leu Ala Gln Ala Glu Gly Asn Arg Val Leu Ala Asp
 65                  70                  75                  80

Gly Glu Asp Leu Thr Ser Phe Leu His Thr Pro Glu Val Asp Arg Val
                     85                  90                  95

Val Ser Ala Val Ala Arg Leu Pro Gly Val Arg Ala Trp Val Asn Arg
                100                 105                 110

Arg Leu Lys Glu Val Pro Pro Phe Val Ala Glu Gly Arg Asp Met
                115                 120                 125

Gly Thr Ala Val Phe Pro Glu Ala Ala His Lys Phe Tyr Leu Thr Ala
                130                 135                 140

Ser Pro Glu Val Arg Ala Trp Arg Arg Ala Arg Glu Arg Pro Gln Ala
145                 150                 155                 160

Tyr Glu Glu Val Leu Arg Asp Leu Leu Arg Arg Asp Glu Arg Asp Lys
                165                 170                 175

Ala Gln Ser Ala Pro Ala Pro Asp Ala Leu Val Leu Asp Thr Gly Gly
                180                 185                 190

Met Thr Leu Asp Glu Val Val Ala Trp Val Leu Ala His Ile Arg Arg
                195                 200                 205

<210> SEQ ID NO 14
<211> LENGTH: 225
<212> TYPE: PRT
<213> ORGANISM: Pyrococcus furiosus

<400> SEQUENCE: 14

Met Arg Ile Val Phe Asp Ile Gly Gly Ser Val Leu Val Pro Glu Asn
  1               5                  10                  15

Pro Asp Ile Asp Phe Ile Lys Glu Ile Ala Tyr Gln Leu Thr Lys Val
                 20                  25                  30

Ser Glu Asp His Glu Val Ala Val Val Gly Gly Gly Lys Leu Ala
                 35                  40                  45

Arg Lys Tyr Ile Glu Val Ala Glu Lys Phe Asn Ser Ser Glu Thr Phe
 50                  55                  60

Lys Asp Phe Ile Gly Ile Gln Ile Thr Arg Ala Asn Ala Met Leu Leu
 65                  70                  75                  80

Ile Ala Ala Leu Arg Glu Lys Ala Tyr Pro Val Val Val Glu Asp Phe
                 85                  90                  95

Trp Glu Ala Trp Lys Ala Val Gln Leu Lys Lys Ile Pro Val Met Gly
                100                 105                 110

Gly Thr His Pro Gly His Thr Thr Asp Ala Val Ala Ala Leu Leu Ala
                115                 120                 125

Glu Phe Leu Lys Ala Asp Leu Leu Val Val Ile Thr Asn Val Asp Gly
                130                 135                 140

Val Tyr Thr Ala Asp Pro Lys Lys Asp Pro Thr Ala Lys Lys Ile Lys
145                 150                 155                 160

Lys Met Lys Pro Glu Glu Leu Leu Glu Ile Val Gly Lys Gly Ile Glu
                165                 170                 175

Lys Ala Gly Ser Ser Val Ile Asp Pro Leu Ala Ala Lys Ile Ile
                180                 185                 190

Ala Arg Ser Gly Ile Lys Thr Ile Val Ile Gly Lys Glu Asp Ala Lys
                195                 200                 205

Asp Leu Phe Arg Val Ile Lys Gly Asp His Asn Gly Thr Thr Ile Glu
                210                 215                 220
```

Pro
225

```
<210> SEQ ID NO 15
<211> LENGTH: 207
<212> TYPE: PRT
<213> ORGANISM: Thermotoga maritima

<400> SEQUENCE: 15
```

| | | | | | | | | | | | | | | | |
|---|---|---|---|---|---|---|---|---|---|---|---|---|---|---|---|
| Met | Lys | Gly | Gln | Leu | Phe | Val | Ile | Cys | Gly | Pro | Ser | Gly | Ala | Gly | Lys |
| 1 | | | | 5 | | | | | 10 | | | | | 15 | |
| Thr | Ser | Ile | Ile | Lys | Glu | Val | Leu | Lys | Arg | Leu | Asp | Asn | Val | Val | Phe |
| | | | 20 | | | | | 25 | | | | | 30 | | |
| Ser | Val | Ser | Cys | Thr | Thr | Arg | Pro | Lys | Arg | Pro | His | Glu | Glu | Asp | Gly |
| | | | 35 | | | | | 40 | | | | | 45 | | |
| Lys | Asp | Tyr | Phe | Phe | Ile | Thr | Glu | Glu | Phe | Leu | Lys | Arg | Val | Glu | |
| | 50 | | | | | 55 | | | | | 60 | | | | |
| Arg | Gly | Glu | Phe | Leu | Glu | Trp | Ala | Arg | Val | His | Gly | His | Leu | Tyr | Gly |
| 65 | | | | | 70 | | | | | 75 | | | | | 80 |
| Thr | Leu | Arg | Ser | Phe | Val | Glu | Ser | His | Ile | Asn | Glu | Gly | Lys | Asp | Val |
| | | | | 85 | | | | | 90 | | | | | 95 | |
| Val | Leu | Asp | Ile | Asp | Val | Gln | Gly | Ala | Leu | Ser | Val | Lys | Lys | Lys | Tyr |
| | | | 100 | | | | | 105 | | | | | 110 | | |
| Ser | Asn | Thr | Val | Phe | Ile | Tyr | Val | Ala | Pro | Pro | Ser | Tyr | Ala | Asp | Leu |
| | | | 115 | | | | | 120 | | | | | 125 | | |
| Arg | Glu | Arg | Ile | Leu | Lys | Arg | Gly | Thr | Glu | Lys | Glu | Ala | Asp | Val | Leu |
| | 130 | | | | | 135 | | | | | 140 | | | | |
| Val | Arg | Leu | Glu | Asn | Ala | Lys | Trp | Glu | Leu | Met | Phe | Met | Asp | Glu | Phe |
| 145 | | | | | 150 | | | | | 155 | | | | | 160 |
| Asp | Tyr | Ile | Val | Val | Asn | Glu | Asn | Leu | Glu | Asp | Ala | Val | Glu | Met | Val |
| | | | | 165 | | | | | 170 | | | | | 175 | |
| Val | Ser | Ile | Val | Arg | Ser | Glu | Arg | Ala | Lys | Val | Thr | Arg | Asn | Gln | Asp |
| | | | 180 | | | | | 185 | | | | | 190 | | |
| Lys | Ile | Glu | Arg | Phe | Lys | Met | Glu | Val | Lys | Gly | Trp | Lys | Lys | Leu | |
| | | | 195 | | | | | 200 | | | | | 205 | | |

```
<210> SEQ ID NO 16
<211> LENGTH: 142
<212> TYPE: PRT
<213> ORGANISM: Aquifex aeolicus

<400> SEQUENCE: 16
```

| | | | | | | | | | | | | | | | |
|---|---|---|---|---|---|---|---|---|---|---|---|---|---|---|---|
| Met | Ala | Val | Glu | Arg | Thr | Leu | Ile | Ile | Val | Lys | Pro | Asp | Ala | Met | Glu |
| 1 | | | | 5 | | | | | 10 | | | | | 15 | |
| Lys | Gly | Ala | Leu | Gly | Lys | Ile | Leu | Asp | Arg | Phe | Ile | Gln | Glu | Gly | Phe |
| | | | 20 | | | | | 25 | | | | | 30 | | |
| Gln | Ile | Lys | Ala | Leu | Lys | Met | Phe | Arg | Phe | Thr | Pro | Glu | Lys | Ala | Gly |
| | | | 35 | | | | | 40 | | | | | 45 | | |
| Glu | Phe | Tyr | Tyr | Val | His | Arg | Glu | Arg | Pro | Phe | Phe | Gln | Glu | Leu | Val |
| | 50 | | | | | 55 | | | | | 60 | | | | |
| Glu | Phe | Met | Ser | Ser | Gly | Pro | Val | Val | Ala | Ala | Val | Leu | Glu | Gly | Glu |
| 65 | | | | | 70 | | | | | 75 | | | | | 80 |
| Asp | Ala | Ile | Lys | Arg | Val | Arg | Glu | Ile | Ile | Gly | Pro | Thr | Asp | Ser | Glu |
| | | | | 85 | | | | | 90 | | | | | 95 | |
| Glu | Ala | Arg | Lys | Val | Ala | Pro | Asn | Ser | Ile | Arg | Ala | Gln | Phe | Gly | Thr |
| | | | 100 | | | | | 105 | | | | | 110 | | |

-continued

```
Asp Lys Gly Lys Asn Ala Ile His Ala Ser Asp Ser Pro Glu Ser Ala
        115                 120                 125
Gln Tyr Glu Ile Cys Phe Ile Phe Ser Gly Leu Glu Ile Val
    130                 135                 140
```

US 10,858,385 B2

METHODS AND COMPOSITIONS FOR NUCLEOSIDE TRIPHOSPHATE AND RIBONUCLEIC ACID PRODUCTION

RELATED APPLICATION

This application is a continuation of international application number PCT/US2018/055353 filed Oct. 11, 2018, which claims the benefit under 35 U.S.C. § 119(e) of U.S. provisional application No. 62/571,071, filed Oct. 11, 2017, each of which is incorporated by reference herein in its entirety.

BACKGROUND

Ribonucleic acid (RNA) comprises repeating units of ribonucleotides and plays a role in key cellular processes, including gene expression and protein synthesis. Thus, RNA is an attractive target for modulating fundamental processes of the cell, for example, RNA vaccines that induce a cellular immune response. Low-cost production of RNA on a commercial scale (e.g., grams to kilograms), however, is challenging due in part to the cost of the starting material (e.g., nucleoside triphosphates (NTPs)) and reaction components (e.g., DNA template and polymerase). Providing high-quality RNA at commercially relevant scales requires cost efficient production of both NTPs and RNA.

SUMMARY

Provided herein are systems, methods, compositions (e.g., cells, cell lysates, reagents, and reaction mixtures), and kits for low-cost production (biosynthesis) of NTPs and/or RNAs, using biosynthetic pathways developed to utilize low-cost substrates (e.g., cellular RNA, nucleobases, nucleosides, nucleoside monophosphates (NMPs), and/or nucleoside diphosphates (NDPs)), recombinant and/or endogenous enzymes (e.g., kinases and/or polymerases), and energy sources (e.g., NTPs, polyphosphate, and/or pyrophosphate). The production of NTPs and/or RNA, in some embodiments, is achieved using in vitro and/or cell-free lysate systems designed to minimize (e.g., reduce, inhibit, and/or remove) undesired enzymatic activities, thus increasing efficiency of the process and yield of the desired end product.

The biosynthetic pathways described herein typically utilize polyphosphate kinase and polyphosphate as an alternative to endogenous pathway enzymes and phosphate sources.

Thus, some aspects of the present disclosure provide methods and compositions for producing NTPs that comprise incubating in a reaction mixture NDPs (e.g., ADP, CDP, GDP, and/or UDP), a polyphosphate kinase (e.g., PPK2), and a polyphosphate (e.g., hexametaphosphate) under conditions suitable for the production of NTPs. As shown in FIG. 2A, PPK transfers a phosphate from polyphosphate to ADP, CDP, GDP, and UDP, resulting in production of ATP, CTP, GDP, and UTP. In some embodiments, this reaction mixture further comprises a NDP kinase (e.g., ndk).

Other aspects of the present disclosure provide systems, methods, compositions, and kits for producing NTPs that comprise incubating in a reaction mixture NMPs (e.g., 5'-NMPs, such as 5'-AMP, 5'-CMP, 5'-GMP, and/or 5'-UMP), a polyphosphate kinase, and a polyphosphate under conditions suitable for the production of NTPs. In some embodiments, the reaction mixture further comprises a NMP kinase or a NDP kinase (e.g., ndk). In some embodiments, the reaction mixture further comprises a NMP kinase (e.g., adk, cmk, gmk, and/or pyrH) and a NDP kinase (e.g., ndk).

Still other aspects of the present disclosure provide systems, methods, compositions, and kits for producing NTPs that comprise incubating in a reaction mixture nucleosides (e.g., adenosine, cytidine, guanosine, and/or uridine), a polyphosphate kinase, and a polyphosphate under conditions suitable for the production of NTPs. In some embodiments, the reaction mixture further comprises a nucleoside kinase, a NMP kinase, or a NDP kinase. In some embodiments, the reaction mixture further comprises a nucleoside kinase, a NMP kinase. and a NDP kinase.

Further aspects of the present disclosure provide systems, methods, compositions, and kits for producing NTPs that comprise incubating in a reaction mixture nucleobases (e.g., adenine, cytosine, guanine, and/or uracil), a phosphoribosyltransferase, a phosphoribosylpyrophosphate, a polyphosphate kinase, and a polyphosphate under conditions suitable for the production of NTPs. In some embodiments, the reaction mixture further comprises a nucleoside kinase, a NMP kinase, or a NDP kinase. In some embodiments, the reaction mixture further comprises a nucleoside kinase, a NMP kinase. and a NDP kinase.

In some embodiments, the starting material (e.g., NMPs, NDPs, and/or nucleosides) for the biosynthesis of NTPs is produced from cellular RNA. Thus, some aspects of the present disclosure provide systems, methods, compositions, and kits for producing NTPs that comprise (a) incubating in a reaction mixture cellular RNA (e.g., obtained from unicellular or multicellular organisms), a polynucleotide phosphorylase (PNPase), and inorganic phosphate under conditions suitable for the production of nucleoside diphosphates (NDPs); (b) eliminating the PNPase (and optionally eliminating other undesired enzymatic activities); and (c) incubating in the resulting reaction mixture the NDPs, a polyphosphate kinase, and a polyphosphate under conditions suitable for the production of NTPs. In some embodiments, the reaction mixture of step (c) further comprises a NDP kinase. Alternatively, the methods may comprise (a) incubating in a reaction mixture cellular ribonucleic acid (RNA), a PNPase, inorganic phosphate, a polyphosphate kinase, and a polyphosphate under conditions suitable for the production of nucleoside diphosphates (optionally wherein the reaction mixture further comprises a NDP kinase); (b) eliminating the PNPase; and (c) incubating the reaction mixture under conditions suitable for the production of NTPs. In some embodiments, the required pathway enzymes (e.g., polyphosphate kinase and/or NDP kinase) can withstand the elimination conditions (e.g., exposure to high temperature or a chemical inhibitor) such that they retain their activity (for example, at least 50% of their activity) following exposure to the conditions used to eliminate (e.g., reduce, inhibit and/or remove) the PNPase.

Other aspects of the present disclosure provide systems, methods, compositions, and kits for producing NTPs that comprise (a) incubating in a first reaction mixture cellular RNA and a ribonuclease (RNase, for example RNase R or Nuclease P1) under conditions suitable for the production of NMPs (e.g., 5'-NMPs); (b) eliminating the RNase (and optionally v other undesired enzymatic activities); and (c) incubating in the resulting reaction mixture the NMPs, a polyphosphate kinase, and a polyphosphate under conditions suitable for the production of NTPs. In some embodiments, the reaction mixture of step (c) further comprises a NMP kinase, a NDP kinase, or both a NMP kinase and a NDP kinase. Alternatively, the methods may comprise (a) incubating in a reaction mixture cellular RNA, a RNase, a polyphosphate kinase, and a polyphosphate under conditions suitable for the production of NMPs (e.g., 5'-NMPs); (b) eliminating the RNase; and (c) incubating the reaction mixture under conditions suitable for the production of NTPs.

The NTPs produced herein are used, in some embodiments, for the production of RNA (e.g., mRNA or double-stranded RNA). This may be achieved, for example, by adding DNA template and polymerase (e.g., T7 RNA polymerase) to any of the reaction mixtures used for the production of NTP, as described herein. Alternatively, the NTPs may be isolated and combined with DNA template and polymerase in a separate reaction mixture to produce RNA. Thus, the present disclosure also provides methods and compositions for the production of RNA.

In any of the biosynthetic pathways described herein the nucleobases, nucleosides, NMPs, NDPs, or NTPs, when used as the starting substrate, may be chemically synthesized, a product of fermentation, or produced by other means.

The polyphosphate kinase used in the systems, reaction mixtures, and methods described herein may be selected from any of the polyphosphate kinases listed in Table 2 or 12. In some embodiments, the polyphosphate kinase comprises a Class III polyphosphate kinase 2 from *Deinococcus geothermalis*.

The polyphosphate may be any polyphosphate that serves as a substrate for a pathway enzymes. In some embodiments, the polyphosphate is hexametaphosphate.

In embodiments where cellular RNA is used, the cellular RNA comprises, for example, ribosomal RNA, messenger RNA, and/or transfer RNA. The cellular RNA may be from a unicellular organism (e.g., bacteria or yeast) or a multicellular organism (e.g., plants).

Enzymes of the biosynthetic pathways useful in the present disclosure may be obtained from (isolated and/or purified) a (at least one) cell lysate prepared from, for example, cells (e.g., engineered cells) that express enzymes of the pathway (e.g., nucleases (such as RNases and/or PNPases), polyphosphate kinases, NMP kinases, NDP kinase, and/or polymerases). Exemplary methods for preparing these cell lysates are described herein. Alternatively, the reaction mixture may comprise a cell lysate (a single cell lysate or a mixture of cell lysates) prepared from cells (e.g., engineered cells) that express enzymes of the pathway. That is, a complete reaction may be performed in a cell lysate or a mixture of cell lysates containing recombinant enzymes and/or endogenous enzymes of the pathway as well as other reaction components (e.g., polyphosphate) required for the production of NTPs. In some embodiments, a (at least one) purified pathway enzyme is added to a reaction mixture.

For reaction mixtures that include cell lysate(s) or enzymes obtained from cell lysate(s), it may be advantageous to eliminate undesired native enzymatic activities using any of the elimination methods described herein. Undesired native enzymatic activities include, for example, phosphatases, nucleases, proteases, deaminases, oxidoreductases, and hydrolases. In some embodiments, native enzymatic activity is eliminated via genetic modification, enzyme secretion from a cell, localization (e.g., periplasmic targeting), and/or protease targeting. In other embodiments, native enzymatic activity is eliminated via temperature, pH, salt, detergent, alcohol or other solvents, and/or chemical inhibitors. In yet other embodiments, native enzymatic activity is eliminated via separation, precipitation, filtration, capture, and/or chromatography.

The details of several embodiments of the invention are set forth in the accompanying Examples, Figures and the Detailed Description. Other features, objects, and advantages of the invention will be apparent from the description and from the claims.

BRIEF DESCRIPTION OF THE DRAWINGS

FIG. 15A presents the three enzymatic reactions for ATP production from citrate and pyrophosphate. FIG. 15B presents the overall chemical reaction. The meaning of the abbreviations is as follows: $PP_i$=inorganic pyrophosphate, PEP=phosphoenolpyruvate, $CO_2$=carbon dioxide, $P_i$=inorganic phosphate, ATP=adenosine triphosphate, and AMP=adenosine monophosphate.

DETAILED DESCRIPTION

Figure 1A:
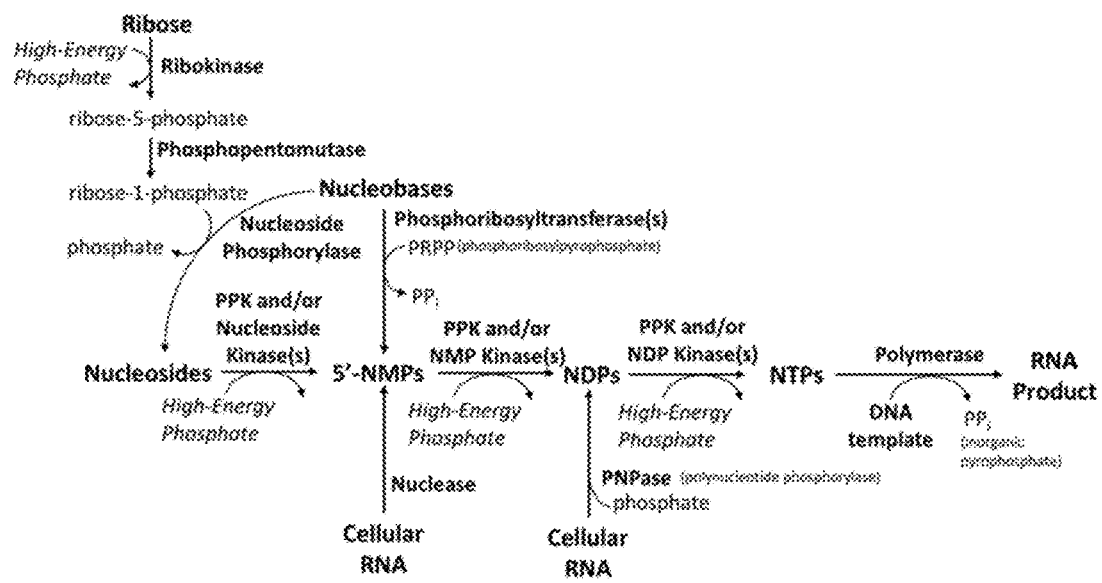
FIG. 1A shows biosynthetic pathways for the production of nucleoside triphosphates (NTPs), and downstream ribonucleic acid (RNA) using nucleotide starting materials.

The present disclosure provides, in some aspects, biosynthetic pathways for the production of NTPs and/or RNA that utilize cost-effective reaction components, such as cellular RNA substrates or monomeric substrates such as nucleobases, nucleosides, NMPs, or NDPs, recombinant and/or purified pathway enzymes (e.g., phosphoribosyltransferases, nucleoside phosphorylases, ribokinases, phosphopentomutaes, nucleases, polyphosphate kinases, NMP kinases, NDP kinases, nucleoside kinases, RNA polymerases), sources of high energy phosphate (e.g., polyphosphate), and/or DNA templates.

Reaction Components

Cellular RNA.

Cellular RNA includes, for example, messenger RNA (mRNA), transfer RNA (tRNA), and ribosomal RNA (rRNA) obtained from cellular material (biomass). Cellular RNA may be obtained from any source of cellular material including, but not limited to, unicellular organisms (e.g., bacteria and yeast) and multicellular organisms (e.g., plants and animals), either from fermentation or from a process waste stream, for example, cellular RNA obtained from a lysate expressing an enzyme (e.g., a kinase).

Nucleobases.

A nucleobase is a nitrogenous base component of a nucleoside or nucleotide. Nucleobases function as fundamental units of the genetic code. Nucleobases include adenine (A), cytosine (C), guanine (G), thymine (T), and uracil (U). Nucleobases include modified nucleobases including, but not limited to, pseudouridine (Ψ), dihydrouridine (D), and 7-methylguanosine ($m^7G$).

Nucleosides.

A nucleoside is a nucleobase linked to a five-carbon sugar (e.g., a ribose). Examples of nucleosides include adenosine, cytidine, guanosine, thymidine and uridine.

Nucleotides.

A nucleotide includes a nucleoside and a phosphate group. A nucleoside having one phosphate group is a nucleoside monophosphate (NMP), which include adenosine monophosphate (AMP), cytidine monophosphate (CMP), guanosine monophosphate (GMP), thymidine monophosphate (TMP), and uridine monophosphate (UMP). A nucleoside having two phosphate groups is a nucleoside diphosphate (NDP), which include adenosine diphosphate (ADP), cytidine diphosphate (CDP), guanosine diphosphate (GDP), thymidine diphosphate (TDP), and uridine diphosphate (UDP). A nucleoside having three phosphate groups is a nucleoside triphosphate (NTP), which include adenosine triphosphate (ATP), cytidine triphosphate (CTP), guanosine triphosphate (GTP), thymidine triphosphate (TTP), and uridine triphosphate (UTP).

Phosphoribosyltransferases.

Phosphoribosyltransferases, such as adenine phosphoribosyltransferase (APRTase), is involved in the nucleotide salvage pathway in cells, which provides an alternative to nucleotide biosynthesis. APRTase catalyzes the following reaction in the purine nucleotide salvage pathway: Adenine+Phosphoribosyl Pyrophosphate (PRPP)→Adenosine 5' monophosphate (AMP)+Pyrophosphate (PPi).

Ribokinases.

Ribokinase is an enzyme that transfers phosphate from a high-energy phosphate source (e.g., ATP or polyphosphate) to D-ribose forming D-ribose-5-phosphate. Examples include the rbsK gene product of *E. coli* and the QT17_05185 gene product of *Thermus* sp. 2.9.

Phosphopentomutases.

Phosphopentomutase is an enzyme that transfers phosphate within a ribose-phosphate molecule. Specifically, phosphoribomutase catalyzes the reversible interconversion of D-ribose-1-phosphate and D-ribose-5-phosphate. Examples include the deoB gene product of *E. coli* and the TM0167 gene product of *Thermotoga maritima*.

Nucleoside Phosphorylases.

Nucleoside phosphorylases are enzymes that catalyze the following reversible reaction —nucleobase+D-ribose-1-phosphate←→nucleoside+inorganic phosphate. Purine nucleoside phosphorylase catalyze such a reaction with purine nucleobases (e.g., adenine, guanine) and purine nucleosides (e.g., adenosine, guanosine). Pyrimidine nucleoside phosphorylases catalyze such a reaction with pyrimidine nucleobases (e.g., cytosine, uracil) and pyrimidine nucleosides (e.g, cytidine, uridine). Examples of nucleoside phosphorylases include the deoD, xapA, and udp gene products of *E. coli*, as well as the TtPNPI, TtPNPII, and TtPyNP, enzymes of *Thermus thermophilus* HB27.

Polynucleotide Phosphorylases.

Polynucleotide phosphorylase (PNPase) is a bifunctional enzyme with a phosphorolytic 3' to 5' exoribonuclease activity and a 3'-terminal oligonucleotide polymerase activity. PNPase is capable of catalyzing the degradation of RNA into nucleoside 5' diphosphates (NDPs) using inorganic phosphate as a co-substrate. Use of high concentrations of inorganic phosphate while employing PNPase to degrade RNA may simultaneously drive PNPase activity while reducing potential NDP yield loss due to phosphatase activities that might be present in the reaction mixture, as inorganic phosphate is known to inhibit such undesirable activities. In some embodiments, a PNPase is used, optionally in conjunction with one or more helicases, to catalyze degradation of RNA into NDPs. Adding a helicase may improve PNPase-meditated depolymerization of cellular RNA by improving accessibility of structured RNA.

Nucleases.

Nucleases are enzymes that cleave the phosphodiester bonds in the backbone of DNA (DNases) or RNA (RNases). Thus, ribonucleases (RNases) are capable of catalyzing the degradation of RNA into nucleoside monophosphates (NMPs). Non-limiting examples of enzymes that may be used to depolymerize RNA, as provided herein, are provided in Table 1. In some embodiments, more than one nuclease is used in a reaction mixture to depolymerize RNA. In some embodiments, 2, 3, 4, or 5 different nucleases are used in a reaction mixture.

TABLE 1

Examples of Enzymes for RNA Depolymerization

| Enzyme | Organism | EC # | UniProt | Reference |
|---|---|---|---|---|
| Nuclease P1 (P1 Nuclease) | *Penicillium citrinum* | 3.1.30.1 | P24289 | 1, 2, 3 |
| RNase II | *Escherichia coli* | 3.1.13.1 | P30850 | 4, 5 |
| RNase III | *Escherichia coli* | 3.1.26.3 | P0A7Y0 | 6, 7, 8 |
| RNase R | *Pseudomonas putida* or *Escherichia coli* | 3.1.13.— | R9V9M9 P21499 | 9 |
| RNase JI | *Bacillus subtilis* | 3.1.4.1 | Q45493 | 10, 11 |
| NucA | *Serratia marcescens* | 3.1.30.2 | P13717 | 12, 13, 14 |
| RNase T | *Escherichia coli* | 3.1.27.3 | P30014 | 15, 16, 17 |
| RNase E | *Escherichia coli* | 3.1.26.12 | P21513 | 18, 19 |
| PNPase | *Escherichia coli* | 2.7.7.8 | P05055 | 55 |

Kinases.

Kinases, generally, are enzymes that catalyze the transfer of phosphate groups from a high-energy phosphate-donating molecule (e.g., ATP, GTP, UTP, CTP, or polyphosphate containing n phosphate groups in the polymer) to specific substrates/molecules. This process produces a phosphorylated substrate and a dephosphorylated form of the high-energy phosphate-donating molecule (e.g., ADP, GDP, UDP, CDP, or polyphosphate containing n−1 phosphate groups in the polymer). Non-limiting examples of kinases for use as provided herein include NMP kinases, NDP kinases, nucleoside kinases, and polyphosphate kinases.

Polyphosphate Kinases.

A polyphosphate kinase is an enzyme that catalyzes the transfer of phosphate group(s) from high-energy, phosphate-donating molecules, such as polyphosphate (PolyP$_n$), to specific substrates/molecules. This process is referred to as phosphorylation, where the substrate gains a phosphate group and the high-energy, phosphate-donating molecule donates a phosphate group. This transesterification produces a phosphorylated substrate and a phosphate-donating molecule lacking the donated phosphate group, such as PolyP$_{n-1}$. The polyphosphate kinases of the present disclosure, in some embodiments, convert nucleosides to NMPs, NMPs to NDPs, and/or NDPs to NTPs. Non-limiting examples of polyphosphate kinases are provided in Table 2. In some embodiments, more than one polyphosphate kinase is used in a reaction mixture. In some embodiments, 2, 3, 4, or 5 different polyphosphate kinases are used in a reaction mixture.

TABLE 2

Examples of Polyphosphate Kinases

| Enzyme | Organism | GenBank # UniProt # | Sequence Identification Number | Reference |
|---|---|---|---|---|
| Thermophiles | | | | |
| PPK2 | *Deinococcus geothermalis* DSM 11300 | WP_011531362.1 | SEQ ID NO: 1 | 20 |
| PPK2 | *Meiothermus ruber* DSM 1279 | ADD29239.1 | SEQ ID NO: 2 | 20 |

TABLE 2-continued

Examples of Polyphosphate Kinases

| | | | | |
|---|---|---|---|---|
| PPK2 | *Meiothermus silvanus* DSM 9946 | WP_013159015.1 | SEQ ID NO: 3 | 20 |
| PPK2 | *Thermosynechococcus elongatus* BP-1 | NP_682498.1 | SEQ ID NO: 4 | 20 |
| PPK2 | *Anaerolinea thermophila* UNI-1 | WP_013558940 | SEQ ID NO: 5 | |
| PPK2 | *Caldilinea aerophila* DSM 14535 | WP_014433181 | SEQ ID NO: 6 | |
| PPK2 | *Chlorobaculum tepidum* TLS | NP_661973.1 | SEQ ID NO: 7 | |
| PPK2 | *Oceanithermus profundus* DSM 14977 | WP_013458618 | SEQ ID NO: 8 | |
| PPK2 | *Roseiflexus castenholzii* DSM 13941 | WP_012120763 | SEQ ID NO: 9 | |
| PPK2 | *Roseiflexus* sp. RS-1 | WP_011956376 | SEQ ID NO: 10 | |
| PPK2 | *Truepera radiovictrix* DSM 17093 | WP_013178933 | SEQ ID NO: 11 | |
| Solvent-tolerant organisms | | | | |
| PPK1 | *Pseudomonas putida* DOT-T1E | AFO50238.1 I7BEV8 | | 42 |
| PPK1 | *Escherichia coli* K-12 | AAC75554.1 P0A7B1 | | |
| PPK1 | *Clostridium acetobutylicum* ATCC 824 | NP_347259.1 Q97LE0 | | 43 |

Acidophiles

| | | |
|---|---|---|
| PPK1 | *Thermosynechococcus elongatus* | WP_011056068 |
| PPK1 | *Acidithiobacillus ferrooxidans* | WP_064219446 |
| PPK1 | *Acidithiobacillus thiooxidans* | WP_031572361 |
| PPK1 | *Bacillus acidicola* | WP_066264350 |
| PPK1 | *Acetobacter aceti* | GAN58028 |
| PPK2 | *Acetobacter aceti* | WP_077811826.1 |
| PPK2 | *Acidithiobacillus thiooxidans* | WP_051690689.1 |
| PPK2 | *Acidithiobacillus ferrooxidans* | WP_064219816.1 |

Alkaliphiles

| | | |
|---|---|---|
| PPK1 | *Thioalkalivibrio denitrificans* | WP_077277945.1 |

Psychrophiles

| | | |
|---|---|---|
| PPK1 | *Psychromonas ingrahamii* | WP_041766473.1 |
| PPK2 | *Psychrobacter arcticus* | WP_083756052.1 |
| PPK2 | *Psychroserpens jangbogonensis* | WP_033960485.1 |
| PPK2 | *Cryobacterium psychrotolerans* | WP_092324020.1 |
| PPK2 | *Nocardioides psychrotolerans* | WP_091116082.1 |
| PPK2 | *Pseudomonas psychrophila* | WP_019411115.1 |

Nucleoside Kinases. Nucleoside kinases catalyze a phosphoryl transfer from a high-energy phosphate-donating molecule (e.g., a nucleotide triphosphate) to an R—OH acceptor, which is typically the 5'-hydroxyl group of the sugar moiety of the nucleoside (e.g., adenosine, guanosine, cytidine, uridine). This process converts a nucleoside to a NMP (e.g., AMP, CMP, GMP, UMP). In some embodiments, the nucleoside kinase catalyzes the transfer of phosphate from a phosphate-donating molecule to adenosine to produce adenosine monophosphate (AMP). In some embodiments, the nucleoside kinase catalyzes the transfer of phosphate from a phosphate-donating molecule to cytidine to produce cytidine monophosphate (CMP). In some embodiments, the nucleoside kinase catalyzes the transfer of phosphate from a phosphate-donating molecule to guanosine to produce guanosine monophosphate (GMP). In some embodiments, the nucleoside kinase catalyzes the transfer of phosphate from a phosphate-donating molecule to uridine to produce uridine monophosphate (UMP). Non-limiting examples of nucleoside kinases are provided in Table 3. In some embodiments, more than one nucleoside kinase is used in a reaction mixture. In some embodiments, 2, 3, 4, or 5 different nucleoside kinases are used in a reaction mixture.

TABLE 3

Examples of Nucleoside Kinases

| Enzyme | Organism | GenBank # UniProt # | Reference |
|---|---|---|---|
| Thermophiles | | | |
| Nucleoside kinase | *Thermoplasma acidophilum* | CAC12009.1 Q9HJT3 | 21 |

TABLE 3-continued

Examples of Nucleoside Kinases

| Enzyme | Organism | GenBank # UniProt # | Reference |
|---|---|---|---|
| Nucleoside kinase | Methanocaldococcus jannaschii | AAB98396.1 Q57849 | 22 |
| Nucleoside kinase | Burkholderia thailandensis | ABC38537.1 AIP24308.1 Q2SZE4 | 23 |
| Uridine-cytidine kinase (Y93H mutant) | Thermus thermophilus | BAD70401.1 Q5SKR5 | 24 |
| Uridine kinase | Caldilinea aerophila | WP_014432899.1 | |
| Uridine kinase | Geobacillus stearothermophilus | WP_043905564.1 | |
| Uridine kinase | Meiothermus ruber | WP_013014613.1 | |

NMP Kinases.

A nucleoside monophosphate kinase (NMP kinase) is an enzyme that catalyzes the transfer of the terminal phosphoryl group from a nucleoside triphosphate (NTP), usually ATP, to the phosphoryl group on a nucleoside monophosphate (e.g., AMP, CMP, GMP, UMP). This process converts a NMP to a NDP (e.g., ADP, CDP, GDP, UDP). In some embodiments, the NMP kinase catalyzes the transfer of phosphate from a phosphate-donating molecule to AMP to produce adenosine diphosphate (ADP). In some embodiments, the NMP kinase catalyzes the transfer of phosphate from a phosphate-donating molecule to CMP to produce cytidine diphosphate (CDP). In some embodiments, the NMP kinase catalyzes the transfer of phosphate from a phosphate-donating molecule to GMP to produce guanosine diphosphate (GDP). In some embodiments, the NMP kinase catalyzes the transfer of phosphate from a phosphate-donating molecule to UMP to produce uridine diphosphate (UDP). Non-limiting examples of NMP kinases are provided in Table 4. In some embodiments, more than one NMP kinases is used in a reaction mixture. In some embodiments, 2, 3, 4, or 5 different NMP kinases are used in a reaction mixture.

TABLE 4A

Examples of AMP kinase enzymes

| Enzyme | Organism | GenBank # UniProt # | Sequence Identification Number | Reference |
|---|---|---|---|---|
| Thermophiles | | | | |
| Adk | Thermus thermophilus | Q72I25 | SEQ ID NO: 12 | 25, 26 |
| Adk | Pyrococcus furiosus | Q8U207 | | 27 |
| Solvent-tolerant organisms | | | | |
| Adk | Pseudomonas putida DOT-T1E | AFO48764.1 I7CAA9 | | 42 |
| Adk | Escherichia coli K-12 W3110 | BAE76253.1 P69441 | | 44 |
| Adk1 | Aspergillus niger CBS 513.88 | CAK45139.1 A2QPN9 | | 45 |
| Adk1 | Saccharomyces cerevisiae ATCC 204508/S288c | AAC33143.1 P07170 | | 46 |
| Adk | Clostridium acetobutylicum ATCC 824 | AAK81051.1 Q97EJ9 | | 43 |
| Adk | Halobacterium salinarum ATCC 700922 | AAG19963.1 Q9HPA7 | | 32 |
| Acidophiles | | | | |
| Adk | Acidithiobacillus thiooxidans | WP_024894015.1 | | |
| Adk | Acidithiobacillus ferrooxidans | WP_064218420.1 | | |
| Adk | Acetobacter aceti | WP_077811596.1 | | |
| Adk | Bacillus acidicola | WP_066267988.1 | | |
| Adk | Sulfolobus solfataricus | WP_009991241.1 | | |

TABLE 4A-continued

Examples of AMP kinase enzymes

| Enzyme | Organism | GenBank # UniProt # | Sequence Identification Number | Reference |
|---|---|---|---|---|
| | | Alkaliphiles | | |
| Adk | Thioalkalivibrio | WP_019570706.1 | | |
| Adk | Amphibacillus xylanus | WP_015008883.1 | | |
| | | Psychrophiles | | |
| Adk | Colwellia psychrerythraea (Vibrio psychroerythus) | WP_033093471.1 Q47XA8 | | 28 |
| Adk | Psychromonas ingrahamii | WP_011769361 A1STI3 | | |
| Adk | Pseudoalteromonas haloplanktis | CAI86283 Q3IKQ1 | | 29 |
| Adk | Psychrobacter arcticus | WP_011280822 | | 30 |
| Adk | Pseudomonas syringae | WP_004406317.1 Q4ZWV2 | | 31 |
| | | Halophiles | | |
| Adk | Halobacterium halobium | WP_010903261.1 Q9HPA7 | | 32 |

TABLE 4B

Examples of CMP kinase enzymes

| Enzyme | Organism | GenBank # UniProt # | Sequence Identification Number | Reference |
|---|---|---|---|---|
| | | Thermophiles | | |
| Cmk | Thermus thermophilus | Q5SL35 | SEQ ID NO: 13 | 33 |
| Cmk | Pyrococcus furiosus | Q8U2L4 | | 27 |
| | | Solvent-tolerant organisms | | |
| Cmk | Pseudomonas putida DOT-T1E | AFO48857.1 I7BXE2 | | 42 |
| Cmk | Escherichia coli K-12 MG1655 | AAC73996.1 P0A6I0 | | 47 |
| Cmk | Clostridium acetobutylicum ATCC 824 | AAK79812.1 Q97I08 | | 43 |
| Cmk | Halobacterium salinarum ATCC 700922 | AAG19965.1 Q9HPA5 | | 34 |
| | | Acidophiles | | |
| Cmk | Bacillus acidicola | WP_066270173 | | |
| Cmk | Acetobacter aceti | WP_010667744 | | |
| Cmk | Acidithiobacillus thiooxidans | WP_024892761.1 | | |
| Cmk | Acidithiobacillus ferrooxidans | WP_064220349.1 | | |
| Cmk | Metallosphaera sedula | WP_011921264.1 | | |
| | | Alkaliphiles | | |
| Cmk | Amphibacillus xylanus | WP_015009966.1 | | |
| Cmk | Thioalkalivibrio denitrificans | WP_077278466.1 | | |
| | | Psychrophiles | | |
| Cmk | Colwellia psychrerythraea (Vibrio psychroerythus) | WP_011043148.1 Q482G4 | | 28 |

TABLE 4B-continued

Examples of CMP kinase enzymes

| Enzyme | Organism | GenBank # UniProt # | Sequence Identification Number | Reference |
|---|---|---|---|---|
| Cmk | *Pseudoalteromonas haloplanktis* | CAI86499.1 Q3ILA1 | | 29 |
| Cmk | *Psychrobacter arcticus* | AAZ19343.1 Q4FRL5 | | 30 |
| Cmk | *Psychromonas ingrahamii* | ABM04716 A1SZ01 | | |
| Cmk | *Pseudomonas syringae* | YP_236713 Q4ZQ97 | | 31 |
| Halophiles | | | | |
| Cmk | *Halobacterium salinarum* | Q9HPA5 | | 34 |

TABLE 4C

Examples of UMP kinase enzymes

| Enzyme | Organism | GenBank # UniProt # | Sequence Identification Number | Reference |
|---|---|---|---|---|
| Thermophiles | | | | |
| PyrH | *Pyrococcus furiosus* | Q8U122 | SEQ ID NO: 14 | 35, 36 |
| PyrH | *Thermus thermophilus* | P43891 | | 33 |
| Solvent-tolerant organisms | | | | |
| PyrH | *Pseudomonas putida* DOT-T1E | AFO48412.1 I7BW46 | | 42 |
| PyrH | *Escherichia coli* K-12 MG1655 | CAA55388.1 P0A7E9 | | 48 |
| An13g00440 | *Aspergillus niger* CBS 513.88 | CAK41445.1 A2R195 | | 45 |
| URA6 | *Saccharomyces cerevisiae* ATCC 204508/S288c | AAA35194.1 P15700 | | 49 |
| PyrH | *Clostridium acetobutylicum* ATCC 824 | AAK79754.1 Q97I64 | | 43 |
| PyrH | *Halobacterium salinarum* ATCC 700922 | AAG20182.1 Q9HNN8 | | 34 |
| Acidophiles | | | | |
| PyrH | *Picrophilus torridus* | WP_048059653 | | |
| PyrH | *Metallosphaera sedula* | WP_012021705 | | |
| PyrH | *Ferroplasma* | WP_009886950.1 | | |
| PyrH | *Thermoplasma acidophilum* | WP_010900913 | | |
| PyrH | *Sulfolobus solfataricus* | WP_009992427 | | 37 |
| PyrH | *Acetobacter aceti* | WP_042788648 | | |
| Alkaliphiles | | | | |
| PyrH | *Thioalkalivibrio* sp. HK1 | WP_081759172.1 | | |
| PyrH | *Amphibacillus xylanus* | WP_015010200.1 | | |
| Psychrophiles | | | | |
| PyrH | *Colwellia psychrerythraea* (Vibrio psychroerythus) | WP_011042391.1 Q485G8 | | 28 |
| PyrH | *Pseudoalteromonas haloplanktis* | CR954246.1 Q3IIX6 | | 29 |
| PyrH | *Psychrobacter arcticus* | AAZ19383.1 Q4FRH5 | | 30 |
| PyrH | *Psychromonas ingrahamii* | ABM04676.1 A1SYW1 | | |
| PyrH | *Pseudomonas syringae* | YP_234434 Q4ZWS6 | | 31 |

TABLE 4C-continued

Examples of UMP kinase enzymes

| Enzyme | Organism | GenBank # UniProt # | Sequence Identification Number | Reference |
|---|---|---|---|---|
| Halophiles | | | | |
| PyrH | *Halobacterium salinarum* | WP_010903483.1 Q9HNN8 | | 34 |

TABLE 4D

Examples of GMP kinase enzymes

| Enzyme | Organism | GenBank # UniProt # | Sequence Identification Number | Reference |
|---|---|---|---|---|
| Thermophiles | | | | |
| Gmk | *Thermotoga maritima* | Q9X215 | SEQ ID NO: 15 | 38 |
| Gmk | *Thermus thermophilus* | Q5SI18 | | 33 |
| Solvent-tolerant organisms | | | | |
| Gmk | *Pseudomonas putida* DOT-T1E | AFO49847.1 I7C087 | | 42 |
| Gmk | *Escherichia coli* K-12 | AAB88711.1 P60546 | | 50 |
| An08g00300 | *Aspergillus niger* CBS 513.88 | CAK45182.1 A2QPV2 | | 45 |
| GUK1 | *Saccharomyces cerevisiae* ATCC 204508/S288c | AAA34657.1 P15454 | | 51 |
| Gmk | *Clostridium acetobutylicum* ATCC 824 | AAK79684.1 Q97ID0 | | 43 |
| Acidophiles | | | | |
| Gmk | *Acidithiobacillus ferrooxidans* | WP_064219869.1 | | |
| Gmk | *Acidithiobacillus thiooxidans* | WP_010637919.1 | | |
| Gmk | *Bacillus acidicola* | WP_066264774.1 | | |
| Gmk | *Acetobacter aceti* | WP_018308252.1 | | |
| Alkaliphiles | | | | |
| Gmk | *Amphibacillus xylanus* | WP_015010280.1 | | |
| Gmk | *Thioalkalivibrio sulfidiphilus* | WP_018953989.1 | | |
| Psychrophiles | | | | |
| Gmk | *Colwellia psychrerythraea* (Vibrio psychroerythus) | AAZ24463 Q47UB3 | | 28 |
| Gmk | *Pseudoalteromonas haloplanktis* | Q3IJH8 | | 29 |
| Gmk | *Psychrobacter arcticus* | WP_011280984.1 Q4FQY7 | | 30 |
| Gmk | *Psychromonas ingrahamii* | ABM05306 A1T0P1 | | |
| Gmk | *Pseudomonas syringae* | WP_003392601.1 Q4ZZY8 | | 31 |

NDP Kinases.

A nucleoside diphosphate kinase (NDP kinase) is an enzyme that catalyzes the exchange of terminal phosphate between different NDPs (e.g., ADP, CDP, GDP, UDP) and nucleoside triphosphates (NTP) in a reversible manner to produce NTPs (e.g., ATP, CTP, GTP, UTP). In some embodiments, the NDP kinase catalyzes the transfer of phosphate from a phosphate-donating molecule to ADP to produce adenosine triphosphate (ATP). In some embodiments, the NDP kinase catalyzes the transfer of phosphate from a phosphate-donating molecule to CDP to produce cytidine triphosphate (CTP). In some embodiments, the NDP kinase catalyzes the transfer of phosphate from a phosphate-donating molecule to GDP to produce guanosine triphosphate (GTP). In some embodiments, the NDP kinase catalyzes the transfer of phosphate from a phosphate-donating molecule to UDP to produce uridine triphosphate (UTP). Non-limiting examples of NDP kinases are provided in Table 5. In some embodiments, more than one NDP kinase is used in a reaction mixture. In some embodiments, 2, 3, 4 or 5 different NDP kinases are used in a reaction mixture.

polyphosphate kinase 1 (PPK1) family, which transfers high-energy phosphate from polyphosphate to ADP to form ATP. This ATP is subsequently used by NMP kinases (e.g., AMP kinase, UMP kinase, GMP kinase, and CMP kinase) to convert NMPs to their cognate ribonucleotide diphosphates (NDPs). Furthermore, ATP is subsequently used by nucleotide diphosphate kinase to convert NDPs to NTPs.

TABLE 5

Examples of NDP Kinases

| Enzyme | Organism | GenBank # UniProt # | Sequence Identification Number | Reference |
|---|---|---|---|---|
| Thermophiles | | | | |
| Ndk | *Aquifex aeolicus* | O67528 | SEQ ID NO: 16 | |
| Solvent-tolerant organisms | | | | |
| Ndk | *Pseudomonas putida* DOT-T1E | AFO50002.1 I7C0T7 | | 42 |
| Ndk | *Escherichia coli* K-12 | CAA40780.1 P0A763 | | 53 |
| An09g05870 | *Aspergillus niger* CBS 513.88 | CAK40394.1 A2QUJ6 | | 45 |
| YNK1 | *Saccharomyces cerevisiae* ATCC 204508/S288c | AAS56589.1 P36010 | | |
| Ndk | *Clostridium acetobutylicum* ATCC 824 | ABR36342.1 A6M162 | | 43 |
| Ndk | *Halobacterium salinarum* ATCC 700922 | BAB17308.1 P61136 | | 53 |
| Acidophiles | | | | |
| Ndk | *Acidithiobacillus thiooxidans* | WP_024892623.1 | | |
| Ndk | *Acetobacter aceti* | WP_042787791.1 | | |
| Ndk | *Picrophilus* | WP_011178084.1 | | |
| Ndk | *Thermoplasma acidophilum* | WP_010901523.1 | | |
| Ndk | *Sulfolobus solfataricus* | WP_009990482.1 | | |
| Ndk | *Bacillus acidicola* | WP_066262668.1 | | |
| Ndk | *Ferroplasma* | WP_009887649.1 | | |
| Ndk | *Metallosphaera sedula* | WP_011921175.1 | | |
| Psychrophiles | | | | |
| Ndk | *Psychromonas ingrahamii* | WP_011771565.1 A1SZU8 | | 39 |
| Ndk | *Colwellia psychrerythraea* | WP_011044987.1 Q47WB6 | | 28 |
| Ndk | *Psychrobacter arcticus* | WP_011279964.1 Q4FTX1 | | 30 |
| Ndk | *Pseudoalteromonas haloplanktis* | CAI89189.1 Q3ID15 | | |
| Halophiles | | | | |
| Ndk | *Halobacterium salinarum* | WP_010902835.1 P61136 | | 40 |
| Ndk | *Natrialba magadii* | WP_004214013.1 D3SY02 | | 41 |

Non-limiting examples of kinases that convert NDP to NTP include nucleoside diphosphate kinase, polyphosphate kinase, and pyruvate kinase. As discussed herein, thermostable variants of the foregoing enzymes are encompassed by the present disclosure. In some embodiments, the NDP kinase(s) is/are obtained from *Aquifex* aeolicus.

Phosphorylation of NMPs to NTPs occurs, in some embodiments, through the polyphosphate-dependent kinase pathway, where high-energy phosphate is transferred from polyphosphate to ADP via a polyphosphate kinase (PPK). In some embodiments, the polyphosphate kinase belongs to the In some embodiments, the polyphosphate kinase belongs to the polyphosphate kinase 2 (PPK2) family. In some embodiments, the polyphosphate kinase belongs to a Class I PPK2 family, which transfers high-energy phosphate from polyphosphate to NDPs to form NTPs. ATP produced by the system is used as a high-energy phosphate donor to convert NMPs to NDPs. In some embodiments, the polyphosphate kinase belongs to a Class III PPK2 family, which transfers high-energy phosphate from polyphosphate to NMPs and NDPs to form NTPs. In some embodiments, Class III PPK2 is used alone to produce NTPs from NMPs. In other embodiments, Class III PPK2 is used in combination with other kinases. Class III PPK2 produces ATP from ADP, AMP, and polyphosphate, which is subsequently used by NMP and NDP kinases to convert NMPs to NTPs.

Non-limiting examples of PPK2 enzymes for use as provided herein are listed in Table 2. Thus, in some embodiments, the PPK2 enzymes are thermostable. For example, the PPK2 enzymes may be thermostable Class III PPK2 enzymes, which favor ATP synthesis over polyphosphate polymerization, and convert both ADP and AMP to ATP. In some embodiments, the PPK2 enzymes are used to convert a polyphosphate, such as hexametaphosphate to ATP, at rates ranging, for example, from 10 to 800 mM per hour (e.g., 10, 15, 20, 25, 50, 75, 100, 150, 200, 250, 300, 350, 400, 450, 500, 550, 600, 650, 700, 750, or 800 mM per hour).

Polyphosphate and Other High Energy Phosphates.

High energy phosphate molecules (phosphate-donating molecules) release energy upon hydrolysis of high energy bond, thereby providing an energy source for biochemical reactions. Polyphosphate (PolyP$_n$) and other high energy phosphate molecules may be used as phosphate sources for production of NTPs, and downstream production of RNA, as described herein. PolyP$_n$, for example, comprises repeating units of phosphate (PO$_4$) linked together by shared oxygen atoms. Phosphorylation of specific substrates/molecules by kinases of the present disclosure involves donation of a phosphate group from PolyP$_n$, thereby producing PolyP$_{n-1}$.

The present disclosure is not limited by the number of phosphate groups in the polyphosphate. In some embodiments, PolyP$_n$ comprises at least 3 phosphate groups (PolyP$_3$). In some embodiments, PolyP$_n$ comprises at least 4, at least 5, at least 6, at least 7. at least 8, at least 9, or at least 10 phosphate groups. In some embodiments, PolyP$_n$ is hexametaphosphate.

Other examples of high energy phosphate molecules include, but are not limited to NTP (e.g., ATP), NDP (e.g., ADP), NMP (e.g., AMP), phosphoenolpyruvate, 1,3-bisphosphoglycerate, phosphocreatine, phosphoenol pyruvate, glucose 1-phosphate, fructose 6-phosphate, and glucose 6-phosphate. In some embodiments, more than one high energy phosphate is used in a reaction mixture. In some embodiments, 2, 3, 4, or 5 different high energy phosphates are used in a reaction mixture.

Templates.

A DNA template includes a promoter, optionally an inducible promoter, operably linked to nucleotide sequence encoding a desired RNA product and, optionally, a transcriptional terminator. A DNA template is typically provided on a vector, such as a plasmid, although other template formats may be used (e.g., linear DNA templates generated by polymerase chain reaction (PCR), chemical synthesis, or other means known in the art). In some embodiments, more than one DNA template is used in a reaction mixture. In some embodiments, 2, 3, 4, or 5 different DNA templates are used in a reaction mixture.

A promotor or a terminator may be a naturally-occurring sequence or an engineered sequence. In some embodiments, an engineered sequence is modified to enhance transcriptional activity. In some embodiments, the promotor is a naturally-occurring sequence. In other embodiments, the promoter is an engineered sequence. In some embodiments, the terminator is a naturally-occurring sequence. In other embodiments, the terminator is an engineered sequence.

Polymerases.

Polymerases are enzymes that synthesize polymers of nucleic acids. Polymerases of the present disclosure include DNA-dependent RNA polymerases and RNA-dependent RNA polymerases. Non-limiting examples of polymerases are provided in Table 6. In some embodiments, a polymerase is a RNA polymerase, such as a T7 RNA polymerase. In some embodiments, more than one polymerase is used in a reaction mixture. In some embodiments, 2, 3, 4, or 5 different polymerases are used in a reaction mixture.

TABLE 6

Examples of RNA Polymerases

| Enzyme | Organism | GenBank # UniProt # |
|---|---|---|
| T7 RNA Polymerase | Bacteriophage T7 | NP_041960.1 P00573 |
| Φ6 RdRP | Bacteriophage Φ6 | P11124 |
| T3 RNA polymerase | Bacteriophage T3 | NP_523301.1 Q778M8 |
| SP6 Polymerase | Bacteriophage SP6 | Y00105.1 P06221 |
| rpoA | *Escherichia coli* - K12 MG1655 | P0A7Z4 |
| rpoB | *Escherichia coli* - K12 MG1655 | P0A8V2 |
| rpoC | *Escherichia coli* - K12 MG1655 | P0A8T7 |

RNA Products.

RNA produced by the methods provided herein may be any form of RNA, including single-stranded RNA (ssRNA) and double-stranded RNA (dsRNA). Non-limiting examples of single-stranded RNA include messenger RNA (mRNA), micro RNA (miRNA), small interfering RNA (siRNA), and antisense RNA. Double-stranded RNA herein includes wholly double-stranded molecules that do not contain a single-stranded region (e.g., a loop or overhang), as well as partially double-stranded molecules that contain a double-stranded region and a single-stranded region (e.g., a loop or overhang). Thus, short hairpin RNA (shRNA) may be produced by the methods of the present disclosure.

RNA produced by the methods provided herein may be modified as described herein. In some embodiments, RNA is produced according to a method described herein and subsequently modified. In some embodiments, RNA is produced according to a method described herein using a modified starting material. In some embodiments, the modified starting material is a modified nucleobase. In some embodiments, the modified starting material is a modified nucleoside. In some embodiments, the modified starting material is a modified nucleotide.

In some embodiments, modified RNA comprises a backbone modification. In some instances, backbone modification results in a longer half-life for the RNA due to reduced nuclease-mediated degradation. This is turn results in a longer half-life. Examples of suitable backbone modifications include but are not limited to phosphorothioate modifications, phosphorodithioate modifications, p-ethoxy modifications, methylphosphonate modifications, methylphosphorothioate modifications, alkyl- and aryl-phosphates (in which the charged phosphonate oxygen is replaced by an alkyl or aryl group), alkylphosphotriesters (in which the charged oxygen moiety is alkylated), peptide nucleic acid (PNA) backbone modifications, locked nucleic acid (LNA) backbone modifications, and the like. These modifications may be used in combination with each other and/or in combination with phosphodiester backbone linkages.

Alternatively or additionally, RNA may comprise other modifications, including modifications at the base or the sugar moieties. Examples include RNA having sugars which are covalently attached to low molecular weight organic groups other than a hydroxyl group at the 3' position and other than a phosphate group at the 5' position (e.g., a 2'-O-alkylated ribose), RNA having sugars such as arabinose instead of ribose. RNA also embrace substituted purines and pyrimidines such as C-5 propyne modified bases (Wagner et al., Nature Biotechnology 14:840-844, 1996). Other purines and pyrimidines include but are not limited to 5-methylcytosine, 2-aminopurine, 2-amino-6-chloropurine, 2,6-diaminopurine, hypoxanthine. Other such modifications are well known to those of skill in the art.

NTP Production Pathways

Provided herein are systems, methods, compositions, and kits for the production of NTPs through various different enzymatic pathways, each of which utilize energy sources as described herein, and low-cost starting materials in the reaction mixture. These enzymatic pathways can be extended, in some embodiments, to the production of RNA (e.g., mRNA or double-stranded RNA) by adding a DNA template and polymerase to the reaction mixture (see, e.g., FIG. 1).

It should be understood that any of the pathway enzymes described herein (e.g., nucleases, kinases, and/or polymerases) may be obtained from unmodified (native) or engineered cells. In some embodiments, the pathway enzyme(s) are secreted from the cells (e.g., the cells are engineered to secrete the enzyme(s)). In other embodiments, the pathway enzymes are obtained from cell lysate(s) of the cells. In some embodiments, the pathway enzymes are components of cell lysate(s) of the cells, in which case, the cell lysate(s) are added to or serve as the reaction mixture in a biosynthetic reaction. In instances where cell lysate(s) is/are used in or serve as the reaction mixture, the cell lysate may be exposed to conditions to eliminate undesired enzymatic activities, as described below, before producing the product (NTP and/or RNA) of interest.

Conversion of NDP to NTP.

Figure 2A:
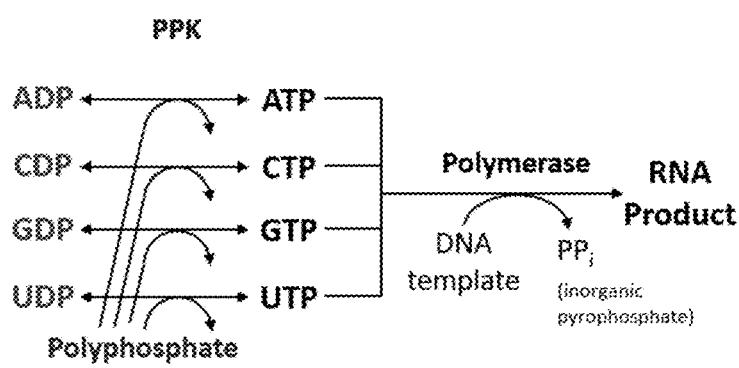
FIG. 2A shows a biosynthetic pathway for the production of NTPs, and downstream RNA, using nucleoside diphosphates (NDPs) as the starting materials.

In some aspects, NTPs are produced using NDPs as substrates, as depicted in FIG. 2A. For example, NTP production methods may include incubating in a reaction mixture NDPs, a (e.g., 1, 2, 3, or 4) polyphosphate kinase, and a (e.g., 1, 2, 3, or 4) polyphosphate under conditions suitable for the production of NTPs. In some embodiments, the reaction mixture for NTP production includes a NDP kinase (see, e.g., Table 5). In some embodiments, the NTP production reaction mixture may also include a nucleoside kinase.

Conversion of NMP to NTP.

Figure 2B:
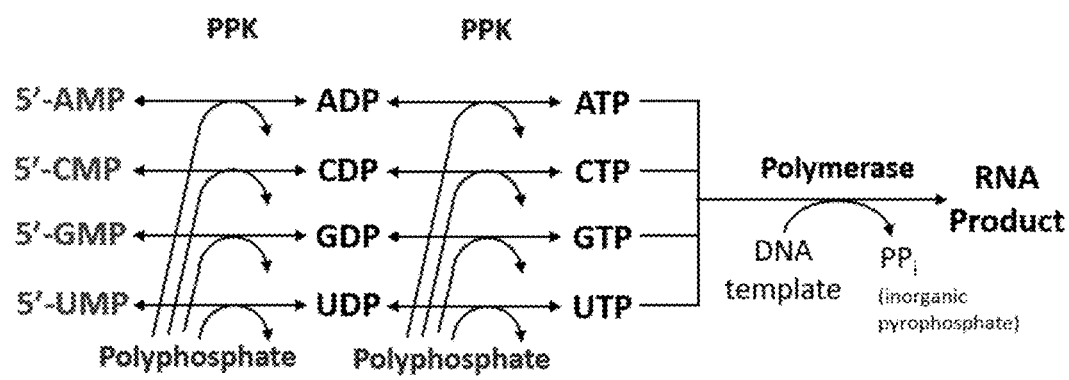
FIG. 2B shows a biosynthetic pathway for the production of NTPs, and downstream RNA, using 5' nucleoside monophosphates (5'-NMPs) as the starting materials.

In some aspects, NTPs are produced using 5' NMPs as substrates, as depicted in FIG. 2B. For example, NTP production methods may include incubating in a reaction mixture 5'-NMPs, a (e.g., 1, 2, 3, or 4) polyphosphate kinase, and a (e.g., 1, 2, 3, or 4) polyphosphate under conditions suitable for the production of NTPs. In some embodiments, the reaction mixture for NTP production includes a NMP kinase (see, e.g., Table 4) and/or a NDP kinase (see, e.g., Table 5). In some embodiments, the NTP production reaction mixture may also include a nucleoside kinase.

Conversion of Nucleosides to NTP.

Figure 2C:
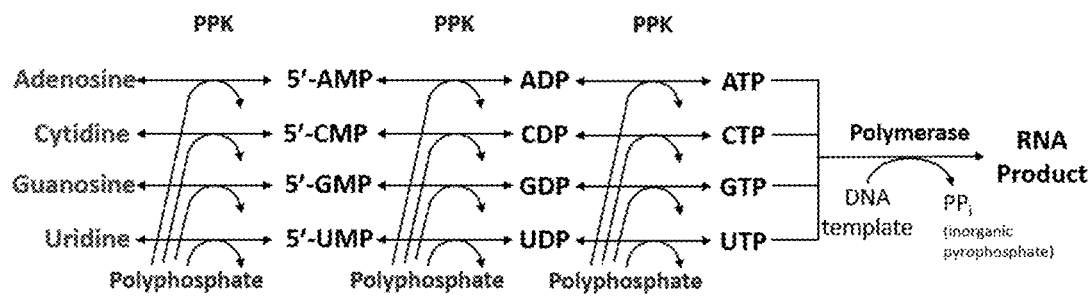
FIG. 2C shows a biosynthetic pathway for the production of NTPs, and downstream RNA, using nucleosides as the starting materials.

In some aspects, NTPs are produced using nucleosides as substrates, as depicted in FIG. 2C. For example, NTP production methods may include incubating in a reaction nucleosides, a (e.g., 1, 2, 3, or 4) polyphosphate kinase, and a (e.g., 1, 2, 3, or 4) polyphosphate under conditions suitable for the production of NTPs. In some embodiments, the NTP production reaction mixture may also include a nucleoside kinase (see, e.g., Table 3) and/or a NMP kinase (see, e.g., Table 4) and/or a NDP kinase (see, e.g., Table 5).

Conversion of Nucleobases to NTP.

Figure 2D:
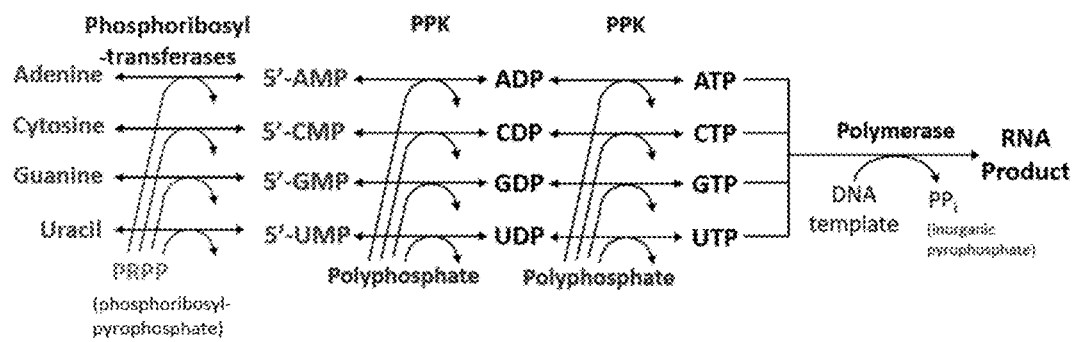
FIG. 2D shows a biosynthetic pathway for the production of NTPs, and downstream RNA, using nucleobases as the starting materials.

In some aspects, NTPs are produced using nucleobases as substrates, as depicted in FIG. 2D. For example, NTP production methods may include incubating in a reaction mixture nucleobases, a (e.g., 1, 2, 3, or 4) phosphoribosyltransferase, a phosphoribosylpyrophosphate, a (e.g., 1, 2, 3, or 4) polyphosphate kinase, and a (e.g., 1, 2, 3, or 4) polyphosphate under conditions suitable for the production of NTPs. In some embodiments, the NTP production reaction mixture may also include a NMP kinase (see, e.g., Table 4) and/or a NDP kinase (see, e.g., Table 5). In some embodiments, the NTP production reaction mixture may also include a nucleoside kinase.

In some embodiments, a biosynthetic pathway for the production of NTPs and/or RNA may use cellular RNA as the substrate, by either first depolymerizing the cellular RNA into NDPs or first depolymerizing the cellular RNA into NMPs.

Conversion of Nucleobases and Ribose to NTP.

Figure 2E:
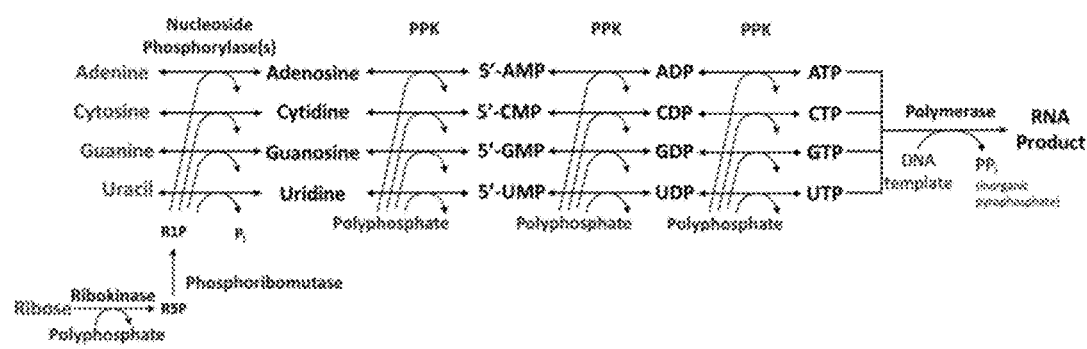
FIG. 2E shows a biosynthetic pathway for the production of NTPs, and downstream RNA, using nucleobases and ribose as the starting materials.

In some aspects, NTPs are produced using nucleobases as substrates, as depicted in FIG. 2E. For example, NTP production methods may include incubating in a reaction nucleobases, D-ribose, ribokinase, phosphopentomutase, at least one (e.g., 1, 2, 3, or 4) nucleoside phosphorylase, at least one (e.g., 1, 2, 3, or 4) polyphosphate kinase, and at least one (e.g., 1, 2, 3, or 4) polyphosphate under conditions suitable for the production of NTPs. In some embodiments, the NTP production reaction mixture may also include at least one NMP kinase (see, e.g., Table 3) and/or at least one NDP kinase (see, e.g., Table 4) and/or a nucleoside kinase.

Conversion of Cellular RNA into NTP Via NDP.

Figure 3A:
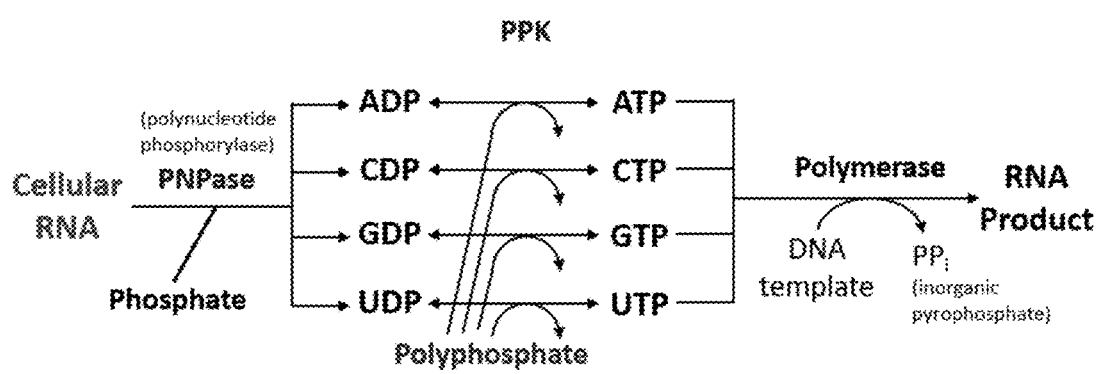
FIG. 3A shows a biosynthetic pathway for the production of NTPs, and downstream RNA, using cellular RNA as the starting material. In this pathway, a polynucleotide phosphorylase is used to degrade cellular RNA into NDPs.

In some aspects, NTP is produced using cellular RNA as a substrate by first breaking down (degrading/depolymerizing) the cellular RNA into NDPs and then converting NDPs into NTPs, as depicted in FIG. 3A. For example, NTP production methods may include incubating in a reaction mixture cellular RNA, a polynucleotide phosphorylase (PNPase), and phosphate under conditions suitable for the production of NDPs. To proceed to the production of NTPs, the reaction mixture, in some embodiments, also comprises a polyphosphate kinase and polyphosphate. Thus, the methods further comprise incubating the reaction mixture under conditions suitable for the production of NTPs. In some embodiments, the reaction mixture further comprises a NDP kinase. In some embodiments, the NTP production reaction mixture may also include a nucleoside kinase.

Conversion of Cellular RNA into NTP Via NMP.

Figure 3B:
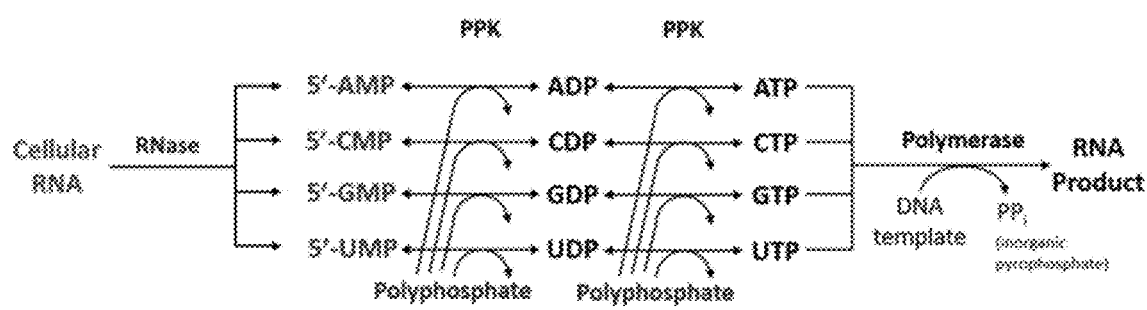
FIG. 3B shows a biosynthetic pathway for the production of NTPs, and downstream RNA, using cellular RNA as the starting material. In this pathway, a ribonuclease is used to degrade cellular RNA into NMPs.
Figure 4A:
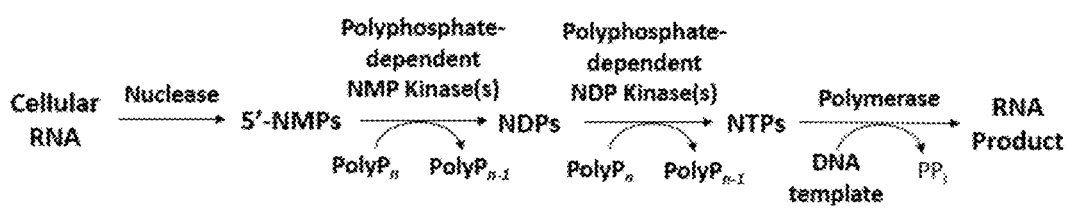
FIG. 4A shows a biosynthetic pathway for the production of NTPs, and downstream RNA, using only polyphosphate kinases.
Figure 4B:
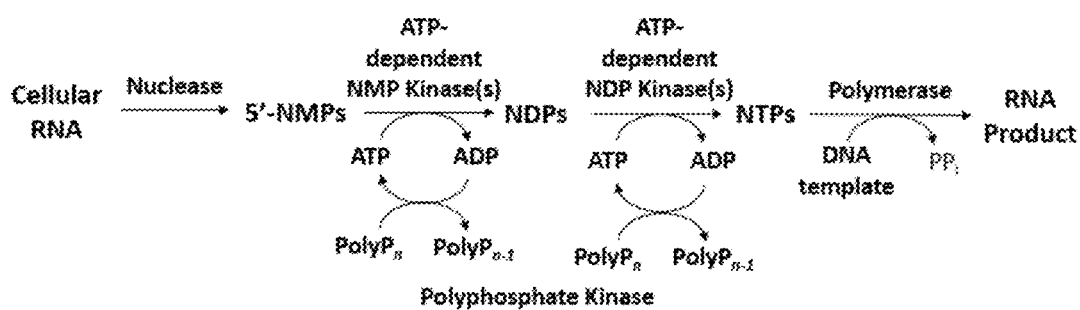
FIG. 4B shows a biosynthetic pathway for the production of NTPs, and downstream RNA, using both polyphosphate kinases (e.g., PPK2) and ATP/ADP-dependent kinases (e.g., NMP kinases such as adk, cmk, gmk, and/or pyrH, and/or NDP kinases such as ndk).
Figure 5:
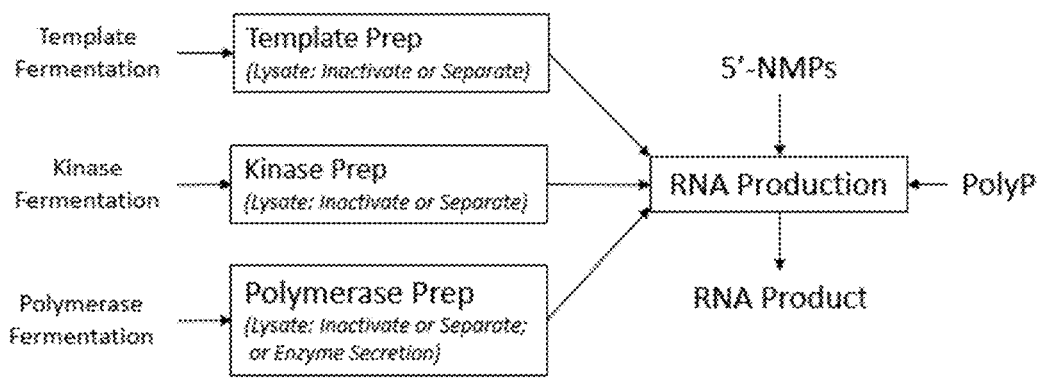
FIG. 5 shows a biosynthetic pathway for the production of RNA starting from 5'-NMPs.
Figure 6:
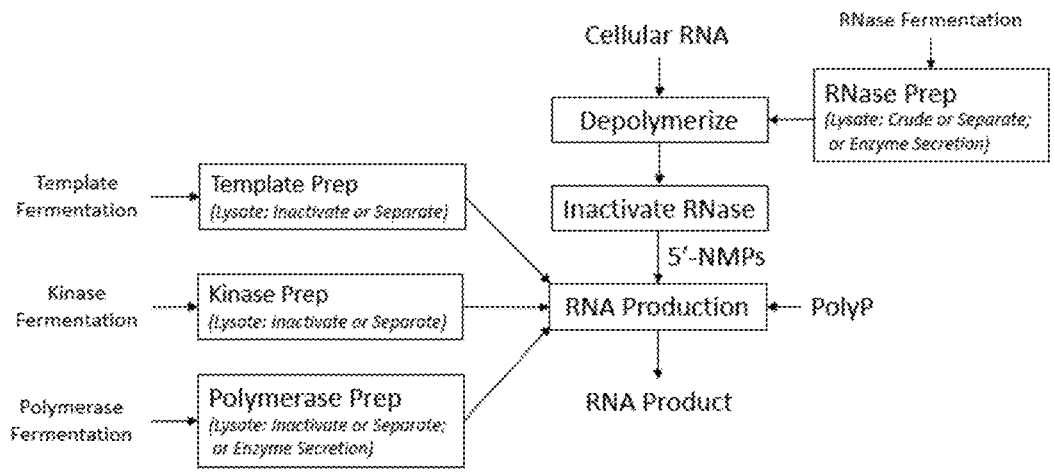
FIG. 6 shows a biosynthetic pathway for the production of RNA starting from cellular RNA. The schematic shows an example in which the template, the kinase, and the polymerase are added during a RNA production reaction.
Figure 7:
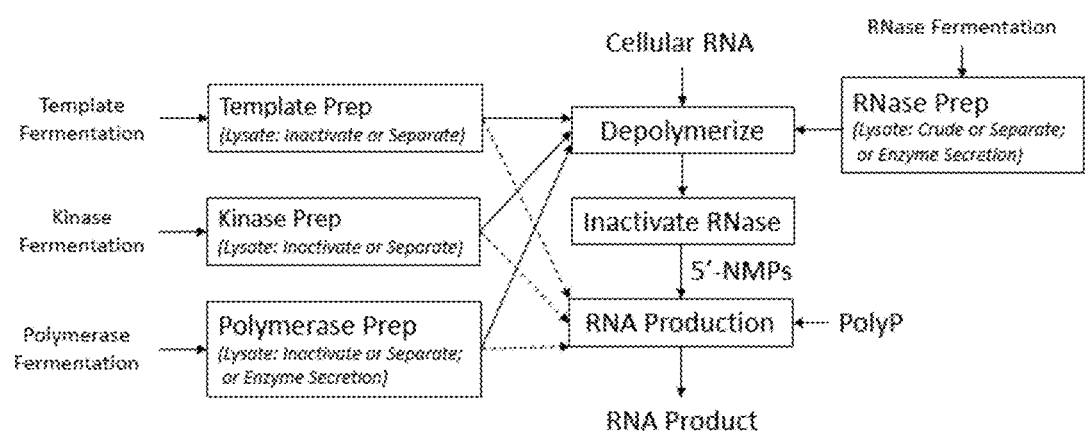
FIG. 7 shows a biosynthetic pathway for the production of RNA starting from cellular RNA. The schematic shows an example in which the template may be added during the depolymerization phase or the RNA production phase, the kinase may be added during the depolymerization phase or the RNA production phase, and the polymerase may added during the depolymerization phase or the RNA production phase.

In some aspects, NTP is produced using cellular RNA as a substrate by first breaking down the cellular RNA into 5'-NMPs and then converting NMPs to NDPs and NDPs to NTPs, as depicted in FIG. 3B. For example, NTP production methods may include incubating in a reaction mixture cellular RNA, and a ribonuclease under conditions suitable for the production of 5'-NMPs. To proceed to the production of NTPs, the reaction mixture, in some embodiments, also comprises a polyphosphate kinase, and a polyphosphate. Thus, the methods further comprise incubating the reaction mixture under conditions suitable for the production of NTPs. In some embodiments, the reaction mixture further comprises a NDP kinase. In some embodiments, the NTP production reaction mixture may also include a nucleoside kinase. Alternatively, NTP production methods may include incubating in a reaction mixture cellular RNA, a ribonuclease that cleaves RNA into 3'-NMPs, and an appropriate phosphatase (e.g. alkaline phosphatase or others) under conditions suitable for the production of nucleosides. The phosphatase would then be eliminated before proceeding to the production of NTPs.

RNA Production Pathways

Figure 1B:
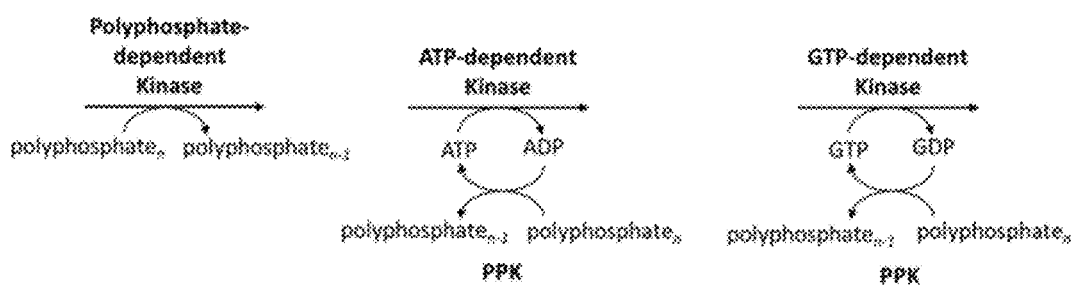
FIG. 1B shows examples of high-energy phosphate strategies where polyphosphate is fed to the reaction mixture.
Figure 1C:
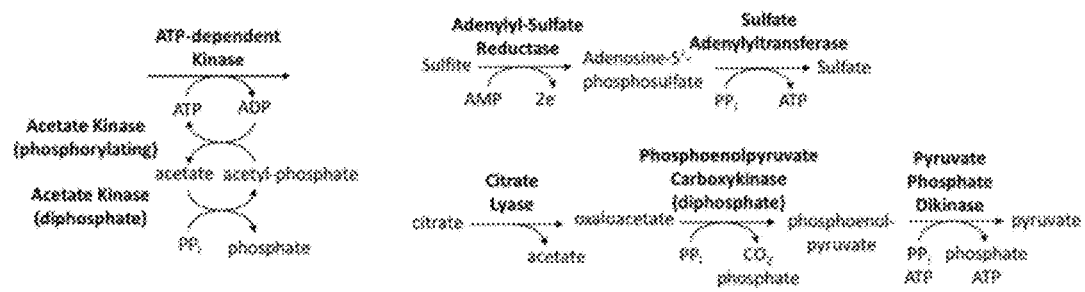
FIG. 1C shows examples of additional high-energy phosphate strategies.

As shown in FIG. 1, RNA (e.g., mRNA or double-stranded RNA) may be produced through various different enzymatic pathways, each of which utilize energy sources as described herein, and low-cost starting materials in the reaction mixture(s). Thus, systems, methods, compositions, and kits for the production of RNA are provided herein.

Conversion of NDP to RNA.

In some aspects, RNA is produced using NDPs as substrates, as depicted in FIG. 2A. For examples, RNA production methods may include incubating in a reaction mixture NDPs, a polyphosphate kinase, a polyphosphate, a DNA template, and a RNA polymerase under conditions suitable for the production of RNA. In some embodiments, the RNA production reaction mixture may also include a NDP kinase (see, e.g., Table 5). In some embodiments, the RNA production reaction mixture may also include a nucleoside kinase Conversion of NMP to RNA.

In some aspects, RNA is produced using 5' NMPs as substrates, as depicted in FIG. 2B. For example, RNA production methods may include incubating in a reaction mixture 5' NMPs, a polyphosphate kinase, a polyphosphate, a DNA template, and a RNA polymerase under conditions suitable for the production of RNA. In some embodiments, the RNA production reaction mixture may also include a NMP kinase (see, e.g., Table 4) and/or a NDP kinase (see, e.g., Table 5). In some embodiments, the RNA production reaction mixture may also include a nucleoside kinase Conversion of Nucleosides to RNA. In some aspects, RNA is produced using nucleosides as substrates, as depicted in FIG. 2C. For example, RNA production methods may include incubating in a reaction mixture nucleosides, a polyphosphate kinase, a polyphosphate, a DNA template, and a RNA polymerase under conditions suitable for the production of RNA. In some embodiments, the RNA production reaction mixture may also include a nucleoside kinase (see, e.g., Table 3) and/or a NMP kinase (see, e.g., Table 4) and/or a NDP kinase (see, e.g., Table 5).

Conversion of Cellular RNA into RNA Via NDP.

In some aspects, RNA is produced using cellular RNA as a substrate by first breaking down the cellular RNA into NDPs, as depicted in FIG. 3A. For example, RNA production methods may include incubating in a reaction mixture cellular RNA, a polynucleotide phosphorylase (PNPase), and phosphate under conditions suitable for the production of NDPs. Before proceeding to the production of RNA, it may be advantageous to eliminate the PNPase to avoid degrading the end product. Thus, the methods may further comprise eliminating the a PNPase, and incubating in the reaction mixture, or in a second reaction mixture, the NDPs, a polyphosphate kinase, a polyphosphate, a DNA template, and a polymerase under conditions suitable for the production of RNA. In some embodiments, the reaction mixture further comprises a NDP kinase. In some embodiments, the RNA production reaction mixture may also include a nucleoside kinase In some embodiments, these pathway enzymes are capable of withstanding elimination conditions, as discussed below, and, thus, all reaction components are included in a single (one-step) reaction mixture. For example, a RNA production method may comprise (a) incubating in a reaction mixture cellular RNA, a PNPase, phosphate, a polyphosphate kinase, a polyphosphate, a DNA template, and a polymerase under conditions suitable for the production of NDPs (optionally wherein the reaction mixture further comprises a NDP kinase), (b) eliminating the a PNPase, and (c) incubating the reaction mixture under conditions suitable for the production of RNA.

Conversion of Cellular RNA into RNA Via NMP.

In some aspects, RNA is produced using cellular RNA as a substrate by first breaking down the cellular RNA into 5' NMPs, as depicted in FIG. 3B. For example, RNA production methods may include incubating in a reaction mixture cellular RNA and a ribonuclease under conditions suitable for the production of 5' NMPs. Before proceeding to the production of RNA, it may be advantageous to eliminate the ribonuclease to avoid degrading the end product. Thus, the methods may further comprise eliminating the a ribonuclease, and incubating in the reaction mixture, or in a second reaction mixture, the 5' NMPs, a polyphosphate kinase, a polyphosphate, a DNA template, and a polymerase under conditions suitable for the production of RNA. In some embodiments, the reaction mixture further comprises a NMP kinase and/or a NDP kinase. In some embodiments, the RNA production reaction mixture may also include a nucleoside kinase In some embodiments, these pathway enzymes are capable of withstanding elimination conditions, as discussed below, and, thus, all reaction components are included in a single (one-step) reaction mixture. For example, a RNA production method may comprise (a) incubating in a reaction mixture cellular RNA, a ribonuclease, a polyphosphate kinase, a polyphosphate, a DNA template, and a polymerase under conditions suitable for the production of NMPs (optionally wherein the reaction mixture further comprises a NMP kinase and/or a NDP kinase), (b) eliminating the a ribonuclease, and (c) incubating the reaction mixture under conditions suitable for the production of RNA.

Conversion of Nucleobases to RNA.

In some aspects, RNA is produced using nucleobases as substrates, as depicted in FIG. 2D. For example, RNA production methods may include incubating in a reaction mixture nucleobases, a (e.g., 1, 2, 3, or 4) phosphoribosyltransferase, a phosphoribosylpyrophosphate, a polyphosphate kinase, a polyphosphate, a DNA template, and a RNA polymerase under conditions suitable for the production of RNA. In some embodiments, the RNA production reaction mixture may also include a NMP kinase (see, e.g., Table 4) and/or a NDP kinase (see, e.g., Table 5). In some embodiments, the RNA production reaction mixture may also include a nucleoside kinase Conversion of Nucleobases and Ribose to RNA.

In some aspects, RNA is produced using nucleobases as substrates, as depicted in FIG. 2E. For example, RNA production methods may include incubating in a reaction mixture nucleobases, D-ribose, ribokinase, phosphopentomutase, at least one (e.g., 1, 2, 3, or 4) nucleoside phosphorylase, at least one polyphosphate kinase, at least one polyphosphate, at least one DNA template, and at least one RNA polymerase under conditions suitable for the production of RNA. In some embodiments, the RNA production reaction mixture may also include at least one NMP kinase (see, e.g., Table 3) and/or at least one NDP kinase (see, e.g., Table 4) and/or a nucleoside kinase.

Enzyme Sources

Any (e.g., one, two, three, or more) or all of the pathway enzymes provided herein (e.g., nucleases, kinases, polymerases, etc.) may be endogenous (unmodified) enzymes or recombinant enzymes expressed by a cell. In some embodiments, the pathway enzymes are provided as a component of a cell lysate, which is included in a reaction mixture. In some embodiments, the pathway enzymes are purified from a cell lysate an included in a reaction mixture. In some embodiments, a pathway enzyme is provided as a component of a cell lysate and a pathway enzyme is purified from a cell lysate. In some embodiments, a pathway enzyme is secreted and optionally purified from cell broth.

In some embodiments, a pathway enzyme (e.g., nucleases, kinases, polymerases, etc.) is an endogenous enzyme purified from a cell and included a reaction mixture as a purified enzyme. In some embodiments, a pathway enzyme (e.g., nucleases, kinases, polymerases, etc.) is an endogenous enzyme provided as a component of a cell lysate that is included in a reaction mixture. In some embodiments, a pathway enzyme (e.g., nucleases, kinases, polymerases, etc.) is a recombinant enzyme purified from a cell and included a reaction mixture as a purified enzyme. In some embodiments, a pathway enzyme (e.g., nucleases, kinases, polymerases, etc.) is a recombinant enzyme provided as a component of a cell lysate that is included in a reaction mixture. In some embodiments, a pathway enzyme is secreted and optionally purified from cell broth.

The present disclosure also encompasses endogenous enzymes and recombinant enzymes secreted by a cell. Thus, in some embodiments, a pathway enzyme (e.g., nucleases, kinases, polymerases, etc.) is an endogenous enzyme secreted from a cell. In some embodiments, a pathway enzyme (e.g., nucleases, kinases, polymerases, etc.) is a recombinant enzyme secreted from a cell.

Elimination of Undesired Enzymatic Activities

In various embodiments provided herein, enzymes prepared from cells or lysates of cells that express pathway enzymes are used in a reaction mixture for the production of NTP and/or RNA. In these cells or cell lysates, there are enzymes that may have deleterious effects on NTP and/or RNA production. Non-limiting examples of such enzymes include phosphatases, nucleases, proteases, deaminases, oxidoreductases, and/or hydrolases, such as those expressed by *Escherichia coli* cells. Phosphatases remove phosphate groups (e.g., converting NMPs to nucleosides, converting NDPs to NMPs, or converting NTPs to NDPs), which reduce NTP production due to futile cycles of nucleotide phosphorylation/dephosphorylation. Nucleases cleave nucleic acids into monomers or oligomers, which lead to RNA product degradation (e.g., by RNase) and/or DNA template degradation (e.g., by DNase). Proteases cleave proteins into amino acids or peptides, which degrade pathway enzymes. Deaminases remove amino groups, which reduced NTP concentrations by conversion of pathway intermediates to non-useful substrates (e.g., xanthine and hypoxanthine) and can lead to mutations in RNA products (e.g., C to U). Hydrolases (e.g., nucleoside hydrolase or nucleotide hydrolase) cleave nucleosides or nucleotides into base and sugar moieties, which reduce NTP concentrations due to irreversible degradation of nucleotides. Oxidoreductases catalyze the transfer of electrons from one molecule (the oxidant) to another molecule (the reductant). Oxidation and/or reduction reactions can, for example, damage nucleobases in DNA and/or RNA, leading to errors in transcription and/or translation, or damage proteins or enzymes leading to loss of function.

Thus, it is advantageous in many embodiments to eliminate these native enzymatic activities or other undesired enzymatic activities in an enzyme preparation, a cell lysate, and/or a reaction mixture. Herein, "elimination" of enzymatic activities may be partial (e.g., at least 30%, 40%, 50%, 60%, 70%, 80%, or 90% of the activity is eliminated) or complete (100% of the activity is eliminated) of an undesired enzymatic activity. As discussed herein, enzymatic activity may be eliminated by genetic modification, conditional inactivation, and/or physical separation. Other elimination methods may also be used. The undesired enzymatic activity may stem from at least one (e.g., 1, 2, 3, 4 or 5) native (endogenous) enzyme, including but not limited to, phosphatases, nucleases, proteases, deaminases, oxidoreductases, and/or hydrolases.

In some embodiments, undesired phosphatase activity is eliminated in an enzyme preparation, a cell lysate, and/or a reaction mixture. In some embodiments, undesired nuclease activity is eliminated in an enzyme preparation, a cell lysate, and/or a reaction mixture. In some embodiments, undesired protease activity is eliminated in an enzyme preparation, a cell lysate, and/or a reaction mixture. In some embodiments, undesired deaminase activity is eliminated in an enzyme preparation, a cell lysate, and/or a reaction mixture. In some embodiments, undesired hydrolase activity is eliminated in an enzyme preparation, a cell lysate, and/or a reaction mixture.

Undesired (e.g., native) enzymatic activity(ies) may be eliminated using genetic, conditional, or separation approaches. In some embodiments, a genetic approach is used to remove undesired enzymatic activity. Thus, in some embodiments, cells are modified to reduce or eliminate undesired enzymatic activities. Examples of genetic approaches that may be used to reduce or eliminate undesired enzymatic activity include, but are not limited to, secretion, gene knockouts, and protease targeting. In some embodiments, a conditional approach is used to remove undesired enzymatic activity. Thus, in some embodiments, undesired enzymes exhibiting undesired activities remain in an enzyme preparation, a cell lysate, and/or a reaction mixture and are selectively inactivated. Examples of conditional approaches that may be used to reduce or eliminate undesired enzymatic activity include, but are not limited to, changes in temperature, pH, salt, detergent, organic solvent (e.g., alcohol), and the use of chemical inhibitors. In some embodiments, a separation/purification approach is used to remove undesired enzymatic activity. Thus, in some embodiments, undesired enzymes exhibiting undesired activities are physically removed from an enzyme preparation, a cell lysate, and/or a reaction mixture. Examples of separation approaches that may be used to reduce or eliminate undesired enzymatic activity include, but are not limited to, precipitation, immobilization, filtration, and chromatography.

Genetic Approaches.

In some embodiments, cells expressing an enzyme and/or DNA template of a NTP and/or RNA production pathway are modified to reduce or eliminate undesired enzymatic activities. In some embodiments, a gene encoding an enzyme exhibiting an undesired activity is deleted from the cells. In some embodiments, a gene encoding an enzyme exhibiting an undesired activity is mutated such that the resulting gene product is rendered non-functional. In some embodiments, an enzyme exhibiting an undesired activity is modified to include a site-specific protease-recognition sequence in their protein sequence such that the enzyme may be "targeted" and cleaved for inactivation (see, e.g., U.S. Publication No. 2012/0052547 A1, published on Mar. 1, 2012; International Publication No. WO 2015/021058 A2, published Feb. 12, 2015; and International Publication Number WO 2012/030980, published Mar. 8, 2012, each of which is incorporated by reference herein).

Cleavage of an enzyme containing a site-specific protease-recognition sequence results from contact with a cognate site-specific protease that is sequestered in the periplasm of the cell (separate from the target enzyme) during the cell growth phase (e.g., as engineered cells are cultured) and is brought into contact with the enzyme during the ATP production phase (e.g., following cell lysis to produce a cell lysate). Thus, engineered cells of the present disclosure comprise, in some embodiments, (i) an engineered nucleic acid encoding an enzyme exhibiting an undesired activity and includes a site-specific protease-recognition sequence in the protein sequence of the enzyme, and (ii) an engineered nucleic acid encoding a site-specific protease that cleaves the site-specific protease-recognition sequence of the enzyme and includes a periplasmic-targeting sequence. This periplasmic-targeting sequence is responsible for sequestering the site-specific protease to the periplasmic space of the cell until the cell is lysed. Examples of periplasmic-targeting sequences are known.

Examples of proteases that may be used in accordance with the present disclosure include, without limitation, alanine carboxypeptidase, astacin, bacterial leucyl aminopeptidase, cancer procoagulant, cathepsin B, clostripain, cytosol alanyl aminopeptidase, elastase, endoproteinase Brg-C, enterokinase, gastricsin, gelatinase, Gly-X carboxypeptidase, glycyl endopeptidase, human rhinovirus 3C protease, hypodermin C, Iga-specific serine endopeptidase, leucyl aminopeptidase, leucyl endopeptidase, lysC, lysosomal pro-X carboxypeptidase, lysyl aminopeptidase, methionyl aminopeptidase, myxobacter, nardilysin, pancreatic endopeptidase E, picornain 2B, picornain 3C, proendopeptidase, prolyl aminopeptidase, proprotein convertase I, proprotein convertase II, russellysin, saccharopepsin, semenogelase, T-plasminogen activator, thrombin, tissue kallikrein, tobacco etch virus (TEV), togavirin, tryptophanyl aminopeptidase, U-plasminogen activator, V8, venombin B, venombin BB and Xaa-pro aminopeptidase.

Conditional Approaches.

In some embodiments, an enzyme preparation, a cell lysate, and/or a reaction mixture includes an enzyme exhibiting undesired activity that is selectively inactivated. In some embodiments, an enzyme exhibiting undesired activity is selectively inactivated by exposing the enzyme to elimination conditions (e.g., high or low temperature, acidic or basic pH value, high salt or low salt, detergent, and/or organic solvent).

In some embodiments, an enzyme preparation, an enzyme preparation, a cell lysate, and/or a reaction mixture is exposed to a temperature that temporarily or irreversibly inactivates the enzyme exhibiting undesired activity. "Temperature inactivation" refers to the process of heating or cooling an enzyme preparation, a cell lysate, and/or a reaction mixture to a temperature sufficient to inactivate (or at least partially inactivate) native target enzyme. Generally, the process of temperature inactivation involves denaturation of (unfolding of) the deleterious enzyme. The temperature at which an enzyme denature varies among organisms. In E. coli, for example, enzymes generally denature at temperatures above 41° C. The denaturation temperature may be higher or lower than 41° C. for other organisms. Enzymes of a cell lysate, as provide here, may be temperature inactivated at a temperature of 0° C.–95° C., or higher. In some embodiments, enzymes of a cell lysate are temperature inactivated at a temperature of 0-90° C., 0-80° C., 0-70° C., 0-60° C., 0-50° C., 0-40° C., 0-30° C., 0-20° C., 0-10° C., or 0-5° C. In some embodiments, enzymes of a cell lysate are temperature inactivated at a temperature of 5-95° C., 10-95° C., 20-95° C., 30-95° C., 40-95° C., 50-95° C., 60-95° C., 70-95° C., 80-95° C., or 90-95° C. For example, enzymes of a cell lysate may be temperature inactivated at a temperature of approximately 40° C., 42° C., 45° C., 50° C., 55° C., 60° C., 65° C., 70° C., 75° C., 80° C., 85° C., 90° C., or 95° C. In some embodiments, enzymes of a cell lysate are temperature inactivated at a temperature of 50-80° C. In some embodiments, enzymes of a cell lysate are temperature inactivated at a temperature of approximately 70° C. In some embodiments, enzymes of a cell lysate are temperature inactivated at a temperature of approximately 60° C.

In some embodiments, an enzyme preparation, a cell lysate, and/or a reaction mixture is exposed to an acid or base (change in pH) that temporarily or irreversibly inactivates an enzyme exhibiting undesired activity. "Acid or base inactivation" refers to the process of adjusting an enzyme preparation, a cell lysate, and/or a reaction mixture to a pH sufficient to inactivate (or at least partially inactivate) an enzyme. Generally, the process of acid or base inactivation involves denaturation of (unfolding of) the enzyme. The pH at which enzymes denature varies among organisms. In E. coli, for example, native enzymes generally denature at pH above 7.5 or below 6.5. The denaturation pH may be higher or lower than the denaturation pH for other organisms. Enzymes of an enzyme preparation, a cell lysate, and/or a reaction mixture, as provide herein, may be base inactivated at a pH of 7.5-14, or higher. In some embodiments, enzymes of a cell lysate is base inactivated at a pH of 8-14, 8.5-14, 9-14, 9.5-14, 10-14, 10.5-14, 11-14, 11.5-14, 12-14, 12.5-14, 13-14, or 13.5-14. In some embodiments, enzymes of an enzyme preparation, a cell lysate, and/or a reaction mixture are base inactivated at a pH of 7.5-13.5, 7.5-13, 7.5-12.5, 7.5-12, 7.5-11.5, 7.5-11, 7.5-10.5, 7.5-10, 7.5-9.5, 7.5-9, 7.5-8.5, or 7.5-8. For example, enzymes of an enzyme preparation, a cell lysate, and/or a reaction mixture may be base inactivated at a pH of approximately 7.5, 8, 8.5, 9, 9.5, 10, 10.5, 11, 11.5, 12, 12.5, 13, 13.5, or 14. Enzymes of an enzyme preparation, a cell lysate, and/or a reaction mixture, as provide herein, may be acid inactivated at a pH of 6.5-0, or lower. In some embodiments, enzymes of an enzyme preparation, a cell lysate, and/or a reaction mixture are acid inactivated at a pH of 6.5-0.5, 6.5-1, 6.5-1.5, 6.5-2, 6.5-2.5, 6.5-3, 6.5-3.5, 6.5-4, 6.5-4.5, 6.5-5, or 6.5-6. In some embodiments, enzymes of an enzyme preparation, a cell lysate, and/or a reaction mixture are acid inactivated at a pH of 6-0, 5.5-0, 5-0, 4.5-0, 4-0, 3.5-0, 3-0, 2.5-0, 2-0, 1.5-0, 1-0, or 0.5-0. For example, enzymes of an enzyme preparation, a cell lysate, and/or a reaction mixture may be acid inactivated at a pH of approximately 6.5, 6, 5.5, 5, 4.5, 4, 3.5, 3, 2.5, 2, 1.5, 1, 0.5, or 0.

In some embodiments, an enzyme preparation, a cell lysate, and/or a reaction mixture is exposed to a high salt or low salt (change in salt concentration) that temporarily or irreversibly inactivates an enzyme exhibiting undesired activity. "Salt inactivation" refers to the process of adjusting an enzyme preparation, a cell lysate, and/or a reaction mixture to a salt concentration sufficient to inactivate (or partially inactivate) an enzyme. Generally, the process of salt inactivation involves denaturation of (unfolding of) the enzyme. The salt concentration at which enzymes denature varies among organisms. In E. coli, for example, native enzymes generally denature at a salt concentration above 600 mM. The denaturation salt concentration may be higher or lower than the denaturation salt concentration for other organisms. Salts are combinations of anions and cations. Non-limiting examples of cations include lithium, sodium, potassium, magnesium, calcium and ammonium. Non-limiting examples of anions include acetate, chloride, sulfate, and phosphate. Enzymes of an enzyme preparation, a cell lysate, and/or a reaction mixture, as provided herein, may be salt inactivated at a salt concentration of 600-1000 mM, or higher. In some embodiments, enzymes of an enzyme preparation, a cell lysate, and/or a reaction mixture are salt inactivated at a salt concentration of 700-1000 mM, 750-1000 mM, 800-1000 mM, 850-1000 mM, 900-1000 mM, 950-1000 mM. In some embodiments, enzymes of an enzyme preparation, a cell lysate, and/or a reaction mixture are salt inactivated at a salt concentration of 600-950 mM, 600-900 mM, 600-850 mM, 600-800 mM, 600-750 mM, 600-700 mM, or 600-650 mM. For example, enzymes of an enzyme preparation, a cell lysate, and/or a reaction mixture may be salt inactivated at a salt concentration of approximately 600 mM, 650 mM, 700 mM, 750 mM, 800 mM, 850 mM, 900 mM, 950 mM, or 1000 mM. Enzymes of an enzyme preparation, a cell lysate, and/or a reaction mixture, as provided herein, may be salt inactivated at a salt concentration of 400-0 mM, or lower. In some embodiments, enzymes of an enzyme preparation, a cell lysate, and/or a reaction mixture are salt inactivated at a salt concentration of 350-0 mM, 300-0 mM, 250-0 mM, 200-0 mM, 150-0 mM, 100-0 mM, or 50-0 mM. In some embodiments, enzymes of an enzyme preparation, a cell lysate, and/or a reaction mixture are salt inactivated at a salt concentration of 400-50 mM, 400-100 mM, 400-150 mM, 400-200 mM, 400-250 mM, 400-300 mM, or 400-350 mM. For example, enzymes of an enzyme preparation, a cell lysate, and/or a reaction mixture may be salt inactivated at a salt concentration of approximately 400 mM, 350 mM, 300 mM, 250 mM, 200 mM, 150 mM, 100 mM, 50 mM, or 0 mM.

In some embodiments, an organic solvent is added to an enzyme preparation, a cell lysate, and/or a reaction mixture to inactivate an enzyme exhibiting undesired activity. Non-limiting examples of organic solvents include ethanol, methanol, ether, dioxane, acetone, methyl ethyl ketone, acetonitrile, dimethyl sulfoxide, and toluene.

In some embodiments, a detergent is added to an enzyme preparation, a cell lysate, and/or a reaction mixture to inactivate an enzyme exhibiting undesired activity. Non-limiting examples of detergents include sodium dodecyl sulfate (SDS), ethyl trimethylammonium bromide (ETMAB), lauryl trimethyl ammonium bromide (LTAB). and lauryl trimethylammonium chloride (LTAC).

In some embodiments, a chemical inhibitor is added to an enzyme preparation, a cell lysate, and/or a reaction mixture to inactivate an enzyme exhibiting undesired activity. Non-limiting examples of chemical inhibitors include sodium orthovanadate (inhibitor of protein phosphotyrosyl phosphatases), sodium fluoride (inhibitor of phosphoseryl and phosphothreonyl phosphatases), sodium pyrophosphate (phosphatase inhibitor), sodium phosphate, and/or potassium phosphate. In some embodiments, chemical inhibitors are selected from a chemical inhibitor library.

For any of the conditional approaches used herein, it should be understood that any of the pathway enzymes present in the cell lysate or reaction mixture may also be exposed to the elimination conditions (e.g., high or low temperature, acidic or basic pH value, high salt or low salt, detergent and/or organic solvent). Thus, in some embodiments, the pathway enzymes (e.g., polyphosphate kinase, NMP kinase, NDP kinase, and/or polymerase) can withstand elimination conditions. An enzyme is considered to withstand elimination conditions if the enzyme, following exposure to the elimination conditions, retains at least 10% (e.g., at least 20%, at least 30%, at least 40%, at least 50%, at least 60%, at least 70%, at least 80%, or at least 90%) of its enzymatic activity (relative to enzymatic activity prior to exposure to the inactivation condition).

For example, when native enzymes of an enzyme preparation, a cell lysate, and/or a reaction mixture are heat-inactivated (e.g., exposed to a temperature of at least 40° C., or 40-95° C., for at least 2 min, or 2-60 min), the pathway enzymes may be thermostable enzymes. Thus, in some embodiments, at least one of a polyphosphate kinase, NMP kinase, NDP kinase, nucleoside kinase, phosphoribosyltransferase, nucleoside phosphorylase, ribokinase, phosphopentomutase, and polymerase is thermostable. An enzyme (e.g., kinase or polymerase) is considered thermostable if the enzyme (a) retains activity after temporary exposure to high temperatures that denature native enzymes or (b) functions at a high rate after temporary exposure to a medium to high temperature where native enzymes function at low rates. Thermostable enzymes are known, and non-limiting examples of thermostable enzymes for use as provided herein. Other non-limiting examples of pathway enzymes that can withstand elimination conditions are also provided herein.

Separation Approaches.

In some embodiments, a native enzyme exhibiting undesired activity is physically removed from an enzyme preparation, a cell lysate, and/or a reaction mixture. In some embodiments, an enzyme exhibiting undesired activity is precipitated from an enzyme preparation, a cell lysate, and/or a reaction mixture. In some embodiments, an enzyme exhibiting undesired activity is filtered (e.g., based on size) from an enzyme preparation, a cell lysate, and/or a reaction mixture. In some embodiments, an enzyme exhibiting undesired activity is removed from an enzyme preparation, a cell lysate, and/or a reaction mixture via capture and/or chromatography (e.g., by differential affinity to a stationary phase).

In some embodiments, an enzyme exhibiting undesired activity is removed from an enzyme preparation, a cell lysate, and/or a reaction mixture via affinity chromatography. Examples of affinity chromatography include, but are not limited to, Protein A chromatography, Protein G chromatography, metal binding chromatography (e.g., nickel chromatography), lectin chromatography, and GST chromatography.

In some embodiments, an enzyme exhibiting undesired activity is removed from an enzyme preparation, a cell lysate, and/or a reaction mixture via ion exchange chromatography. Examples of anion exchange chromatography (AEX) include, but are not limited to, diethylaminoethyl (DEAE) chromatography, quaternary aminoethyl (QAE) chromatography, and quaternary amine(Q) chromatography. Examples of cation exchange chromatography include, but are not limited to, carboxymethyl (CM) chromatography, sulfoethyl (SE) chromatography, sulfopropyl (SP) chromatography, phosphate (P) chromatography, and sulfonate (S) chromatography.

In some embodiments, an enzyme exhibiting undesired activity is removed from an enzyme preparation, a cell lysate, and/or a reaction mixture via hydrophobic interaction chromatography (HIC). Examples of hydrophobic interaction chromatography include, but are not limited to, Phenyl Sepharose chromatography, Butyl Sepharose chromatography, Octyl Sepharose chromatography, Capto Phenyl chromatography, Toyopearl Butyl chromatography, Toyopearl Phenyl chromatography, Toyopearl Hexyl chromatography, Toyopearl Ether chromatography, and Toyopearl PPG chromatography. Any of the chemistries detailed above could be alternatively be used to immobilize or capture pathway enzymes.

Thermostable Enzymes

Any of the pathway enzymes provided herein (e.g., nucleases, kinases, polymerases, etc.) may be thermostable enzymes. Thermostability refers to the quality of enzymes to resist denaturation at relatively high or low temperature. For example, if an enzyme is denatured (inactivated) at a temperature of 42° C., an enzyme having similar activity (e.g., kinase activity) is considered "thermostable" if it does not denature at 42° C.

An enzyme (e.g., kinase or polymerase) is considered thermostable if the enzyme (a) retains activity after temporary exposure to high temperatures that denature other native enzymes or (b) functions at a high rate after temporary exposure to a medium to high temperature where native enzymes function at low rates.

An enzyme (e.g., kinase or polymerase) is also considered thermostable if the enzyme (a) retains activity after temporary exposure to low temperatures that denature other native enzymes or (b) functions at a high rate after temporary exposure to a medium to low temperature where native enzymes function at low rates.

In some embodiments, a thermostable enzyme retains greater than 10% activity following temporary exposure to relatively high temperature (e.g., higher than 41° C. for kinases obtained from E. coli, higher than 37° C. for many RNA polymerases) that would otherwise denature a similar (non-thermostable) native enzyme. In some embodiments, a thermostable enzyme retains 10-100%, 25-100%, or 50-100% activity following temporary exposure to relatively high temperature that would otherwise denature a similar (non-thermostable) native enzyme. For example, a thermostable enzyme may retain 10-90%, 10-85%, 10-80%, 10-75%, 10-70%, 10-65%, 10-60%, 10-55%, 25-90%, 25-85%, 25-80%, 25-75%, 25-70%, 25-65%, 25-60%, 25-55%, 50-90%, 50-85%, 50-80%, 50-75%, 50-70%, 50-65%, 50-60%, or 50-55% temporary exposure to relatively high temperature that would otherwise denature a similar (non-thermostable) native enzyme. In some embodiments, a thermostable enzyme retains 10%, 15%, 20%, 25%, 30%, 35%, 40%, 45%, 50%, 55%, 60%, 65%, 70%, 75%, 80%, 85%, 90%, 95%, 98%, 99%, or 100% activity following temporary exposure to relatively high temperature that would otherwise denature a similar (non-thermostable) native enzyme.

In some embodiments, a thermostable enzyme retains greater than 50% activity following temporary exposure to relatively low temperature (e.g., lower than 32° C. for kinases obtained from E. coli, lower than 32° C. for many RNA polymerases) that would otherwise denature a similar (non-thermostable) native enzyme. In some embodiments, a thermostable enzyme retains 50-100% activity following temporary exposure to relatively low temperature that would otherwise denature a similar (non-thermostable) native enzyme. For example, a thermostable enzyme may retain 50-90%, 50-85%, 50-80%, 50-75%, 50-70%, 50-65%, 50-60%, or 50-55% activity following temporary exposure to relatively low temperature that would otherwise denature a similar (non-thermostable) native enzyme. In some embodiments, a thermostable enzyme retains 25%, 30%, 35%, 40%, 45%, 50%, 55%, 60%, 65%, 70%, 75%, 80%, 85%, 90%, 95%, 98%, 99%, or 100% activity following temporary exposure to relatively low temperature that would otherwise denature a similar (non-thermostable) native enzyme.

In some embodiments, the activity of a thermostable enzyme after temporary exposure to medium to high temperature (e.g., 42-80° C.) is greater than (e.g., 25%, 30%, 35%, 40%, 45%, 50%, 55%, 60%, 65%, 70%, 75%, 80%, 85%, 90%, 95%, 98%, 99%, or 100% greater than) the activity of a similar (non-thermostable) native enzyme.

In some embodiments, the activity of a thermostable enzyme after temporary exposure to medium to low temperature (e.g., 32-0° C.) is greater than (e.g., 25%, 30%, 35%, 40%, 45%, 50%, 55%, 60%, 65%, 70%, 75%, 80%, 85%, 90%, 95%, 98%, 99%, or 100% greater than) the activity of a similar (non-thermostable) native enzyme.

The activity of a thermostable kinase, for example, may be measured by the amount of NMP or NDP the kinase is able to phosphorylate. Thus, in some embodiments, a thermostable kinase, at relatively high temperature (e.g., 42° C.) converts greater than 50% of NMP to NDP, or greater than 50% of NDP to NTP, in the same amount of time required to complete a similar conversion at 37° C. In some embodiments, a thermostable kinase, at relatively high temperature (e.g., 42° C.) converts greater than 60% of NMP to NDP, or greater than 60% of NDP to NTP, in the same amount of time required to complete a similar conversion at 37° C. In some embodiments, a thermostable kinase, at relatively high temperature (e.g., 42° C.) converts greater than 70% of NMP to NDP, or greater than 70% of NDP to NTP, in the same amount of time required to complete a similar conversion at 37° C. In some embodiments, a thermostable kinase, at relatively high temperature (e.g., 42° C.) converts greater than 80% of NMP to NDP, or greater than 80% of NDP to NTP, in the same amount of time required to complete a similar conversion at 37° C. In some embodiments, a thermostable kinase, at relatively high temperature (e.g., 42° C.) converts greater than 90% of NMP to NDP, or greater than 90% of NDP to NTP, in the same amount of time required to complete a similar conversion at 37° C.

In some embodiments, a thermostable kinase, at relatively low temperature (e.g., 32° C.) converts greater than 50% of NMP to NDP, or greater than 50% of NDP to NTP, in the same amount of time required to complete a similar conversion at 37° C. In some embodiments, a thermostable kinase, at relatively low temperature (e.g., 32° C.) converts greater than 60% of NMP to NDP, or greater than 60% of NDP to NTP, in the same amount of time required to complete a similar conversion at 37° C. In some embodiments, a thermostable kinase, at relatively low temperature (e.g., 32° C.) converts greater than 70% of NMP to NDP, or greater than 70% of NDP to NTP, in the same amount of time required to complete a similar conversion at 37° C. In some embodiments, a thermostable kinase, at relatively low temperature (e.g., 32° C.) converts greater than 80% of NMP to NDP, or greater than 80% of NDP to NTP, in the same amount of time required to complete a similar conversion at 37° C. In some embodiments, a thermostable kinase, at relatively low temperature (e.g., 32° C.) converts greater than 90% of NMP to NDP, or greater than 90% of NDP to NTP, in the same amount of time required to complete a similar conversion at 37° C.

The activity of a thermostable polymerase, for example, is assessed based on fidelity and polymerization kinetics (e.g., rate of polymerization). Thus, one unit of a thermostable T7 polymerase, for example, may incorporate 10 nmoles of NTP into acid insoluble material in 30 minutes at temperatures above 37° C. (e.g., at 50° C.). In another example, one unit of a thermostable T7 polymerase may incorporate 10 nmoles of NTP into acid insoluble material in 30 minutes at temperatures below 32° C. (e.g., at 25° C.)

In some embodiments, thermostable enzymes (e.g., kinases or polymerases) may remain active (able to catalyze a reaction) at a temperature of 42° C. to 80° C., or higher. In some embodiments, thermostable enzymes remain active at a temperature of 42-80° C., 42-70° C., 42-60° C., 42-50° C., 50-80° C., 50-70° C., 50-60° C., 60-80° C., 60-70° C., or 70-80° C. For example, thermostable enzymes may remain active at a temperature of 42° C., 43° C., 44° C., 45° C., 46° C., 47° C., 48° C., 49° C., 50° C., 51° C., 52° C., 53° C., 54° C., 55° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., or 80° C. Thermostable enzymes may remain active at relatively high temperatures for 15 minutes to 48 hours, or longer. For example, thermostable enzymes may remain active at relatively high temperatures for 1, 2, 3, 4, 5, 6, 7, 8, 9, 10, 11, 12, 13, 14, 15, 16, 17, 18, 19, 20, 24, 36, 42, or 48 hours.

In some embodiments, thermostable enzymes (e.g., kinases or polymerases) may remain active (able to catalyze a reaction) at a temperature of 32° C. to 0° C., or lower. In some embodiments, thermostable enzymes remain active at a temperature of 32-5° C., 32-10° C., 32-20° C., 32-25° C., 32-30° C., 30-0° C., 25-0° C., 20-0° C., 10-0° C., or 5-0° C. For example, thermostable enzymes may remain active at a temperature of 32° C., 31° C., 30° C., 29° C., 28° C., 27° C., 26° C., 25° C., 24° C., 23° C., 22° C., 21° C., 20° C., 19° C., 18° C., 17° C., 16° C., 15° C., 14° C., 13° C., 12° C., 10° C., 9° C., 8° C., 7° C., 6° C., 5° C., 4° C., 3° C., 2° C., 1° C., or 0° C. Thermostable enzymes may remain active at relatively low temperatures for 15 minutes to 48 hours, or longer. For example, thermostable enzymes may remain active at relatively low temperatures for 1, 2, 3, 4, 5, 6, 7, 8, 9, 10, 11, 12, 13, 14, 15, 16, 17, 18, 19, 20, 24, 36, 42, or 48 hours.

Non-limiting examples of thermostable NMP kinases are listed in Tables 4A-4D. Other thermostable kinases include thermostable nucleoside diphosphate kinases (see, e.g., Table 5), thermostable pyruvate kinases, and thermostable polyphosphate kinases (see, e.g., Table 2). Other thermostable kinases are encompassed by the present disclosure.

Non-limiting examples of RNA polymerases are listed in Table 6. Other RNA polymerases, including thermostable RNA polymerases, are encompassed by the present disclosure.

Thermostable RNA polymerases may be prepared by modifying wild-type enzymes. Such modifications (e.g., mutations) are known. For example, variant thermostable T7 RNA polymerases may include one or more of the following point mutations: V426L, A702V, V795I, S430P, F849I, S633P, F880Y, C510R, and S767G (EP2377928 and EP1261696A1, each of which is incorporated herein by reference). In some embodiments, a variant thermostable T7 RNA polymerase includes V426L, A702V, and V795I mutations. In some embodiments, a variant thermostable T7 RNA polymerase includes S430P, F849I, S633P, and F880Y mutations. In some embodiments, a variant thermostable T7 RNA polymerase includes F880Y, S430P, F849I, S633P, C510R, and S767G mutations. In some embodiments, a variant thermostable T7 RNA polymerase includes Y639V, H784G, E593G, and V685A mutations. In some embodiments, a variant thermostable T7 RNA polymerase includes S430P, N433T, S633P, F849I, and F880Y mutations. Other variant and recombinant thermostable polymerases are encompassed by the present disclosure.

In some embodiments, a thermostable T7 polymerase is used to produce a RNA of interest. For example, a thermostable T7 polymerase (e.g., incubated at a temperature of 37-60° C.) having a concentration of 0.1-5% total protein may be used to synthesize RNA of interest at a rate of greater than 1 g/L/hr (or, e.g., 1 g/L/hr-20 g/L/hr).

It should be understood that while many embodiments of the present disclosure describe the use of thermostable polymerases/enzymes, other enzymes/polymerases may be used. In some embodiments, polymerase may be exogenously added to heat-inactivated cell lysates, for example, to compensate for any reduction or loss of activity of the thermostable enzyme(s).

Fusion Enzymes

Any of the pathway enzymes provided herein (e.g., nucleases, kinases, polymerases, etc.) may be individual enzymes, enzymes with multiple activities, or fusion enzymes. A fusion enzyme may be created by joining two or more gene or gene segments that code for separate proteins. Translation of this fusion gene results in a single or multiple polypeptides with functional properties derived from each of the original proteins, e.g., a fusion protein that acts as a nuclease, acts as a kinase, and/or acts as a polymerase. Other enzymes may also be expressed as a fusion protein.

Some enzymes that exist in nature are multifunctional (e.g., CMP-UMP kinases). Thus, the term "enzyme" encompasses "enzymatic activities," regardless of how they are supplied.

A fusion enzyme is considered to "act as a nuclease" if the enzyme exhibits nuclease activity (cleaves or depolymerizes a nucleic acid; e.g., RNase R). A fusion enzyme is considered to "act as a kinase" if the enzyme exhibits kinase activity (catalyzes the transfer of a phosphate group from one molecule to another molecule; e.g., polyphosphate kinase). A fusion enzyme is considered to "act as a polymerase" if the enzyme exhibits polymerase activity (assembles nucleotides to produce nucleic acids; e.g., RNA polymerase).

Energy Sources

There are several energy and phosphate sources that may be used, as provided herein, for the production of NTP and/or RNA. Non-limiting examples of sources of phosphate include NTP (e.g., ATP, GTP, UTP, CTP), polyphosphate (e.g., hexametaphosphate), and pyrophosphate (PPi). In some embodiments, NTP, whether chemically synthesized, a product of fermentation, or extracted from a natural source, is included in a reaction mixture for the production of RNA. In some embodiments, polyphosphate and polyphosphate kinase are included in a reaction mixture for the production of NTP and/or RNA. In some embodiments, acetate, ADP, pyrophosphate, and at least two acetate kinases (e.g., acetate kinase (diphosphate) EC 2.7.2.12 and acetate kinase (phosphorylating) EC.7.2.1) are included in a reaction mixture for the production of NTP and/or RNA. In some embodiments, citrate, AMP, pyrophosphate, citrate lyase (the citrate lyase complex), a phosphoenolpyruvate carboxykinase (PEPCK) or a phosphoenolpyruvate carboxylase (PEPC), and a pyruvate phosphate dikinase (PPDK) are included in a reaction mixture for the production of NTP and/or RNA. In some embodiments, sulfite, AMP, pyrophosphate, adenylyl sulfate reductase, and sulfate adenylyltransferase are included in a reaction mixture for the production of NTP and/or RNA. Other energy sources are also encompassed by the present disclosure.

In some embodiments, an energy source is ATP produced from pyrophosphate through cyclical phosphorylation of acetate, from pyrophosphate and citrate, or from pyrophosphate and sulfite. Methods for ATP production from the above pathways are described herein. A summary of the ATP production pathways and pathway enzymes are provided in Table 7 below.

TABLE 7

Summary of Exemplary ATP Production Pathways and Enzymes

| ATP Production Pathway | Enzymes |
| --- | --- |
| ATP production from pyrophosphate through the acetate phosphorylation/dephosphorylation cycle | acetate kinase (diphosphate) (EC 2.7.2.12) acetate kinase (phosphorylating) (EC 2.7.2.1) |
| ATP production from citrate and pyrophosphate | citrate lyase (EC 4.1.3.6) phosphoenolpyruvate carboxykinase (PEPCK) (EC 4.1.1.38) pyruvate phosphate dikinase (PPDK) (EC 2.7.9.1, 2.7.9.2) phosphenolpyruvate carboxylase (PEPC) (EC 4.1.1.31) |
| ATP production from sulfite and pyrophosphate | sulfate adenylytransferase (EC 2.7.7.4) adenylyl sulfate reductase (EC 1.8.99.2) |

Figure 14:
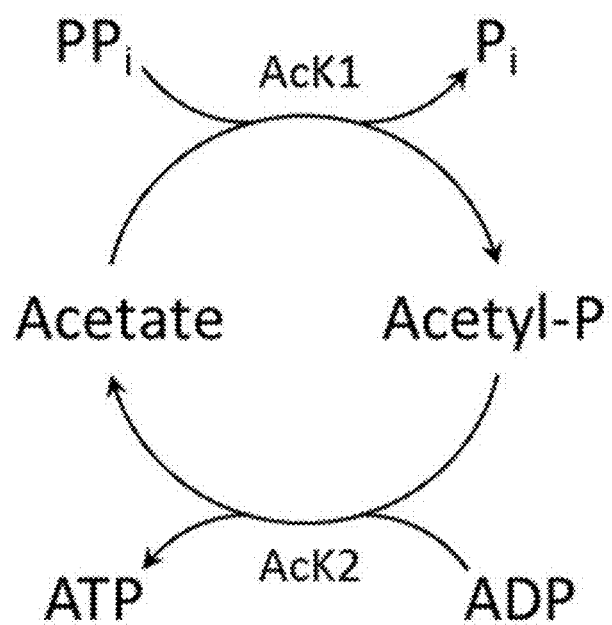
FIG. 14 is a schematic of an enzymatic pathway for production of ATP from pyrophosphate through the cyclical phosphorylation of acetate. The meaning of the abbreviations is as follows: AcK1=first acetate kinase, AcK2=second acetate kinase, $PP_i$=inorganic pyrophosphate, $P_i$=inorganic phosphate, ATP=adenosine triphosphate, ADP=adenosine diphosphate, and Acetyl-P=acetyl-phosphate.

ATP Production from Pyrophosphate and ADP Through an Acetate Phosphorylation/Dephosphorylation Cycle Some aspects of the present disclosure use methods for producing ATP from pyrophosphate (high-energy phosphate donor) and ADP (ultimate energy/phosphate acceptor) through an acetate phosphorylation/dephosphorylation cycle (see, e.g., FIG. 14). The first acetate kinase (AcK1; EC 2.7.2.12) phosphorylates acetate using inorganic pyrophosphate ($PP_i$), which produces acetyl-phosphate and inorganic phosphate ($P_i$). The acetyl-phosphate is then dephosphorylated by a second acetate kinase (AcK2; EC 2.7.2.1), which transfers the high-energy phosphate group from the acetyl-phosphate to ADP and produces ATP and acetate. The resulting acetate is then free to be phosphorylated again by AcK1, thereby completing a reaction cycle.

In some embodiments, the methods of producing ATP from pyrophosphate and ADP include culturing cells engineered to express a first acetate kinase, a second acetate kinase, or two different acetate kinases. In some embodiments, the methods include culturing cells engineered to express a first acetate kinase and a second acetate kinase. In some embodiments, the first acetate kinase and the second acetate kinase are expressed as a single fusion (chimeric) protein.

In some embodiments, at least one of the enzymes is a thermostable enzyme. In some embodiments, at least two of the enzymes are thermostable enzymes. In some embodiments, all of the enzymes are thermostable enzymes. Thus, in some embodiments, the methods include culturing cells engineered to express a thermostable acetate kinase. In other embodiments, the methods include culturing cells engineered to express a first thermostable acetate kinase and a second thermostable acetate kinase.

In some embodiments, the methods of producing ATP from pyrophosphate through the cyclical phosphorylation of acetate include lysing (e.g., thermal, osmotic, mechanical (e.g., sonication), chemical, or enzymatic lysis) the cultured cells to produce at least one (e.g., at least two) cell lysate. It should be understood that multiple cell lysates (and thus multiple cell populations, e.g., from the same organism (e.g., bacteria) or from different organisms (e.g., bacteria, yeast and/or plant) may be used in an enzymatic reaction as provided herein. For example, one cell population may be engineered to express a first acetate kinase of the ATP production pathway, while another cell population may be engineered to express a second acetate kinase of the ATP production pathway. Thus, in some embodiments, the methods comprise culturing a population of cells engineered to express an acetate kinase, and/or culturing a cell population engineered to express at least one additional acetate kinase. Following lysis of the cells, the cell lysates are combined such that the enzymes are present in a single cell lysate/reaction mixture.

In some embodiments, the methods of producing ATP from pyrophosphate through the cyclical phosphorylation of acetate further include heating the cell lysate(s) (or a cell lysate mixture) to a temperature that inactivates native enzymatic activity but does not inactivate any of the thermostable enzymes of the ATP production pathway, to produce a heat-inactivated lysate. The cell lysate(s), in some embodiments, is heated to a temperature of at least 50° C. For example, the cell lysate(s) may be heated to a temperature of at least 55° C., 60° C., 65° C., 70° C., 75° C., 80° C., 85° C., or 90° C. A native enzyme (or other non-thermostable enzyme) is considered inactive, in some embodiments, when its level of activity is reduced by at least 50%. In some embodiments, a native enzyme (or other non-thermostable enzyme) is considered inactive when its level of activity is reduced by at least 55%, 60%, 65%, 70%, 75%, 80%, 85%, 90%, 95%, or 100%.

The cell lysate(s) may be heated for a period of time sufficient to inactive native enzymes (or other non-thermostable enzymes) of the cell. For example, the cell lysate(s) may be heated for at least 2, 3, 4, or at least 5 minutes. In some embodiments, the cell lysate(s) are heated for longer than 5 minutes. In some embodiments, the cell lysate(s) is heated for longer than 15 minutes. In some embodiments, the cell lysate(s) is heated for less than 2 minutes. In some embodiments, the cell lysate(s) are heated for a period of time sufficient to reduce activity of native enzymes (or other non-thermostable enzymes) by at least 50% (e.g., at least 60%, 70%, 80%, or 90%).

Following heat inactivation, in some embodiments, at least one (e.g., at least two or at least three) purified enzymes may be added to the cell lysate/reaction mixture. Thus, a reaction mixture, in some embodiments, may include a combination of enzymes present in the cell lysate (expressed by the engineered host cell(s)) and at least one purified enzyme. At least one purified enzyme may be a first acetate kinase and/or a second acetate kinase. In some embodiments, a cell lysate may be cooled (e.g., to 50° C.) following a heat-inactivation step, prior to adding the purified enzyme(s).

In some embodiments, the methods of producing ATP from pyrophosphate through the cyclical phosphorylation of acetate also include incubating the heat-inactivated lysate(s) in the presence of acetate, adenosine diphosphate (ADP), and an inorganic phosphate to produce ATP. The inorganic phosphate may be, for example, pyrophosphate. Other inorganic phosphates and/or orthophosphate polymers, including but not limited to tripolyphosphate, tetrapolyphosphate, pentapolyphosphate, hexametaphosphate and mixtures thereof, may be used.

Also encompassed herein are cells and cell lysates used for the production of ATP from pyrophosphate through the cyclical phosphorylation of acetate. Thus, an engineered cell (e.g., bacterial cell, yeast cell, and/or plant cell) or cell lysate(s) of the present disclosure may include at least one (e.g., at least two) acetate kinase. In some embodiments, an engineered cell (e.g., bacterial cell, yeast cell, and/or plant cell) or cell lysate(s) of the present disclosure includes at least one (e.g., at least two) thermostable acetate kinase.

In some embodiments, the methods of producing ATP from citrate include lysing (e.g., thermal, osmotic, mechanical (e.g., sonication), chemical, or enzymatic lysis) the cultured cells to produce at least one (e.g., at least two, or three) cell lysate. It should be understood that multiple cell lysates (and thus multiple cell populations, e.g., from the same organism (e.g., bacteria) or from different organisms (e.g., bacteria, yeast and/or plant cells) may be used in an enzymatic reaction as provided herein. For example, one cell population may be engineered to express one or more enzymes of the ATP production pathway, while another cell population (or several other cell populations) may be engineered to express another (at least one other) enzyme of the ATP production pathway. Thus, in some embodiments, the methods comprise culturing a population of cells engineered to express a citrate lyase, culturing a cell population engineered to express a PEPCK (a thermostable PEPCK), and/or culturing a cell population engineered to express a PPDK.

TABLE 8

Exemplary Acetate Kinase Enzymes

| Enzyme Name | Reaction catalyzed | EC No. | Native Organism | NCBI No. |
| --- | --- | --- | --- | --- |
| Acetate kinase | Phosphorylates acetate to acetyl-phosphate | 2.7.2.12 | Entamoeba histolytica | XP_655990.1 |
| Acetate kinase | Phosphorylates ADP to ATP | 2.7.2.1 | Cryptococcus neoformans | XP_012053491.1 |

ATP Production from Pyrophosphate, AMP, and Citrate

Figure 15A:
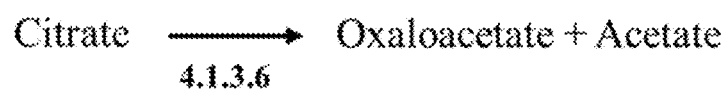
FIG. 15A-15B is a schematic of an enzymatic pathway for production of ATP from citrate.
Figure 15A:
Figure 15A:
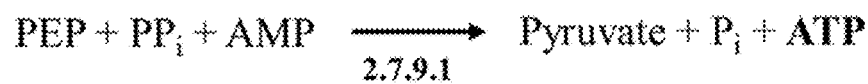
Figure 15B:
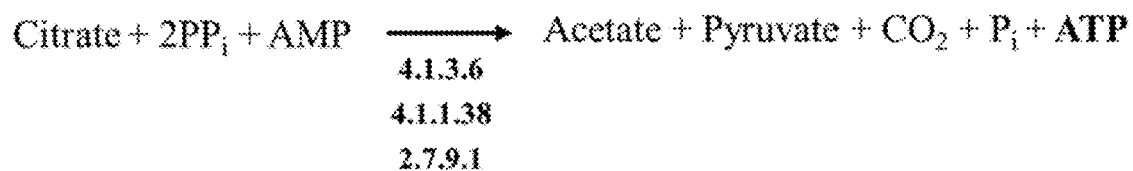

Some aspects of the present disclosure use methods for producing ATP from pyrophosphate, AMP, and citrate (see, e.g., FIGS. 15A-15B). A three-step enzymatic pathway is shown in FIG. 15A. In the first step, citrate lyase converts citrate to acetate and oxaloacetate. In the second step, phosphoenolpyruvate carboxykinase (PEPCK) converts pyrophosphate and oxaloacetate generated in the first step to phosphoenolpyruvate (PEP), carbon dioxide ($CO_2$), and inorganic phosphate (Pt). In the third step, pyruvate phosphate dikinase (PPDK) converts inorganic pyrophosphate ($PP_i$), AMP, and PEP generated in the second step to pyruvate, $P_i$, and ATP. The combined chemical reaction uses one mole of citrate, one mole of AMP, and two moles of $PP_i$ to yield one mole of acetate, one mole of pyruvate, one mole of $CO_2$, two moles of $P_i$, and one mole of ATP (FIG. 15B). Alternatively, phosphenolpyruvate carboxylase (PEPC) may be used to catalyze the carboxylation of PEP to oxaloacetate, which may be reversible under certain conditions.

These methods, in some embodiments, include culturing cells engineered to express a citrate lyase, a PEPCK (or at least one PEPC), a PPDK, or a combination of at least two or at least three of the foregoing enzymes. In some embodiments, citrate lyase and PEPCK (or PEPC), PEPCK (or PEPC) and PPDK, or citrate lyase and PPDK are expressed as a single fusion (chimeric) protein.

In some embodiments, at least one of the enzymes is a thermostable enzyme. In some embodiments, at least two or at least three of the enzymes are thermostable enzymes. In some embodiments, all of the enzymes are thermostable enzymes. Thus, in some embodiments, the methods include culturing cells engineered to express a thermostable citrate lyase, a thermostable PEPCK, a PPDK, or a combination of at least two or at least three of the foregoing thermostable enzymes.

Following lysis of the cells, the cell lysates are combined such that the enzymes are present in a single cell lysate/reaction mixture.

In some embodiments, the methods of producing ATP from citrate further include heating the cell lysate(s) (or a cell lysate mixture) to a temperature that inactivates native enzymatic activity but does not inactivate any of the thermostable enzymes of the ATP production pathway, to produce a heat-inactivated lysate. The cell lysate(s), in some embodiments, is heated to a temperature of at least 50° C. For example, the cell lysate(s) may be heated to a temperature of at least 55° C., 60° C., 65° C., 70° C., 75° C., 80° C., 85° C., or 90° C. A native enzyme (or other non-thermostable enzyme) is considered inactive, in some embodiments, when its level of activity is reduced by at least 50%. In some embodiments, a native enzyme (or other non-thermostable enzyme) is considered inactive when its level of activity is reduced by at least 55%, 60%, 65%, 70%, 75%, 80%, 85%, 90%, 95%, or 100%.

The cell lysate(s) may be heated for a period of time sufficient to inactive native enzymes (or other non-thermostable enzymes) of the cell. For example, the cell lysate(s) may be heated for at least 2, 3, 4, or at least 5 minutes. In some embodiments, the cell lysate(s) are heated for longer than 5 minutes. In some embodiments, the cell lysate(s) are heated for a period of time sufficient to reduce activity of native enzymes (or other non-thermostable enzymes) by at least 50% (e.g., at least 60%, 70%, 80%, or 90%).

Following heat inactivation, in some embodiments, at least one (e.g., at least two or at least three) purified enzymes may be added to the cell lysate/reaction mixture. Thus, a reaction mixture, in some embodiments, may include a combination of enzymes present in the cell lysate (expressed by the engineered host cell(s)) and at least one purified enzyme. At least one purified enzyme may be selected from the group consisting of citrate lyase, PEPCK (or PEPC), and PPDK. In some embodiments, a cell lysate may be cooled (e.g., to 50° C.) following a heat-inactivation step, prior to adding the purified enzyme(s).

In some embodiments, the methods of producing ATP from citrate also include incubating the heat-inactivated lysate(s) in the presence of citrate, adenosine monophosphate (AMP), and inorganic phosphate to produce ATP. The inorganic phosphate may be, for example, pyrophosphate. Other inorganic phosphates and/or orthophosphate polymers, including but not limited to tripolyphosphate, tetrapolyphosphate, pentapolyphosphate, hexametaphosphate and mixtures thereof, may be used.

Also encompassed herein are cells and cell lysates used for the production of ATP from citrate. Thus, an engineered cell (e.g., bacterial cell, yeast cell, and//or plant cell) or cell lysate(s) of the present disclosure may include at least one (e.g., at least two or at least three) enzyme selected from the group consisting of citrate lyase, PEPCK (or PEPC), and PPDK. In some embodiments, an engineered cell (e.g., bacterial cell, yeast cell, and/or plant cell) or cell lysate(s) of the present disclosure includes at least one (e.g., at least two or at least three) enzyme selected from the group consisting of thermostable citrate lyase, thermostable PEPCK (or thermostable PEPC), and thermostable PPDK.

While individual enzymes will differ in their cofactor preferences, there may be instances where biological cofactors such as NAD⁺, NADP⁺, NADH, or NADPH may be used by an enzyme to absorb these electrons. In these instances, cofactors such as these may also be included.

In some embodiments, at least one of the enzymes is a thermostable enzyme. In some embodiments, at least two (of the enzymes are thermostable enzymes. In some embodiments, all of the enzymes are thermostable enzymes. Thus, in some embodiments, the methods include culturing cells engineered to express a thermostable adenylyl sulfate reductase and a thermostable sulfate adenylyltransferase.

In some embodiments, the methods of producing ATP from sulfite include lysing (e.g., thermal, osmotic, mechanical (e.g., sonication), chemical, or enzymatic lysis) the cultured cells to produce at least one (e.g., 2, 3, 4 or 5) cell lysate. It should be understood that multiple cell lysates (and thus multiple cell populations, e.g., from the same organism (e.g., bacteria) or from different organisms (e.g., bacteria, yeast, and/or plant) may be used in an enzymatic reaction as provided herein. For example, one cell population may be engineered to express an adenylyl sulfate reductase, while another cell population (or several other cell populations) may be engineered to express a sulfate adenylyltransferase.

TABLE 9

Exemplary ATP Production from Pyrophosphate and Citrate Pathway Enzymes

| Pathway Step | Enzyme Name | EC No. | Native Organism | NCBI No. |
|---|---|---|---|---|
| 1 | Citrate lyase | 4.1.3.6 | *Escherichia coli* *Caloramator australicus* | AAC28949.1; AAC73717.2; AAC73716.1 CCJ33900.1; CCJ33901.1; CCJ33902.1 |
| 2 | phosphoenolpyruvate carboxykinase (PEPCK); also known as phosphoenolpyruvate carboxytransphosphorylase | 4.1.1.38 | *Propionibacterium freudenreichii* *Entamoeba histolytica* | AJQ89945.1 LC062511.1 XP_654765.1 XP_650862.1 |
| | phosphenolpyruvate carboxylase (PEPC) | 4.1.1.31 | *Pseudomonas fluorescens* | ABA72812.1 |
| 3 | pyruvate phosphate dikinase (PPDK) | 2.7.9.1 | *Clostridium symbiosum* | AAA22917.1 |

ATP Production from Pyrophosphate, AMP, and Sulfite

Figure 16:
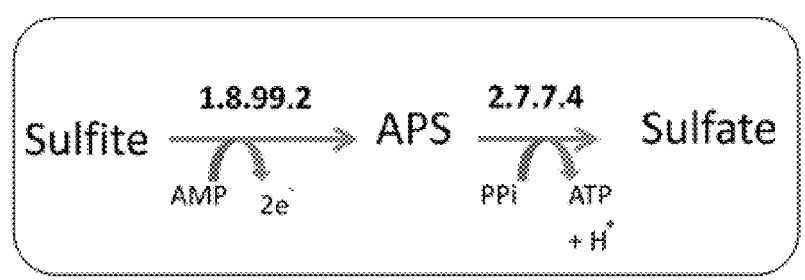
FIG. 16 is a schematic of an enzymatic pathway for production of ATP from sulfite. The meaning of the abbreviations is as follows: ATP=adenosine triphosphate, AMP=adenosine monophosphate, APS=adenosine 5'-phosphosulfate, and $PP_i$=inorganic pyrophosphate.

Some aspects of the present disclosure use methods for producing ATP from pyrophosphate, AMP, and sulfite (see, e.g., FIG. 16). In the first step, adenylyl sulfate reductase converts adenosine monophosphate (AMP) to adenosine 5'-phosphosulfate (APS) with consumption of sulfite. In the second step, sulfate adenylyltransferase catalyzes the conversion of APS to sulfate with generation of ATP and consumption of pyrophosphate.

In some embodiments, the methods of producing ATP from pyrophosphate, AMP, and sulfite include culturing cells engineered to express a adenylyl sulfate reductase, a sulfate adenylyltransferase, or a combination of a adenylyl sulfate reductase and a sulfate adenylyltransferase. In some embodiments, the adenylyl sulfate reductase and the sulfate adenylyltransferase are expressed as a single fusion (chimeric) protein or a bifunctional protein.

In some embodiments, reducing agents may be added that serve as electron sinks. Examples of such reducing agents include but are not limited to the following: dithiothreitol (DTT) or glutathione or ferricyanide or dithioerythritol or Tris-2-carboxyethylphosphine hydrochloride (TCEP).

Thus, in some embodiments, the methods comprise culturing a population of cells engineered to express an adenylyl sulfate reductase, and/or culturing a cell population engineered to express a sulfate adenylyltransferase. Following lysis of the cells, the cell lysates are combined such that the enzymes are present in a single cell lysate/reaction mixture.

In some embodiments, the methods of producing ATP from sulfite further include heating the cell lysate(s) (or a cell lysate mixture) to a temperature that inactivates native enzymatic activity but does not inactivate any of the thermostable enzymes of the ATP production pathway, to produce a heat-inactivated lysate. The cell lysate(s), in some embodiments, is heated to a temperature of at least 50° C. For example, the cell lysate(s) may be heated to a temperature of at least 55° C., 60° C., 65° C., 70° C., 75° C., 80° C., 85° C., or 90° C. A native enzyme (or other non-thermostable enzyme) is considered inactive, in some embodiments, when its level of activity is reduced by at least 50%. In some embodiments, a native enzyme (or other non-thermostable enzyme) is considered inactive when its level of activity is reduced by at least 55%, 60%, 65%, 70%, 75%, 80%, 85%, 90%, 95%, or 100%.

The cell lysate(s) may be heated for a period of time sufficient to inactive native enzymes (or other non-thermostable enzymes) of the cell. For example, the cell lysate(s) may be heated for at least 2, 3, 4, or at least 5 minutes. In some embodiments, the cell lysate(s) are heated for longer than 5 minutes. In some embodiments, the cell lysate(s) are heated for a period of time sufficient to reduce activity of native enzymes (or other non-thermostable enzymes) by at least 50% (e.g., at least 60%, 70%, 80%, or 90%).

Following heat inactivation, in some embodiments, at least one (e.g., at least two or at least three) purified enzymes may be added to the cell lysate/reaction mixture. Thus, a reaction mixture, in some embodiments, may include a combination of cell lysate, enzymes present in the cell lysate (expressed by the engineered host cell(s)), and at least one purified enzyme. At least one purified enzyme may be a first acetate kinase and/or a second acetate kinase. In some embodiments, a cell lysate may be cooled (e.g., to 50° C.) following a heat-inactivation step, prior to adding the purified enzyme(s).

In some embodiments, the methods of producing ATP from sulfite also include incubating the heat-inactivated lysate(s) in the presence of sulfite, adenosine monophosphate (AMP), and inorganic phosphate to produce ATP. The inorganic phosphate may be, for example, pyrophosphate. Other inorganic phosphates and/or orthophosphate polymers, including but not limited to tripolyphosphate, tetrapolyphosphate, pentapolyphosphate, hexametaphosphate and mixtures thereof, may be used.

Also encompassed herein are cells and cell lysates used for the production of ATP. Thus, an engineered cell (e.g., bacterial cell, yeast cell, and/or plant cell) or cell lysate(s) of the present disclosure may include at least one (e.g., at least two) adenylyl sulfate reductase and/or at least one sulfate adenylyltransferase. In some embodiments, an engineered cell (e.g., bacterial cell, yeast cell, and/or plant cell) or cell lysate(s) of the present disclosure includes at least one (e.g., at least two, at least three, or at least four) thermostable adenylyl sulfate reductase and/or at least one thermostable sulfate adenylyltransferase.

Depolymerization of Cellular RNA

In some embodiments, cellular RNA serves as the substrate for the production of NTP and/or RNA. Depolymerization (degradation) of cellular RNA results in a pool comprising nucleoside diphosphates (NDPs) or 5'-nucleoside monophosphates (5'-NMPs), depending on the enzymes used for depolymerization.

Cellular RNA, in some embodiments, is depolymerized into NDPs using, for example, a polynucleotide phosphorylase (PNPase) (see, e.g., Table 1). In some embodiments, the concentration of PNPase used in a reaction mixture is 0.001-10 mg/mL (e.g., 0.001, 0.01, 0.1, 0.2, 0.3, 0.4, 0.5, 0.6, 0.7, 0.8, 0.9, 1.0, 5, or 10 mg/mL). In some embodiments, the concentration of PNPase is a reaction mixture is 0.5-5 mg/mL. In some embodiments, the concentration of PNPase is a reaction mixture is 5 mg/mL. In some embodiments, the concentration of PNPase is a reaction mixture is greater than 10 mg/mL.

Cellular RNA, in other embodiments, is depolymerized into NMPs using, for example, a nuclease (e.g., RNase R or P1 nuclease) (see, e.g., Table 1). Depending on the enzyme, enzymatic depolymerization of RNA may yield 3'-NMPs, 5'-NMPs or a combination of 3'-NMPs and 5'-NMPs. Because it is not possible to polymerize 3'-NTPs (converted from 3'-NDPs, which are converted from 3'-NMPs), enzymes (e.g., RNase R and/or P1 nuclease) that yield 5'-NMPs (which are then converted to 5'-NDPs, and then 5'-NTPs) are preferred. In some embodiments, the concentration of nuclease (e.g., RNase R and/or P1 nuclease) used in a reaction mixture is 0.001-10 mg/mL (e.g., 0.001, 0.01, 0.1, 0.2, 0.3, 0.4, 0.5, 0.6, 0.7, 0.8, 0.9, 1.0, 5, or 10 mg/mL). In some embodiments, the concentration of nuclease in a reaction mixture is 0.0.5-5 mg/mL. In some embodiments, the concentration of nuclease in a reaction mixture is 5 mg/mL. In some embodiments, the concentration of nuclease in a reaction mixture is greater than 10 mg/mL.

The PNPase and/or the RNase, in some embodiments, is obtained from or is a component of a cell lysate of cells that express the PNPase and/or the RNase.

TABLE 10

Exemplary ATP Production from Pyrophosphate, AMP, and Sulfite Pathway Enzymes

| Pathway Step | Enzyme Name | EC No. | Native Organism | NCBI No. | Uniprot ID |
|---|---|---|---|---|---|
| 1 | Adenylyl sulfate reductase | 1.8.99.2 | Archaeoglobus fulgidus | CAA45030.1, CAA45029.1 | Q59115, Q59116 |
|  |  |  | Archaeoglobus profundus | WP_012940649.1, WP_012940650 |  |
|  |  |  | Thermodesulforhabdus norvegica | SFM96889.1 |  |
|  |  |  | Thiobacillus denitrificans | AAQ18138.1, AAQ18139.1 | Q5VLA6, Q5VLA7 |
|  |  |  | Desulfovibrio vulgaris | YP_010068.1, YP_010067.1 | Q59339, Q59338 |
| 2 | Sulfate adenylyltransferase | 2.7.7.4 | Archaeoglobus fulgidus | KUJ93479.1 | A0A124 FBI0 |
|  |  |  | Archaeoglobus profundus | WP_012940652.1 |  |
|  |  |  | Thermodesulforhabdus norvegica | WP_093395234.1, SFM89448.1 |  |
|  |  |  | Thiobacillus denitrificans | AAQ18137.1 |  |
|  |  |  | Desulfovibrio vulgaris | WP_012611243.1, WP_010938590.1 |  |
|  |  |  | Escherichia coli | ANO79304.1 |  |

The amount of cellular RNA required to synthesize a RNA product of interest may vary, depending on, for example, the desired length and yield of the RNA product as well as the nucleotide composition of the RNA product relative to the nucleotide composition of the cellular RNA starting material. Typically, for a bacterial cell or a yeast cell, for example, cellular RNA content ranges from 5-50% of the total cell mass. The percent of total cell mass can be calculated, for example, using the following equation: (kilogram (kg) of RNA/kilogram of dry cell weight)×100%.

Conditions suitable for the production of NMPs and conditions suitable for the production of NDPs are known in the art or may be determined by one of ordinary skill in the art, taking into consideration, for example, optimal conditions for nuclease (e.g., RNase) activity, including pH (e.g., pH 3-8), temperature (e.g., 15° C. to 70° C.), length of time (e.g., 5 min-72 hrs), and salt concentration (e.g., sodium chloride, potassium chloride, sodium acetate, potassium acetate at a concentration of 5 mM to 1 M) of the reaction mixture as well as any exogenous cofactors. In some embodiments, buffer is added to a cell lysate, for example, to achieve a particular pH value and/or salt concentration. Examples of buffers include, without limitation, phosphate buffer, Tris buffer, MOPS buffer, HEPES buffer, citrate buffer, acetate buffer, malate buffer, MES buffer, histidine buffer, PIPES buffer, bis-tris buffer, and ethanolamine buffer.

In some embodiments, a reaction mixture during a RNA depolymerization reaction is incubated for 24 hours at a temperature of 37° C. In some embodiments, a reaction mixture during a RNA depolymerization reaction is incubated for 5-30 min at a temperature of 37° C. In some embodiments, a reaction mixture during a RNA depolymerization reaction has a pH of 7.0 and is incubated for 15 minutes at a temperature of 37° C. In some embodiments, a reaction mixture during a RNA depolymerization reaction may be incubated under conditions that result in greater than 65% conversion of RNA to NDP or RNA to 5'-NMPs. In some embodiments, RNA is converted to NDP or 5'-NMPs at a rate of (or at least) 50 mM/hr, 100 mM/hr or 200 mM/hr. In other embodiments, a reaction mixture during an RNA depolymerization reaction is incubated at a higher temperature (for example, 50° C.-70° C.), as in Example 5.

Polymerization of RNA Product

In some embodiments, NTPs, either produced by a method provided herein or supplied from commercial sources, are used in a biosynthetic pathway for the production of a RNA product of interest. A DNA designed to encode the RNA product serves as the template for the synthesis of the RNA. The DNA template may be engineered, in some instances, to have a transcriptional promoter that selectively drives transcription of the RNA of interest. Polymerization of RNA requires NTPs, a DNA template comprising a transcriptional promoter, and a polymerase (e.g., RNA polymerase) specific to the transcriptional promoter. Typically, a polymerase for use as provided herein is a single subunit polymerase, is highly selective for its cognate transcriptional promoters, has high-fidelity, and is highly efficient.

In some embodiments, the concentration of the DNA template in a reaction mixture is 0.001-10 μg/μl. In some embodiments, the concentration of the DNA template in a reaction mixture is 0.001 μg/μl, 0.05 μg/μl, 0.1 μg/μl, 0.5 μg/μl, 1.0 μg/μl, 5 μg/μl, or 10 μg/μl.

Conditions suitable for the production of RNA are known in the art or may be determined by one of ordinary skill in the art, taking into consideration, for example, optimal conditions for polymerase (e.g., T7 RNA polymerase) activity, including pH (e.g., pH 3-8), temperature (e.g., 15° C. to 70° C.), length of time (e.g., 5 min-72 hrs), and salt concentration (e.g., sodium chloride, potassium chloride, sodium acetate, potassium acetate at a concentration of 5 mM to 1 M) of the reaction mixture as well as any exogenous cofactors. In some embodiments, buffer is added to a cell lysate, for example, to achieve a particular pH value and/or salt concentration. Examples of buffers include, without limitation, phosphate buffer, Tris buffer, MOPS buffer, HEPES buffer, citrate buffer, acetate buffer, malate buffer, MES buffer, histidine buffer, PIPES buffer, bis-tris buffer, and ethanolamine buffer.

In some embodiments, a reaction mixture during a RNA polymerization reaction is incubated for 0.5-24 hours at a temperature of 37° C. In some embodiments, a reaction mixture during a RNA polymerization reaction is incubated for 0.5-24 hours at a temperature of 50° C.

Cells and Cell Lysates

Cells of the present disclosure, in some embodiments, express cellular RNA, enzymes that depolymerizes RNA (e.g., RNases), pathway enzymes (e.g., recombinant enzymes such as polyphosphate kinase), and/or polymerases (e.g., RNA polymerases). In some embodiments, the engineered cells include a DNA template containing a promoter, and optionally a transcriptional terminator, operably linked to a nucleotide sequence encoding a RNA product of interest.

In some embodiments, the cells are engineered cells. Engineered cells are cells that comprise a engineered (e.g., recombinant or synthetic) nucleic acid, or are otherwise modified such that they are structurally and/or functionally distinct from their naturally-occurring counterparts. Thus, a cell that contains an engineered nucleic acid is considered an "engineered cell."

A cell "expresses" a product if the product, encoded by a nucleic acid (e.g., an engineered nucleic acid), is produced in the cell. It is known in the art that gene expression refers to the process by which genetic instructions in the form of a nucleic acid are used to synthesize a product, such as a protein (e.g., an enzyme).

Cells may be prokaryotic cells or eukaryotic cells. In some embodiments, cells are bacterial cells, yeast cells, insect cells, mammalian cells, plant cells, or other types of cells.

Bacterial cells of the present disclosure include, without limitation, *Escherichia* spp., *Streptomyces* spp., *Zymomonas* spp., *Acetobacter* spp., *Citrobacter* spp., *Synechocystis* spp., *Rhizobium* spp., *Clostridium* spp., *Corynebacterium* spp., *Streptococcus* spp., *Xanthomonas* spp., *Lactobacillus* spp., *Lactococcus* spp., *Bacillus* spp., *Alcaligenes* spp., *Pseudomonas* spp., *Aeromonas* spp., *Azotobacter* spp., *Comamonas* spp., *Mycobacterium* spp., *Rhodococcus* spp., *Gluconobacter* spp., *Ralstonia* spp., *Acidithiobacillus* spp., *Microlunatus* spp., *Geobacter* spp., *Geobacillus* spp., *Arthrobacter* spp., *Flavobacterium* spp., *Serratia* spp., *Saccharopolyspora* spp., *Thermus* spp., *Stenotrophomonas* spp., *Chromobacterium* spp., *Sinorhizobium* spp., *Saccharopolyspora* spp., *Agrobacterium* spp., *Pantoea* spp, and *Vibrio natriegens*.

Yeast cells of the present disclosure include, without limitation, engineered *Saccharomyces* spp., *Schizosaccharomyces*, *Hansenula*, *Candida*, *Kluyveromyces*, *Yarrowia* and *Pichia*.

In some embodiments, cells of the present disclosure are *Escherichia coli* cells, *Bacillus subtilis* cells, *Pseudomonas putida* cells, *Saccharomyces cerevisiae* cells, or *Lactobacil*- lus brevis cells. In some embodiments, cells of the present disclosure are *Escherichia coli* cells.

Typically, cells are cultured. Culturing is the process by which cells are grown under controlled conditions, typically outside of their natural environment. For example, cells, such as bacterial cells, may be grown as a cell suspension in liquid nutrient broth, also referred to as liquid culture medium.

Examples of commonly used bacterial *Escherichia coli* growth media include, without limitation, LB (Lysogeny Broth) Miller broth (1% NaCl): 1% peptone, 0.5% yeast extract, and 1% NaCl; LB (Lysogeny Broth) Lennox Broth (0.5% NaCl): 1% peptone, 0.5% yeast extract, and 0.5% NaCl; SOB medium (Super Optimal Broth): 2% peptone, 0.5% Yeast extract, 10 mM NaCl, 2.5 mM KCl, 10 mM $MgCl_2$, 10 mM $MgSO_4$; SOC medium (Super Optimal broth with Catabolic repressor): SOB+20 mM glucose; 2× YT broth (2× Yeast extract and Tryptone): 1.6% peptone, 1% yeast extract, and 0.5% NaCl; TB (Terrific Broth) medium: 1.2% peptone, 2.4% yeast extract, 72 mM $K_2HPO_4$, 17 mM $KH_2PO_4$ and 0.4% glycerol; and SB (Super Broth) medium: 3.2% peptone, 2% yeast extract, and 0.5% NaCl and or Korz medium (Korz, D J et al. 1995).

Examples of high density bacterial *Escherichia coli* growth media include, but are not limited to, DNAGro™ medium, ProGro™ medium, AutoX™ medium, DetoX™ medium, InduX™ medium, and SecPro™ medium.

In some embodiments, cells are cultured under conditions that result in expression of enzymes or nucleic acids. Such culture conditions may depend on the particular product being expressed and the desired amount of the product.

In some embodiments, cells are cultured at a temperature of 30° C. to 40° C. For example, engineered cells may be cultured at a temperature of 30° C., 31° C., 32° C., 33° C., 34° C., 35° C., 36° C., 37° C., 38° C., 39° C. or 40° C. Typically, cells, such as engineered *E. coli* cells, are cultured at a temperature of 37° C.

In some embodiments, cells are cultured for a period of time of 12 hours to 72 hours, or more. For example, engineered cells may be cultured for a period of time of 12, 18, 24, 30, 36, 42, 48, 54, 60, 66, or 72 hours. Typically, cells, such as engineered bacterial cells, are cultured for a period of time of 12 to 24 hours. In some embodiments, cells are cultured for 12 to 24 hours at a temperature of 37° C.

In some embodiments, cells are cultured (e.g., in liquid cell culture medium) to an optical density, measured at a wavelength of 600 nm ($OD_{600}$), of 5 to 200. In some embodiments, cells are cultured to an $OD_{600}$ of 5, 10, 15, 20, 25, 50, 75, 100, 150, or 200.

In some embodiments, cells are cultured to a density of $1\times10^8$ ($OD_{600}<1$) to $2\times10^{11}$ (OD~200) viable cells/ml cell culture medium. In some embodiments, cells are cultured to a density of $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, or $2\times10^{11}$ viable cells/ml. (Conversion factor: OD $1=8\times10^8$ cells/ml).

In some embodiments, cells are cultured in a bioreactor. A bioreactor refers simply to a container in which cells are cultured, such as a culture flask, a dish, or a bag that may be single-use (disposable), autoclavable, or sterilizable. The bioreactor may be made of glass, or it may be polymer-based, or it may be made of other materials.

Examples of bioreactors include, without limitation, stirred tank (e.g., well mixed) bioreactors and tubular (e.g., plug flow) bioreactors, airlift bioreactors, membrane stirred tanks, spin filter stirred tanks, vibromixers, fluidized bed reactors, and membrane bioreactors. The mode of operating the bioreactor may be a batch or continuous processes and will depend on the engineered cells being cultured. A bioreactor is continuous when the feed and product streams are continuously being fed and withdrawn from the system. A batch bioreactor may have a continuous recirculating flow, but no continuous feeding of nutrient or product harvest. For intermittent-harvest and fed-batch (or batch fed) cultures, cells are inoculated at a lower viable cell density in a medium that is similar in composition to a batch medium. Cells are allowed to grow exponentially with essentially no external manipulation until nutrients are somewhat depleted and cells are approaching stationary growth phase. At this point, for an intermittent harvest batch-fed process, a portion of the cells and product may be harvested, and the removed culture medium is replenished with fresh medium. This process may be repeated several times. For production of recombinant proteins and antibodies, a fed-batch process may be used. While cells are growing exponentially, but nutrients are becoming depleted, concentrated feed medium (e.g., 10-15 times concentrated basal medium) is added either continuously or intermittently to supply additional nutrients, allowing for further increase in cell concentration and the length of the production phase. Fresh medium may be added proportionally to cell concentration without removal of culture medium (broth). To accommodate the addition of medium, a fedbatch culture is started in a volume much lower that the full capacity of the bioreactor (e.g., approximately 40% to 50% of the maximum volume).

Some methods of the present disclosure are directed to large-scale (commercial-scale) production of RNA (e.g., mRNA). For large-scale production methods, cells may be grown in liquid culture medium in a volume of 5 liters (L) to 250,000 L, or more. In some embodiments, cells may be grown in liquid culture medium in a volume of greater than (or equal to) 10 L, 100 L, 1000 L, 10000 L, or 100000 L. In some embodiments, cells are grown in liquid culture medium in a volume of 5 L, 10 L, 15 L, 20 L, 25 L, 30 L, 35 L, 40 L, 45 L, 50 L, 100 L, 500 L, 1000 L, 5000 L, 10000 L, 100000 L, 150000 L, 200000 L, 250000 L, or more. In some embodiments, cells may be grown in liquid culture medium in a volume of 5 L to 10 L, 5 L to 15 L, 5 L to 20 L, 5 L to 25 L, 5 L to 30 L, 5 L to 35 L, 5 L to 40 L, 5 L to 45 L, 10 L to 15 L, 10 L to 20 L, 10 L to 25 L, 20 L to 30 L, 10 L to 35 L, 10 L to 40 L, 10 L to 45 L, 10 L to 50 L, 15 L to 20 L, 15 L to 25 L, 15 L to 30 L, 15 L to 35 L, 15 L to 40 L, 15 L to 45 L, or 15 to 50 L. In some embodiments, cells may be grown in liquid culture medium in a volume of 100 L to 300000 L, 100 L to 200000 L, or 100 L to 100000 L.

Typically, culturing of cells is followed by lysing the cells. Lysing is the process by which cells are broken down, for example, by viral, heat, chemical, enzymatic, mechanical, or osmotic mechanisms. A cell lysate is a fluid containing the contents of lysed cells (e.g., lysed engineered cells), including, for example, organelles, membrane lipids, proteins, nucleic acids and inverted membrane vesicles. Cell lysates of the present disclosure may be produced by lysing any population of engineered cells, as provided herein.

Cell lysis can disturb carefully controlled cellular environments, resulting in protein degradation and modification by unregulated endogenous proteases and phosphatases. Thus, in some embodiments, protease inhibitors and/or phosphatase inhibitors and/or nuclease inhibitors and/or hydrolase inhibitors and/or deaminase inhibitors may be added to the cell lysate or cells before lysis, or these activities may be removed by heat inactivation, gene inactivation, or protease targeting.

Cell lysates, in some embodiments, may be combined with a nutrient. For example, cell lysates may be combined with $Na_2HPO_4$, $KH_2PO_4$, $NH_4Cl$, NaCl, $MgSO_4$, $CaCl_2$. Examples of other nutrients include, without limitation, magnesium sulfate, magnesium chloride, magnesium orotate, magnesium citrate, potassium phosphate monobasic, potassium phosphate dibasic, potassium phosphate tribasic, sodium phosphate monobasic, sodium phosphate dibasic, sodium phosphate tribasic, ammonium phosphate monobasic, ammonium phosphate dibasic, ammonium sulfate, ammonium chloride, and ammonium hydroxide.

Cell lysates, in some embodiments, may be combined with a cofactor. For example, cell lysates may be combined with adenosine diphosphate (ADP), adenosine triphosphate (ATP), nicotinamide adenine dinucleotide (NAD+), or other non-protein chemical compounds required for activity of an enzyme (e.g., inorganic ions and coenzymes).

The volume of cell lysate used for a single reaction may vary. In some embodiments, the volume of a cell lysate is 0.001 to 250 $m^3$.

Nucleic Acids

A "nucleic acid" is at least two nucleotides covalently linked together, and in some instances, may contain phosphodiester bonds (e.g., a phosphodiester "backbone"). Nucleic acids (e.g., components, or portions, of nucleic acids) may be naturally occurring or engineered. "Naturally occurring" nucleic acids are present in a cell that exists in nature in the absence of human intervention. "Engineered nucleic acids" include recombinant nucleic acids and synthetic nucleic acids. A "recombinant nucleic acid" refers to a molecule that is constructed by joining nucleic acid molecules (e.g., from the same species or from different species) and, typically, can replicate in a living cell. A "synthetic nucleic acid" refers to a molecule that is biologically synthesized, chemically synthesized, or by other means synthesized or amplified. A synthetic nucleic acid includes nucleic acids that are chemically modified or otherwise modified but can base pair with naturally-occurring nucleic acid molecules. Recombinant and synthetic nucleic acids also include those molecules that result from the replication of either of the foregoing. Engineered nucleic acids may contain portions of nucleic acids that are naturally occurring, but as a whole, engineered nucleic acids do not occur naturally and require human intervention. In some embodiments, a nucleic acid encoding a product of the present disclosure is a recombinant nucleic acid or a synthetic nucleic acid. In other embodiments, a nucleic acid encoding a product is naturally occurring.

An engineered DNA template encoding RNA, as provided herein, may be operably linked to a promoter, which is a control region of a nucleic acid at which initiation and rate of transcription of the remainder of a nucleic acid are controlled. A promoter drives expression or drives transcription of the nucleic acid that it regulates.

A promoter may be one naturally associated with a gene or sequence, as may be obtained by isolating the 5' non-coding sequences located upstream of the coding segment of a given gene or sequence. Such a promoter may be endogenous.

In some embodiments, a coding nucleic acid sequence may be positioned under the control of a recombinant or heterologous promoter, which refers to a promoter that is not normally associated with the encoded sequence in its natural environment. Such promoters may include promoters of other genes; promoters isolated from any other cell; and synthetic promoters or enhancers that are not "naturally occurring" such as, for example, those that contain different elements of different transcriptional regulatory regions and/or mutations that alter expression through methods of genetic engineering that are known in the art. In addition to producing nucleic acid sequences of promoters and enhancers synthetically, sequences may be produced using recombinant cloning and/or nucleic acid amplification technology, including polymerase chain reaction (PCR).

A promoter is considered to be operably linked to a nucleotide sequence when it is in a correct functional location and orientation in relation to the nucleotide sequence it regulates to control ("drive") transcriptional initiation and/or expression of that nucleotide sequence.

Engineered nucleic acids of the present disclosure may contain a constitutive promoter or an inducible promoter. In some embodiments, the constitutive promotor or the inducible promoter is operably linked to a coding sequence, and optionally one or more transcriptional terminators. In some embodiments, the coding sequence encodes a protein or a RNA product. A "constitutive promoter" refers to a promoter that is constantly active in a cell. An "inducible promoter" refers to a promoter that initiates or enhances transcriptional activity when in the presence of, influenced by, or contacted by an inducer or inducing agent, or activated in the absence of a factor that causes repression. Inducible promoters for use in accordance with the present disclosure include any inducible promoter described herein or known to one of ordinary skill in the art. Examples of inducible promoters include, without limitation, chemically/biochemically-regulated and physically-regulated promoters such as organic solvent-regulated promoters, tetracycline-regulated promoters, steroid-regulated promoters, metal-regulated promoters, pathogenesis-regulated promoters, temperature/heat-inducible, phosphate-regulated (e.g., PhoA), and light-regulated promoters.

An engineered DNA template encoding RNA, as provided herein, may also be operably linked to one or more transcriptional terminators, which are control regions of a nucleic acid which cause a polymerase to stop transcribing and dissociate from the DNA template.

A terminator may be one or more sequences naturally associated with a gene or sequence, as may be obtained by isolating the 3'-non-coding sequences located downstream of the coding segment of a given gene or sequence. Such a terminator may be endogenous or engineered for improved termination efficiency. Endogenous and/or engineered terminator sequences from one or more sources can be added in series for improved termination efficiency.

Circular DNA templates encoding RNA may include one or more transcriptional terminators to minimize or prevent transcription of non-template DNA sequence, for example, a sequence that is part of a plasmid backbone.

Engineered nucleic acids may be introduced into host cells using any means known in the art, including, without limitation, transformation, transfection (e.g., chemical (e.g., calcium phosphate, cationic polymers, or liposomes) or non-chemical (e.g., electroporation, sonoporation, impalefection, optical transfection, hydrodynamic transfection)), and transduction (e.g., viral transduction).

Enzymes or other proteins encoded by a naturally-occurring, intracellular nucleic acid may be referred to as "endogenous enzymes" or "endogenous proteins."

Compositions

In some embodiments, a reaction mixture for the production of nucleoside triphosphates (NTPs) comprises nucleoside diphosphates (NDPs), a polyphosphate kinase, and a polyphosphate. In some embodiments, the reaction mixture further comprises a nucleoside kinase and/or a NDP kinase.

In some embodiments, a reaction mixture for the production of NTPs comprises 5' nucleoside monophosphates, a polyphosphate kinase, and polyphosphate. In some embodiments, the reaction mixture further comprises a nucleoside kinase, a NMP kinase, and/or a NDP kinase.

In some embodiments, a reaction mixture for the production of NTPs comprises nucleosides, a polyphosphate kinase, and a polyphosphate. In some embodiments, the reaction mixture further comprises a nucleoside kinase, a NMP kinase, and/or a NDP kinase.

In some embodiments, a reaction mixture for the production of NTPs comprises nucleobases, a phosphoribosyltransferase, a phosphoribosylpyrophosphate, a polyphosphate kinase, and a polyphosphate. In some embodiments, the reaction mixture further comprises a nucleoside kinase, a NMP kinase, and/or a NDP kinase.

In some embodiments, a reaction mixture for the production of NTPs comprises nucleobases, D-ribose, a ribokinase, a phosphopentomutase, a nucleoside phosphorylase, a polyphosphate kinase, and a polyphosphate. In some embodiments, the reaction mixture further comprises a nucleoside kinase, a NMP kinase, and/or a NDP kinase.

In some embodiments, a reaction mixture for the production of ribonucleic acid (RNA) comprises nucleoside diphosphates (NDPs), a polyphosphate kinase, a polyphosphate, a deoxyribonucleic acid (DNA) template, and a polymerase. In some embodiments, the reaction mixture further comprises a nucleoside kinase, a NMO kinase, and/or a NDP kinase.

In some embodiments, a reaction mixture for the production of RNA comprises 5' nucleoside monophosphates, a polyphosphate kinase, a polyphosphate, a deoxyribonucleic acid (DNA) template, and a polymerase. In some embodiments, the reaction mixture further comprises a nucleoside kinase, a NMP kinase, and/or a NDP kinase.

In some embodiments, a reaction mixture for the production of RNA comprises nucleosides, a nucleoside kinase, a polyphosphate kinase, a polyphosphate, a deoxyribonucleic acid (DNA) template, and a polymerase. In some embodiments, the reaction mixture further comprises a nucleoside kinase, a NMP kinase, and/or a NDP kinase.

In some embodiments, a reaction mixture for the production of RNA comprises nucleobases, a phosphoribosyltransferase, a phosphoribosylpyrophosphate, a polyphosphate kinase, a polyphosphate, a deoxyribonucleic acid (DNA) template, and a polymerase. In some embodiments, the reaction mixture further comprises a nucleoside kinase, a NMP kinase, and/or a NDP kinase.

In some embodiments, a reaction mixture for the production of RNA comprises nucleobases, D-ribose, a ribokinase, a phosphopentomutase, a nucleoside phosphorylase, a polyphosphate kinase, a polyphosphate, a deoxyribonucleic acid (DNA) template, and a polymerase. In some embodiments, the reaction mixture further comprises a nucleoside kinase, a NMP kinase, and/or a NDP kinase.

Additional Embodiments

Additional embodiments of the present disclosure are encompassed by the following numbered paragraphs.

1. A method for producing nucleoside triphosphates (NTPs), comprising:
   incubating in a reaction mixture nucleoside diphosphates (NDPs), a polyphosphate kinase, and a polyphosphate under conditions appropriate for the production of NTPs, optionally wherein the reaction mixture further comprises a nucleoside kinase and/or a NDP kinase.

2. The method of paragraph 1, wherein the NDPs comprise ADP, GDP, CDP, and/or UDP.

3. The method of paragraph 1 or 2, wherein the NDPs are chemically synthesized, a product of fermentation, or extracted from a natural source.

4. The method of any one of paragraphs 1-3, wherein the a polyphosphate kinase is selected from PPK1 family enzymes and PPK2 family enzymes.

5. The method of paragraph 4, wherein the polyphosphate kinase comprises a Class III polyphosphate kinase 2 from *Deinococcus geothermalis*.

6. The method of any one of paragraphs 1-5, wherein the polyphosphate comprises hexametaphosphate.

7. The method of any one of paragraphs 1-6, wherein the polyphosphate kinase, the nucleoside kinase, and/or the NDP kinase is prepared from cells that express the polyphosphate kinase, the nucleoside kinase, and/or the NDP kinase.

8. The method of any one of paragraphs 1-7, wherein the reaction mixture comprises a cell lysate or an enzyme preparation from cells that express the polyphosphate kinase, the nucleoside kinase, and/or the NDP kinase.

9. The method of paragraph 8, wherein native enzymatic activity of enzymes in the cell lysate or enzyme preparation have been eliminated.

10. The method of paragraph 9, wherein native enzymatic activity of enzymes in the cell lysate or enzyme preparation have been eliminated via genetic modification, enzyme secretion from a cell, and/or protease targeting.

11. The method of paragraph 9 or 10, wherein native enzymatic activity of enzymes in the cell lysate or enzyme preparation have been eliminated via temperature, pH, salt, detergent, alcohol, and/or chemical inhibitors.

12. The method of any one of paragraphs 9-11, wherein native enzymatic activity of enzymes in the cell lysate or enzyme preparation have been eliminated via separation, precipitation, filtration, capture, and/or chromatography.

13. The method of any one of paragraphs 9-12, wherein the native enzymatic activities are selected from phosphatases, nucleases, proteases, deaminases, oxidoreductases, and hydrolases.

14. The method of any one of paragraphs 1-13, wherein the polyphosphate kinase, the nucleoside kinase, and/or the NDP kinase can withstand elimination conditions.

15. A method for producing nucleoside triphosphates (NTPs), comprising:
   incubating in a reaction mixture 5' nucleoside monophosphates (5' NMPs), a polyphosphate kinase, and a polyphosphate under conditions appropriate for the production of NTPs, optionally wherein the reaction mixture further comprises a nucleoside kinase, a NMP kinase, and/or a NDP kinase.

16. The method of paragraph 15, wherein the 5' NMPs comprise 5' AMP, 5' GMP, 5' CMP and/or 5' UMP.

17. The method of paragraph 15 or 16, wherein the 5' NMPs are chemically synthesized, a product of fermentation, or extracted from a natural source.

18. The method of any one of paragraphs 15-17, wherein the polyphosphate kinase is selected from PPK1 family enzymes and PPK2 family enzymes.

19. The method of paragraph 18, wherein the polyphosphate kinase comprises a Class III polyphosphate kinase 2 from *Deinococcus geothermalis*.

20. The method of any one of paragraphs 15-19, wherein the polyphosphate comprises hexametaphosphate.

21. The method of any one of paragraphs 15-20, wherein the polyphosphate kinase, the nucleoside kinase, the NMP kinase, and/or the NDP kinase is prepared from cells that express the polyphosphate kinase, the nucleoside kinase, the NMP kinase, and/or the NDP kinase.

22. The method of any one of paragraphs 15-21, wherein the reaction mixture comprises a cell lysate or an enzyme preparation from cells that express the polyphosphate kinase, the nucleoside kinase, the NMP kinase, and/or the NDP kinase.

23. The method of paragraph 22, wherein native enzymatic activity of enzymes in the cell lysate have been eliminated.

24. The method of paragraph 23, wherein native enzymatic activity of enzymes in the cell lysate have been eliminated via genetic modification, enzyme secretion from a cell, and/or protease targeting.

25. The method of paragraph 23 or 24, wherein native enzymatic activity of enzymes in the cell lysate have been eliminated via temperature, pH, salt, detergent, alcohol, and/or chemical inhibitors.

26. The method of any one of paragraphs 23-25, wherein native enzymatic activity of enzymes in the cell lysate or enzyme preparation have been eliminated via separation, precipitation, filtration, capture, and/or chromatography.

27. The method of any one of paragraphs 23-26, wherein the native enzymatic activities are selected from phosphatases, nucleases, proteases, deaminases, oxidoreductases, and hydrolases.

28. The method of any one of paragraphs 15-27, wherein the polyphosphate kinase, the nucleoside kinase, the NMP kinase, and/or the NDP kinase can withstand elimination conditions.

29. A method for producing nucleoside triphosphates (NTPs), comprising:
incubating in a reaction mixture nucleosides, a polyphosphate kinase, and a polyphosphate under conditions appropriate for the production of NTPs, optionally wherein the reaction mixture further comprises a nucleoside kinase, a NMP kinase, and/or a NDP kinase.

30. The method of paragraph 29, wherein the nucleosides comprise adenosine, guanosine, cytidine, and/or uridine.

31. The method of paragraph 29 or 30, wherein the nucleosides are chemically synthesized, a product of fermentation, or extracted from a natural source.

32. The method of any one of paragraphs 29-31, wherein the polyphosphate kinase is selected from PPK1 family enzymes and PPK2 family enzymes.

33. The method of paragraph 32, wherein the polyphosphate kinase comprises a Class III polyphosphate kinase 2 from *Deinococcus geothermalis*.

34. The method of any one of paragraphs 29-33, wherein the polyphosphate comprises hexametaphosphate.

35. The method of any one of paragraphs 29-34, wherein the polyphosphate kinase, the nucleoside kinase, the NMP kinase and/or the NDP kinase is prepared from cells that express the polyphosphate kinase, the nucleoside kinase, the NMP kinase, and/or the NDP kinase.

36. The method of any one of paragraphs 29-35, wherein the reaction mixture comprises a cell lysate or an enzyme preparation from cells that express the polyphosphate kinase, the nucleoside kinase, the NMP kinase, and/or the NDP kinase.

37. The method of paragraph 36, wherein native enzymatic activity of enzymes in the cell lysate have been eliminated.

38. The method of paragraph 37, wherein native enzymatic activity of enzymes in the cell lysate have been eliminated via genetic modification, enzyme secretion from a cell, and/or protease targeting.

39. The method of paragraph 37 or 38, wherein native enzymatic activity of enzymes in the cell lysate have been eliminated via temperature, pH, salt, detergent, alcohol, and/or chemical inhibitors.

40. The method of any one of paragraphs 37-39, wherein native enzymatic activity of enzymes in the cell lysate or enzyme preparation have been eliminated via separation, precipitation, filtration, capture, and/or chromatography.

41. The method of any one of paragraphs 37-40, wherein the native enzymatic activities are selected from phosphatases, nucleases, proteases, deaminases, oxidoreductases, and hydrolases.

42. The method of any one of paragraphs 29-41, wherein the polyphosphate kinase, the nucleoside kinase, the NMP kinase, and/or the NDP kinase can withstand elimination conditions.

43. A method for producing nucleoside triphosphates (NTPs), comprising:
incubating in a reaction mixture nucleobases, a phosphoribosyltransferase, a phosphoribosylpyrophosphate, a polyphosphate kinase, and a polyphosphate under conditions appropriate for the production of NTPs, optionally wherein the reaction mixture further comprises a nucleoside kinase, a NMP kinase, and/or a NDP kinase.

44. The method of paragraph 43, wherein the nucleobases comprise adenine, guanidine, cytosine, and/or uracil.

45. The method of paragraph 43 or 44, wherein the nucleobases are chemically synthesized, a product of fermentation, or extracted from a natural source.

46. The method of any one of paragraphs 43-45, wherein the polyphosphate kinase is selected from PPK1 family enzymes and PPK2 family enzymes.

47. The method of paragraph 46, wherein the polyphosphate kinase comprises a Class III polyphosphate kinase 2 from *Deinococcus geothermalis*.

48. The method of any one of paragraphs 43-47, wherein the polyphosphate comprises hexametaphosphate.

49. The method of any one of paragraphs 43-48, wherein the polyphosphate kinase, the nucleoside kinase, the NMP kinase and/or the NDP kinase is prepared from cells that express the polyphosphate kinase, the nucleoside kinase, the NMP kinase, and/or the NDP kinase.

50. The method of any one of paragraphs 43-49, wherein the reaction mixture comprises a cell lysate or an enzyme preparation from cells that express the polyphosphate kinase, the nucleoside kinase, the NMP kinase, and/or the NDP kinase.

51. The method of paragraph 50, wherein native enzymatic activity of enzymes in the cell lysate have been eliminated.

52. The method of paragraph 51, wherein native enzymatic activity of enzymes in the cell lysate have been eliminated via genetic modification, enzyme secretion from a cell, and/or protease targeting.

53. The method of paragraph 51 or 52, wherein native enzymatic activity of enzymes in the cell lysate have been eliminated via temperature, pH, salt, detergent, alcohol, and/or chemical inhibitors.

54. The method of any one of paragraphs 51-53, wherein native enzymatic activity of enzymes in the cell lysate or enzyme preparation have been eliminated via separation, precipitation, filtration, capture, and/or chromatography.

55. The method of any one of paragraphs 51-54, wherein the native enzymatic activities are selected from phosphatases, nucleases, proteases, deaminases, oxidoreductases, and hydrolases.

56. The method of any one of paragraphs 43-55, wherein the polyphosphate kinase, the nucleoside kinase, the NMP kinase, and/or the NDP kinase can withstand elimination conditions.

57. A method for producing nucleoside triphosphates (NTPs), comprising:
incubating in a reaction mixture nucleobases, ribose, ribokinase, phosphopentomutase, a nucleoside phosphorylase, a polyphosphate kinase, and a polyphosphate under conditions appropriate for the production of NTPs, optionally wherein the reaction mixture further comprises a nucleoside kinase, a NMP kinase, and/or a NDP kinase.

58. The method of paragraph 57, wherein the nucleobases comprise adenine, guanidine, cytosine, and/or uracil.

59. The method of paragraph 57 or 58, wherein the nucleobases are chemically synthesized, a product of fermentation, or extracted from a natural source.

60. The method of any one of paragraphs 57-59, wherein the polyphosphate kinase is selected from PPK1 family enzymes and PPK2 family enzymes.

61. The method of paragraph 60, wherein the polyphosphate kinase comprises a Class III polyphosphate kinase 2 from *Deinococcus geothermalis*.

62. The method of any one of paragraphs 57-61, wherein the polyphosphate comprises hexametaphosphate.

63. The method of any one of paragraphs 57-62, wherein the ribokinase, the phosphopentomutase, the nucleoside phosphorylase, the polyphosphate kinase, the nucleoside kinase, the NMP kinase, and/or the NDP kinase is prepared from cells that express the ribokinase, the phosphopentomutase, the nucleoside phosphorylase, the polyphosphate kinase, the nucleoside kinase, the NMP kinase, and/or the NDP kinase.

64. The method of any one of paragraphs 57-63, wherein the reaction mixture comprises a lysate prepared from cells that express the ribokinase, the phosphopentomutase, the nucleoside phosphorylase, the polyphosphate kinase, the nucleoside kinase, the NMP kinase, and/or the NDP kinase.

65. The method of paragraph 64, wherein native enzymatic activity of enzymes in the cell lysate have been eliminated.

66. The method of paragraph 65, wherein native enzymatic activity of enzymes in the cell lysate have been eliminated via genetic modification, enzyme secretion from a cell, and/or protease targeting.

67. The method of paragraph 65 or 66, wherein native enzymatic activity of enzymes in the cell lysate have been eliminated via temperature, pH, salt, detergent, organic solvent, and/or chemical inhibitors.

68. The method of any one of paragraphs 65-67, wherein native enzymatic activity of enzymes in the cell lysate or enzyme preparation have been eliminated via separation, precipitation, filtration, capture, and/or chromatography.

69. The method of any one of paragraphs 65-68, wherein the native enzymatic activities are selected from phosphatases, nucleases, proteases, deaminases, oxidoreductases, and hydrolases.

70. The method of any one of paragraphs 57-69, wherein the ribokinase, the phosphopentomutase, the nucleoside phosphorylase, the polyphosphate kinase, the NMP kinase, the NDP kinase, and/or the nucleoside kinase is modified to withstand elimination conditions.

71. A method for producing nucleoside triphosphates (NTPs), comprising:
incubating in a reaction mixture cellular ribonucleic acid (RNA), a polynucleotide phosphorylase (PNPase), inorganic phosphate, a polyphosphate kinase, and a polyphosphate under conditions appropriate for the production of NDPs and NTPs, optionally wherein the reaction mixture further comprises a nucleoside kinase and/or a NDP kinase.

72. The method of paragraph 71, wherein the cellular RNA comprises ribosomal RNA, messenger RNA, and/or transfer RNA.

73. The method of paragraph 61 or 72, wherein the cellular RNA is from a unicellular organism or a multicellular organism.

74. The method of any one of paragraphs 71-73, wherein the polyphosphate kinase is selected from PPK1 family enzymes and PPK2 family enzymes.

75. The method of paragraph 74, wherein the polyphosphate kinase comprises a Class III polyphosphate kinase 2 from *Deinococcus geothermalis*.

76. The method of any one of paragraphs 71-75, wherein the polyphosphate comprises hexametaphosphate.

77. The method of any one of paragraphs 71-76, wherein the PNPase, the polyphosphate kinase, the nucleoside kinase, and/or the NDP kinase is prepared from cells that express the PNPase, the polyphosphate kinase, the nucleoside kinase, and/or the NDP kinase.

78. The method of any one of paragraphs 71-77, wherein the reaction mixture comprises a cell lysate or an enzyme preparation from cells that express the PNPase, the polyphosphate kinase, the nucleoside kinase, and/or the NDP kinase.

79. The method of paragraph 78, wherein native enzymatic activity of enzymes in the cell lysate have been eliminated.

80. The method of paragraph 79, wherein native enzymatic activity of enzymes in the cell lysate have been eliminated via genetic modification, enzyme secretion from a cell, and/or protease targeting.

81. The method of paragraph 79 or 80, wherein native enzymatic activity of enzymes in the cell lysate have been eliminated via temperature, pH, salt, detergent, alcohol, and/or chemical inhibitors.

82. The method of any one of paragraphs 79-81, wherein native enzymatic activity of enzymes in the cell lysate or enzyme preparation have been eliminated via separation, precipitation, filtration, capture, and/or chromatography.

83. The method of any one of paragraphs 79-82, wherein the native enzymatic activities are selected from phosphatases, nucleases, proteases, deaminases, oxidoreductases, and hydrolases.

84. The method of any one of paragraphs 79-83, wherein the PNPase, the polyphosphate kinase, the nucleoside kinase, and/or the NDP kinase can withstand elimination conditions.

85. A method for producing nucleoside triphosphates (NTPs), comprising:
(a) incubating in a reaction mixture cellular ribonucleic acid (RNA), a ribonuclease, a polyphosphate kinase, and a polyphosphate under conditions appropriate for the production of 5' NMPs and NTPs, optionally wherein the reaction mixture further comprises a nucleoside kinase, a NMP kinase, and/or a NDP kinase.

86. The method of paragraph 85, wherein the cellular RNA comprises ribosomal RNA, messenger RNA, and/or transfer RNA.

87. The method of paragraph 85 or 86, wherein the cellular RNA is from a unicellular organism or a multicellular organism.

88. The method of any one of paragraphs 85-87, wherein the polyphosphate kinase is selected from PPK1 family enzymes and PPK2 family enzymes.

89. The method of paragraph 88, wherein the polyphosphate kinase comprises a Class III polyphosphate kinase 2 from *Deinococcus geothermalis*.

90. The method of any one of paragraphs 85-89, wherein the polyphosphate comprises hexametaphosphate.

91. The method of any one of paragraphs 85-90, wherein the ribonuclease, the polyphosphate kinase, the nucleoside kinase, the NMP kinase, and/or the NDP kinase is prepared from cells that express the ribonuclease, the polyphosphate kinase, the nucleoside kinase, the NMP kinase, and/or the NDP kinase.

92. The method of any one of paragraphs 85-91, wherein the reaction mixture comprises a cell lysate or an enzyme preparation from cells that express the ribonuclease, the polyphosphate kinase, the nucleoside kinase, the NMP kinase, and/or the NDP kinase.

93. The method of paragraph 92, wherein native enzymatic activity of enzymes in the cell lysate have been eliminated.

94. The method of paragraph 93, wherein native enzymatic activity of enzymes in the cell lysate have been eliminated via genetic modification, enzyme secretion from a cell, and/or protease targeting.

95. The method of paragraph 93 or 94, wherein native enzymatic activity of enzymes in the cell lysate have been eliminated via temperature, pH, salt, detergent, alcohol, and/or chemical inhibitors.

96. The method of any one of paragraphs 93-95, wherein native enzymatic activity of enzymes in the cell lysate or enzyme preparation have been eliminated via separation, precipitation, filtration, capture, and/or chromatography.

97. The method of any one of paragraphs 93-96, wherein the native enzymatic activities are selected from phosphatases, nucleases, proteases, deaminases, oxidoreductases, and hydrolases.

98. The method of any one of paragraphs 93-97, wherein the ribonuclease, the polyphosphate kinase, the nucleoside kinase, the NMP kinase, and/or the NDP kinase can withstand elimination conditions.

99. A method for producing ribonucleic acid (RNA), comprising:
incubating in a reaction mixture nucleoside diphosphates (NDPs), a polyphosphate kinase, a polyphosphate, a DNA template encoding a RNA of interest, and a RNA polymerase under conditions appropriate for the production of the RNA of interest, optionally wherein the reaction mixture further comprises a nucleoside kinase and/or a NDP kinase.

100. The method of paragraph 99, wherein the NDPs comprise ADP, GDP, CDP, and/or UDP.

101. The method of paragraph 99 or 100, wherein the NDPs are chemically synthesized, a product of fermentation, or extracted from a natural source.

102. The method of any one of paragraphs 99-101, wherein the polyphosphate kinase is selected from PPK1 family enzymes and PPK2 family enzymes.

103. The method of paragraph 102, wherein the polyphosphate kinase comprises a Class III polyphosphate kinase 2 from *Deinococcus geothermalis*.

104. The method of any one of paragraphs 99-103, wherein the polyphosphate comprises hexametaphosphate.

105. The method of any one of paragraphs 99-104, wherein the polyphosphate kinase, the DNA template, the polymerase, the nucleoside kinase, and/or the NDP kinase is prepared from cells that express the polyphosphate kinase, the DNA template, the polymerase, the nucleoside kinase, and/or the NDP kinase.

106. The method of any one of paragraphs 99-105, wherein the reaction mixture comprises a cell lysate or an enzyme preparation from cells that express the polyphosphate kinase, the DNA template, the polymerase, the nucleoside kinase, and/or the NDP kinase.

107. The method of paragraph 106, wherein native enzymatic activity of enzymes in the cell lysate or enzyme preparation have been eliminated.

108. The method of paragraph 107, wherein native enzymatic activity of enzymes in the cell lysate or enzyme preparation have been eliminated via genetic modification, enzyme secretion from a cell, and/or protease targeting.

109. The method of paragraph 107 or 108, wherein native enzymatic activity of enzymes in the cell lysate or enzyme preparation have been eliminated via temperature, pH, salt, detergent, alcohol, and/or chemical inhibitors.

110. The method of any one of paragraphs 107-109, wherein native enzymatic activity of enzymes in the cell lysate or enzyme preparation have been eliminated via separation, precipitation, filtration, capture, and/or chromatography.

111. The method of any one of paragraphs 107-110, wherein the native enzymatic activities are selected from phosphatases, nucleases, proteases, deaminases, oxidoreductases, and hydrolases.

112. The method of any one of paragraphs 99-111, wherein the polyphosphate kinase, the polymerase, the nucleoside kinase, and/or the NDP kinase can withstand elimination conditions.

113. The method of any one of paragraphs 99-112, wherein the polymerase comprises a RNA polymerase.

114. A method for producing ribonucleic acid (RNA), comprising:
incubating in a reaction mixture 5' nucleoside monophosphates (5' NMPs), a polyphosphate kinase, a polyphosphate, a DNA template encoding a RNA of interest, and a polymerase under conditions appropriate for the production of the RNA of interest, optionally wherein the reaction mixture further comprises a nucleoside kinase, a NMP kinase, and/or a NDP kinase.

115. The method of paragraph 114, wherein the 5' NMPs comprise 5' AMP, 5' GMP, 5' CMP and/or 5' UMP.

116. The method of paragraph 114 or 115, wherein the 5' NMPs are chemically synthesized, a product of fermentation, or extracted from a natural source.

117. The method of any one of paragraphs 114-116, wherein the polyphosphate kinase is selected from PPK1 family enzymes and PPK2 family enzymes.

118. The method of paragraph 117, wherein the polyphosphate kinase comprises a Class III polyphosphate kinase 2 from *Deinococcus geothermalis*.

119. The method of any one of paragraphs 114-118, wherein the polyphosphate comprises hexametaphosphate.

120. The method of any one of paragraphs 114-119, wherein the polyphosphate kinase, the nucleoside kinase, the NMP kinase, the NDP kinase, the DNA template, and/or the polymerase is prepared from cells that express the polyphosphate kinase, the nucleoside kinase, the NMP kinase, the NDP kinase, the DNA template, and/or the polymerase.

121. The method of any one of paragraphs 114-120, wherein the reaction mixture comprises a cell lysate or an enzyme preparation from cells that express the polyphosphate kinase, the nucleoside kinase, the NMP kinase, the NDP kinase, the DNA template, and/or the polymerase.

122. The method of paragraph 121, wherein native enzymatic activity of enzymes in the cell lysate have been eliminated.

123. The method of paragraph 122, wherein native enzymatic activity of enzymes in the cell lysate have been eliminated via genetic modification, enzyme secretion from a cell, and/or protease targeting.

124. The method of paragraph 122 or 123, wherein native enzymatic activity of enzymes in the cell lysate have been eliminated via temperature, pH, salt, detergent, alcohol, and/or chemical inhibitors.

125. The method of any one of paragraphs 122-124, wherein native enzymatic activity of enzymes in the cell lysate or enzyme preparation have been eliminated via separation, precipitation, filtration, capture, and/or chromatography.

126. The method of any one of paragraphs 122-125, wherein the native enzymatic activities are selected from phosphatases, nucleases, proteases, deaminases, oxidoreductases, and hydrolases.

127. The method of any one of paragraphs 114-126, wherein the polyphosphate kinase, the nucleoside kinase, the NMP kinase, the NDP kinase, and/or the polymerase can withstand elimination conditions.

128. The method of any one of paragraphs 114-127, wherein the polymerase comprises a RNA polymerase.

129. A method for producing ribonucleic acid (RNA), comprising:
incubating in a reaction mixture nucleosides, a polyphosphate kinase, a polyphosphate, a DNA template encoding a RNA of interest, and/or a polymerase under conditions appropriate for the production of the RNA of interest, optionally wherein the reaction mixture further comprises a nucleoside kinase, a NMP kinase, and/or a NDP kinase.

130. The method of paragraph 129, wherein the nucleosides comprise adenosine, guanosine, cytidine, and/or uridine.

131. The method of paragraph 129 or 130, wherein the nucleosides are chemically synthesized, a product of fermentation, or extracted from a natural source.

132. The method of any one of paragraphs 129-131, wherein the polyphosphate kinase is selected from PPK1 family enzymes and PPK2 family enzymes.

133. The method of paragraph 132, wherein the polyphosphate kinase comprises a Class III polyphosphate kinase 2 from *Deinococcus geothermalis*.

134. The method of any one of paragraphs 129-133, wherein the polyphosphate comprises hexametaphosphate.

135. The method of any one of paragraphs 129-134, wherein the polyphosphate kinase, the nucleoside kinase, the NMP kinase, the NDP kinase, the DNA template, and/or the polymerase is prepared from cells that express the least one polyphosphate kinase, the nucleoside kinase, the polyphosphate, the nucleoside kinase, the NMP kinase, the NDP kinase, the DNA template, and/or the polymerase.

136. The method of any one of paragraphs 129-135, wherein the reaction mixture comprises a cell lysate or an enzyme preparation from cells that express the least one polyphosphate kinase, the nucleoside kinase, the NMP kinase, the NDP kinase, the DNA template, and/or the polymerase.

137. The method of paragraph 136, wherein native enzymatic activity of enzymes in the cell lysate have been eliminated.

138. The method of paragraph 137, wherein native enzymatic activity of enzymes in the cell lysate have been eliminated via genetic modification, enzyme secretion from a cell, and/or protease targeting.

139. The method of paragraph 137 or 138, wherein native enzymatic activity of enzymes in the cell lysate have been eliminated via temperature, pH, salt, detergent, alcohol, and/or chemical inhibitors.

140. The method of any one of paragraphs 137-139, wherein native enzymatic activity of enzymes in the cell lysate or enzyme preparation have been eliminated via separation, precipitation, filtration, capture, and/or chromatography.

141. The method of any one of paragraphs 137-140, wherein the native enzymatic activities are selected from phosphatases, nucleases, proteases, deaminases, oxidoreductases, and hydrolases.

142. The method of any one of paragraphs 129-141, wherein the least one polyphosphate kinase, the polyphosphate, the nucleoside kinase, the NMP kinase, the NDP kinase, and/or the polymerase can withstand elimination conditions.

143. The method of any one of paragraphs 129-142, wherein the polymerase comprises a RNA polymerase.

144. A method for producing ribonucleic acid (RNA), comprising:
incubating in a reaction mixture nucleobases, a phosphoribosyltransferase, a phosphoribosylpyrophosphate, a polyphosphate kinase, and a polyphosphate, a DNA template encoding a RNA of interest, and/or a polymerase under conditions appropriate for the production of the RNA of interest, optionally wherein the reaction mixture further comprises a nucleoside kinase, a NMP kinase, and/or a NDP kinase.

145. The method of paragraph 144, wherein the nucleobases comprise adenine, guanidine, cytosine, and/or uracil.

146. The method of paragraph 144 or 145, wherein the nucleobases are chemically synthesized, a product of fermentation, or extracted from a natural source.

147. The method of any one of paragraphs 144-146, wherein the polyphosphate kinase is selected from PPK1 family enzymes and PPK2 family enzymes.

148. The method of paragraph 148, wherein the polyphosphate kinase comprises a Class III polyphosphate kinase 2 from *Deinococcus geothermalis*.

149. The method of any one of paragraphs 144-148, wherein the polyphosphate comprises hexametaphosphate.

150. The method of any one of paragraphs 144-149, wherein the phosphoribosyltransferase, the polyphosphate kinase, the nucleoside kinase, a NMP kinase, the NDP kinase, the DNA template, and/or the polymerase is prepared from cells that express the phosphoribosyltransferase, the polyphosphate kinase, the nucleoside kinase, the NMP kinase, the NDP kinase, the DNA template, and/or the polymerase.

151. The method of any one of paragraphs 144-150, wherein the reaction mixture comprises a cell lysate or an enzyme preparation from cells that express the phosphoribosyltransferase, the polyphosphate kinase, the nucleoside kinase, the NMP kinase, the NDP kinase, the DNA template, and/or the polymerase.

152. The method of paragraph 151, wherein native enzymatic activity of enzymes in the cell lysate have been eliminated.

153. The method of paragraph 152, wherein native enzymatic activity of enzymes in the cell lysate have been eliminated via genetic modification, enzyme secretion from a cell, and/or protease targeting.

154. The method of paragraph 152 or 153, wherein native enzymatic activity of enzymes in the cell lysate have been eliminated via temperature, pH, salt, detergent, alcohol, and/or chemical inhibitors.

155. The method of any one of paragraphs 152-154, wherein native enzymatic activity of enzymes in the cell lysate or enzyme preparation have been eliminated via separation, precipitation, filtration, capture, and/or chromatography.

156. The method of any one of paragraphs 152-155, wherein the native enzymatic activities are selected from phosphatases, nucleases, proteases, deaminases, oxidoreductases, and hydrolases.

157. The method of any one of paragraphs 144-156, wherein the phosphoribosyltransferase, the polyphosphate kinase, the nucleoside kinase, the NMP kinase, the NDP kinase, and/or the polymerase can withstand elimination conditions.

158. The method of any one of paragraphs 144-157, wherein the polymerase comprises a RNA polymerase.

159. A method for producing ribonucleic acid (RNA), comprising:
incubating in a reaction mixture nucleobases, a ribose, a ribokinase, a phosphopentomutase, a nucleoside phosphorylase, a polyphosphate kinase, a polyphosphate, a DNA template encoding a RNA of interest, and a polymerase under conditions appropriate for the production of the RNA of interest, optionally wherein the reaction mixture further comprises a nucleoside kinase, a NMP kinase, and/or at least one NDP kinase.

160. The method of paragraph 159, wherein the nucleobases comprise adenine, guanidine, cytosine, and/or uracil.

161. The method of paragraph 159 or 160, wherein the nucleobases are chemically synthesized, a product of fermentation, or extracted from a natural source.

162. The method of any one of paragraphs 159-161, wherein the polyphosphate kinase is selected from PPK1 family enzymes and PPK2 family enzymes.

163. The method of paragraph 162, wherein the polyphosphate kinase comprises a Class III polyphosphate kinase 2 from *Deinococcus geothermalis*.

164. The method of any one of paragraphs 159-163, wherein the polyphosphate comprises hexametaphosphate.

165. The method of any one of paragraphs 159-164, wherein the ribokinase, the phosphopentomutase, the nucleoside phosphorylase, the polyphosphate kinase, the nucleoside kinase, the NMP kinase, the NDP kinase, the DNA template, and/or the polymerase is from at least one lysate prepared from engineered cells modified to express the ribokinase, the phosphopentomutase, the nucleoside phosphorylase, the polyphosphate kinase, the nucleoside kinase, the NMP kinase, the NDP kinase, the DNA template, and/or the polymerase.

166. The method of any one of paragraphs 159-165, wherein the reaction mixture a lysate prepared from cells that express the ribokinase, the phosphopentomutase, the nucleoside phosphorylase, the polyphosphate kinase, the nucleoside kinase, the NMP kinase, the NDP kinase, the DNA template, and/or the polymerase.

167. The method of paragraph 166, wherein native enzymatic activity of enzymes in the cell lysate have been eliminated.

168. The method of paragraph 167, wherein native enzymatic activity of enzymes in the cell lysate have been eliminated via genetic modification, enzyme secretion from a cell, and/or protease targeting.

169. The method of paragraph 167 or 168, wherein native enzymatic activity of enzymes in the cell lysate have been eliminated via temperature, pH, salt, detergent, organic solvent, and/or chemical inhibitors.

170. The method of any one of paragraphs 167-169, wherein native enzymatic activity of enzymes in the cell lysate or enzyme preparation have been eliminated via separation, precipitation, filtration, capture, and/or chromatography.

171. The method of any one of paragraphs 167-170, wherein the native enzymatic activities are selected from phosphatases, nucleases, proteases, deaminases, oxidoreductases, and hydrolases.

172. The method of any one of paragraphs 159-171, wherein the ribokinase, the phosphopentomutase, the nucleoside phosphorylase, the polyphosphate kinase, the nucleoside kinase, the NMP kinase, the NDP kinase, and/or the polymerase is modified to withstand elimination conditions.

173. The method of any one of paragraphs 159-172, wherein the at least one polymerase comprises at least one RNA polymerase.

174. A method for producing ribonucleic acid (RNA), comprising:
(a) incubating in a reaction mixture cellular ribonucleic acid (RNA), a polynucleotide phosphorylase (PNPase), and inorganic phosphate under conditions appropriate for the production of nucleoside diphosphates (NDPs);
(b) eliminating the PNPase; and
(c) incubating in the reaction mixture, or in a second reaction mixture, the NDPs, a polyphosphate kinase, a polyphosphate, a DNA template encoding a RNA of interest, and a polymerase under conditions appropriate for the production of the RNA of interest, optionally wherein the reaction mixture of step (c) further comprises a nucleoside kinase and/or a NDP kinase.

175. The method of paragraph 174, wherein the cellular RNA comprises ribosomal RNA, messenger RNA, and/or transfer RNA.

176. The method of paragraph 174 or 175, wherein the cellular RNA is from a unicellular organism or a multicellular organism.

177. The method of any one of paragraphs 174-176, wherein the polyphosphate kinase is selected from PPK1 family enzymes and PPK2 family enzymes.

178. The method of paragraph 177, wherein the polyphosphate kinase comprises a Class III polyphosphate kinase 2 from *Deinococcus geothermalis*.

179. The method of any one of paragraphs 174-178, wherein the polyphosphate comprises hexametaphosphate.

180. The method of any one of paragraphs 174-179, wherein the PNPase is prepared from cells that express the PNPase.

181. The method of any one of paragraphs 174-180, wherein the reaction mixture of (a) comprises a cell lysate prepared from cells that express the PNPase.

182. The method of paragraph 181, wherein step (b) comprises eliminating the PNPase via temperature, pH, salt, detergent, alcohol, and/or chemical inhibitors.

183. The method of paragraph 181 or 182, wherein step (b) comprises eliminating the PNPase via wherein native enzymatic activity of enzymes in the cell lysate or enzyme preparation have been eliminated via separation, precipitation, filtration, capture, and/or chromatography.

184. The method of any one of paragraphs 174-183, wherein the polyphosphate kinase, the nucleoside kinase, the NDP kinase, the DNA template, and/or the polymerase is prepared from cells that express the polyphosphate kinase, the nucleoside kinase, the NDP kinase, the DNA template, and/or the polymerase.

185. The method of any one of paragraphs 174-183, wherein the reaction mixture of step (c) comprises a cell lysate prepared from cells that express the polyphosphate kinase, the nucleoside kinase, the NDP kinase, the DNA template, and/or the polymerase.

186. The method of paragraph 185, wherein native enzymatic activity of enzymes in the cell lysate of step (c) have been eliminated.

187. The method of paragraph 186, wherein native enzymatic activity of enzymes in the cell lysate have been eliminated via genetic modification, enzyme secretion from a cell, and/or protease targeting.

188. The method of paragraph 186 or 187, wherein native enzymatic activity of enzymes in the cell lysate have been eliminated via temperature, pH, salt, detergent, alcohol, and/or chemical inhibitors.

189. The method of any one of paragraphs 186-188, wherein native enzymatic activity of enzymes in the cell lysate have been eliminated via separation, precipitation, filtration, capture, and/or chromatography.

190. The method of any one of paragraphs 186-189, wherein the native enzymatic activities are selected from phosphatases, nucleases, proteases, deaminases, oxidoreductases, and hydrolases.

191. The method of any one of paragraphs 186-190, wherein the polyphosphate kinase, the nucleoside kinase, the NDP kinase, and/or the polymerase can withstand elimination conditions.

192. The method of any one of paragraphs 174-191, wherein the polymerase comprises a RNA polymerase.

193. A method for producing ribonucleic acid (RNA), comprising:
(a) incubating in a reaction mixture cellular ribonucleic acid (RNA), a polynucleotide phosphorylase (PNPase), inorganic phosphate, a polyphosphate kinase, a polyphosphate, a DNA template encoding a RNA of interest, and a polymerase under conditions appropriate for the production of nucleoside diphosphates, optionally wherein the reaction mixture further comprises a nucleoside kinase and/or a NDP kinase;
(b) eliminating the PNPase; and
(c) incubating the reaction mixture under conditions appropriate for the production of the RNA of interest.

194. The method of paragraph 193, wherein the cellular RNA comprises ribosomal RNA, messenger RNA, and/or transfer RNA.

195. The method of paragraph 193 or 194, wherein the cellular RNA is from a unicellular organism or a multicellular organism.

196. The method of any one of paragraphs 193-195, wherein the polyphosphate kinase is selected from PPK1 family enzymes and PPK2 family enzymes.

197. The method of paragraph 196, wherein the polyphosphate kinase comprises a Class III polyphosphate kinase 2 from *Deinococcus geothermalis*.

198. The method of any one of paragraphs 193-197, wherein the polyphosphate comprises hexametaphosphate.

199. The method of any one of paragraphs 193-198, wherein the PNPase, the polyphosphate kinase, the nucleoside kinase, the NDP kinase, the DNA template, and/or the polymerase is prepared from cells that express the PNPase, the polyphosphate kinase, the nucleoside kinase, the NDP kinase, the DNA template, and/or the polymerase.

200. The method of any one of paragraphs 193-199, wherein the reaction mixture of (a) comprises a cell lysate prepared from cells that express the PNPase, the polyphosphate kinase, the nucleoside kinase, the NDP kinase, the DNA template, and/or the polymerase.

201. The method of paragraph 200, wherein step (b) comprises eliminating the PNPase and native enzymatic activities in the cell lysate via temperature, pH, salt, detergent, alcohol, and/or chemical inhibitors.

202. The method of paragraph 200 or 201, wherein step (b) comprises eliminating the PNPase and native enzymatic activities in the cell lysate via separation, precipitation, filtration, capture, and/or chromatography.

203. The method of any one of paragraphs 200-202, wherein step (b) comprises eliminating native enzymatic activities in the cell lysate via genetic modification, enzyme secretion from a cell, and/or protease targeting.

204. The method of any one of paragraphs 201-203, wherein the native enzymatic activities are selected from phosphatases, nucleases, proteases, deaminases, oxidoreductases, and hydrolases.

205. The method of any one of paragraphs 201-204, wherein the polyphosphate kinase, the nucleoside kinase, the NDP kinase, and/or the polymerase can withstand elimination conditions.

206. The method of any one of paragraphs 193-205, wherein the polymerase comprises a RNA polymerase.

207. A method for producing ribonucleic acid (RNA), comprising:
(a) incubating in a reaction mixture cellular ribonucleic acid (RNA) and a ribonuclease under conditions appropriate for the production of 5' nucleoside monophosphates (5' NMPs);
(b) eliminating the ribonuclease; and
(c) incubating in the reaction mixture, or in a second reaction mixture, the 5' NMPs, a polyphosphate kinase, a polyphosphate, a DNA template encoding a RNA of interest, and a polymerase under conditions appropriate for the production of the RNA of interest, optionally wherein the reaction mixture of step (c) further comprises a nucleoside kinase, a NMP kinase, and/or a NDP kinase.

208. The method of paragraph 207, wherein the cellular RNA comprises ribosomal RNA, messenger RNA, and/or transfer RNA.

209. The method of paragraph 207 or 208, wherein the cellular RNA is from a unicellular organism or a multicellular organism.

210. The method of any one of paragraphs 207-209, wherein the polyphosphate kinase is selected from PPK1 family enzymes and PPK2 family enzymes.

211. The method of paragraph 210, wherein the polyphosphate kinase comprises a Class III polyphosphate kinase 2 from *Deinococcus geothermalis*.

212. The method of any one of paragraphs 207-211, wherein the polyphosphate comprises hexametaphosphate.

213. The method of any one of paragraphs 207-212, wherein the ribonuclease is prepared from cells that express the ribonuclease.

214. The method of any one of paragraphs 207-213, wherein the reaction mixture of (a) comprises a cell lysate prepared from cells that express the ribonuclease.

215. The method of paragraph 214, wherein step (b) comprises eliminating the ribonuclease via temperature, pH, salt, detergent, alcohol, and/or chemical inhibitors.

216. The method of paragraph 214 or 215, wherein step (b) comprises eliminating the ribonuclease via separation, precipitation, filtration, capture, and/or chromatography.

217. The method of any one of paragraphs 207-216, wherein the polyphosphate kinase, the nucleoside kinase, the NMP kinase, the NDP kinase, the DNA template, and/or the polymerase is prepared from cells that express the polyphosphate kinase, the nucleoside kinase, the NMP kinase, the NDP kinase, the DNA template, and/or the polymerase.

218. The method of any one of paragraphs 207-216, wherein the reaction mixture of step (c) comprises a cell lysate prepared from cells that express the polyphosphate kinase, the nucleoside kinase, the NMP kinase, the NDP kinase, the DNA template, and/or the polymerase.

219. The method of paragraph 218, wherein native enzymatic activity of enzymes in the cell lysate of step (c) have been eliminated.

220. The method of paragraph 219, wherein native enzymatic activity of enzymes in the cell lysate have been eliminated via genetic modification, enzyme secretion from a cell, and/or protease targeting.

221. The method of paragraph 219 or 220, wherein native enzymatic activity of enzymes in the cell lysate have been eliminated via temperature, pH, salt, detergent, alcohol, and/or chemical inhibitors.

222. The method of any one of paragraphs 219-221, wherein native enzymatic activity of enzymes in the cell lysate have been eliminated via separation, precipitation, filtration, capture, and/or chromatography.

223. The method of any one of paragraphs 219-222, wherein the native enzymatic activities are selected from phosphatases, nucleases, proteases, deaminases, oxidoreductases, and hydrolases.

224. The method of any one of paragraphs 219-223, wherein the polyphosphate kinase, the nucleoside kinase, the NMP kinase, the NDP kinase, and/or the polymerase can withstand elimination conditions.

225. The method of any one of paragraphs 207-224, wherein the polymerase comprises at least on RNA polymerase.

226. A method for producing ribonucleic acid (RNA), comprising:
(a) incubating in a reaction mixture cellular ribonucleic acid (RNA), a ribonuclease, a polyphosphate kinase, a polyphosphate, a DNA template encoding a RNA of interest, and a polymerase under conditions appropriate for the production of 5' nucleoside monophosphates (5' NMPs);
(b) eliminating the ribonuclease; and
(c) incubating the reaction mixture under conditions appropriate for the production of the RNA of interest.

227. The method of paragraph 226, wherein the cellular RNA comprises ribosomal RNA, messenger RNA, and/or transfer RNA.

228. The method of paragraph 226 or 214, wherein the cellular RNA is from a unicellular organism or a multicellular organism.

229. The method of any one of paragraphs 226-228, wherein the polyphosphate kinase is selected from PPK1 family enzymes and PPK2 family enzymes.

230. The method of paragraph 229, wherein the polyphosphate kinase comprises a Class III polyphosphate kinase 2 from *Deinococcus geothermalis*.

231. The method of any one of paragraphs 226-230, wherein the polyphosphate comprises hexametaphosphate.

232. The method of any one of paragraphs 226-231, wherein the ribonuclease, the polyphosphate kinase, the nucleoside kinase, the NMP kinase, the NDP kinase, the DNA template, and/or the polymerase is prepared from cells that express the ribonuclease, the polyphosphate kinase, the nucleoside kinase, the NMP kinase, the NDP kinase, the DNA template, and/or the polymerase.

233. The method of any one of paragraphs 227-232, wherein the reaction mixture of (a) comprises a cell lysate prepared from cells that express the ribonuclease, the polyphosphate kinase, the nucleoside kinase, the NMP kinase, the NDP kinase, the DNA template, and/or the polymerase.

234. The method of paragraph 233, wherein step (b) comprises eliminating the ribonuclease and native enzymatic activities in the cell lysate via temperature, pH, salt, detergent, alcohol, and/or chemical inhibitors.

235. The method of paragraph 233 or 234, wherein step (b) comprises eliminating the ribonuclease and native enzymatic activities in the cell lysate via separation, precipitation, filtration, capture, and/or chromatography.

236. The method of any one of paragraphs 233-235, wherein step (b) comprises eliminating native enzymatic activities in the cell lysate via genetic modification, enzyme secretion from a cell, and/or protease targeting.

237. The method of any one of paragraphs 234-236, wherein the native enzymatic activities are selected from phosphatases, nucleases, proteases, deaminases, oxidoreductases, and hydrolases.

238. The method of any one of paragraphs 234-237, wherein the polyphosphate kinase, the nucleoside kinase, the NMP kinase, the NDP kinase, and/or the polymerase can withstand elimination conditions.

239. The method of any one of paragraphs 226-238, wherein the polymerase comprises a RNA polymerase.

EXAMPLES

Example 1—Cell-Free Synthesis of RNA Starting from Either Lysate RNA or Purified *E. coli* RNA Materials and Methods
Strains and Lysates

*E. coli* strain BL21(DE3) was transformed with pET-Duet-1 vectors encoding codon-optimized versions of the following enzymes: RNase R ($K_{544}R$) from *E. coli* (EcRNR), UMP kinase from *Pyrococcus furiosus* (PfPyrH), CMP kinase from *Thermus thermophilus* (TthCmk), GMP kinase from *Thermotoga maritima* (TmGmk), NDP kinase from *Aquifex aeolicus* (AaNdk), and Class III polyphosphate kinase 2 from *Deinococcus geothermalis* (DgPPK2). All enzymes, except for DgPPK2, contained N-terminal hexahistidine tags. The resulting strains were grown in a 37° C. batch fermentation process in Korz media supplemented with 40 g/L glucose and 50 mg/L carbenicillin until $OD_{600}=20$, induced with 0.8 mM isopropyl β-D-1-thiogalactopyranoside (IPTG), and grown for an additional 1 hour before harvest via centrifugation. After harvest, biomass pellets were stored at −80° C.

Biomass pellets were then used to prepare cell lysates. Lysates were prepared by thawing biomass pellets on ice, then resuspending in 1.5 volumes resuspension buffer. For the strain expressing EcRNR, biomass was resuspended in 58.8 mM potassium phosphate dibasic. For strains expressing PfPyrH, TthCmk, TmGmk, and AaNdk, biomass was resuspended in 50 mM Tris-HCl (pH 8.5) with 50 mM NaCl.

For the strain expressing DgPPK2, biomass was resuspended in 100 mM MOPS-NaOH (pH 7.0). For all strains, biomass was lysed by 2-3 passes of mechanical homogenization at 15,000 psi at 4° C. Lysates were then clarified by centrifugation at 16,000×g for 1 hour at 4° C.

Extraction and Purification of E. coli RNA

RNA was extracted and purified from high-density E. coli lysates (protein concentration: 40-50 mg/mL) according to established protocols (Mohanty, B. K., Giladi, H., Maples, V. F., & Kushner, S. R. (2008). Analysis of RNA decay, processing, and polyadenylation in Escherichia coli and other prokaryotes. Methods in Enzymology, 447, 3-29).

Protein Expression and Purification

E. coli strain BL21(DE3) was transformed with a pBAD24 vector encoding a thermostable mutant T7 RNA polymerase with an N-terminal hexahistidine tag. The resulting strain was cultivated in baffled shake flasks using lysogeny broth (LB) media supplemented with 50 mg/L carbenicillin. Cultures were grown at 37° C. with shaking until OD600=0.6, then induced with 0.2% (w/v) L-arabinose and grown for an additional 4 hours. Biomass was then harvested by centrifugation and stored at −80° C. prior to lysis. Lysates were prepared by thawing biomass pellets on ice, resuspending in 1.5 volumes equilibration/wash buffer (20 mM sodium phosphate pH 7.4, 500 mM sodium chloride, 30 mM imidazole), and 2-3 passes of mechanical homogenization at 15,000 psi and 4° C. Lysates were then clarified by centrifugation. Recombinant protein was purified by fast protein liquid chromatography (FPLC) using an AKTAPrime Plus equipped with a HisTrap HP column (GE Healthcare Life Sciences) following standard protocols. Fractions containing recombinant protein were then combined and buffer exchanged by dialysis into 2× phosphate buffered saline (PBS) supplemented with 5 mM DTT and 0.01% Triton X-100. Post-dialysis, protein stocks were diluted with an equal volume of glycerol and stored at −20° C.

For E. coli RNase R, cultures were grown, expression was induced, and lysates were prepared following the protocols described herein. The enzyme was then purified following the protocols described herein, except that the purified enzyme was buffer-exchanged by dialysis into 2×PBS supplemented with 500 mM NaCl prior to mixing with glycerol.

DNA Template Preparation

Linear DNA templates were amplified from synthetic DNA by PCR and purified using solid-phase reversible immobilization (SPRI) on paramagnetic beads. Plasmid DNA templates were prepared by cloning the sequence of interest into a suitable plasmid vector, transforming the resulting plasmid into E. coli strain DH10b, culturing the transformants in LB media, and purifying the plasmids using Plasmid Maxi or Giga kits (Qiagen).

Cell-Free RNA Synthesis from Lysate RNA

Lysates expressing EcRNR, TthCmk, PfPyrH, TmGmk, AaNdk, and DgPPK2 were each diluted to 42 mg/mL in 50 mM Tris, 50 mM NaCl (pH 7.0), then combined in equal proportion. Depolymerization of RNA in the lysates was initiated by adding an equal volume of 3 mM ethylenediaminetetraacetic acid (EDTA) in 50 mM Tris, 50 mM NaCl (pH 7.0) and incubating at 37° C. for 15 minutes. Depolymerization was monitored by quantifying acid-soluble nucleotides by absorbance at 260 nm. Magnesium sulfate and sodium hexametaphosphate were added to the lysates to final concentrations of 30 mM and 1 mM, respectively, then the lysates were incubated at 70° C. for 15 minutes to inactivate EcRNR and endogenous E. coli enzymes. After 15 minutes, the temperature was reduced to 50° C. and the reaction was assembled with the following composition:

TABLE 11

Reaction Conditions

| | |
|---|---|
| Magnesium sulfate | 30 mM |
| Sodium hexametaphosphate | 4 mM |
| Kinase lysates | 21 g/L total protein |
| Spermidine | 2 mM |
| Template DNA | 25 mg/L |
| RNA polymerase | 0.3 g/L |

Reactions were incubated at 50° C. for 2 hours, treated with TURBO DNase (Thermo Fisher), and analyzed by agarose gel electrophoresis.

Cell-Free RNA Synthesis from Purified E. coli RNA

Purified E. coli RNA (approximately 8 g/L) was depolymerized by incubating with 1 g/L purified E. coli RNase R in a buffer containing 50 mM Tris-HCl (pH 7.0), 50 mM sodium chloride, and 2 mM magnesium sulfate. The depolymerization reaction was incubated at 37° C. for 30 minutes and monitored by quantifying acid-soluble nucleotides by absorbance at 260 nm. After 30 minutes, the depolymerization reaction was combined with the TthCmk, TmGmk, PfPyrH, AaNdk, and DgPPK2 lysates each diluted in 50 mM Tris-HCl (pH 7.0), 50 mM NaCl, and mixed in equal proportion. Magnesium sulfate and sodium hexametaphosphate were then added to final concentrations of 30 mM and 1 mM, respectively, and the reaction heated to 70° C. for 15 minutes. After heat inactivation, reactions were assembled as described herein with the following composition:

TABLE 12

Reaction Conditions

| | |
|---|---|
| Magnesium sulfate | 30 mM |
| Sodium hexametaphosphate | 4 mM |
| Kinase lysates | 13 g/L total protein |
| Spermidine | 2 mM |
| Template DNA | 25 mg/L |
| RNA polymerase | 0.3 g/L |

Results

Figure 8A:
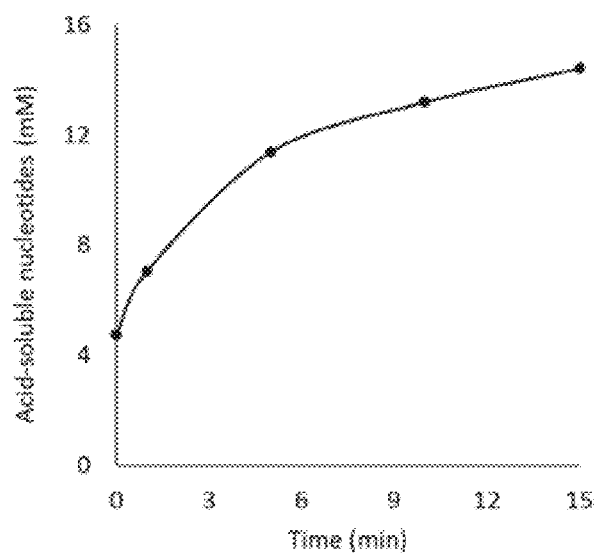
FIG. 8A shows a graph of acid-soluble nucleotides (mM) produced over time during depolymerization of RNA from *E. coli* lysates using overexpressed RNase R. Acid-soluble nucleotides were measured by UV absorbance.
Figure 8B:
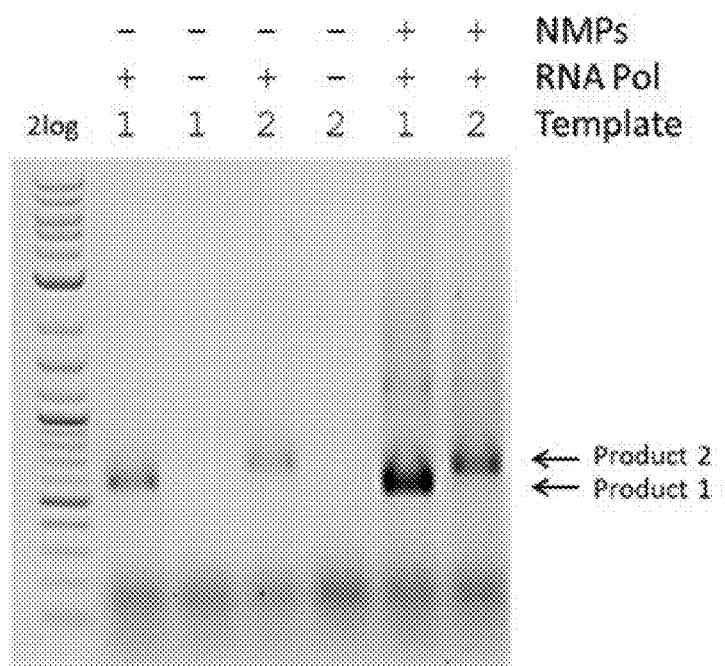
FIG. 8B shows an agarose gel of RNA products produced in reactions comprising RNA polymerase and NMPs produced by depolymerization (−NMPs) or purified NMPs (+NMPs, 4 mM each). Abbreviations: −2 log: 2-log DNA ladder (New England Biolabs), NMPs: equimolar mix of 5'-NMPs, RNA Pol: thermostable T7 RNA polymerase, Template 1: Linear DNA template, Template 2: Plasmid DNA template.

Cell-free synthesis of RNA was performed using lysate RNA as a substrate. RNA from pooled lysates overexpressing pathway enzymes was first depolymerized by overexpressed E. coli RNase R (EcRNR), an exonuclease that produces 5' NMPs. Depolymerization was rapid, producing approximately 14 mM acid-soluble nucleotides after 15 minutes (FIG. 8A). The lysate mix containing pathway enzymes and 5' NMPs was then heat treated to inactivate EcRNR and endogenous E. coli enzymes, while the thermostable pathway enzymes remained active. After heat inactivation, the RNA synthesis reaction was assembled, incubated at 50° C., and visualized on an agarose gel (FIG. 8B). Reactions with two different templates, including a linear PCR product (Template 1) and a hairpin template encoded on a plasmid (Template 2), yielded distinct bands on an agarose gel (FIG. 8B). No bands were observed in the conditions without RNA polymerase. As a positive control, reactions were performed where purified 5' NMPs (4 mM each AMP, CMP, GMP, and UMP) were added. These reactions produced products that migrated at the same size as reactions using NMPs produced by depolymerizing RNA.

Figure 9A:
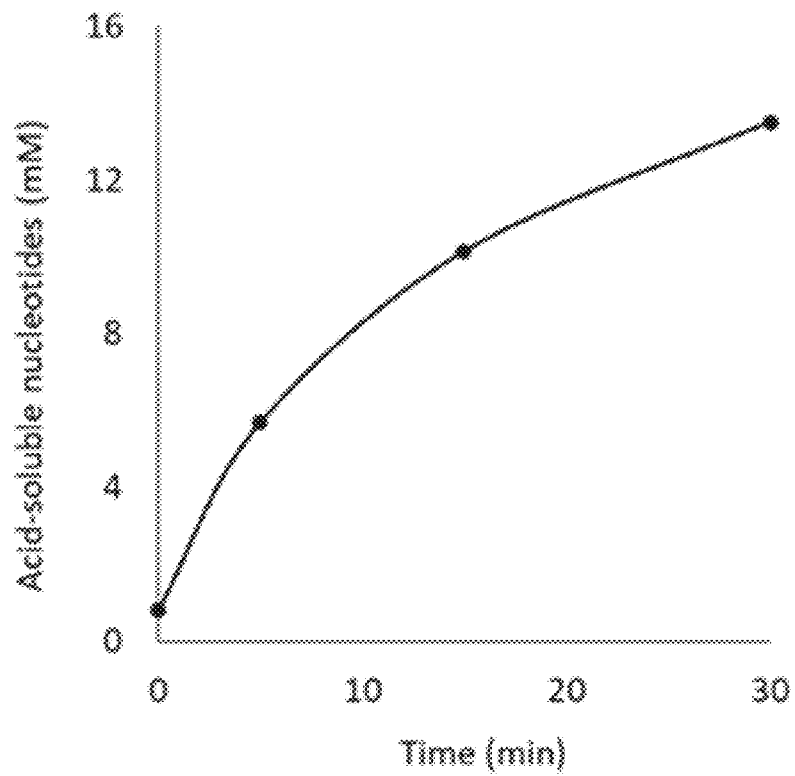
FIG. 9A shows a graph of acid-soluble nucleotides (mM) produced over time during depolymerization of purified RNA using 1 mg/mL purified RNase R. Acid-soluble nucleotides were measured by UV absorbance.
Figure 9B:
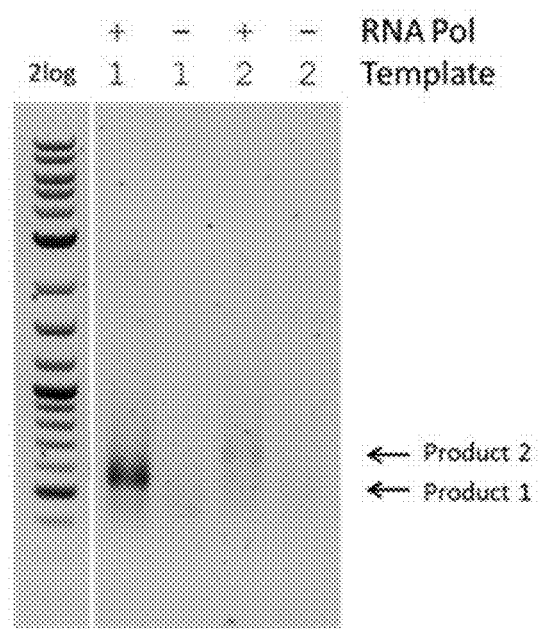
FIG. 9B shows an agarose gel of RNA products produced in reactions comprising RNA polymerase and NMPs produced by depolymerization of purified RNA. As a negative control, reaction were performed in the absence of RNA polymerase. Abbreviations: −2 log: 2-log DNA ladder (New England Biolabs), NMPs: equimolar mix of 5'-nucleoside monophosphates, RNA Pol: thermostable T7 RNA polymerase, Template 1: Linear DNA template, Template 2: Plasmid DNA template.

Cell-free synthesis of RNA was also performed using purified *E. coli* RNA as substrate. RNA was first incubated with purified *E. coli* RNase R ($K_{544}R$) to release 5' NMPs (FIG. 9A). After 30 minutes, the depolymerization reaction was combined with a lysate mix containing pathway enzymes and heat treated to inactivate EcRNR and endogenous *E. coli* enzymes, while the thermostable pathway enzymes remained active. After heat inactivation, the RNA synthesis reaction was assembled, incubated at 50° C., and visualized on an agarose gel (FIG. 9B). Reactions with two different templates, including a linear PCR product (Template 1) and a hairpin template encoded on a plasmid (Template 2), yielded defined bands on an agarose gel, though yields appeared lower for Template 2 (FIG. 9B). Again, no bands were observed in the conditions without RNA polymerase.

Taken together, these results demonstrate that cell-free RNA synthesis can be used to produce an RNA of interest from a variety of NMP source material, including high-purity purchased NMPs, NMPs produced by enzymatic depolymerization of lysate RNA, and NMPs produced by enzymatic depolymerization of purified RNA.

Example 2—Cell-Free Synthesis of RNA Using a Non-Thermostable Wild-Type Polymerase or a Thermostable Polymerase Mutant, and Purified NMPs as a Substrate Materials and Methods Biomass, lysates, purified proteins, and DNA template were prepared as described herein. Cell-free synthesis of RNA was performed essentially as described in Example 1, except that EcRNR was omitted and 4 mM each AMP, CMP, GMP, and UMP were added to the reaction.

Results

Figure 10:
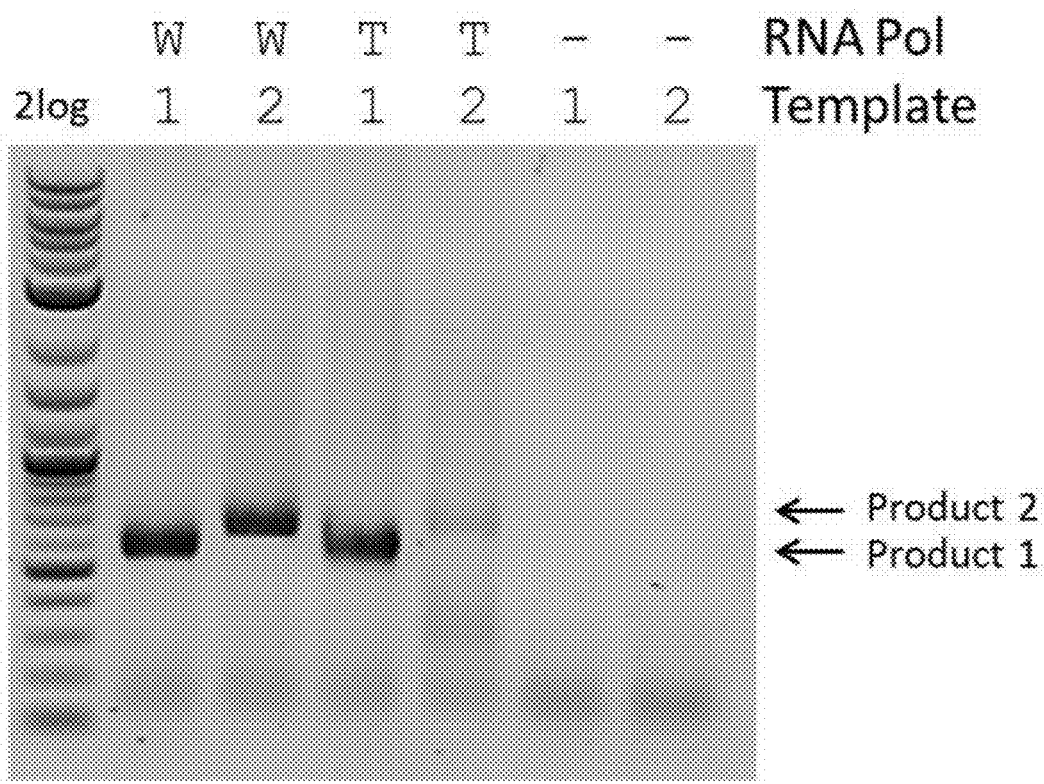
FIG. 10 shows an agarose gel of RNA products produced by cell-free RNA synthesis using a wild-type polymerase (W) or a thermostable polymerase mutant (T) at 37° C. Abbreviations: −2 log: 2-log DNA ladder (New England Biolabs), W: wild-type T7 RNA polymerase (New England Biolabs), T: thermostable T7 RNA polymerase, Template 1: Linear DNA template, Template 2: Plasmid DNA template.

Cell-free synthesis of RNA was performed using purified NMPs as a substrate at a 37° C. reaction temperature. Lysates containing pathway enzymes were assembled and heat treated to inactivate endogenous *E. coli* enzymes, while the thermostable pathway enzymes remained active. After heat inactivation, the reaction was assembled using either wild-type T7 RNA polymerase or a thermostable mutant, incubated at 37° C. for 2 hours, and visualized on an agarose gel (FIG. 10). Reactions with two different templates, including a linear PCR product (Template 1) and a hairpin template encoded on a plasmid (Template 2), yielded distinct bands with both polymerases. At 37° C., RNA yield (based on gel band intensity) appeared greater with the wild-type polymerase than the thermostable mutant, especially with Template 2. No bands were observed in the conditions without RNA polymerase.

These results demonstrate that the RNA polymerase used for cell-free RNA synthesis does not need to be thermostable, and that RNA can be produced using a wild-type T7 RNA polymerase in a 37° C. reaction.

Example 3—Cell-Free Synthesis of RNA Using a Class III Polyphosphate Kinase 2 from *Deinococcus geothermalis* (DgPPK2) and NMPs as a Substrate Materials and Methods Cell-free RNA synthesis reactions were assembled essentially as described in Example 2, with the following composition:

TABLE 13

| Reaction Conditions | |
| --- | --- |
| Magnesium sulfate | 45 mM |
| Sodium hexametaphosphate | 13 mM |
| DgPPK2 lysate | 7 g/L total protein |
| Template DNA | 50 mg/L |
| Spermidine | 2 mM |
| RNA polymerase | 0.3 g/L |

As a positive control, a 5-enzyme lysate system containing uridylate kinase, cytidylate kinase, guanylate kinase, nucleotide diphosphate kinase and a polyphosphate kinase was used in the reaction according to Examples 1-2. The dsRNA synthesized in the reactions was purified via an adapted RNASwift extraction protocol and quantitated using a reverse phase ion pair chromatography as described herein (Nwokeji, A. O., Kilby, P. M., Portwood, D. E., & Dickman, M. J. (2016). RNASwift: A rapid, versatile RNA extraction method free from phenol and chloroform. *Analytical Biochemistry*, 512, 36-46).

Results

Cell-free synthesis of RNA was performed in reactions comprising DgPPK2 as the sole kinase in the reaction, and NMPs as a substrate. As a positive control, RNA was synthesized in the presence of the 5-enzyme lysate system containing uridylate kinase, cytidylate kinase, guanylate kinase, nucleotide diphosphate kinase, and polyphosphate kinase. Control reaction were performed in the absence of polymerase.

Figure 11A:
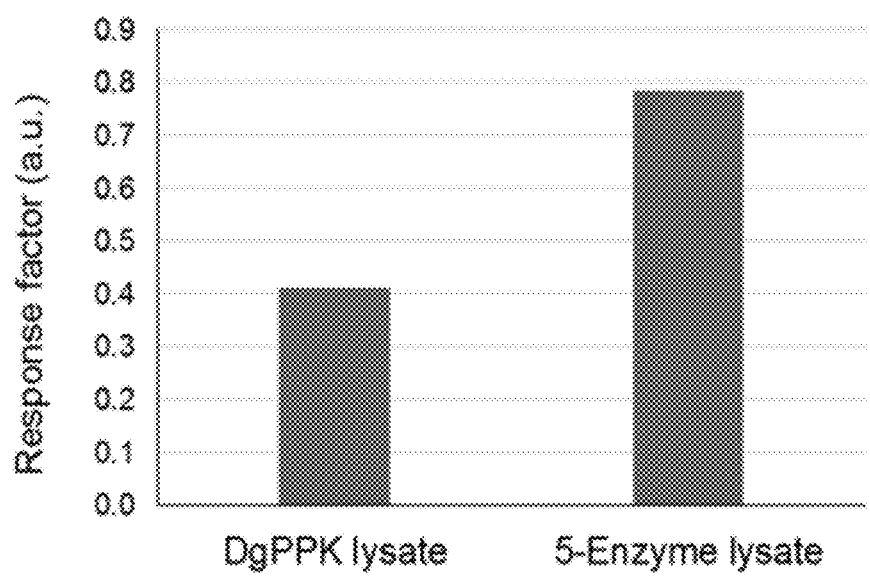
FIG. 11A shows a plot of the response factor (calculated as ratio of area of the dsRNA of interest to that of a commercially-available dsRNA internal standard) of the reactions comprising either DgPPK2 as a sole kinase or the 5-enzyme lysate system.
Figure 11B:
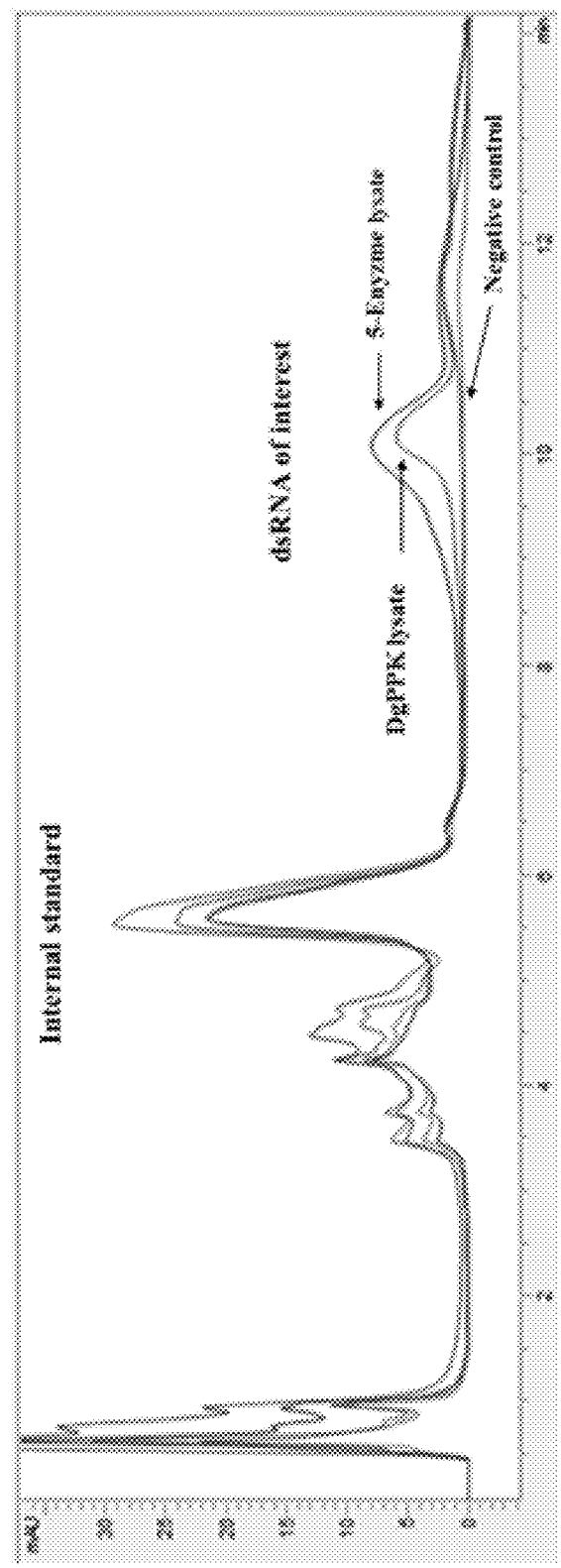
FIG. 11B shows HPLC chromatograms of the dsRNA product produced in reactions comprising DgPPK2 lysate, 5-enzyme lysate system, and the negative controls without T7 RNA polymerase.

The response factor for each reaction was determined. The response factor was calculated as ratio of area of the dsRNA of interest to that of a commercially-available dsRNA internal standard. Comparison of the response factors demonstrated that reactions containing DgPPK2 as the sole kinase synthesized ~48% of the dsRNA synthesized that was synthesized in reactions containing the 5-enzyme lysate system (FIG. 11A). The dsRNA product synthesized in the DgPPK2 reaction and the 5-enzyme lysate system reaction were analyzed by HPLC. The HPLC chromatograms of the dsRNA product from the reactions were similar demonstrating that the dsRNA product produced by the DgPPK2-only system was similar to the product produced by the 5-enzyme system (FIG. 11B).

Taken together, these results demonstrate that the DgPPK2 could be used as a sole kinase to synthesize cell-free dsRNA from NMPs or NDPs.

Example 4—Depolymerization of RNA from Various Sources Using Purified RNase R or Purified Nuclease P1

Materials and Methods

Extraction and Purification of RNA and Nuclease

RNA was extracted and purified from high-density *E. coli* lysates (protein concentration: 40-50 mg/mL) according to established protocols (Mohanty, B. K., Giladi, H., Maples, V. F., & Kushner, S. R. (2008). Analysis of RNA decay, processing, and polyadenylation in *Escherichia coli* and other prokaryotes. *Methods in Enzymology*, 447, 3-29).

RNA from *Vibrio* was purified from *V. natriegens* cell broth using RNASwift Protocol (Nwokeji, A. O., Kilby, P. M., Portwood, D. E., & Dickman, M. J. (2016). RNASwift: A rapid, versatile RNA extraction method free from phenol and chloroform. *Analytical Biochemistry*, 512, 36-46).

Yeast derived RNA extract was purchased from commercial sources. The RNA powder was ~85% to ~90% pure and required no further purification. RNase R was purified from an *E. coli* strain overexpressing RNase R and grown to high cell density. Proteins were purified by immobilized metal affinity chromatography using HisTrap HP columns connected to an AKTAPrime Plus FPLC system (GE Healthcare). Purified Nuclease P1, a 5' phosphodiesterase, was obtained from commercial sources.

Depolymerization of RNA with Exogenous Nuclease

*E. coli* RNA, *V. natriegens* RNA, Yeast derived RNA powder resuspended in nuclease-free water (RNA content of 11 mg/mL), RNase R solution (1 mg/mL in 300 mM potassium phosphate buffer pH 7.4, 200 mM KCl, 2 mM $MgCl_2$) and Purified Nuclease P1 (also referred 5' phosphodiesterase) (1-2 mg/mL in 100 mM potassium phosphate buffer pH 7.4, 1 mM $ZnCl_2$, 10 mM $MgCl_2$) were pre-equilibrated at 2° C. before initiating the reaction. At time t=0, 50 μL of RNA and 50 μL nuclease solution were mixed and the reaction initiated by transferring to a preheated 37° C. block. After initiation, reactions were incubated at 37° C. and periodically sampled by transferring 10 μL to acid quench solution (90 μL of 0.2M sulfuric acid) on ice. After completion of the time course, quenched samples were clarified by centrifugation at 3,200×g for 20 minutes at 2° C. Depolymerization was first quantified by absorbance of acid-soluble nucleotides at 260 nm. The total nucleotide pool (e.g., 100% depolymerization) was determined by alkaline hydrolysis of RNA: 50 μL RNA was combined with 150 μL of 0.2M potassium hydroxide, then heated to 99° C. for 20 minutes. Alkaline-hydrolyzed samples were then quenched and analyzed as described above. Depolymerization was also quantified by LC-MS analysis of 5', 2', and 3' NMPs: 10 μL of sample was quenched in 30 μL 100% acetonitrile and diluted into 500 μL of deionized water containing 10 μM adipic acid used as internal standard. The sample was then centrifuged and passed through a 0.2 μm filter before LC-MS analysis.

Nucleotide Analysis

Analysis of 2', 3', and 5' NMPs was performed by mass spectrometry and liquid chromatography using an ABSCIEX API 5000 Mass spectrometer and a standard Agilent 1200 HPLC equipped with Sequant Zinc-hilic column (2.1×50 mm, 3 μm i.d.). The mobile phases consisted of 20 mM ammonium acetate in 90% acetonitrile (A) and 20 mM ammonium acetate in 10% acetonitrile (B). The separation method consisted of the following: starting gradient of 6% B followed by a gradient to 8.5% B over 600 seconds, a gradient to 13% B over 400 seconds, followed by a gradient from to 20% B over 60 seconds, a wash at 50% B for 60 seconds, and finally, re-equilibration at 6% B for 220 seconds. Quantitation was performed in negative mode electro-spray ionization (ESI) using the following mass spec transitions: 2'3'5' AMP: 346.1-134.1, 2'3'5' UMP: 323.0-97, 2'3'5' CMP: 322-97, 2'3'5' GMP: 362.1-211. Peak areas were compared to standard curves consisting of purified compounds (purchased from Sigma-Aldrich except for 2' and 3' CMP, UMP, and GMP which were purchased from Biolog Life Science Institute) and normalized to an internal standard (adipic acid) that was spiked into the samples prior to analysis. For analysis of samples, standard curves were prepared in deionized water, diluted with internal standard and filtered as in the sample preparation steps described herein.

Results

Figure 12A:
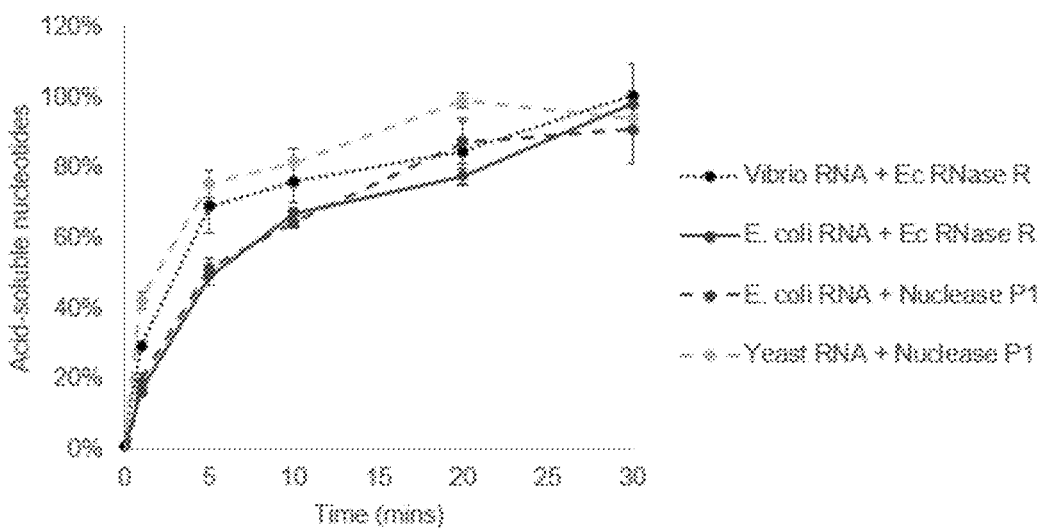
FIG. 12A shows a graph of acid-soluble nucleotides (mM) produced over time during depolymerization of various sources of RNA using purified RNase R or Nuclease P1. Acid-soluble nucleotides were measured by UV absorbance.
Figure 12B:
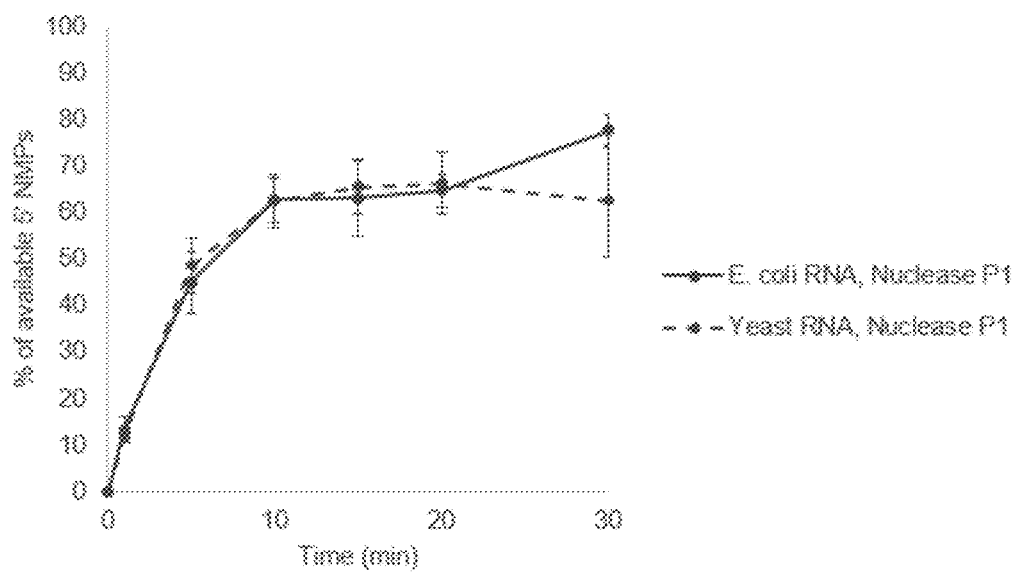
FIG. 12B shows a graph of the percent of available 5'-NMPs produced over time during depolymerization of RNA from E. coli or yeast using Nuclease P1. Percent of available 5'-NMPs was determined by LC-MS.

*V. natriegens* RNA was digested using purified *E. coli* RNase R, and *E. coli* RNA and yeast-derived RNA extract were digested using both *E. coli* RNase R and Nuclease P1. Depolymerization was monitored by release of acid-soluble nucleotides. Treatment of *E. coli* and *V. natriegens* RNA with RNase R showed a time-dependent conversion of RNA to acid-soluble nucleotides reaching ~98 to ~100% depolymerization after 30 minutes of incubation (FIG. 12A). Treatment of yeast-derived RNA extract reached ~94% depolymerization with Nuclease P1 (FIG. 12A). Also, treatment of *E. coli* RNA with Nuclease P1 resulted in ~90% depolymerization (FIG. 12A). Subsequent analyses by LC-MS revealed release of 5' NMPs in *E. coli* RNA and yeast-derived RNA extract treated with Nuclease P1 (FIG. 12B)

These results demonstrate that varying sources of RNA (e.g., Vibrio RNA, *E. coli* RNA, and yeast RNA) can be digested to 5' NMP using different nucleases (e.g., RNase R and Nuclease P1).

Example 5—Effects of Temperature and Lysate Inactivation on RNA Depolymerization Materials and Methods Strains and Lysates Strain GL17-086 (BL21(DE3).ΔtolC.Δph[DE3]1+2*.Δph[285p]*.ΔfhuA*.ΔlamB*ma::tolC) and strain GL17-109 (BL21(DE3). ΔtolC.Δph[DE3]1+2*.Δph[285p]*.ΔfhuA*.ΔlamB*.Δrna*.ΔphoA*.ΔappA*.Δamn*.ΔnagD*.ΔushA::tolC) were used in the study described herein. For both strains, 1 L cultures were grown under batch-growth conditions in KORZ media (5 g/L $(NH_4)_2SO_4$, 15.7 g/L $K_2HPO_4$, 4.2 g/L $KH_2PO_4$, 1.7 g/L citric acid, 0.6 g/L $MgSO_4$, 0.1% Thiamine-HCl, 0.01% Pluronic, trace metals, and 40 g/L glucose) for approximately seven hours. After growth the cells were centrifuged at 6000 g for 20 minutes and then stored at −80° C. Frozen biomass was thawed in 1.5× volumes of a 58.8 mM dibasic potassium phosphate solution and lysed by passing through an EmulsiFlex C3 homogenizer (Avestin) for 3 passes, recirculating, with pulses of 15000-20000 psi. Lysate was clarified by spinning at 15000 g for 1 hour at 4° C. The lysate was then stored at −80° C. in single-use aliquots.

Analysis of RNA Polymerization Products at Various Temperatures

Frozen lysates for both strains (086 and 109) were incubated at varying temperatures to profile the RNA depolymerization products and their potential degradation. Lysate aliquots were thawed on ice and then dispensed into PCR strip-tubes. Tubes were then incubated at 40° C., 50° C., 60° C., and 70° C. up to an hour with intermittent sampling. The initial to timepoint was taken by quenching while the lysates were still on ice. For all other times, samples were quenched in 5× volumes of acetonitrile with 60 μl diluted into 500 μl of a 50 μM adipic acid solution in 50 mM ammonium acetate, and then run on an LC-QQQ. Using MRM, all four main nucleotides and their associated derivates (ATP, ADP, AMP, adenine, adenosine, GTP, GDP, GMP, guanine, guanosine, CTP, CDP, CMP, cytidine, cytosine, UTP, UDP, UMP, uridine, and uracil) were quantified at each timepoint. Base hydrolysis of lysates, where RNA is completely hydrolyzed down to NMPs, was performed by incubating the lysate in 3× volumes of 0.2M NaOH at 99° C. for 20 minutes. It was then neutralized with an equal volume of 150 mM HCl and 20 μl of this solution was diluted into 200 μl of a 50 mM ammonium acetate solution with 50 μM adipic acid. Base hydrolyzed lysate values represent 100% depolymerization. Under some conditions these lysates were incubated as-is, and in others conditions the lysates were mixed with either 0.5 mg/ml Nuclease P1 (Sigma N8630) or RNase R. RNase R was prepared as follows: cells were resuspended in 1.5× volumes of lysis buffer (50 mM potassium phosphate, pH=7.4, 500 mM NaCl, 20 mM imidazole), lysed in an EmulsiFlex C3 Homogenizer (Avestin) for three passes at 15000-25000 psi, clarified for one hour at 16000 g, 4° C. The supernatant was then purified via FPLC, then dialyzed overnight in 2×PBS. Precipitated protein post-dialysis was recovered by adding 500 mM NaCl, mixed with glycerol to yield a 50% glycerol solution for aliquoting and storing at −20° C.

Analysis of Dilution Effects and Pre-Heat-Kill Effects on RNA Depolymerization

Experiments were performed with the lysate of GL17-109, prepared as described herein. Lysates were prepared under a wide range of conditions. Common across all conditions, reactions received an added 150 mM potassium phosphate (pH=7.4), 100 mM KCl, and 0.1 mM $ZnCl_2$, and all of the following conditions were tested with RNase R, Nuclease P1, or no exogenous nuclease added. Both nuclease stock solutions were made as described previously. Depolymerization reactions were carried out under 80% and 50% lysate dilutions into water. These were screened with 0.5 or 0.31 mg/ml, respectively, of exogenous nuclease spiked in. Lysate mixtures were also prepared by making a 1 mg/ml nuclease lysate and mixing it into a non-spiked lysate yielding 0.064 and 0.04 mg/ml nuclease in 80% dilution conditions, or 0.04 and 0.025 mg/ml nuclease in 50% dilution conditions. Lastly, conditions were tested where lysates that did not contain added nuclease were heat killed at 70° C. for 15 minutes and then mixed with either purified nuclease, or the still-active 1 mg/ml nuclease lysate. Samples were incubated at 37° C. for 30 minutes and sampled by quenching in 5× volumes of acetonitrile, and diluting into 1 ml of a 50 μM adipic acid solution in 50 mM ammonium acetate. The quench solution was then spun down, filtered through a 0.2 μm filter plate, and the filtrate was run on an LC-QQQ to measure NMPs, nucleosides, and nucleobases.

Results

RNA nucleases (RNases) are known to have activity profiles that span temperature profiles more broadly than many other enzymes from mesophilic sources, occasionally showing activity up to 60° C. despite originating from an organism evolved to grow at 37° C. To evaluate the impact of elevated temperatures on RNA depolymerization in an *E. coli* lysate, two separate studies were conducted. First, lysates from two separate strains were incubated at temperatures greater than 37° C. over the course of an hour, with or without the addition of one of two RNases-RNase R or RNase P1. The second study involved eliminating a lysate to remove deleterious enzymatic activities and mixing this inactive lysate with an active lysate to study potential impacts on RNA depolymerization, or mixing exogenous nucleases into the inactivated lysate.

Figure 13:
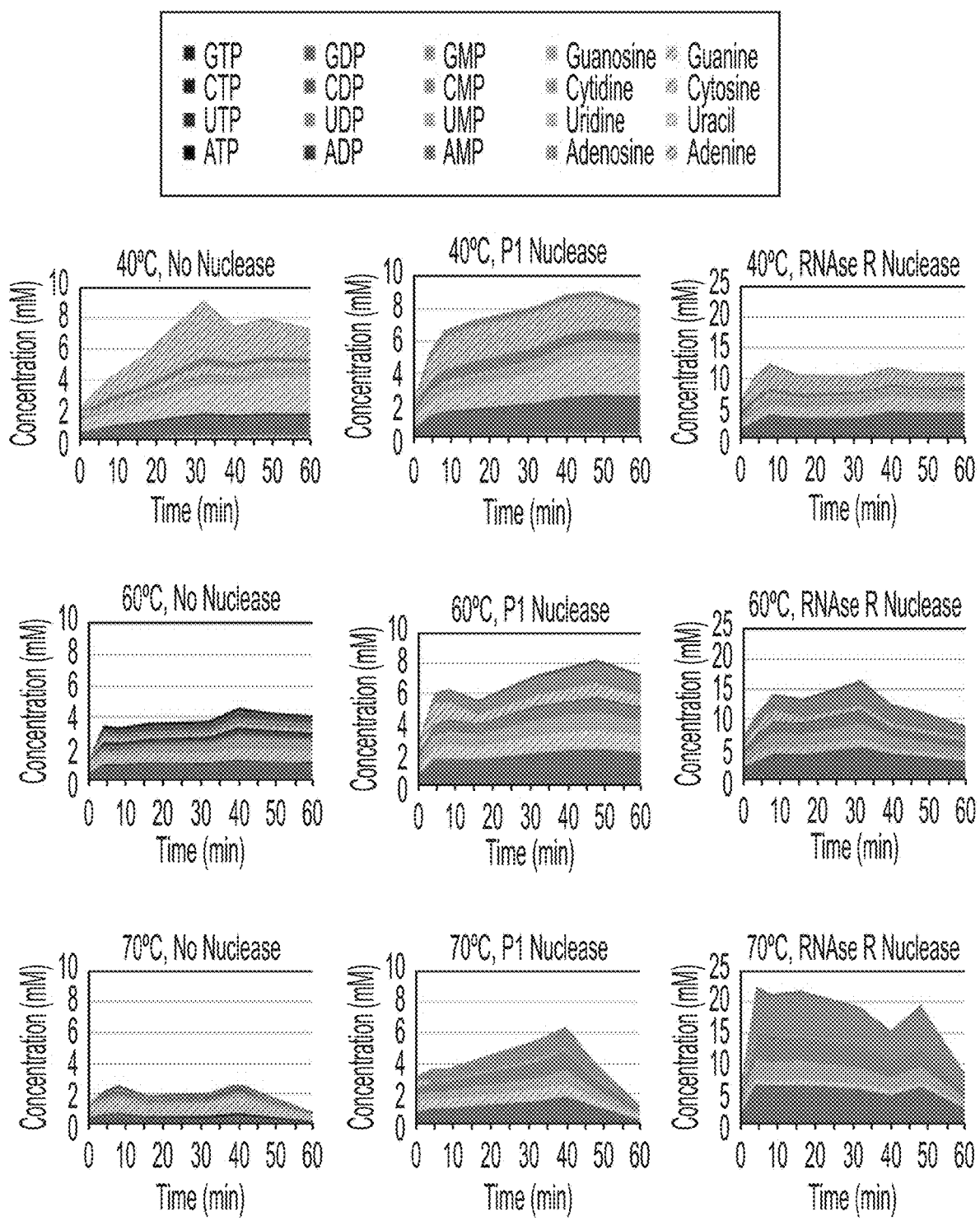
FIG. 13 shows nucleomic profile plots for RNA depolymerization across different temperatures of the lysate from GL17-109. Cumulative concentrations of the 20 analytes are shown. Nucleosides are shown in a white-speckled pattern, and were minimally produced. Data for 50° C. was collected but is not shown.

Improved depolymerization was observed when lysates were incubated at 60° C. and 70° C. (FIG. 13). Depolymerization improved in several ways. When RNA depolymerizes, it predominantly produces NMPs. In an active lysate, however, theses NMPs continue to be degraded by other enzymes, with a very large accumulation of two main products—guanosine and uracil. Incubating lysates at 60° C. and 70° C. significantly decreased the accumulation of these nucleobases, even in lysates that did not receive exogenous RNase R or Nuclease P1 (FIG. 13). As each mole of nucleobase correlates to an irreversible loss of NMPs from RNA, this demonstrated improved NMP stability in lysates. Additionally, when exogenous nuclease is added under these temperature conditions, dramatic improvement in net NMP accumulation is seen, as shown in FIG. 13 at 70° C. with RNase R added. Base hydrolysis of the GL17-109 lysate showed a maximum concentration of 32.6 mM NMPs. Correcting for dilution of the added nuclease, the accumulation of ~22 mM NMPs seen at 70° C. with RNase R is a 75% yield. Assuming that tRNA represents about 15% of the total RNA pool and that it is inaccessible to these nucleases, this would represent a 94% yield of all accessible RNA. Depolymerization in GL17-086 was poorer across the board than GL17-109, likely due to the greater phosphorylytic activity (data not shown).

The impacts of pre-heat kill and lysate dilutions showed a small benefit, but only under a more heavily diluted lysate. In this study, two types of lysates were made—a "reagent" lysate, which contains the RNA to be depolymerized, and the "catalyst" lysate, containing exogenous nuclease (RNase R or Nuclease P1). Many different conditions were evaluated, as shown in Table 14 below, to determine their impact on RNA depolymerization. Lysates that were diluted to only 80% showed similar depolymerization performance, regardless of whether portions of the lysate were heat-killed or not. However, lysates that were diluted to 50% performed slightly better when a large portion of the RNA was in an inactivated lysate. Across all of the conditions tested at this dilution, an average depolymerization yield improvement of 2.7% was observed. The performance of the depolymerization reaction under these conditions does not show a dramatic improvement, but by performing equivalently or only slightly better, this does leave the possibility open for implementing a pre-depolymerization heat kill should other parts of the process require it, for example halting growth of any unlysed cells that may remain in the culture or reducing the protein content of the lysate if a pelleting step is included after heat-treatment.

TABLE 14

Summary of RNA depolymerization yields across varying mixtures of lysates, nucleases, and inactivated lysates. Percent yields are based on a basis of 32.6 mM NMPs, as quantified through lysate base hydrolysis of RNA.

| | No Pre-Heat Kill | | Pre-Heat Kill | |
| --- | --- | --- | --- | --- |
| Reaction | % Depol. Yield (RNase R) | % Depol. Yield (Nuclease $P_1$) | % Depol. Yield (RNase R) | % Depol. Yield (Nuclease $P_1$) |
| 80% background lysate + 0.5 mg/mL Nuclease | 26 | 40 | 27 | 40 |
| 72% background lysate + 8% of 1 mg/mL nuclease lysate (0.064 mg/mL nuclease final) | 26 | 33 | 22 | 30 |

TABLE 14-continued

Summary of RNA depolymerization yields across varying mixtures of lysates, nucleases, and inactivated lysates. Percent yields are based on a basis of 32.6 mM NMPs, as quantified through lysate base hydrolysis of RNA.

| | No Pre-Heat Kill | | Pre-Heat Kill | |
|---|---|---|---|---|
| Reaction | % Depol. Yield (RNase R) | % Depol. Yield (Nuclease $P_1$) | % Depol. Yield (RNase R) | % Depol. Yield (Nuclease $P_1$) |
| 75% background lysate + 5% of 1 mg/mL nuclease lysate (0.04 mg/mL nuclease final) | 29 | 31 | 24 | 29 |
| 80% background lysate - no nuclease control | 18 | 23 | 10 | 10 |
| 50% background lysate + 0.31 mg/mL Nuclease | 41 | 49 | 44 | 56 |
| 46% background lysate + 4% of 1 mg/mL nuclease lysate (0.04 mg/mL nuclease final) | 33 | 41 | 40 | 36 |
| 47.5% background lysate + 2.5% of 1 mg/mL nuclease lysate (0.025 mg/mL nuclease final) | 27 | 37 | 27 | 41 |
| 50% background lysate - no nuclease control | 20 | 34 | 10 | 12 |

Example 6: Cell-Free Production of RNA Using Various Nucleotide Sources

Materials and Methods

Yeast RNA powder obtained from commercial sources was dissolved in water at 45-60 g/L and depolymerized using 1.2 g/L P1 nuclease at 70° C., pH 5.5-5.8 for 1 hour in the presence of 0.05 mM zinc chloride. The resulting depolymerized material was clarified by centrifugation and filtered using a 10 kDa MWCO filter. The resulting stream contained 5' nucleotide monophosphates (NMPs) at a total concentration of ~90-100 mM (~20-25 mM each AMP, CMP, GMP, and UMP).

*E. coli* BL21(DE3) derivatives carrying pBAD24-derived vectors encoding individual kinase enzymes (TthCmk, PfPyrH, TmGmk, AaNdk, and DgPPK2) were cultivated in fermentations with Korz media supplemented with 50 mg/L carbenicillin using standard techniques [Korz, D. J., Rinas, U., Hellmuth, K., Sanders, E. A., & Deckwer, W. D. (1995). Simple fed-batch technique for high cell density cultivation of *Escherichia coli*. Journal of biotechnology, 39(1), 59-65.]. Protein expression was induced by adding L-arabinose. After harvest, lysates were prepared in 60 mM phosphate buffer using high-pressure homogenization, resulting in mixtures of approximately 40 g/L total protein.

*E. coli* BL21(DE3) derivatives carrying pUC19-derived vectors containing one or more transcriptional templates (each consisting of a T7 promoter, target sequence, and one or more transcriptional terminators) encoding a 524 bp double-stranded RNA sequence. Cells were cultivated in fermentations in Korz media using standard techniques [Phue, J. N., Lee, S. J., Trinh, L., & Shiloach, J. (2008). Modified *Escherichia coli* B (BL21), a superior producer of plasmid DNA compared with *Escherichia coli* K (DH5alpha). Biotechnology and bioengineering, 101(4), 831.]. After harvest, lysates were created by high pressure homogenization, diluted, and heat-treated following similar procedures.

*E. coli* BL21(DE3) derivatives carrying pBAD24-derived vectors encoding thermostable T7 RNA polymerase enzymes were cultivated, enzyme expression was induced, and lysates were prepared using similar procedures. Polymerase enzymes were partially purified using two steps of ammonium sulfate fractionation.

Reactions were assembled in 30 mM phosphate buffer, pH 7 according to Table 15.

TABLE 15

Reaction Conditions

| Nucleotide source | Depolymerized cellular RNA | NMPs | NDPs |
|---|---|---|---|
| Nucleotides | 15% v/v | 4 mM each | 4 mM each |
| Magnesium sulfate | | 45 mM | |
| Sodium hexametaphosphate | | 13 mM | |
| Kinase lysates | | 2 g/L total protein | |
| Template DNA lysate | | 5.4% v/v | |
| RNA polymerase | | 0.1 g/L | |

In assembling the cell-free reactions, lysates containing kinase enzymes and template DNA were diluted, combined in equal proportion, and mixed with reaction additives such as magnesium sulfate and sodium hexametaphosphate. Lysates were incubated at 70° C. for 15 minutes to inactivate other enzymatic activities while preserving the activities of the overexpressed kinases. Cell-free reactions were initiated by the addition of RNA polymerase, incubated at 48° C. for 1 hour, and analyzed according to established protocols [Nwokeoji, A. O., Kilby, P. M., Portwood, D. E., & Dickman, M. J. (2016). RNASwift: A rapid, versatile RNA extraction method free from phenol and chloroform. Analytical biochemistry, 512, 36].

Results

Figure 17:
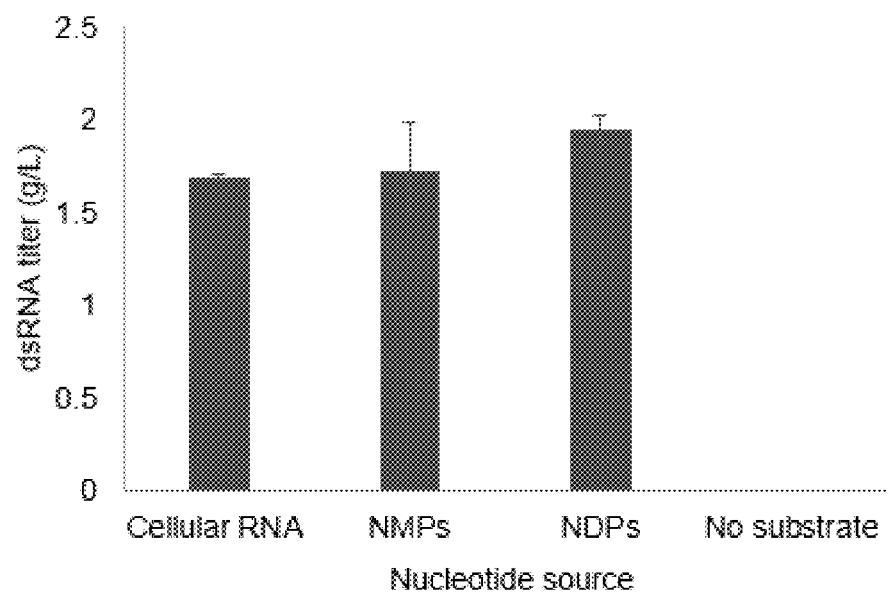
FIG. 17 is a graph showing that cell-free synthesis of dsRNA produces similar product titers regardless of nucleotide source.

Cell-free RNA synthesis reactions were performed using cellular RNA, an equimolar mix of nucleoside 5'-monophosphates (AMP, CMP, GMP, UMP), or an equimolar mix of 5' nucleoside diphosphates (ADP, CDP, GDP, UDP). Similar titers of dsRNA product were produced for each nucleotide source (FIG. 17).

These results demonstrate that the cell-free reactions described herein can be used to synthesize RNA from multiple sources of nucleotides, including cellular RNA, nucleoside 5'-monophosphates, and nucleoside diphosphates.

Example 7: Cell-Free Production of RNA Using Wild-Type RNA Polymerase

Materials and Methods

E. coli BL21(DE3) derivatives carrying pBAD24-derived vectors encoding hexahistidine-tagged thermostable or wild-type T7 RNA polymerase enzymes were cultivated, enzyme expression was induced, and lysates were prepared using procedures described herein. Polymerase enzymes were purified by fast protein liquid chromatography (FPLC) as described herein. Cell-free reactions were performed as described herein except that reactions were performed at a range of temperatures (37-48° C.) for 2 hours. Titers of dsRNA product were quantified as described herein.

Results

Figure 18:
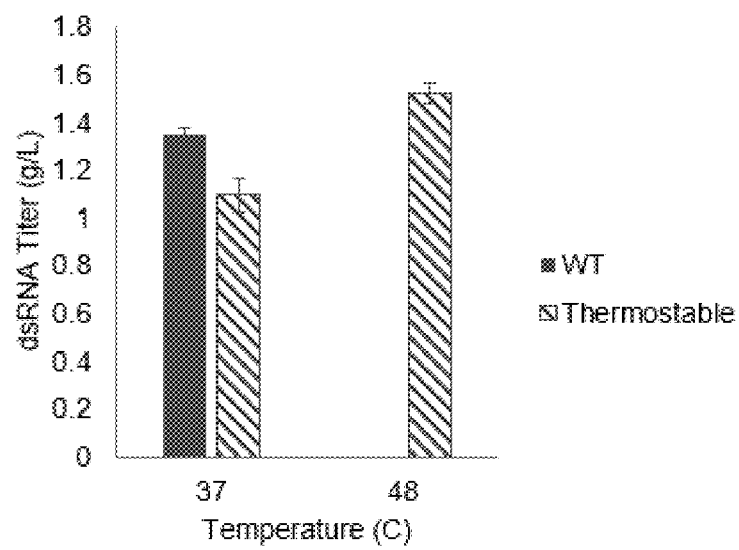
FIG. 18 is a graph showing that cell-free synthesis of dsRNA results in comparable product titers with wild-type and thermostable mutant RNA polymerases at mesophilic reaction temperature.

Cell-free RNA synthesis reactions were performed using wild-type T7 RNA polymerase or a thermostable mutant (FIG. 18). Reactions performed with the thermostable mutant produced dsRNA product at 37° C. and 48° C. In contrast, reactions performed with the wild-type polymerase produced product at 37° C. but not 48° C.

These results demonstrate that the cell-free reactions described herein do not require thermostable RNA polymerases provided they are incubated at appropriate temperatures.

Example 8: Cell-Free Production of NTPs Using Various Nucleotide Sources

Materials and Methods

Cell-free reactions were performed as described in Example 6, except the template DNA lysate and RNA polymerase were omitted. Nucleotides were analyzed by HPLC using an adaptation of published methods [de Korte, D., Haverkort, W. A., Roos, D., & van Gennip, A. H. (1985). Anion-exchange high performance liquid chromatography method for the quantitation of nucleotides in human blood cells. Clinica chimica acta; international journal of clinical chemistry, 148(3), 185.]

Results

Figure 19:
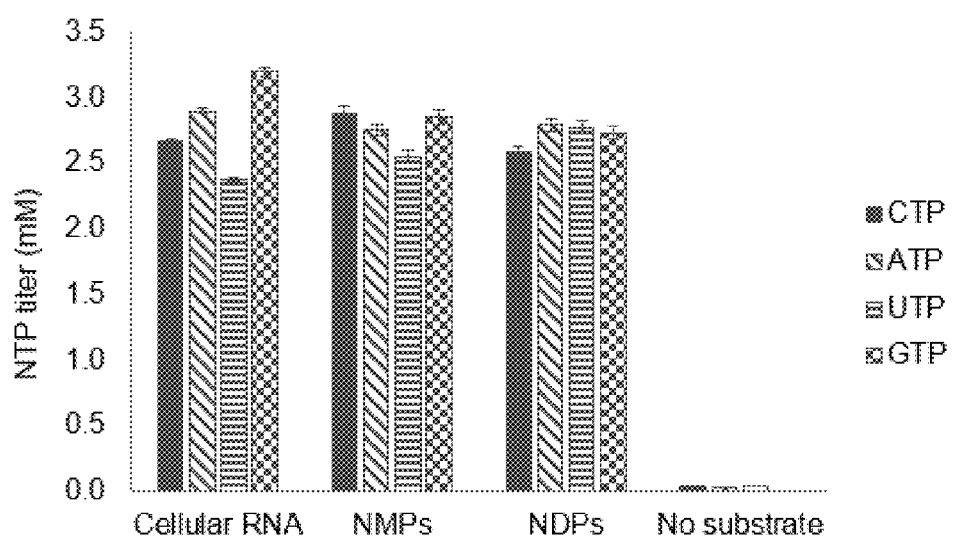
FIG. 19 is a graph showing that cell-free synthesis of NTPs results in similar NTP titers regardless of nucleotide source after a 1 hour incubation at 48° C. For each source of nucleotides (cellular RNA, purified NMPs, or purified NDPs), a quantity of substrate sufficient to provide approximately 4 mM of each nucleotide was added to the reaction. For example, reactions with NDPs comprised 4 mM each ADP, CDP, GDP, and UDP.

Cell-free reactions to produce nucleotide 5'-triphosphates (NTPs: ATP, CTP, GTP and UTP) were performed using cellular RNA, an equimolar mix of nucleoside 5'-monophosphates (AMP, CMP, GMP, UMP), or an equimolar mix of 5' nucleoside diphosphates (ADP, CDP, GDP, UDP). Similar titers of each NTP were produced for each nucleotide source (FIG. 19).

These results demonstrate that the cell-free reactions described herein can also be used to produce NTPs simply by omitting the RNA polymerase and DNA template. Similarly to the cell-free reactions producing RNA described in Example 6, cell-free reactions producing NTPs can utilize multiple sources of nucleotides, including cellular RNA, nucleoside 5'-monophosphates, and nucleoside diphosphates.

REFERENCES

1. Maekewa K., Tsunasawa S., Dibo G., Sakiyama F. 1991. Primary structure of nuclease P1 from *Penicillium citrinum*. Eur. J. Biochem. 200:651-661.
2. Volbeda A., Lahm A., Sakiyama F., Suck D. 1991. Crystal structure of *Penicillium citrinum* P1 nuclease at 2.8-A resolution. EMBO J. 10:1607-1618(1991)
3. Romier C., Dominguez R., Lahm A., Dahl O., Suck D. 1998. Recognition of single-stranded DNA by nuclease P1: high resolution crystal structures of complexes with substrate analogs. Proteins 32:414-424
4. Cheng Z. F., Deutscher M. P. 2002. Purification and characterization of the *Escherichia coli* exoribonuclease RNase R. Comparison with RNase II. J. Biol. Chem. 277:21624-21629.
5. Zilhao R., Camelo L., Arraiano C. M. 1993. DNA sequencing and expression of the gene mb encoding *Escherichia coli* ribonuclease II. Mol. Microbiol. 8:43-51
6. March P. E., Ahnn J., Inouye M. 1985. The DNA sequence of the gene (mc) encoding ribonuclease III of *Escherichia coli*. Nucleic Acids Res. 13:4677-4685
7. Chen S. M., Takiff H. E., Barber A. M., Dubois G. C., Bardwell J. C., Court D. L. 1990. Expression and characterization of RNase III and Era proteins. Products of the rnc operon of *Escherichia coli*. J. Biol. Chem. 265:2888-2895
8. Robertson H. D., Webster R. E., Zinder N. D. 1968. Purification and properties of ribonuclease III from *Escherichia coli*. J. Biol. Chem. 243:82-91.
9. Molina L., Bernal P., Udaondo Z., Segura A., Ramos J. L. 2013. Complete Genome Sequence of a *Pseudomonas putida* Clinical Isolate, Strain H8234. Genome Announc. 1: E00496-13; and Cheng, Z. F. and M. P. Deutscher. 2002. Purification and characterization of the *Escherichia coli* exoribonuclease RNAse R. Comparison with RNAse II. J Biol Chem. 277(24).
10. Even S., Pellegrini O., Zig L., Labas V., Vinh J., Brechemmier-Baey D., Putzer H. 2005. Ribonucleases J1 and J2: two novel endoribonucleases in *B. subtilis* with functional homology to *E. coli* RNase E. Nucleic Acids Res. 33:2141-2152.
11. Li de la Sierra-Gallay I., Zig L., Jamalli A., Putzer H. 2008. Structural insights into the dual activity of RNase J. Nat. Struct. Mol. Biol. 15:206-212.
12. Ball T. K., Saurugger P. N., Benedick M. J. 1987. The extracellular nuclease gene of *Serratia marcescens* and its secretion from *Escherichia coli*. Gene 57:183-192.
13. Biedermann K., Jepsen P. K., Riise E., Svendsen I. 1989. Purification and characterization of a *Serratia marcescens* nuclease produced by *Escherichia coli*. Carlsberg Res. Commun. 54:17-27.
14. Shlyapnikov S. V., Lunin V. V., Perbandt M., Polyakov K. M., Lunin V. Y., Levdikov V. M., Betzel C., Mikhailov A. M. 2000. Atomic structure of the *Serratia marcescens* endonuclease at 1.1 A resolution and the enzyme reaction mechanism. Acta Crystallogr. D 56:567-572.
15. Zuo Y., Deutscher M. P. 2002. Mechanism of action of RNase T. I. Identification of residues required for catalysis, substrate binding, and dimerization. J. Biol. Chem. 277:50155-50159.
16. Zuo Y., Zheng H., Wang Y., Chruszcz M., Cymborowski M., Skarina T., Savchenko A., Malhotra A., Minor W. 2007. Crystal structure of RNase T, an exoribonuclease involved in tRNA maturation and end turnover. Structure 15:417-428.
17. Huang S., Deutscher M. P. 1992. Sequence and transcriptional analysis of the *Escherichia coli* rnt gene encoding RNase T. J. Biol. Chem. 267:25609-25613.
18. Chauhan A. K., Miczak A., Taraseviciene L., Apirion D. 1991. Sequencing and expression of the mc gene of *Escherichia coli*. Nucleic Acids Res. 19:125-129.

19. Cormack R. S., Genereaux J. L., Mackie G. A. 1993. RNase E activity is conferred by a single polypeptide: overexpression, purification, and properties of the ams/rne/hmp1 gene product. Proc. Natl. Acad. Sci. U.S.A. 90:9006-9010.

20. Motomura, K., Hirota, R., Okada, M., Ikeda, T., Ishida, T., & Kuroda, A. (2014). A New Subfamily of Polyphosphate Kinase 2 (Class III PPK2) Catalyzes both Nucleoside Monophosphate Phosphorylation and Nucleoside Diphosphate Phosphorylation, *Applied and Environmental Microbiology*, 80(8), 2602-2608. http://doi.org/10.1128/AEM.03971-13

21. Elkin, S. R., Kumar, A., Price, C. W., & Columbus, L. (2013). A Broad Specificity Nucleoside Kinase from *Thermoplasma acidophilum*. *Proteins*, 81(4), 568-582. doi.org/10.1002/prot.24212

22. Hansen, T., Arnfors, L., Ladenstein, R., & Schönheit, P. (2007). The phosphofructokinase-B (MJ0406) from *Methanocaldococcus jannaschii* represents a nucleoside kinase with a broad substrate specificity. Extremophiles, 11(1), 105.

23. Ota, H., Sakasegawa, S., Yasuda, Y., Iniarnura, S., & Tamura, T. (2008). A novel nucleoside kinase from *Burkholderia thailandensis*: a member of the phosphofructokinase B-type family of enzymes. *The FEBS journal*, 275(23), 5865.

24. Tomoike, F., Nakagawa, N., Kuramitsu, S., & Masui, R. (2011). A single amino acid limits the substrate specificity of *Thermus thermophilus* uridine-cytidine kinase to cytidine. *Biochemistry*, 50(21), 4597.

25. Henne A., Brueggemann H., Raasch C., Wiezer A., Hartsch T., Liesegang H., Johann A., Lienard T., Gohl O., Martinez-Arias R., Jacobi C., Starkuviene V., Schlenczeck S., Dencker S., Huber R., Klenk H.-P., Kramer W., Merkl R., Gottschalk G., Fritz H.-J. 2004. The genome sequence of the extreme thermophile *Thermus thermophilus*. Nat. Biotechnol. 22:547-553.

26. Tan Z W, Liu J, Zhang X F, Meng F G, Zhang Y Z. Nan Fang Yi Ke Da Xue Xue Bao. 2010. Expression, purification and enzymatic characterization of adenylate kinase of *Thermus thermophilus* HB27 in *Escherichia coli*. January; 30(1):1-6

27. Maeder D. L., Weiss R. B., Dunn D. M., Cherry J. L., Gonzalez J. M., DiRuggiero J., Robb F. T. 1999. Divergence of the hyperthermophilic archaea *Pyrococcus furiosus* and *P. horikoshii* inferred from complete genomic sequences. Genetics 152:1299-1305.

28. Methé, B. A., Nelson, K. E., Deming, J. W., Momen, B., Melamud, E., Zhang, X., . . . Fraser, C. M. (2005). The psychrophilic lifestyle as revealed by the genome sequence of *Colwellia psychrerythraea* 34H through genomic and proteomic analyses. *Proceedings of the National Academy of Sciences of the United States of America*, 102(31), 10913-10918. doi.org/10.1073/pnas.0504766102

29. Médigue, C., Krin, E., Pascal, G., Barbe, V., Bernsel, A., Bertin, P. N., . . . Danchin, A. (2005). Coping with cold: The genome of the versatile marine *Antarctica* bacterium *Pseudoalteromonas haloplanktis* TAC125. *Genome Research*, 15(10), 1325-1335. doi.org/10.1101/gr.4126905

30. Ayala-del-Río, H. L., Chain, P. S., Grzymski, J. J., Ponder, M. A., Ivanova, N., Bergholz, P. W., . . . Tiedje, J. M. (2010). The Genome Sequence of *Psychrobacter arcticus* 273-4, a Psychroactive Siberian Permafrost Bacterium, Reveals Mechanisms for Adaptation to Low-Temperature Growth. *Applied and Environmental Microbiology*, 76(7), 2304-2312. doi.org/10.1128/AEM.02101-09

31. Feil, H., Feil, W. S., Chain, P., Larimer, F., DiBartolo, G., Copeland, A., . . . Lindow, S. E. (2005). Comparison of the complete genome sequences of *Pseudomonas syringae* pv. *syringae* B728a and pv. tomato DC3000. *Proceedings of the National Academy of Sciences of the United States of America*, 102(31), 11064-11069. doi.org/10.1073/pnas.0504930102

32. Song, S., Inouye, S., Kawai, M., Fukami-Kobayashi, K., Gō, M., & Nakazawa, A. (1996). Cloning and characterization of the gene encoding *Halobacterium halobium* adenylate kinase. *Gene*, 175(1), 65-70.

33. Masui R., Kurokawa K., Nakagawa N., Tokunaga F., Koyama Y., Shibata T., Oshima T., Yokoyama S., Yasunaga T., Kuramitsu S. Complete genome sequence of *Thermus thermophilus* HB8. Submitted (November-2004) to the EMBL/GenBank/DDBJ databases.

34. Ng, W. V., Kennedy, S. P., Mahairas, G. G., Berquist, B., Pan, M., Shukla, H. D., . . . DasSarma, S. (2000). Genome sequence of *Halobacterium* species NRC-1. *Proceedings of the National Academy of Sciences of the United States of America*, 97(22), 12176-12181.

35. Marco-Marin C., Escamilla-Honrubia J. M., Rubio V. 2005. First-time crystallization and preliminary X-ray crystallographic analysis of a bacterial-archaeal type UMP kinase, a key enzyme in microbial pyrimidine biosynthesis. Biochim. Biophys. Acta 1747:271-275.

36. Marco-Marin C., Escamilla-Honrubia J. M., Rubio V. 2005. First-time crystallization and preliminary X-ray crystallographic analysis of a bacterial-archaeal type UMP kinase, a key enzyme in microbial pyrimidine biosynthesis. Biochim. Biophys. Acta 1747:271-275.

37. Jensen, K. S., Johansson, E., & Jensen, K. F. (2007). Structural and enzymatic investigation of the *Sulfolobus solfataricus* uridylate kinase shows competitive UTP inhibition and the lack of GTP stimulation. *Biochemistry*, 46(10), 2745-2757.

38. Nelson K. E., Clayton R. A., Gill S. R., Gwinn M. L., Dodson R. J., Haft D. H., Hickey E. K., Peterson J. D., Nelson W. C., Ketchum K. A., McDonald L. A., Utterback T. R., Malek J. A., Linher K. D., Garrett M. M., Stewart A. M., Cotton M. D., Pratt M. S. Fraser C. M. 1999. Evidence for lateral gene transfer between Archaea and Bacteria from genome sequence of *Thermotoga maritima*. Nature 399:323-329.

39. Riley, M., Staley, J. T., Danchin, A., Wang, T. Z., Brettin, T. S., Hauser, L. J., . . . Thompson, L. S. (2008). Genomics of an extreme psychrophile, *Psychromonas ingrahamii*. *BMC Genomics*, 9, 210. doi.org/10.1186/1471-2164-9-210

40. Ishibashii, M., Tokunaga, H., Hirakuka, K., Yonezawa, Y., Tsurumani, H., Arakawa, T., & Tokunaga, M. (2001). NaCl-activated nucleoside diphosphate kinase from extremely halophilic archaeon, *Halobacterium salinarum*, maintains native conformation without salt. *FEBS letters*, 493(2-3), 134.

41. Polosina, Y. Y., Zamyatkin, D. F., Kostyukova, A. S., Filimonov, V. V., & Fedorov, O. V. (2002). Stability of *Natrialba magadii* NDP kinase: comparisons with other halophilic proteins. *Extremophiles: life under extreme conditions*, 6(2), 135.

42. Polosina, Y. Y., Zamyatkin, D. F., Kostyukova, A. S., Filimonov, V. V., & Fedorov, O. V. (2002). Stability of

*Natrialba magadii* NDP kinase: comparisons with other halophilic proteins. *Extremophiles: life under extreme conditions,* 6(2), 135.
43. Udaondo, Z., Molina, L., Daniels, C., Gomez, M. J., Molina-Henares, M. A., Matilla, M. A., . . . Ramos, J. L. (2013). Metabolic potential of the organic-solvent tolerant *Pseudomonas putida* DOT-T1E deduced from its annotated genome. *Microbial Biotechnology,* 6(5), 598-611. http://doi.org/10.1111/1751-7915.12061
44. Nölling, J., Breton, G., Omelchenko, M. V., Makarova, K. S., Zeng, Q., Gibson, R., Smith, D. R. (2001). Genome Sequence and Comparative Analysis of the Solvent-Producing Bacterium *Clostridium acetobutylicum. Journal of Bacteriology,* 183(16), 4823-4838. http://doi.org/10.1128/113.183.16.4823-4838.2001
45. Brune, M., Schumann, R., & Wittinghofer, F. (1985). Cloning and sequencing of the adenylate kinase gene (adk) of *Escherichia coli, Nucleic Acids Research,* 13(19), 7139-7151.
46. Pel, H. J., de Winde, J. H., Archer, D. B., Dyer, P. S., Hofmann, G., Schaap, P. J., . . . & Andersen, M. R. (2007). Genome sequencing and analysis of the versatile cell factory *Aspergillus niger* CBS 513.88. *Nature biotechnology,* 25(2), 221.
47. Magdolen, V., Oechsner, U, &. Bandlow, W. (1987). The complete nucleotide sequence of the gene coding for yeast adenylate kinase. *Current genetics,* 12(6), 405.
48. Pedersen, S., Skouv, J., Kajitani, M., & Ishihama, A. (1984). Transcriptional organization of the rpsA operon of *Escherichia coli. Molecular & general genetics: MGG,* 196(1), 135.
49. Smallshaw, J., & Kelln, R. A. (1992). Cloning, nucleotide sequence and expression of the *Escherichia coli* K-12 pyrH gene encoding UMP kinase. *Genetics (Life Sci. Adv.),* 11, 59-65.
50. Liljelund, P., Sanni, A., Friesen, J. D., &. Lacroute, F. (1989). Primary structure of the *S. cerevisiae* gene encoding uridine monophosphokinase. *Biochemical and biophysical research communications,* 165(1), 464.
51, Gentry, D., Bengra, C., Ikehara, K., & Cashel, M. (1993). Guanylate kinase of *Escherichia coli* K-12. *The Journal of biological chemistry,* 268(19), 14316.
52. Konrad, M. (1992). Cloning and expression of the essential gene for guanylate kinase from yeast. *The Journal of biological chemistry,* 267(36), 25652.
53. Hama, H., Almaula, N., Lerner, C. G., Inouye, S., & Inouye, M. (1991). Nucleoside diphosphate kinase from *Escherichia coli*; its overproduction and sequence comparison with eukaryotic enzymes. *Gene,* 105(1), 31.
54. Besir, H., Zeth, K., Bracher, A., Heider, U., Ishibashi, M., Tokunaga, M., & Oesterhelt, D. (2005). Structure of a halophilic nucleoside diphosphate kinase from *Halobacterium salinarum. FEBS letters,* 579(29), 6595.
55. Deutscher, M. & Reuven N. (1991). Enzymatic basis for hydrolytic versus phosphorolytic mRNA degradation in *Escherichia coli* and *Bacillus subtilis. PNAS,* 88, 3277-3280.
56. Nwokeji, A. O., Kilby, P. M., Portwood, D. E., & Dickman, M. J. (2016). RNASwift: A rapid, versatile RNA extraction method free from phenol and chloroform. Analytical Biochemistry, 512, 36-46.
57. Mohanty, B. K., Giladi, H., Maples, V. F., & Kushner, S. R. (2008). Analysis of RNA decay, processing, and polyadenylation in *Escherichia coli* and other prokaryotes. *Methods in Enzymology,* 447, 3-29.
58. Korz, D. J., Rinas, U., Hellmuth, K., Sanders, E. A., & Deckwer, W. D. (1995). Simple fed-batch technique for high cell density cultivation of *Escherichia coli.* Journal of biotechnology, 39(1), 59-654
59. Phue, J. N., Lee, S. J., Trinh, L., & Shiloach, J. (2008). Modified *Escherichia coli* B (BL21), a superior producer of plasmid DNA compared with *Escherichia coli* K (DH5alpha). Biotechnology and bioengineering, 101(4), 831.
60. de Korte, D., Haverkort, W. A., Roos, D., & van Gennip, A. H. (1985). Anion-exchange high performance liquid chromatography method for the quantitation of nucleotides in human blood cells. Clinica chimica acta; international journal of clinical chemistry, 148(3), 185.]

```
                              Sequences

Deinococcus geothermalis DSM 11300 PPK2
                                                   (SEQ ID NO: 1)
MQLDRYRVPPGQRVRLSNWPTDDDGGLSKAEGEALLPDLQQRLANLQERLYAESQ
QALLIVLQARDAGGKDGTVKHVIGAFNPSGVQVSNFKVPTEEERAHDFLWRIHRQTP
RLGMIGVFNRSQYEDVLVTRVHHLIDDQTAQRRLKHICAFESLLTDSGTRIVKFYLHI
SPEEQKKRLEARLADPSKHWKFNPGDLQERAHWDAYTAVYEDVLTTSTPAAPWYV
VPADRKWFRNLLVSQILVQTLEEMNPQFPAPAFNAADLRIV Meiothermus ruber DM 1279 PPK2
                                                   (SEQ ID NO: 2)
MGFCSIEFLMGAQMKKYRVQPDGRFELKRFDPDDTSAFEGGKQAALEALAVLNRRL
EKLQELLYAEGQHKVLVVLQAMDAGGKDGTIRVVFDGVNPSGVRVASFGVPTEQE
LARDYLWRVHQQVPRKGELVIFNRSHYEDVLVVRVKNLVPQQVWQKRYRHIREFE
RMLADEGTTILKFFLHISKDEQRQRLQERLDNPEKRWKFRMGDLEDRRLWDRYQEA
YEAAIRETSTEYAPWYVIPANKNWYRNWLVSHILVETLEGLAMQYPQPETASEKIVIE Meiothermus silvanus DSM 9946 PPK2
                                                   (SEQ ID NO: 3)
MAKTIGATLNLQDIDPRSTPGFNGDKEKALALLEKLTARLDELQEQLYAEHQHRVLV
ILQGMDTSGKDGTIRHVFKNVDPLGVRVVAFKAPTPPELERDYLWRVHQHVPANGE
LVIFNRSHYEDVLVARVHNLVPPAIWSRRYDHINAFEKMLVDEGTTVLKFFLHISKEE
QKKRLLERLVEADKHWKFDPQDLVERGYWEDYMEAYQDVLDKTHTQYAPWHVIP
ADRKWYRNLQVSRLLVEALEGLRMKYPRPKLNIPRLKSELEKM Thermosynechococcus elongatus BP-1 PPK2
                                                   (SEQ ID NO: 4)
MIPQDFLDEINPDRYIVPAGGNFHWKDYDPGDTAGLKSKVEAQELLAAGIKKLAAY
QDVLYAQNIYGLLIIFQAMDAAGKDSTIKHVMSGLNPQACRVYSFKAPSAEELDHDF
LWRANRALPERGCIGIFNRSYYEEVLVVRVHPDLLNRQQLPPETKTKHIWKERFEDIN
```

| Sequences |
|---|
| HYERYLTRNGILILKFFLHISKAEQKKRFLERISRPEKNWKFSIEDVRDRAHWDDYQQ<br>AYADVFRHTSTKWAPWHIIPANHKWFARLMVAHFIYQKLASLNLHYPMLSEAHREQ<br>LLEAKALLENEPDED |

Anaerolinea thermophila UNI-1 PPK2

(SEQ ID NO: 5)

MGEAMERYFIKPGEKVRLKDWSPDPPKDFEGDKESTRAAVAELNRKLEVLQERLYA
ERKHKVLVILQGMDTSGKDGVIRSVFEGVNPQGVKVANFKVPTQEELDHDYLWRV
HKVVPGKGEIVIFNRSHYEDVLVVRVHNLVPPEVWKKRYEQINTQFERLLHETGTTIL
KFFLFISREEQKQRLLERLADPAKHWKFNPGDLKERALWEEYEKAYEDVLSRTSTEY
APWILVPADKKWYRDWVISRVLVETLEGLEIQLPPPLADAETYRRQLLEEDAPESR

Caldilinea aerophila DSM 14535 PPK2

(SEQ ID NO: 6)

MDVDRYRVPPGSTIHLSQWPPDDRSLYEGDKKQGKQDLSALNRRLETLQELLYAEG
KHKVLIILQGMDTSGKDGVIRHVFNGVNPQGVKVASFKVPTAVELAHDFLWRIHRQ
TPGSGEIVIFNRSHYEDVLVVRVHGLVPPEVWARRYEHINTAFEKLLVDEGTTILKFFL
HISKEEQRQRLLERLEMPEKRWKFSVGDLAERKRWDEYMAAYEAVLSKTSTEYAP
WYIVPSDRKWYRNLVISHVIINALEGLNMRYPQPEDIAFDTIVIE

Chlorobaculum tepidum TLS PPK2

(SEQ ID NO: 7)

MKLDLDAFRIQPGKKPNLAKRPTRIDPVYRSKGEYHELLANHVAELSKLQNVLYAD
NRYAILLIFQAMDAAGKDSAIKHVMSGVNPQGCQVYSFKHPSATELEHDFLWRTNC
VLPERGRIGIFNRSYYEEVLVVRVHPEILEMQNIPHNLAHNGKVWDHRYRSIVSHEQ
HLHCNGTRIVKFYLHLSKEEQRKRFLERIDDPNKNWKFSTADLEERKFWDQYMEAY
ESCLQETSTKDSPWFAVPADDKKNARLIVSRIVLDTLESLNLKYPEPSPERRKELLDIR
KRLENPENGK

Oceanithermus profundus DSM 14977 PPK2

(SEQ ID NO: 8)

MDVSRYRVPPGSGFDPEAWPTREDDDFAGGKKEAKKELARLAVRLGELQARLYAE
GRQALLIVLQGMDTAGKDGTIRHVFRAVNPQGVRVTSFKKPTALELAHDYLWRVH
RHAPARGEIGIFNRSHYEDVLVVRVHELVPPEVWGRRYDHINAFERLLADEGTRIVK
FFLHISKDEQKRRLEARLENPRKHWKFNPADLSERARWGDYAAAYAEALSRTSSDR
APWYAVPADRKWQRNRIVAQVLVDALEAMDPRFPRVDFDPASVRVE

Roseiflexus castenholzii DSM 13941 PPK2

(SEQ ID NO: 9)

MYAQRVVPGMRVRLHDIDPDANGGLNKDEGRARFAELNAELDVMQEELYAAGIHA
LLLILQGMDTAGKDGAIRNVMLNLNPQGCRVESFKVPTEEELAHDFLWRVHRVVPR
KGMVGVFNRSHYEDVLVVRVHSLVPESVWRARYDQINAFERLLADTGTIIVKCFLHI
SKEEQEQRLLARERDVSKAWKLSAGDWRERAFWDDYMAAYEEALTRCSTDYAPW
YIIPANRKWYRDLAISEALVETLRPYRDDWRRALDAMSRARRAELEAFRAEQHAME
GRPQGAGGVSRR

Roseiflexus sp. RS-1 PPK2

(SEQ ID NO: 10)

MHYAHTVIPGTQVRLRDIDPDASGGLTKDEGRERFASFNATLDAMQEELYAAGVHA
LLLILQGMDTAGKDGAIRNVMHNLNPQGCRVESFKVPTEEELAHDFLWRVHKVVPR
KGMVGVFNRSHYEDVLVVRVHSLVPEHVWRARYDQINAFERLLTDTGTIIVKCFLHI
SKDEQEKRLLAREQDVTKAWKLSAGDWRERERWDEYMAAYEEALTRCSTEYAPW
YIIPANRKWYRDLAISEVLVETLRPYRDDWQRALDAMSQARLAELKAFRHQQTAGA
TRL

Truepera radiovictrix DSM 17093 PPK2

(SEQ ID NO: 11)

MSQGSAKGLGKLDKKVYARELALLQLELVKLQGWIKAQGLKVVVLFEGRDAAGK
GSTITRITQPLNPRVCRVVALGAPTERERTQWYFQRYVHHLPAAGEMVLFDRSWYN
RAGVERVMGFCTEAEYREFLHACPTFERLLLDAGIILIKYWFSVSAAEQERRMRRRN
ENPAKRWKLSPMDLEARARWVAYSKAKDAMFYHTDTKASPWYVVNAEDKRRAH
LSCIAHLLSLIPYEDLTPPPLEMPPRDLAGADEGYERPDKAHQTWVPDYVPPTR

Thermus thermophilus Adk (SEQ ID NO: 12)

MDVGQAVIFLGPPGAGKGTQASRLAQELGFKKLSTGDILRDHVARGTPLGERVRPIM
ERGDLVPDDLILELIREELAERVIFDGFPRTLAQAEALDRLLSETGTRLLGVVLVEVPE
EELVRRILRRAELEGRSDDNEETVRRRLEVYREKTEPLVGYYEARGVLKRVDGLGTP
DEVYARIRAALGI

Thermus thermophilus Cmk (SEQ ID NO: 13)

MRGIVTIDGPSASGKSSVARRVAAALGVPYLSSGLLYRAAAFLALRAGVDPGDEEGL
LALLEGLGVRLLAQAEGNRVLADGEDLTSFLHTPEVDRVVSAVARLPGVRAWVNR

Sequences

```
RLKEVPPPFVAEGRDMGTAVFPEAAHKFYLTASPEVRAWRRARERPQAYEEVLRDL
LRRDERDKAQSAPAPDALVLDTGGMTLDEVVAWVLAHIRR

Pyrococcus furiosus PyrH
                                                 (SEQ ID NO: 14)
MRIVFDIGGSVLVPENPDIDFIKEIAYQLTKVSEDHEVAVVVGGGKLARKYIEVAEKF
NSSETFKDFIGIQITRANAMLLIAALREKAYPVVVEDFWEAWKAVQLKKIPVMGGTH
PGHTTDAVAALLAEFLKADLLVVITNVDGVYTADPKKDPTAKKIKKMKPEELLEIVG
KGIEKAGSSSVIDPLAAKIIARSGIKTIVIGKEDAKDLFRVIKGDHNGTTIEP Thermotoga maritima Gmk
                                                 (SEQ ID NO: 15)
MKGQLFVICGPSGAGKTSIIKEVLKRLDNVVFSVSCTTRPKRPHEEDGKDYFFITEEEF
LKRVERGEFLEWARVHGHLYGTLRSFVESHINEGKDVVLDIDVQGALSVKKKYSNT
VFIYVAPPSYADLRERILKRGTEKEADVLVRLENAKWELMFMDEFDYIVVNENLED
AVEMVVSIVRSERAKVTRNQDKIERFKMEVKGWKKL Aquifex aeolicus Ndk
                                                 (SEQ ID NO: 16)
MAVERTLIIVKPDAMEKGALGKILDRFIQEGFQIKALKMFRFTPEKAGEFYYVHRERP
FFQELVEFMSSGPVVAAVLEGEDAIKRVREIIGPTDSEEARKVAPNSIRAQFGTDKGK
NAIHASDSPESAQYEICFIFSGLEIV
```

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The terms "about" and "substantially" preceding a numerical value mean±10% of the recited numerical value.

Where a range of values is provided, each value between the upper and lower ends of the range are specifically contemplated and described herein.

What is claimed is:

1. A method for producing ribonucleic acid (RNA) comprising:
   (a) incubating (i) cellular RNA, wherein the cellular RNA comprises ribosomal RNA, messenger RNA, and/or transfer RNA, and (ii) a ribonuclease to produce 5' nucleoside monophosphates (NMPs);
   (b) eliminating the ribonuclease; and
   (c) incubating the 5' NMPs with polyphosphate kinase (PPK), polyphosphate, deoxyribonucleic acid (DNA) template encoding a RNA of interest, and RNA polymerase to produce the RNA of interest.

2. The method of claim 1, wherein the ribonuclease is Nuclease P1 or RNase R.

3. The method of claim 1, wherein the 5' NMPs include 5' AMP, 5' GMP, 5' CMP, and/or 5' UMP.

4. The method of claim 1, wherein the ribonuclease is eliminated via temperature, pH, salt, detergent, alcohol, chemical inhibitors, separation, precipitation, filtration, capture, and/or chromatography.

5. The method of claim 1, wherein the PPK is a PPK1 family enzyme or a PPK2 family enzyme.

6. The method of claim 1, wherein the PPK is a Class III PPK2 enzyme from *Deinococcus geothermalis* (SEQ ID NO: 1).

7. The method of claim 1, wherein the polyphosphate is selected from the group consisting of tetrapolyphosphates, pentapolyphosphates, and hexametaphosphates.

8. The method of claim 1, wherein step (c) comprises an enzyme preparation or cell lysate obtained from cells that produce the PPK, the deoxyribonucleic acid (DNA) template, and/or the RNA polymerase.

9. The method of claim 8, wherein activity of native enzymes in the cell lysate or enzyme preparation has been eliminated via genetic modification, enzyme secretion from a cell, protease targeting, temperature, pH, salt, detergent, alcohol, chemical inhibitors, separation, precipitation, filtration, capture, and/or chromatography.

10. The method of claim 9, wherein the native enzymes are selected from the group consisting of phosphatases, nucleases, proteases, deaminases, oxidoreductases, and hydrolases.

11. A method for producing ribonucleic acid (RNA) comprising:
    (a) incubating (i) cellular RNA and (ii) a ribonuclease to produce 5' nucleoside monophosphates (NMPs);
    (b) eliminating the ribonuclease; and
    (c) incubating the 5' NMPs with at least one NMP kinase, at least one NDP kinase, at least one polyphosphate kinase (PPK), polyphosphate, deoxyribonucleic acid (DNA) template encoding a RNA of interest, and RNA polymerase to produce the RNA of interest.

12. The method of claim 11, wherein the cellular RNA comprises ribosomal RNA, messenger RNA, and/or transfer RNA.

13. The method of claim 11, wherein the ribonuclease is Nuclease P1 or RNase R.

14. The method of claim 11, wherein the 5' NMPs include 5' AMP, 5' GMP, 5' CMP, and/or 5' UMP.

15. The method of claim 11, wherein the ribonuclease is eliminated via temperature, pH, salt, detergent, alcohol, chemical inhibitors, separation, precipitation, filtration, capture, and/or chromatography.

16. The method of claim 11, wherein the at least one NMP kinase is an AMP kinase, a CMP kinase, a UMP kinase, or a GMP kinase.

17. The method of claim 16, wherein the at least one NMP kinase is AMP kinase from *Thermus thermophilus* (SEQ ID NO: 12), CMP kinase from *Thermus thermophilus* (SEQ ID NO: 13), UMP kinase from *Pyrococcus furiosus* (SEQ ID NO: 14), and/or GMP kinase from *Thermotoga maritima* (SEQ ID NO: 15).

18. The method of claim 11, wherein the at least one NDP kinase is from *Aquifex aeolicus* (SEQ ID NO: 16).

19. The method of claim 11, wherein the at least one PPK is a PPK1 family enzyme or a PPK2 family enzyme.

20. The method of claim 19, wherein the at least one PPK is a Class III PPK2 enzyme from *Deinococcus geothermalis* (SEQ ID NO: 1).

21. The method of claim 11, wherein the polyphosphate is selected from the group consisting of tetrapolyphosphates, pentapolyphosphates, and hexametaphosphates.

22. The method of claim 11, wherein step (c) comprises an enzyme preparation or cell lysate obtained from cells that produce the PPK, the NMP kinase, the NDP kinase, the deoxyribonucleic acid (DNA) template, and/or the RNA polymerase.

23. The method of claim 11, wherein activity of native enzymes in the cell lysate or enzyme preparation has been eliminated via genetic modification, enzyme secretion from a cell, protease targeting, temperature, pH, salt, detergent, alcohol, chemical inhibitors, separation, precipitation, filtration, capture, and/or chromatography.

24. The method of claim 23, wherein the native enzymes are selected from the group consisting of phosphatases, nucleases, proteases, deaminases, oxidoreductases, and hydrolases.

25. A method for producing ribonucleic acid (RNA) comprising:
    (a) incubating (i) cellular RNA and (ii) Nuclease P1 to produce 5' nucleoside monophosphates (NMPs);
    (b) eliminating the Nuclease P1; and
    (c) incubating the 5' NMPs with at least one NMP kinase, at least one NDP kinase, a Class III PPK2 enzyme from *Deinococcus geothermalis* (SEQ ID NO: 1), polyphosphate, deoxyribonucleic acid (DNA) template encoding a RNA of interest, and RNA polymerase to produce the RNA of interest.

26. The method of claim 25, wherein the at least one NMP kinase is AMP kinase from *Thermus thermophilus* (SEQ ID NO: 12), CMP kinase from *Thermus thermophilus* (SEQ ID NO: 13), UMP kinase from *Pyrococcus furiosus* (SEQ ID NO: 14), and/or GMP kinase from *Thermotoga maritima* (SEQ ID NO: 15).

27. The method of claim 25, wherein the at least one NDP kinase is from *Aquifex aeolicus* (SEQ ID NO: 16).

28. A method for producing ribonucleic acid (RNA) comprising:
   (a) incubating (i) cellular RNA and (ii) a ribonuclease to produce 5' nucleoside monophosphates (NMPs);
   (b) eliminating the ribonuclease, wherein the ribonuclease is eliminated via temperature, pH, salt, detergent, alcohol, chemical inhibitors, separation, precipitation, filtration, capture, and/or chromatography; and
   (c) incubating the 5' NMPs with polyphosphate kinase (PPK), polyphosphate, deoxyribonucleic acid (DNA) template encoding a RNA of interest, and RNA polymerase to produce the RNA of interest.

29. The method of claim 28, wherein the ribonuclease is Nuclease P1 or RNase R.

30. The method of claim 28, wherein the PPK is a PPK1 family enzyme or a PPK2 family enzyme.

* * * * *